(12) United States Patent
Snell et al.

(10) Patent No.: US 9,314,517 B2
(45) Date of Patent: *Apr. 19, 2016

(54) PARASITE VACCINE

(75) Inventors: William J. Snell, Richardson, TX (US); Yanjie Liu, Dallas, TX (US); Oliver Billker, Oxford (GB); Robert E. Sinden, Wokingham (GB); Rita Tewari, Nottingham (GB)

(73) Assignees: IMPERIAL INNOVATIONS LTD, London (GB); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 95 days.

This patent is subject to a terminal disclaimer.

(21) Appl. No.: 12/899,507

(22) Filed: Oct. 6, 2010

(65) Prior Publication Data

US 2011/0091526 A1    Apr. 21, 2011

Related U.S. Application Data

(63) Continuation of application No. 11/856,036, filed on Sep. 15, 2007, now Pat. No. 8,216,593.

(60) Provisional application No. 60/845,122, filed on Sep. 16, 2006.

(51) Int. Cl.
| | | |
|---|---|---|
| *A61K 39/018* | (2006.01) | |
| *A61K 39/002* | (2006.01) | |
| *A61K 39/005* | (2006.01) | |
| *A61K 39/12* | (2006.01) | |
| *A61K 39/15* | (2006.01) | |
| *C07K 14/44* | (2006.01) | |
| *A61K 39/012* | (2006.01) | |
| *A61K 39/015* | (2006.01) | |
| *A61K 39/00* | (2006.01) | |

(52) U.S. Cl.
CPC ............ *A61K 39/018* (2013.01); *A61K 39/002* (2013.01); *A61K 39/005* (2013.01); *A61K 39/012* (2013.01); *A61K 39/015* (2013.01); *C07K 14/44* (2013.01); *A61K 2039/55566* (2013.01); *A61K 2039/55572* (2013.01)

(58) Field of Classification Search
None
See application file for complete search history.

(56) References Cited

U.S. PATENT DOCUMENTS

| | | | |
|---|---|---|---|
| 4,683,195 A | | 7/1987 | Mullis et al. |
| 4,683,202 A | | 7/1987 | Mullis |
| 4,877,612 A | | 10/1989 | Berger et al. |
| 4,965,188 A | | 10/1990 | Mullis et al. |
| 6,248,329 B1 * | | 6/2001 | Chandrashekar et al. . 424/191.1 |
| 6,617,156 B1 * | | 9/2003 | Doucette-Stamm et al. ............ 435/320.1 |
| 6,660,498 B1 | | 12/2003 | Hui et al. |
| 7,410,637 B2 | | 8/2008 | Sayre et al. |
| 8,216,593 B2 | | 7/2012 | Snell et al. |
| 2003/0211089 A1 | | 11/2003 | Sayre et al. |
| 2005/0220822 A1 * | | 10/2005 | Hoffman et al. ........... 424/272.1 |
| 2012/0027857 A1 * | | 2/2012 | Abramovic et al. .......... 424/480 |
| 2013/0084607 A1 * | | 4/2013 | Harding et al. ................. 435/97 |

FOREIGN PATENT DOCUMENTS

| | | |
|---|---|---|
| WO | 01/08335 A1 | 2/2001 |
| WO | 2008034121 A2 | 3/2008 |

OTHER PUBLICATIONS

Herbert et al eds, The Dictionary of Immunology, definition of "vaccine", Academic Press, 1995.*
Oplinger et al NIH record vol. LVII No. 9.*
Struik and Riley, Immunological Reviews 2004, vol. 201:268-290.*
Tongren et al. Trends in Parasitology vol. 20 Dec. 2004 p. 604-610.*
Chenik et al. Parasitology (published online Jan. 3, 2006), 132,493-509.*
Uniprot Accession No. Q1X7J9, May 2006.*
Antony et al. Drug Development and Industrial Pharmacy, 23(4), 417-418, 1997.*
Berge et al., 66 J. Pharm. Sci. 1-19 (1977)).*
VanWijk. Cardiovascular Research 59(2003) 277-287.*
http://www.britannica.com/EBchecked/topic/17885/alum retrieved Jul. 2, 2014.*
Crowley et al. PSTT vol. 2, No. 6, pp. 237-243, Jun. 1999.*
Kola et al. Journal of Chemical and Pharmaceutical Sciences, vol. 6 issue 3 p. 161-169, 2013.*
Newman et al. Vaccine Adjuvants. Exp. Opin. Ther. Patents (2000) 10(3):279-314.*
Abbas, A.K., et al., "Cellular and Molecular Immunology," Philadelphia: W.B. Saunders Company, (2000), Chapter 15, pp. 360-362.
Adachi, Jun, et al., "MOLPHY Version 2.3—Programs for Molecular Phylogenetics Based on Maximum Liklihood," Mol; Phylogen and Evol., Inst. Stat. Math., Tokyo, (1996), 150 pages.
Altschul, Stephen F., et al., "Gapped BLAST and PSI-BLAST: A New Generation of Protein Database Search Programs," Nucleic Acids Research, (1997), vol. 25, No. 17, pp. 3389-3402.
Billker, Oliver, et al., "Calcium and a Calcium-Dependent Protein Kinase Regulate Gamete Formation and Mosquito Transmission in a Malaria Parasite," Cell, May 14, 2004, vol. 117, pp. 503-514.
Breman, Joel G., et al., Conquering the Intolerable Burden of Malaria: What's New, What's Needed: A Summary, Am. J. Trop. Med. Hyg., (2004), pp. 1-15.
Dessens, Johannes T., et al., "SOAP, A Novel Malaria Ookinete Protein Involved in Mosquito Midgut Invasion and Oocyst Development," Molecular Microbiology, (2003), 49(2):319-329.
Fang, Su-Chiung, et al., Cell Size Checkpoint Control by the Retinoblastoma Tumor Suppressor Pathway, PLOS Genetics, Oct. 2006, vol. 2, Issue 10, pp. 1565-1579.

(Continued)

Primary Examiner — Oluwatosin Ogunbiyi
(74) Attorney, Agent, or Firm — Edwin S. Flores; Daniel J. Chalker; Chalker Flores, LLP

(57) ABSTRACT

Compositions and methods for the development and use of a vaccine that includes one or more FusM antigens in a carrier adapted to trigger a FusM-specific immune response in the human blood stream are disclosed herein.

11 Claims, 12 Drawing Sheets

(56) References Cited

OTHER PUBLICATIONS

Goodenough, Ursula W., et al., "Isolation and Genetic Analysis of Mutant Strains of Chlamydomonas Reinhardt Defective in Gametic Differentiation," Genetics, Feb. 1976, 82:169-186.

Greenspan, Neil S., et al., "Structural Analysis: Defining Epitopes: It's Not as Easy as it Seems," Nature Biotechnology, Oct. 1999, vol. 17, pp. 936-937.

Harlow, J., et al., "Antibodies—A Laboratory Manual," (1988), Chapter 3, pp. 23-74.

Inoue, Naokazu, et al., "The Immunoglobulin Superfamily Protein Izumo is Required for Sperm to Fuse with Eggs," Nature, Mar. 10, 2005, vol. 434, pp. 234-238.

International Search Report and Written Opinion for Application PCT/US07/78595, dated Apr. 16, 2008, 21 pages.

Johnson, Mark A., et al., "Arabidopsis Hapless Mutations Define Essential Gametophytic Functions," Genetics, Oct. 2004, 168:972-982.

Kindle, Karen L., et al., "Stable Nuclear Transformation of Chlamydomonas Using the Chlamydomonas Gene for Nitrate Reductase," The Journal of Cell Biology, Dec. 1989, vol. 109, No. 6, pp. 2589-2601.

Li, S., et al., "Viral Vectors for Malaria Vaccine Development," Vaccine, (2007), 25:2567-2574.

Liu, Yao-Guang, et al., "Efficient Isolation and Mapping fo Arabidopsis Thaliana T_DNA Insert Junctions by Thermal Asymmetric Interlaced PCR," The Plant Journal, (1995), 8(3):457-463.

Mahjoub, Moe R., et al., "A NIMA-Related Kinase, Fa2p, Localizes to a Novel Site in the Proximal Cilia of Chlamydomonas and Mouse Kidney Cells," Molecular Biology of the Cell, Nov. 2004, vol. 15, pp. 5172-5286.

Matsuzaki, Motomichi, et al., "Genome Sequence of the Ultrasmall Univellar Red Alga *Cyanidioschyzon merolae* 10D," Nature, Apr. 8, 2004, vol. 428, pp. 653-657.

Misamore, M. J., et al., "The Chlamydomonas Fus1 Protein is Present on the Mating Type Plus Fusion Organelle and Required for a Critical Membrane Adhesion Event During Fusion with Minus Gametes." Mol Biol Cell (2003), 6:2530-2542.

Mori, T., et al., "Generative Cell Specific 1 is Essential for Angiosperm Fertilization." Nat Cell Biol (2006), 8:64-71.

Nelson, Julie, A.E., et al., "The CRY1 Gene in Chlamydomonas Reinhardtii: Structure and Use as a Dominant Selectable Marker for Nuclear Transformation," Molecular and Cellular Biology, Jun. 1994, vol. 14, No. 6, pp. 4011-4019.

Pan, J., et al., "Signal Transduction During Fertilization in the Unicellular Green Alga, *Chlamydomonas*." Curr Opin Microbiol. (2000), 3:596-602.

Pei, Jimin, et al., "Al2CO: Calculation of Positional Conservation in a Protein Sequence Alignment," Bioinformatics, (2001), vol. 17, No. 8, pp. 700-712.

Pei, Jimin, et al., "PROMALS: Towards Accurate Multiple Sequence Alignments of Distantly Related Proteins," Bioinformatics, (2007), vol. 23, No. 7, pp. 802-808.

Pollock, S. V., et al., "Rubisco Activase is Required for Optimal Photosynthesis in the Green Alga *Chlamydomonas reinhardtii* in a Low-$CO_2$ Atmosphere," Plant Physiol, (2003), 133:1854-1861.

Reininger, L., et al., "A Nima-Related Protein Kinase is Essential for Completion of the Sexual Cycle of Malaria Parasites." J Biol Chem., (2005), 280:31957-31964.

Schmidt, Heiko A., et al., "TREE-PUZZLE: Maximum Likelihood Phylogenetic Analysis Using Quartets and Parallel Computing," Bioinformatics, (2002), vol. 18, No. 3, pp. 502-504.

Silflow, Carolyn D., et al., "The Vfl1 Protein in Chlamydomonas Localizes in a Rotationally Asymmetric Pattern at the Distal Ends of the Basal Bodies," The Journal of Cell Biology, Apr. 2, 2001, vol. 153, No. 1, pp. 63-74.

The Dictionary of Immunology, Definition of Vaccine Herbert et al. Eds, Academic Press, 1995.

Dessens, et al. "CTRP is essential for mosquito infection by malaria ookinetes" EMBO J 18, 6221-7 (1999).

Ferris, et al. "A sex recognition glycoprotein is encoded by the plus mating-type gene fus1 of Chlamydomonas reinhardtii" Aug. 1996, Mol Biol Cell 7, 1235-1248.

Liu, et al. "Amplification of genomic sequences flanking T-DNA insertions by thermal asymmetric interlaced polymerase chain reaction" (2005) Methods Mol Biol 286, 341-348.

Milek, et al. "Immunological properties of recombinant proteins of the transmission blocking vaccine candidate, Pfs48/45, of the human malaria parasite *Plasmodium falciparum* produced in *Escherichia coli*" Apr. 1998, Parasite Immunol 8:377-85.

Oplinger, A., "NIAID Tackles Malaria in Vaccine Lab," NIH Record, (May 6, 2005), vol. LVII, No. 9.

Struik, S. S., "Does Malaria Suffer from Lack of Memory?" Immunological Reviews (2004), 201:268-290.

Tongren, J. E., Malaria Vaccines: If at First You Don't Succeed, Trends in Parasitology (Dec. 2004), 20:604-610.

\* cited by examiner

FIG. 1F

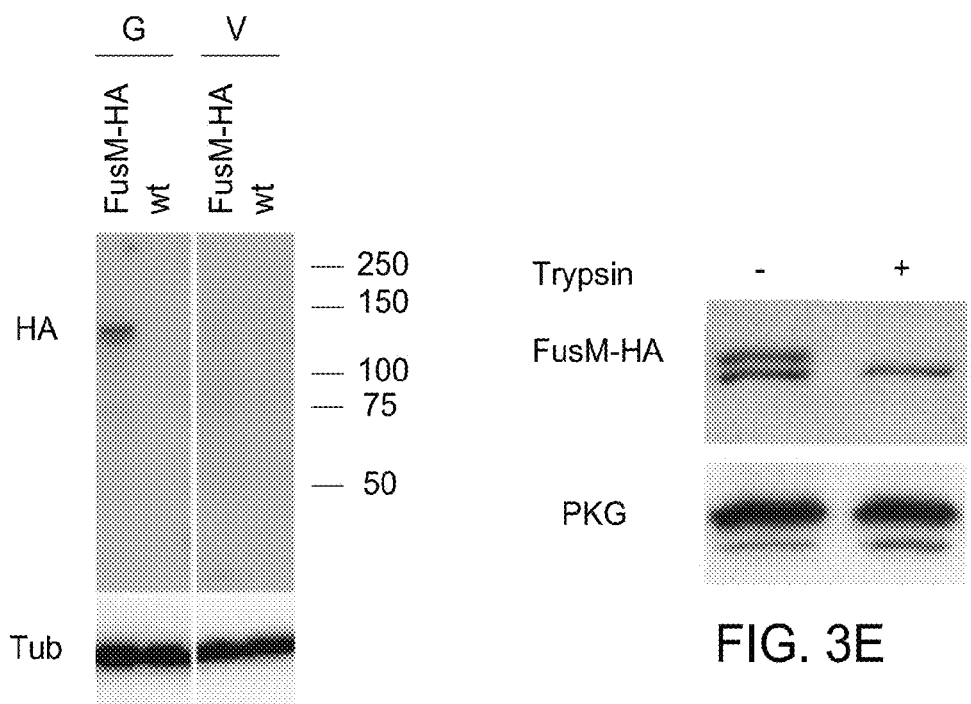
FIG. 3D
FIG. 3E
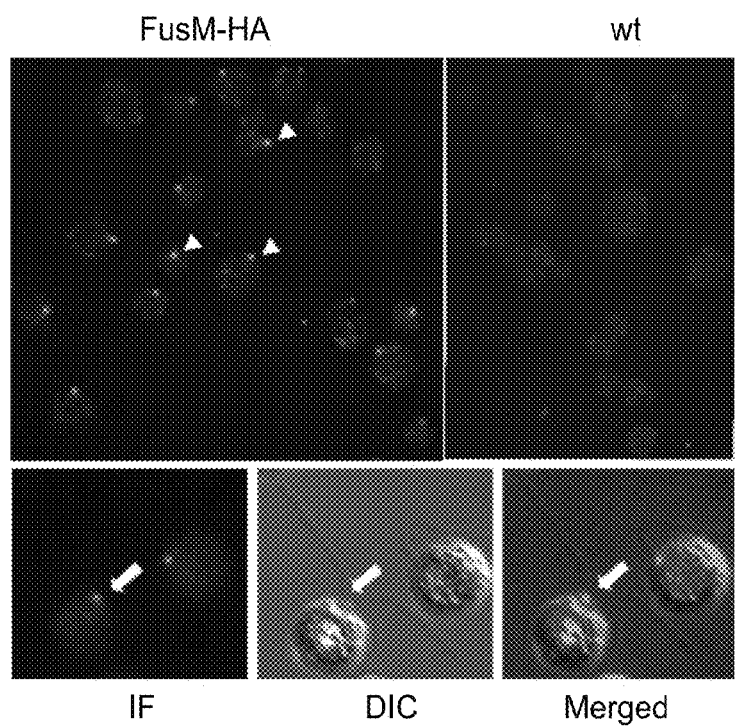
FIG. 3F

PARASITE VACCINE

CROSS-REFERENCE TO RELATED APPLICATIONS

This application claims priority to and is a Continuation Application of U.S. patent application Ser. No. 11/856,036 filed Sep. 15, 2007, now U.S. Pat. No. 8,216,593 issued Jul. 10, 2012 which claims priority to U.S. Provisional Patent Application Ser. No. 60/845,122, filed Sep. 16, 2006, the entire contents of each of which are incorporated herein by reference.

STATEMENT OF FEDERALLY FUNDED RESEARCH

This invention was made with U.S. Government support under Contract No. R01GM56778-6 awarded by the NIH. The government has certain rights in this invention.

TECHNICAL FIELD OF THE INVENTION

The present relates to vaccination against parasites, and more particularly, compositions and methods for the therapeutic use of FusM protein and portions thereof to vaccinate patients and patient populations.

BACKGROUND OF THE INVENTION

Without limiting the scope of the invention, its background is described in connection with anti-parasitic vaccines.

Malaria and related parasitic diseases continue to bring misery to much of the world's population. Malaria and related parasitic protozoa cause untold human misery worldwide. It is estimated that over 1 billion people are infected with the malaria-causing organism, *Plasmodium*, and 3 million persons die each year from the disease (Breman et al., 2004). Those who do not die endure long suffering. The disease causes billions of dollars in lost productivity. Humans with Sleeping Sickness, Chagas disease, Cryptosporidiosis, and Toxoplasmosis also suffer greatly. Many people die from the diseases, or lose their ability to be productive members of their communities. Similarly, these and other parasites annually kill large numbers of the vertebrates (cows, sheep, goats, sheep, pigs, and chickens) that are human primary food sources worldwide (Roberts and Janovy, 2005).

Several methods are being used to roll back malaria and other of these parasitic diseases, including reduction of insect vectors, drugs, and vaccines. None of these are completely effective, though, and it is estimated that more humans are infected now with malaria than were infected 20 years ago. One problem with existing vaccines is that they target surface antigens of poorly understood or unknown function. In addition, the targets mutate and render the organism resistant to the vaccine. Therefore, new discoveries and new approaches are essential to combat malaria and related parasitic protozoan diseases.

SUMMARY OF THE INVENTION

The present invention includes vaccines, constructions, host cells, and vectors that include or express one or more protozoan FusM antigens for use with, e.g., a carrier adapted to trigger a FusM-specific immune response. The skilled artisan may also recognize that FusM has been referred to as HAP2 (Hapless 2) or GCS1 (generative cell specific 1). In one embodiment, the present invention is a vaccine having at least a portion of a protozoan FusM mating protein that is immunogenic; and a carrier. The vaccine may also include an adjuvant, a pharmaceutically acceptable salt, an excipient, a preservative, a binder or a pharmaceutically acceptable liquid. The FusM protein is obtained from a protozoan that has been heat-killed, attenuated, chemically-inactivated, mechanically inactivated or combinations thereof, e.g., the FusM protein may be recombinant, and the portion of the FusM protein may even be selected to trigger a cytotoxic T-cell immune response, a humoral immune response, a mucosal immune response or a combination thereof. The vaccine may include a FusM protein may be lyophilized, vacuum-dried, vacuum heat-dried, freeze-sprayed or combinations thereof. Examples of carriers for the vaccine include an excipient, an adjuvant, an absorption enhancer, a release-rate controlling polymer, a stability enhancer, or combinations thereof. In one example, the FusM protein is inserted for expression in a carrier virus, an attenuated bacterium or an attenuated blood-stage/sporozoite. In another example, the FusM protein may be inserted as gene or gene fragments that are expressed in a carrier virus. The carrier may be an adjuvant selected from Complete Freund's Adjuvant, Incomplete Freund's Adjuvant, alum, a carrier virus, high molecular weight polysaccharides, glycoproteins, microparticles, liposomes, and combinations thereof.

Examples of protozoan sources for the vaccine include those selected from the group consisting of the Phylum Apicomplexa or the Class Kinetoplastida. More particular examples of the sources for the protein, genes and/or antigen include protozoans selected from the group consisting of the Phylum Apicomplexa further defined as comprising *Babesia* sp., *Cryptosporidium* sp., *Plasmodium* sp., and *Toxoplasma* sp. *Plasmodium* sp., *Plasmodium falciparum, Plasmodium vivax, Cryptosporidium parvum, Cryptosporidium hominis, Eimeria* sp., *Eimeria tenella, Theileria* sp., *Theileria parva, Toxoplasma* sp. and *Toxoplasma gondii*. Other examples include protozoans selected from the Class Kinetoplastida, further defined as comprising *Trypanosoma brucei* subspecies, *Trypanosoma cruzi, Leishmania* sp., and *Leishmania major*. The vaccine may be formulated for oral, subcutaneous, intramuscular, nasal, intradermal, pulmonary, intraalveolar, intravaginal, intrarectal, intraperitoneal or intravenous administration. Examples of portions of a protozoan FusM mating protein may be selected from SEQ ID NOS 1-14, or enough contiguous nucleic acids or amino acids to generate an immunogenic FusM antigen.

Another embodiment of the present invention includes a method for modulating a protozoan population by identifying a human population in need of reduction in a protozoan population; and vaccinating a majority of the population with a vaccine comprising an immunogenic portion of a FusM protein. Another method of the present invention includes a method of providing immunity to a vertebrate host by vaccinating the host with an antigen comprising a polypeptide that causes immunity against a protozoan FusM protein. The immunity may be innate immunity, passive immunity, active immunity or a combination thereof. For use with the method, the protozoan is selected from the group consisting of the Phylum Apicomplexa or the Class Kinetoplastida, Phylum Apicomplexa further defined as comprising *Babesia* sp., *Cryptosporidium* sp., *Plasmodium* sp., and *Toxoplasma* sp. *Plasmodium* sp., *Plasmodium falciparum, Plasmodium vivax, Cryptosporidium parvum, Cryptosporidium hominis, Eimeria* sp., *Eimeria tenella, Theileria* sp., *Theileria parva, Toxoplasma* sp. and *Toxoplasma gondii* or even Class Kinetoplastida, further defined as comprising *Trypanosoma brucei, Trypanosoma cruzi, Leishmania* sp., and *Leishmania*

*major*. The host that is vaccinated may be a human, a dog, a cat, a monkey, a horse, a cow, a pig or a chicken.

Another embodiment of the present invention is a vaccine against malaria comprising at least a portion of a protozoan FusM protein that is immunogenic, wherein the protozoan is selected from the group consisting of *Plasmodium* sp., *Plasmodium falciparum*, *Plasmodium vivax*, and *Plasmodium berghei*, *Plasmodium ovale* and *Plasmodium malariae*. Another embodiment is a transmission-blocking vaccine that includes an amount of an anti-FusM antibody or a fragment thereof sufficient to passively block the majority of the mating of a protozoan in vivo. The antibody or a fragment thereof is administered to a patient in need of passive immunity. The present invention also includes an inhibitor of protozoan mating by providing a medicament (and the use thereof) that includes an anti-FusM antibody or fragment thereof. In one aspect, the antibody or fragment thereof is disposed in a carrier that is suitable for aerosol delivery, immediate release, time-release dosage, mixed-release or suitable for release into a water reservoir.

Another embodiment of the present invention includes a method for screening anti-parasitic drugs by obtaining one or more FusM mutant proteins; contacting the one or more FusM mutant proteins with one or more candidate agents that to determine if they inhibit the formation of a FusM complex, and further isolating and characterizing the candidate agents for those that prevent gamete formation of parasites. The method may also include the step of testing the one or more candidate agents for toxicity in vertebrates. The method may also include the step of testing the one or more candidate agents for toxicity in humans. The method may also include the step of characterizing the molecular structure of the one or more candidate agents.

Yet another embodiment of the present invention includes a live-attenuated mutant protozoan vaccine comprising a protozoan that is blocked developmentally phenotypically or chemically at the gamete phase, such that the host raises immunity to the FusM protein. Other embodiment includes an isolated nucleic acid molecule, the complementary sequence of which hybridizes fully, under highly stringent conditions (aqueous buffer, 65° C.) to the nucleotide sequences set forth in SEQ ID NO: 1 to 14, wherein the nucleic acid molecule encodes a protozoan mating protein antigen, wherein the protozoan mating protein antigen encodes a protein that triggers an immune response in a mammal, or even an isolated nucleic acid molecule that encodes a FusM mating protein comprising the nucleotide sequence of SEQ ID NO: 11 to 20. The isolated nucleic acid molecule comprising a nucleotide sequence which encodes a protein comprising the amino acid sequence of SEQ ID NOS.: 1-14 or the amino acid expressed therefrom. Another embodiment of the present invention is an expression vector comprising the isolated nucleic acid molecule of SEQ ID NOS.: 1 to 14, operably linked to a promoter. Another embodiment is a recombinant vector, transformed or transfected with the isolated nucleic acid molecule of SEQ ID NOS.: 1 to 14 or the amino acid expressed therefrom. The recombinant vector is further defined as a live, attenuated virus, bacterium or protozoan vector; a heat-killed virus, bacterium or protozoan vector; a chemically inactivated virus, bacterium or protozoan vector; a mechanically inactivated virus, bacterium or protozoan vector; or combinations thereof.

BRIEF DESCRIPTION OF THE DRAWINGS

For a more complete understanding of the features and advantages of the present invention, reference is now made to the detailed description of the invention along with the accompanying figures and in which:

Figure 1F:
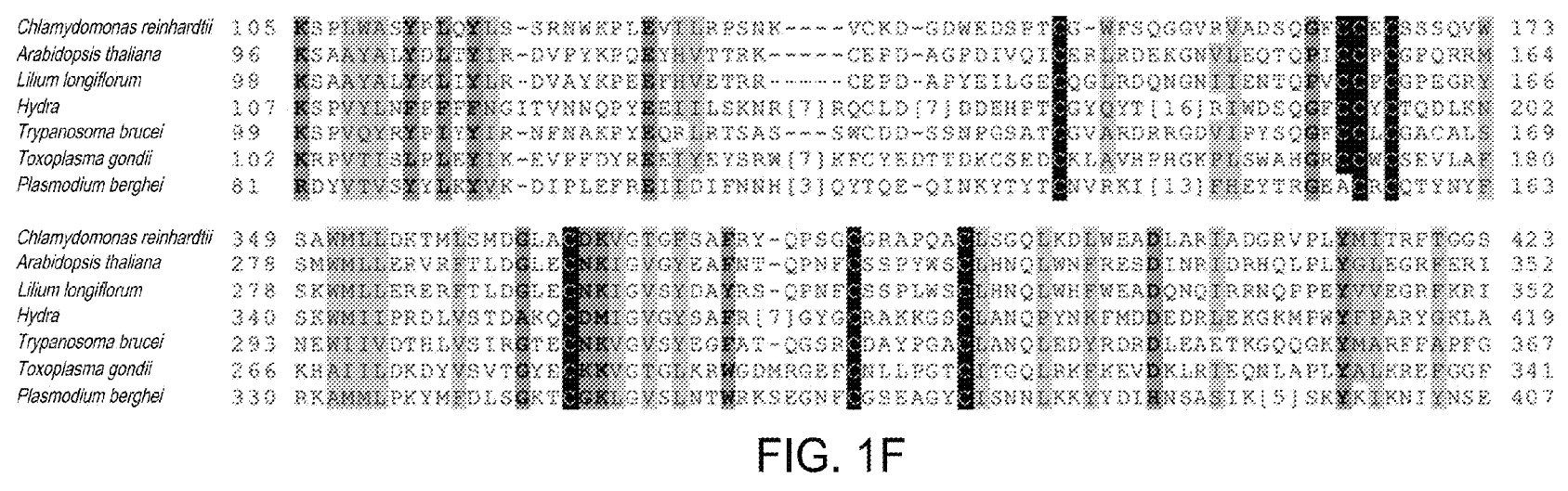

FIGS. 1A to 1F. FusM is required for fertilization in *Chlamydomonas* and phylogenetically conserved in many eukaryotes. (FIG. 1A) Differential interference contrast microscopy (DIC) images of (left panel) a quadriflagellated zygote formed from fusion of a wt female gamete with a wt male gamete and (right panel) a wt female gamete undergoing flagellar adhesion with a 63B10 male, but failing to fuse. (FIG. 1B) Structure of the FusM gene and location of the aphVIII plasmid. (FIG. 1C) PCR using primers p1/p2 and p1-p17 showing the absence of intact FusM in 63B10 gametes and its reappearance in several 63B10 gametes rescued for fusion with the wt FusM gene. (FIG. 1D) Large aggregates of zygotes were present only in mixtures of wt female and male gametes and wt female and 63B10 male gametes rescued with the wt FusM gene (63B10-C9). (FIG. 1E) Phylogenetic tree illustrating the relationships of FusM proteins from several species. (FIG. 1F) Alignment of two conserved regions of FusMs from several species (SEQ ID NOs.: 1-14, respectively). Positions with conserved cysteines are in black background, other conserved positions are in gray background. Uncharged residues in positions with mainly hydrophobic residues are in yellow background. Residues in long loops are not shown in this figure and are replaced by brackets that indicate the number of residues in the loop. The numbers of beginning and ending residues for the regions are shown. See Table S1 for the full alignments of the proteins (SEQ ID NOS: 46-73).

(FIG. 2A) Structure of the *Plasmodium* FusM gene and gene replacement construct. Short arrows indicate oligonucleotides used for PCR genotyping. (FIG. 2B) Southern hybridization of EcoRI-digested genomic DNA using the 5' targeting sequence as a probe. Arrowheads indicate diagnostic 2.8 kb (wt) and 5.0 kb (FusM) bands. (FIG. 2C) Diagnostic PCR with genomic DNA templates and oligonucleotides 525/526 to test for the presence of FusM, and oligonucleotides 524/70 to detect a unique 1 kb product across the integration site. (FIG. 2D) RT-PCR detection of FusM transcript in parasite lines and stages (the expected larger product from genomic DNA includes one intron). (FIG. 2E) Representative images of midguts from *A. stephensi* mosquitoes 10 d after feeding on wt and fusm infected mice (scale bar, 100 µm) and bar chart showing average numbers of oocysts per gut (error bar=s.e.m., n=47 wt or fusm-exposed mosquitoes from 3 independent experiments). The overall prevalence of infection was 87% for wt, and 0% for fusm. (FIG. 2F) Immunofluorescence images of live 20 h *Plasmodium* cultures immunostained for the macrogamete/zygote marker P28 as described (24). Elongate ookinetes (asterisks) were absent from the fusm mutant (scale bar, 10 µm), which possessed only round macrogametes. The bar chart shows ookinete conversion rates for wt and fusm clone 8. Conversion rate is expressed as the percentage of P28-positive parasites that had progressed to the ookinete stage (error bar=s.d.; n=3).

FIGS. 3A to 3F. FusM is present at the surface of the male mating structure in *Chlamydomonas* and has a male-specific function late in fertilization in both *Chlamydomonas* and *Plasmodium*. (FIG. 3A) Unlike *Chlamydomonas* fusm males, which failed to fuse when mixed with wt females, *Chlamydomonas* fusm females were capable of fusion with wt males (see Methods for strategy used to generate females missing the wt FusM and containing only the mutant fusm). The upper panel shows Southern hybridization of wt and mutant strains, documenting that the fusm females contained only the disrupted FusM gene. The upper, wt FusM Not1 fragment is 5.3 kb and the lower fragment from the 63B10 allele is 1.3 kb. The lower panel shows the percent of the indicated gametes that fused when mixed with wt gametes of the opposite sex. (FIG. 3B) In vitro malaria ookinete conversion analysis demonstrates that the *Plasmodium* fusm mutant shows productive cross-fertilization with the nek4 sterility mutant, which produces functional males only, and not with cdpk4, which produces functional females only (error bar=s.d.; n=3). The ookinete conversion rates are about half that of wt, because only 50% of the female gametes are competent to be fertilized. (FIG. 3C) *Chlamydomonas* FusM functions after gamete activation. 63B10 gametes were incubated with wt females, flagella isolated from wt females, db-cAMP, or medium (control) and the percent of cells that were activated was determined by measuring cell wall loss. (FIG. 3D) Immunoblotting with an anti-HA antibody documents that 63B10 cells rescued with HA-tagged FusM expressed FusM-HA protein only in the gamete phase of their life cycle. (FIG. 3E) Immunoblotting with anti-HA antibody shows that the upper form of FusM-HA on live FusM-HA gametes was sensitive to treatment with 0.01% trypsin for 20 min at room temperature. (FIG. 3F) Anti-HA immunostaining combined with DIC microscopy of FusM-HA gametes shows that FusM-HA is expressed between the two flagella at the site of the male mating structure.

(FIG. 4A) Activated live 63B10 gametes, like activated live wt males, adhered via their mating structures to activated, fixed, fluorescently tagged imp2 females, which are incapable of flagellar adhesion (upper panel, differential interference microscopy; lower panel, fluorescence; arrowheads indicate the imp2 females). The percent (+/−s.e.m.) of imp2 gametes forming pairs when mixed with an excess of activated 63B10 or wt males is shown below the figure (average from 2 independent experiments; n=150-200 imp2 cells examined in each). Similar results were obtained when the agglutinin mutant imp5 was used (not shown). Between 0 and 6% pairs were detected in controls in which activated live imp2 gametes were mixed with the fixed imp2 gametes (not shown). (FIG. 4B) FusM is essential for membrane merger. The plasma membranes of activated female gametes were labeled with the fluorescent lipid PKH26, mixed with wt or 63B10 male gametes, and the live cells were examined by epifluorescence and DIC microscopy. (FIG. 4C) Efficiency of exflagellation, gamete adhesion and gamete fusion in wt, p48/45, and fusm strains of *Plasmodium* (error bar=s.d.; n=3 experiments, each examining 100 gametocytes).

Figure 1B:
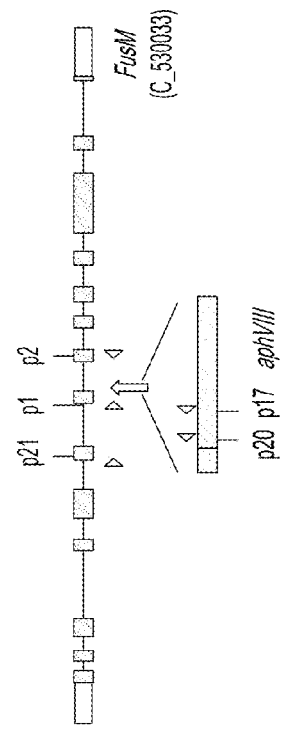
Figure 1D:
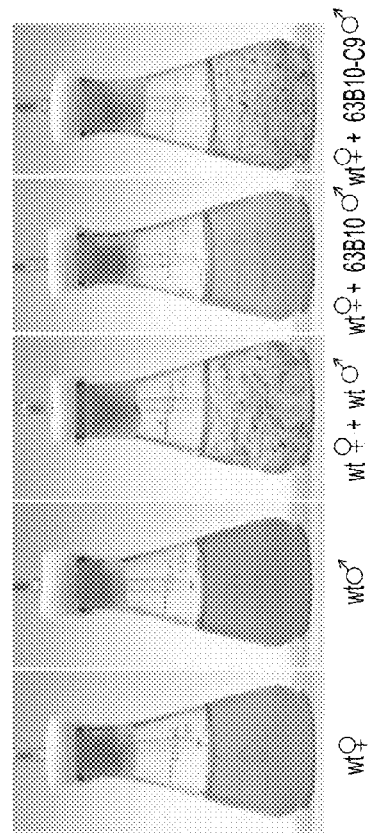
Figure 1A:
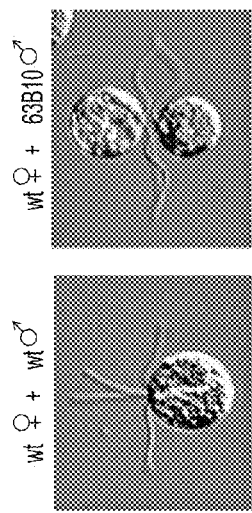
Figure 1C:
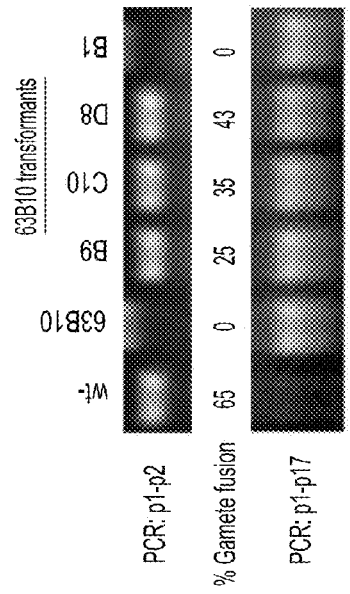
Figure 1E:
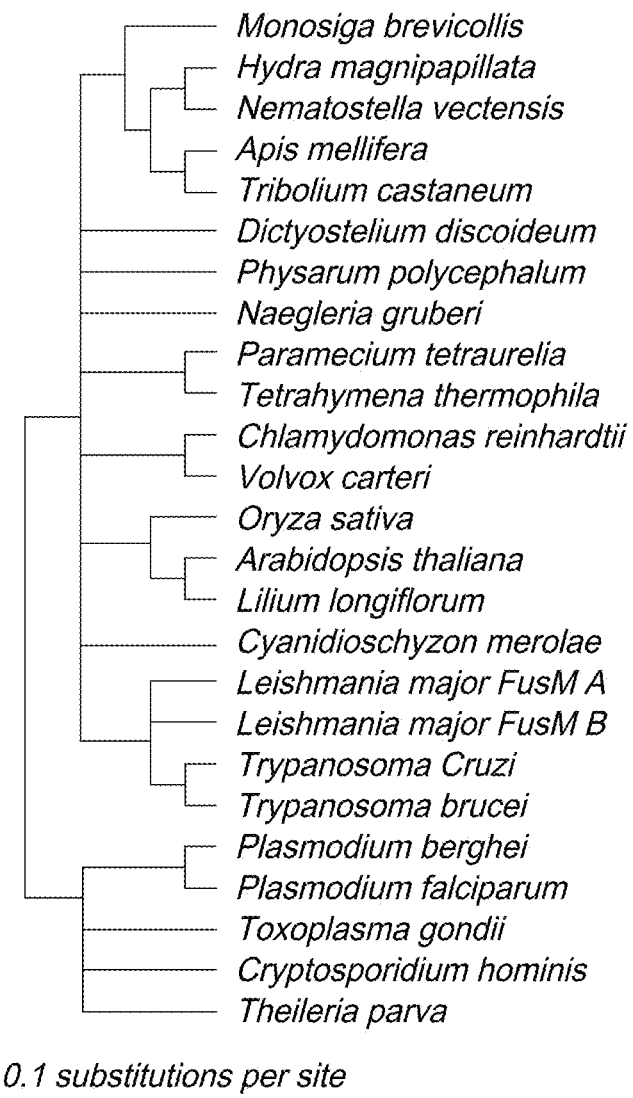
Figure 2A:
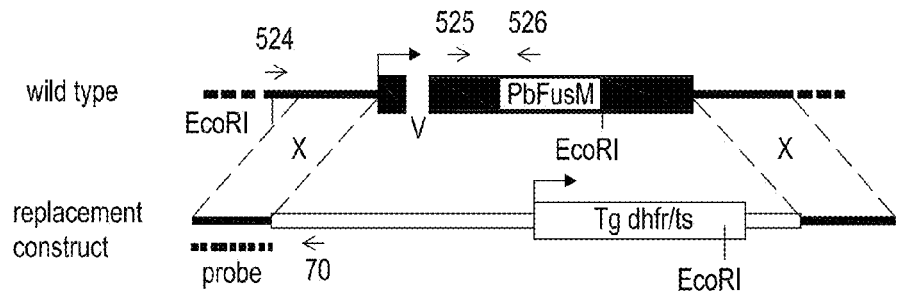
FIGS. 2A to 2F. FusM is essential for sexual development and mosquito transmission of *P. berghei*.
Figure 2B:
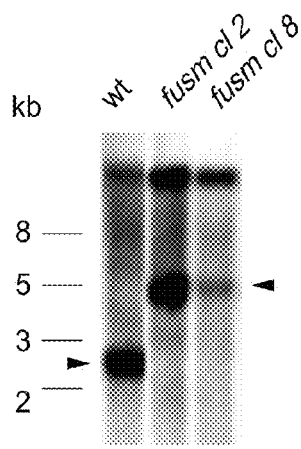
Figure 2C:
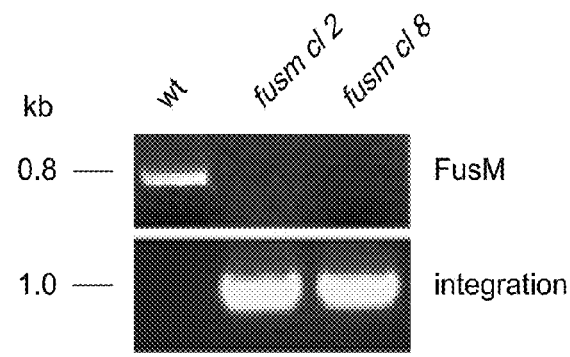
Figure 2D:
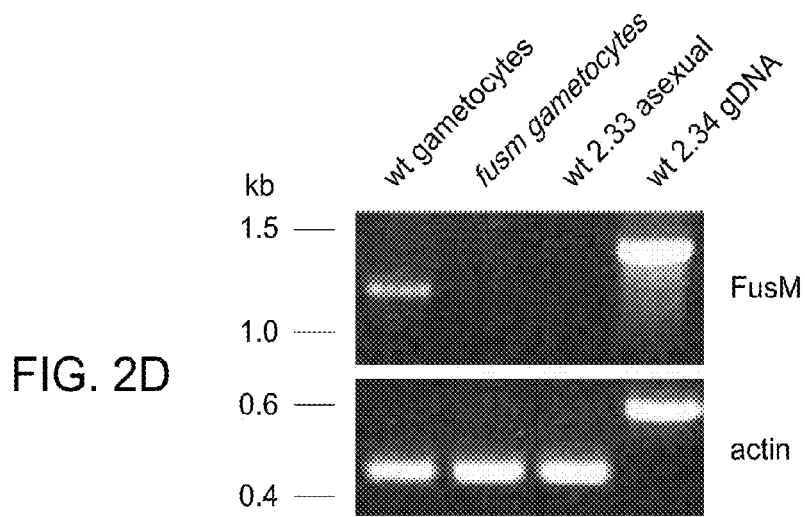
Figure 2E:
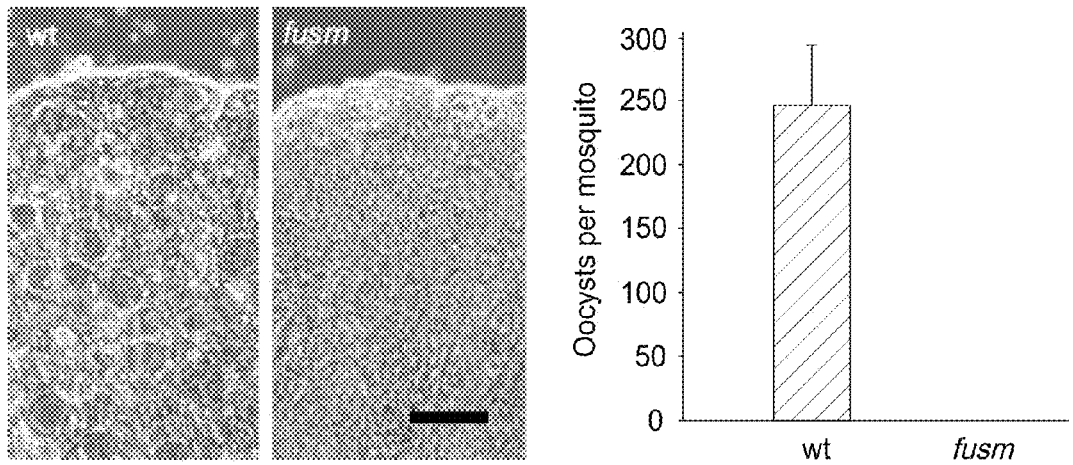
Figure 2F:
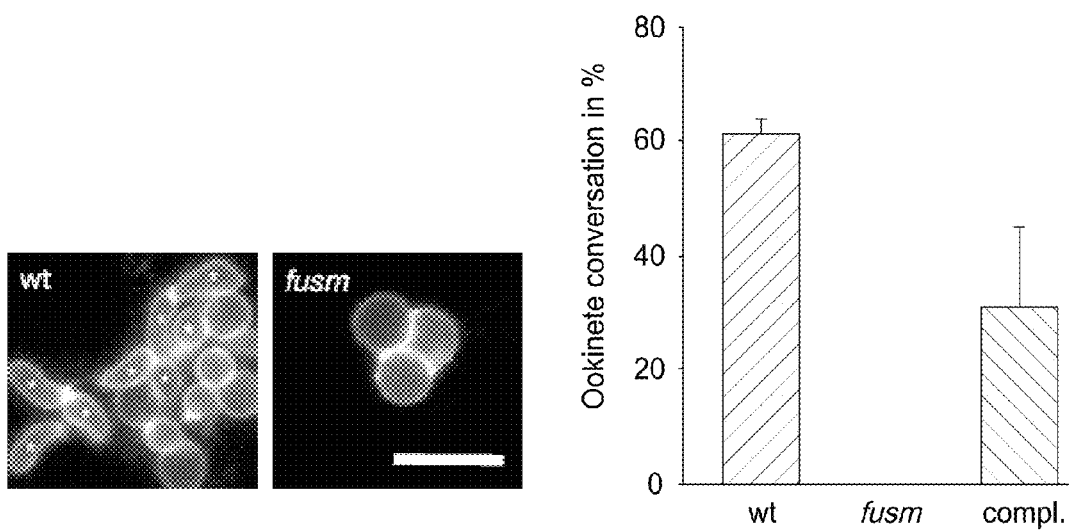

Table S1 includes the following amino acid sequences, SEQ ID NO.:46-73.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

A number of vaccines have a short shelf life and must be stored at refrigeration temperatures. Optimally, a vaccine should have a long shelf life when stored at room temperatures, however, live vaccines tend to require storage at cold temperatures (even when the vaccine is lyophilized), due to the fact that the number of viable vaccine units drops with prolonged storage at warmer temperatures. While killed or dead vaccines are more stable than live vaccines, live attenuated vaccines are more often used for intestinal vaccination due to the long-term, residual immunity that they provide and the low infectivity of the vaccine.

In general, only a few vaccines are administered orally, the only commonly used oral vaccine is the attenuated polio virus. While the attenuated virus may be killed by acid conditions in the stomach, the vaccine has been formulated in a manner that sufficient viable virus particles pass through the stomach to be active in the small intestine.

As used herein, the term "antigen" refers to a molecule with one or more epitopes that stimulate a host's immune system to make a secretory, humoral and/or cellular antigen-specific response against FusM (also known as HAP2 (Hapless 2) or GCS1 (generative cell specific 1)), or to a DNA molecule that is capable of producing such an antigen in a vertebrate. The term is also used interchangeably with "immunogen." For example, a specific antigen can be complete protein, portions of a protein, peptides, fusion proteins, glycosylated proteins and combinations thereof. For use with the present invention, one or more FusM antigens (native protein or protein fragment), may be provided directly or as part of a recombinant nucleic acid expression system to provide an antigenic FusM product to trigger a host immune response. The FusM antigen may further be a DNA molecule which produces the FusM antigen in the host.

As used herein, the term "gene" refers to a functional protein, polypeptide or peptide-encoding nucleic acid unit, e.g., the FusM encoding nucleic acids. As will be understood by those in the art, this functional term includes genomic sequences, cDNA sequences, probes, oligonucleotides or fragments thereof (and combinations thereof), as well as gene products, including those that may have been designed and/or altered by the user. Purified genes, nucleic acids, protein and the like are used to refer to these entities when identified and separated from at least one contaminating nucleic acid or protein with which it is ordinarily associated.

As used herein, the term "host cell" refers to cells that have been engineered to contain nucleic acid segments or altered segments, whether archeal, prokaryotic, or eukaryotic. Thus, engineered, or recombinant cells, are distinguishable from naturally occurring cells that do not have the recombinantly introduced genes. In one specific example of the present invention, the host cell has been modified by the introduction of exogenous nucleic acids that alter the expression of FusM, e.g., introduce a non-binding mutant of FusM. Alternatively, the host cell is a wild-type protozoan that has been mutated to express a mutant form of the FusM protein or to block the protozoan in a "mating state", e.g., a *Plasmodium* sp. that is non-pathogenic in humans that over-expresses the FusM and/or the FusM target for the vaccine of the present invention.

As used herein, the expressions "cell" and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Different designations for the type and source for a cell, e.g., protozoan, prokaryotic, etc., will be clear to those of skill in the art from the designation of the cell within the context of the discussion and the examples of the present invention.

As used herein, the term "plasmids" refers to extrachromosomal, at least partially self-replicating nucleic acids. Plasmids are designated by a lower case p preceded and/or followed by capital letters and/or numbers that name the plasmid. Many plasmids are commercially available, are publicly available on an unrestricted basis, or can be constructed from such available plasmids in accord with published procedures. In addition, other equivalent plasmids are known in the art and will be apparent to the ordinary artisan.

As used herein, the term "protein-protein complex" or "protein complex" refers to an association of more than one protein. The proteins of the complex may be associated by a variety of methods, or by any combination of methods, including but not limited to functional, stereochemical, conformational, biochemical, or electrostatic association. It is intended that the term encompass associations of any number of proteins.

As used herein, the terms "protein", "polypeptide" and "peptide" refer to compounds comprising amino acids joined via peptide bonds and are used interchangeably.

As used herein, the term "transformation," refers to a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome.

As used herein, the term "transfection" refers to the introduction of foreign DNA into eukaryotic cells. Transfection may be accomplished by a variety of means known to the art including, e.g., calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Thus, the term "stable transfection" or "stably transfected" refers to the introduction and integration of foreign DNA into the genome of the transfected cell. The term "stable transfectant" refers to a cell which has stably integrated foreign DNA into the genomic DNA. The term also encompasses cells which transiently express the inserted DNA or RNA for limited periods of time. Thus, the term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

As used herein, the term "selectable marker" refers to the use of a gene that encodes an enzymatic activity and which confers the ability to grow in medium lacking what would otherwise be an essential nutrient (e.g., the HIS3 gene in yeast cells); in addition, a selectable marker may confer resistance to an antibiotic or drug upon the cell in which the selectable marker is expressed. A review of the use of selectable markers in mammalian cell lines is provided in Sambrook, J., et al., Molecular Cloning: A Laboratory Manual, 2nd ed., Cold Spring Harbor Laboratory Press, New York (1989) pp. 16.9-16.15.

As used herein, the term "vector" is used in reference to nucleic acid molecules that transfer DNA segment(s) from one cell to another. The term "vehicle" is sometimes used interchangeably with "vector." The term "vector" as used herein also includes expression vectors in reference to a recombinant DNA molecule containing a desired coding sequence and appropriate nucleic acid sequences necessary for the expression of the operably linked coding sequence in a particular host organism. Nucleic acid sequences necessary for expression in prokaryotes or eukaryotes usually include a promoter, an operator (optional), and a ribosome binding site, often along with other sequences. Eukaryotic cells are known to use promoters, enhancers, and termination and polyadenylation signals. Another, and different, way in which the term "vector," is used herein refers to the insect or other host that serves to deliver a parasite between organisms, e.g., mosquitoes are common "vectors" for parasites that are transmitted between humans or animals via the mosquito "vector." Other vectors include, e.g., fleas, mites, flies and the like, as will be known to those of skill in the art. Finally, the term "vector" may be used to describe the use of a carrier or other delivery system or organism to deliver the antigen(s) of the present invention to a host in order to trigger an immune response as part of a vaccine. Non-limiting examples of these vaccine vectors include viruses, bacteria, protozoans, cells (e.g., homologous or heterologous), etc., which may be live, live-attenuated, heat-killed, mechanically-killed, chemically-killed, recombinant (e.g., peptides, proteins and the like), as will be known to those skilled in the art of vaccine preparation. The skilled artisan will readily recognize the type of "vector" to which this specification and claims refer based on the description of the materials and methods used and described herein.

As used herein, the term "amplify", when used in reference to nucleic acids refers to the production of a large number of copies of a nucleic acid sequence by any method known in the art. Amplification is a special case of nucleic acid replication involving template specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer may be single stranded for maximum efficiency in amplification but may alternatively be double stranded. If double stranded, the primer is first treated to separate its strands before being used to prepare extension products. The primer must be sufficiently long to prime the synthesis of extension products in the presence of the inducing agent. The exact lengths of the primers chosen will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g. ELISA, as well as enzyme-based histochemical assays), fluorescent, radioactive, and luminescent systems. It is not intended that the present invention be limited to any particular detection system or label.

As used herein, the term "target" when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as DCTP or DATP, into the amplified segment). In addition to genomic DNA, any oligonucleotide sequence can be amplified with the appropriate set of primer molecules. In particular the amplified segments created by the PCR process itself are, themselves, efficient templates for subsequent PCR amplifications.

As used herein, the term "immunological response" refers to a composition or vaccine that includes a FusM antigen and that triggers in the host a cellular- and/or antibody-mediated immune response to FusM-derived antigens. Usually, such a response may include antibody production (e.g., in the intestinal tract, from germinal centers in lymph nodes, etc.), B cell proliferation, helper T cells, cytotoxic T cell proliferation, Natural Killer activation specifically to FusM antigen or antigens against the FusM target itself and/or fluids, secretions, tissues, cells or hosts infected therewith.

As used herein, the terms "vaccine composition" or "vaccine" refer to a FusM antigen that is used to stimulate the immune system of a vertebrate, e.g., a bird, a fish, a mammal, or even a human, so that current harm is alleviated, or protection against future harm is provided by an adaptive immune response. An immune response may also be provided passively, by transferring immune protection (e.g., antibodies) from one "immunized" host to the recipient that has not been challenged by the antigen and/or is unable to generate an immune response to the antigen. An immune response may also carry from the host into the vector, wherein the antibodies that are ingested by the vector along with the parasites block parasite mating.

As used herein, the term "immunization" refers to the process of inducing a continuing protective level of antibody and/or cellular immune response which is directed against a FusM antigen, either before or after exposure of the host to FusM.

As used herein, the term "homology" refers to the extent to which two nucleic acids are complementary. There may be partial or complete homology. A partially complementary sequence is one that at least partially inhibits a completely complementary sequence from hybridizing to a target nucleic acid and is referred to using the functional term "substantially homologous." The degree or extent of hybridization may be examined using a hybridization or other assay (such as a competitive PCR assay) and is meant, as will be known to those of skill in the art, to include specific interaction even at low stringency.

A nucleic acid having a sequence that is "substantially homologous" to a FusM antigen of SEQ ID NO:X" is defined herein as an oligonucleotide sequence that exhibits greater than or equal to 75, 80, 85, 90 or 95% identity to the sequence of SEQ ID NO:X when sequences having a length of 20, 50, 100 bp or larger are compared. The equivalent term may be used to describe an amino acid sequence, that is, that a sequence may be "substantially homologous" at the amino acid level.

As used herein, the terms "altered", or "alterations" or "modified" refer to nucleic acid or amino acid sequences and includes changes such as insertions, deletions, substitutions, fusions with related or unrelated sequences, such as might occur by the hand of man, or those that may occur naturally such as polymorphisms, alleles and other structural types that lead to an antigenic or immunogenic peptide or protein that is substantially homologous or identical to a parasitic FusM. Alterations encompass genomic DNA and RNA sequences that may differ with respect to their hybridization properties using a given hybridization probe. Alterations of polynucleotide sequences for FusM, or fragments thereof, include those that increase, decrease, or have no effect on functionality. Alterations of polypeptides refer to those that have been changed by recombinant DNA engineering, chemical, or biochemical modifications, such as amino acid derivatives or conjugates, or post-translational modifications.

As used herein, the term "immunogen" refers to a antigen that is capable of initiating lymphocyte activation resulting in an antigen-specific immune response. An immunogen therefore includes any molecule which contains one or more epitopes that will stimulate a host's immune system to initiate a secretory, humoral and/or cellular antigen-specific response.

As used herein, the term "antibody" refers to polyclonal and monoclonal antibody preparations, as well as preparations including hybrid antibodies, altered antibodies, $F(ab')_2$ fragments, F(ab) fragments, Fv fragments, single domain antibodies, chimeric antibodies, humanized antibodies, and functional fragments thereof which exhibit immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, $F(ab')_2$, Fv, and other fragments that exhibit immunological binding properties of the parent monoclonal antibody molecule.

Methods of making polyclonal and monoclonal antibodies are known in the art. Polyclonal antibodies are generated by immunizing a suitable animal, such as a mouse, rat, rabbit, sheep or goat, with an antigen of interest. In order to enhance immunogenicity, the antigen can be linked to a carrier prior to immunization. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the antigen may be conjugated to a bacterial toxoid, such as toxoid from diphtheria, tetanus, cholera, etc., in order to enhance the immunogenicity thereof. Rabbits, sheep, mice, rats, hamsters, horses, cows and goats are often used for the preparation of polyclonal sera when large volumes of sera are desired. These animals are good design choices also because of the availability of labeled anti-host antibodies. Immunization is performed by mixing or emulsifying the antigen in saline, preferably in an adjuvant such as Complete Freund's Adjuvant ("CFA") and injected. The animal is boosted 2-6 weeks later with one or more injections of the antigen in saline, often with the antigen emulsified with Incomplete Freund's adjuvant ("IFA"). Antibodies may also be generated by in vitro immunization, using methods known in the art. Polyclonal antisera is then obtained from the immunized animal.

Monoclonal antibodies are generally prepared using the method of Kohler and Milstein, Nature (1975) 256:495-497, or a modification thereof. Typically, a mouse, hamster, huMouse or rat is immunized as described above. However, rather than bleeding the animal to extract serum, the spleen (and optionally several large lymph nodes) is removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice).

As used herein, the terms "antigen-binding site" or "binding portion" refer to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439-473.

As used herein, the term "Fab'," refers to a polypeptide that is a heterodimer of the variable domain and the first constant domain of an antibody heavy chain, plus the variable domain and constant domain of an antibody light chain, plus at least one additional amino acid residue at the carboxy terminus of the heavy chain $C_H1$ domain including one or more cysteine residues. $F(ab')_2$ antibody fragments are pairs of Fab' antibody fragments which are linked by a covalent bond(s). The Fab' heavy chain may include a hinge region. This may be any desired hinge amino acid sequence. Alternatively the hinge may be entirely omitted in favor of a single cysteine residue or, a short (about 1-10 residues) cysteine-containing polypeptide. In certain applications, a common naturally occurring antibody hinge sequence (cysteine followed by two prolines and then another cysteine) is used; this sequence is found in the hinge of human $IgG_1$ molecules (E. A. Kabat, et al., Sequences of Proteins of Immunological Interest 3rd edition (National Institutes of Health, Bethesda, Md., 1987)). In other embodiments, the hinge region is selected from another desired antibody class or isotype. In certain preferred embodiments of this invention, the C-terminus of the $C_H1$ of Fab' is fused to the sequence Cys X X (X preferably is Ala, although it may be any other residue such as Arg, Asp, or Pro; one or both X amino acid residues may be deleted).

As used herein, the term "hinge region" refers to an amino acid sequence located between $C_H1$ and $C_H2$ in native immunoglobulins or any sequence variant thereof. Analogous regions of other immunoglobulins will be employed, although it will be understood that the size and sequence of the hinge region may vary widely. For example, the hinge region of a human $IgG_1$ is only about 10 residues, whereas that of human $IgG_3$ is about 60 residues.

As used herein, the term Fv refers to a covalently or non-covalently-associated heavy and light chain heterodimer which does not contain constant domains. As used herein, the terms "Fv-SH" or "Fab'-SH" refers to an Fv or Fab' polypeptide having a cysteinyl free thiol. The free thiol is in the hinge region, with the light and heavy chain cysteine residues that ordinarily participate in inter-chain bonding being present in their native form. In the most preferred embodiments of this invention, the Fab'-SH polypeptide composition is free of heterogenous proteolytic degradation fragments and is substantially (greater than about 90 mole percent) free of Fab' fragments wherein heavy and light chains have been reduced or otherwise derivatized so as not to be present in their native state, e.g. by the formation of aberrant disulfides or sulfhydryl addition products.

As used herein, the term "humanized antibody" refers to an immunoglobulin amino acid sequence variant or fragment thereof that is capable of binding to a predetermined antigen and that includes an FR region having substantially the amino acid sequence of a human immunoglobulin and a CDR having substantially the amino acid sequence of a non-human immunoglobulin or a sequence engineered to bind to a preselected antigen.

As used herein, the term "control sequences" refers to DNA sequences necessary for the expression of an operably linked coding sequence in a particular host organism. The control sequences that are suitable for prokaryotes, for example, include a promoter, optionally an operator sequence, a ribosome binding site, and transcriptional terminators. Highly regulated inducible promoters that suppress Fab' polypeptide synthesis at levels below growth-inhibitory amounts while the cell culture is growing and maturing, for example, during the log phase may be used.

As used herein, a nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it effects the transcription of the sequence; or a ribosome binding site is operably linked to e coding sequence if it is positioned so as to facilitate translation. Generally, "operably linked" means that the DNA sequences being linked are contiguous and, in the case of a secretory leader, contiguous and in same reading frame. Enhancers do not have to be contiguous. Linking is accomplished by ligation at convenient restriction sites. If such sites do not exist, then synthetic oligonucleotide adaptors or linkers are used in accord with conventional practice.

As used herein, the term "transgene" refers to such heterologous nucleic acid, e.g., heterologous nucleic acid in the form of, e.g., an expression construct (e.g., for the production of a "knock-in" transgenic animal) or a heterologous nucleic acid that upon insertion within or adjacent a target gene results in a decrease in target gene expression (e.g., for production of a "knock-out" transgenic animal). A "knock-out" of a gene means an alteration in the sequence of the gene that results in a decrease of function of the target gene, preferably such that target gene expression is undetectable or insignificant. Transgenic knock-out animals include a heterozygous knock-out of a target gene, or a homozygous knock-out of a target gene.

As used herein, the terms "Knock-out" and "conditional knock-out" refer to the alteration of a target gene that can be activated by exposure of the animal to a substance that promotes target gene alteration, introduction of an enzyme that promotes recombination at the target gene site (e.g., Cre in the Cre-lox system), or other method for directing the target gene alteration.

As used herein, the term "knock-in" refers to an alteration in a host cell genome that results in altered expression (e.g., increased or decreased expression) of a target gene, e.g., by introduction of an additional copy of the target gene, or by operatively inserting a regulatory sequence that provides for enhanced expression of an endogenous copy of the target gene. "Knock-in" transgenics include heterozygous knock-in of the target gene or a homozygous knock-in of a target gene and include conditional knock-ins.

The present invention is also directed to protein or peptide compositions, free from total cells and other peptides, which comprise a purified protein or peptide which incorporates an epitope that is immunologically cross-reactive with one or more anti-FusM antibodies.

The skilled artisan will recognize that epitopes may be mapped by simple deletion constructs that incorporate one or more epitope(s) that are immunologically cross-reactive with FusM. The peptide or protein antigen may include a primary, secondary or tertiary structure similar to an epitope located within the FusM polypeptide. The level of similarity will generally be to such a degree that monoclonal or polyclonal antibodies directed against the FusM polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of cytotoxic or helper T-cell-stimulating immunodominant epitopes against FusM, and/or their functional equivalents, may be suitable for use in vaccines. For example, the skilled artisan may employ the methods of Hopp (U.S. Pat. No. 4,554,101, relevant portions incorporated herein by reference), which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101, relevant portions incorporated herein by reference). The amino acid sequence of these "epitopic core sequences" may then be readily incorporated into peptides, either through the application of peptide synthesis or recombinant technology.

Peptides for T cell epitopes for use with the present invention will generally be on the order of 8 to 20 amino acids in length, and more preferably about 8 to about 15 amino acids in length. Depending on the Major Histocompatibility (MHC) of the host, shorter or longer antigenic cytotoxic of helper T-cell-stimulating peptides will provide advantages in certain circumstances, for example, in the preparation of vaccines or in immunologic detection assays. Exemplary advantages include the ease of preparation and purification, the relatively low cost and improved reproducibility of production, and advantageous biodistribution.

For example, synthetic peptides may be made that include modified and/or extended epitopic/immunogenic core sequences which result in a "universal" epitopic peptide directed to FusM. These epitopic core sequences are identified herein in particular aspects as hydrophilic regions of the FusM polypeptide antigen. It is proposed that these regions represent those which are most likely to promote T-cell or B-cell stimulation, and, hence, elicit specific antibody production.

The identification of epitopic core sequences is known to those of skill in the art, for example, as described by Hopp (U.S. Pat. No. 4,554,101, relevant portions incorporated herein by reference), which teaches the identification and preparation of epitopes from amino acid sequences on the basis of hydrophilicity. Moreover, numerous computer programs are available for use in predicting antigenic portions of proteins (see e.g., Jameson & Wolf, 1988; Wolf et al., 1988). Computerized peptide sequence analysis programs (e.g., DNAStar Software, DNAStar, Inc., Madison, Wis.) may also be useful in designing synthetic peptides in accordance with the present disclosure.

Synthesis of epitopic sequences or peptides that include antigenic epitopes within their sequence are readily achieved using conventional synthetic techniques such as the solid phase method (e.g., through the use of commercially available peptide synthesizer such as an Applied Biosystems ABI 433A Peptide Synthesizer). Peptide antigens synthesized in this manner may then be aliquotted in predetermined amounts and stored in conventional manners, such as in aqueous solutions or in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C. or frozen. Of course, where the peptides are stored in a lyophilized or powdered state, they may be stored virtually indefinitely, e.g., in metered aliquots that may be rehydrated with a predetermined amount of water (e.g., distilled) or buffer prior to use.

As used herein, the terms a "pharmacologic dose" or "therapeutically effective dose" refer to an amount sufficient to gives a desired physiological effect.

For oral therapeutic administration, the FusM antigen(s) may be incorporated with excipients and/or adjuvants and used in the form of ingestible tablets, buccal tables, troches, capsules, elixirs, suspensions, syrups, wafers, and the like. Such compositions and preparations should include at least 0.1% weight percent of the FusM antigen(s). The percentage of the compositions and preparations may, of course, be varied and may conveniently be between about 2 to about 60% of the weight of the unit. When targeting for mucosal immunity, the FusM antigen of the present invention may be provided along with any or a number of known vectors and/or carrier that produce a mucosal immune response, e.g., as taught by V. Gerdts, et al., Mucosal Delivery of Vaccines in Domestic Animals, Vet. Res. 37 (2006) 487-510, relevant portions incorporated herein by reference. The amount of the FusM antigen(s) may be selected and may be increased or decreased, as will be know to those of skill in the art of vaccination, depending on the therapeutically useful results of one or more vaccinations such that a suitable dosage will be obtained that is immunogenic, that is, it triggers an immune response.

The FusM antigen(s) may also be administered parenterally or intraperitoneally. Solutions of the FusM antigen(s) (or vectors that deliver the FusM antigen(s)) may be provided as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable, oral or other use include sterile aqueous solutions or dispersions and sterile powders for FusM vaccine delivery.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The FusM antigen(s) may be included for intramuscular, subcutaneous or even for transdermal administration and may include a reservoir adapted to retain during storage and release in operation the particles containing the FusM antigen(s) of the present invention. It will be appreciated that a wide variety of transdermal devices have been described in the art and are suitable for use in the present invention. An exemplary transdermal device generally includes a reservoir defined by an impermeable backing layer and a membrane. The backing layer and the membrane are joined together about the outer periphery of the device. These layers may be joined by an adhesive, a heat seal or the like. The transdermal device may also include an adhesive layer to attach the device to the skin of a subject. A release liner will generally cover the adhesive that the user removes prior to use of the device to expose adhesive layer.

Example 1

Identification of a family of protist plasma membrane proteins whose expression is restricted to male gametes and whose function is essential for the life cycle of parasitic protozoa. It has been found that FusM is a critical mating protein involved in the fusion of parasite gametes.

The present invention includes the identification of a novel family of cell surface gamete fusion proteins, named FusM, whose members are present in several species of parasitic protozoa. These proteins are critical for gamete fusion and have been targeted for the manufacture of a vaccine to prevent zygote formation. It is shown herein that the FusM family is a heretofore unrecognized candidate for transmission-blocking vaccines. FusM was found to be essential for gamete fusion in a related protist, the green alga, *Chlamydomonas reinhardtii*, an important model organism for investigating fertilization.

Using bioinformatics analysis and techniques, it was found that these proteins are conserved in parasitic protozoa. It is demonstrated herein that the parasitic protozoan FusM is critical for cell surface gamete fusion. FusM homologues are present in the following parasitic protozoa: *Plasmodium falciparum* and *Plasmodium vivax* (both responsible for malaria in humans), *Plasmodium berghei* (causative agent of rodent malaria)(the skilled artisan will recognize that all malaria species should include FusM, including *P. malariae* and *P. ovale*), *Trypansosoma brucei* subspecies (African Sleeping Sickness in humans), *Trypanosoma cruzi* (Chagas disease, a human disease in the Americas), *Cryptosporidium parvum* (Cryptosporidiosis in humans), *Eimeria tenella* (Coccidiosis in poultry), *Theileria* (Theileriosis, which causes heavy losses of ruminants in Africa, Asia, and Europe), and *Toxoplasma gondii* (Toxoplasmosis in humans). Previous studies reported that a FusM protein homolog (designated HAP2 [Johnson et al., 2004] or GCS1 [Mori et al., 2006]) was essential for fertilization in the mustard plant *Arabidopsis thaliana* but no functional results with the protein were shown beyond angiosperms.

The present inventors first demonstrated that *Chlamydomonas* FusM is essential for the final step in fertilization, fusion of the male with the female gamete of *Chlamydomonas* and that it is required only by male gametes. The inventors sought to disrupt the parasitic protozoan FusM. Using these parasitic protozoan FusM mutants it is demonstrated herein that FusM is essential in the male gamete for fusion of male and female gametes in *Plasmodium berghei*, a *Plasmodium* that infects mouse and that is used as a well-described and recognized model for the human form of malaria. In all *Plasmodium* species, fusion of male and female gametes to form zygotes is absolutely essential for transmission of the disease (through a mosquito) from one human to another. It was found that disruption of FusM function interferes with the life cycle of these organisms at the last step of gamete interactions, gamete fusion, and made it possible to develop anti-FusM vaccines that will interfere with transmission of devastating animal and human diseases.

It was found by the present inventors that the FusM protein is expressed by gametes in *Plasmodium* where its function in fertilization is essential for completion of the life cycle and transmission. It has been demonstrated that other proteins in this location can be successfully used as targets for vaccination (Quakyi et al., 1987; Milek et al., 1998). It has also been demonstrated that antibodies against proteins of analogous function in mammals block fertilization (Inoue et al., 2005). Antibodies or other molecular ligands that directly or indirectly interfere with FusM function will block the life cycle of the *Plasmodium*. Furthermore, the finding that FusM is essential for gamete fusion in two distantly related organisms, *Chlamydomonas* and *Plasmodium*, coupled with the presence of FusM family members in the *Apicomplexans* and *Kinetoplastids*, predict that FusM family members will have similar functions in these organisms. Thus, antibodies or other molecular ligands that directly or indirectly interfere with the function of FusM family members in the *Apicomplexans* and *Kinetoplastids* also have significant potential to block the life cycles of these organisms.

Discovery and characterization of FusM in the flagellated protozoa, *Chlamydomonas reinhardtii*. The molecular mechanisms that underlie the fusion of male and female gametes during fertilization in eukaryotes have been difficult to investigate. Until the report last year of the mouse sperm protein Izumo (Inoue et al., 2005), which does not have homologs in protists, only one other gamete fusion protein had been identified in any eukaryotic organism. That protein was Fus1 and it is required in female gametes for zygote formation in the unicellular green alga, *Chlamydomonas reinhardtii* (Ferris et al., 1996; Misamore et al., 2003). The mechanisms of gamete fusion are important to understand as part of the goal of identifying fundamental cellular and molecular mechanisms in fertilization that are common across species. Because the Fus1 gene is unique to *Chlamydomonas*, the present inventors isolated, characterized and identified the fusion protein in male gametes, anticipating that it would be more widely distributed in nature. Using insertional mutagenesis to randomly disrupt genes in the male strain of *Chlamydomonas* and bioassays to screen the mutants for cells whose gametes would recognize and become activated during interactions with female gametes but would be unable to fuse, the present inventors were able to identify the FusM protein. It was found that the gene FusM is essential for gamete fusion in *Chlamydomonas*. Moreover, its was found that FusM is a member of a gene family that is present in several parasitic protozoa that cause devastating human and animal diseases, including *Plasmodium*, the causative agent of malaria.

Materials and Methods. Culturing *Chlamydomonas*, mutagenesis, and screening for fusion mutants. Growth of *Chlamydomonas* vegetative cells and gametes, induction of gametogenesis, and assay of gamete adhesion, gamete activation and gamete fusion to form a zygote have been described previously (Pan and Snell, 2000). Insertional mutagenesis with a plasmid encoding a bacterially-derived paromomycin resistance gene was carried out as described (Pollock et al., 2003) using male strain B215. Over 6,000 insertional mutant clones that grew on paromomycin were analyzed. The clones were screened using phase contrast microscopy for cells that produced male gametes that could adhere to female gametes but were unable to fuse. One fusion-defective, insertional mutant clone, 63B10, was selected for further characterization.

Identification of the gene disrupted in fusion-defective clone 63B10. Genomic DNA from clone 63B10 was used as a template in TAIL PCR reactions to identify genomic DNA adjacent to the plasmid DNA that was used for insertional mutagenesis (Liu et al., 2005). The PCR product was cloned and sequenced using standard methods and contained 0.12 kb of genomic DNA. A BLAST search of version 2 of the *Chlamydomonas* genome database genome.jgi-psf.org/chlre2/chlre2.home.html showed that the 0.12 kb sequence was present in gene model C_530033. From a BAC clone containing this gene model, an 8.3 kb fragment was cloned that contained only gene model C_530033. To confirm that disruption of C_530033 indeed was responsible for the fusion-defective phenotype, a wild-type gene was introduced into the 63B10 mutant using co-transformation with the NIT gene (Kindle et al., 1989). Of 48 clones that grew on the selective medium, 4 clones produced gametes that were capable of gamete fusion (range=20-60% fusion). Using PCR methods it was shown that all 4 clones had received the wild-type gene, thereby confirming that C_530033 was essential for gamete fusion. The gene was named FusM, for fusion protein, male.

Expression of CrFusM transcripts is sex-specific and gamete-specific and essential for fusion in male gametes only. Analysis of genomic DNA showed that the FusM gene was not sex-linked but was present in both the male and female strains. To determine the pattern of expression of the gene, PCR methods were used. RT-PCR using mRNA isolated from wild-type male and female cells in the vegetative and gametic stages of their life cycle showed that FusM transcripts were present only in male gametes. In an independent approach, wild-type female gametes were crossed with a 63B10 male gamete that had been rescued for fusion with the wild-type FusM gene. Using PCR, the inventors screened for female progeny of meiosis that contained only the disrupted form of FusM. When mixed with wild-type male gametes, these FusM defective female gametes were fully capable of gamete fusion. Therefore, FusM is essential for fusion activity of only male gametes in *Chlamydomonas*.

CrFusM is not required for the initial steps in gamete interactions, including gamete recognition and gamete activation; it is essential only for gamete fusion. When male and female gametes of *Chlamydomonas* are mixed together they adhere to each other via their flagella. Flagellar adhesion triggers a complex flagellar signaling pathway within the flagella of each gamete that stimulates production of cAMP leading to activation of the gametes for cell fusion. The activated gametes release enzymes that degrade the extracellular matrix and both gametes reorganize fusogenic membrane specializations on their plasma membranes at the apical ends of the cell. Flagellar adhesion brings the fusogenic membranes into close contact, followed immediately by fusion of the plasma membranes of the two gametes. Within seconds the two gametes merge their cytoplasmic contents, reorient their flagella, and become a zygote (Goodenough, 1991). It was found that 63B10 gametes were incapable of gamete fusion. Next, the step in fertilization at which the blockage occurred was identified. By use of bright field and phase contrast microscopy, it was found that 63B10 male gametes underwent flagellar adhesion with wild-type female gametes that was indistinguishable from flagellar adhesion of wild-type male gametes. Bioassays that detect the presence of the extracellular matrix, showed that the 63B10 gametes also degraded their extracellular matrix when incubated with a cell-permeable form of cAMP or when mixed with wild-type female gametes, thereby demonstrating that they were capable of gamete activation. Moreover, addition of the membrane-permeable form of cAMP to 63B10 gametes adhering to wild-type female gametes did not rescue gamete fusion. Therefore, FusM was dispensable for gamete adhesion and gamete activation, and was essential only for fusion of the plasma membranes of the interacting gametes.

FusM family members are present in higher plants, primitive multicellular animals, and parasitic protozoa, including *Plasmodium*. By use of bioinformatics methods, including BLAST searches, FusM family members in *Oryza sativa* (rice), *Zea mays* (corn) and most other higher plants whose genomes are publicly available were also identified. FusM family members were also identified in *Hydra* and the Startlet Sea Anemone, but not in other multicellular animals to date. FusM is present in many non-parasitic unicellular protozoa, including *Tetrahymena thermophile* and *Dictyostelium discoideum*. Finally, FusM family members are present in many parasitic protozoa, including *Plasmodium falciparum*. *Plasmodium vivax*, *Plasmodium berghei*, *Trypansosoma brucei*, *Trypanosoma cruzi*, *Cryptosporidium hominis*, *Eimeria tenella*, *Theileria parva*, and *Toxoplasma gondii*. FIG. 1 shows an alignment of the sequences of FusM family members in several of these parasitic protozoa, SEQ ID NOS, 1-10, respectively.

TABLE 1

Properties of FusM mutants of *Chlamydomonas* and *Plasmodium*

| Organism | Asexual growth | Gametogenesis | Initial gamete interactions | Female gamete fusion | Male gamete fusion | Zygote maturation |
|---|---|---|---|---|---|---|
| *Chlamydomonas* | Wild type phenotype | Wild type phenotype | Wild type phenotype | Wild type phenotype | None | None |
| *Plasmodium* | Wild type phenotype | Wild type phenotype | Wild type phenotype | Wild type phenotype | None | None |

The *Plasmodium* FusM is a microgamete (male gamete) fusion protein. Although several important cellular and molecular events of the sexual phase of the life cycle of *Plasmodium* have been elucidated, the proteins that accomplish gamete interactions and gamete fusion have not been identified. Fertilization in *Plasmodium* occurs in the gut of mosquito after it has ingested the blood of an infected host. Once in the environment of the mosquito gut, male gametocytes (microgametocytes) and female gametocytes (macrogametocytes) within the red blood cells of the ingested blood meal are released from the cells and are stimulated to undergo gametogenesis to form male gametes (microgametes) and female gametes (macrogametes), events that are completed within 10-15 minutes. The male gametes possess a single flagellum which they use for propulsion. Upon collision with a female gamete (which is immotile), the male gamete adheres transiently and then fuses with the female gamete to become a zygote. The zygote elongates to become an ookinete, which migrates through the wall of the gut where it becomes an oocyst. Further meiotic and mitotic divisions eventually produce sporozoites that migrate to the salivary gland from which they are injected into a new host at the next feeding, thereby transmitting the disease (Sinden, 1983). To identify a possible role for FusM in *Plasmodium* sexual reproduction, molecular methods were used to disrupt the *Plasmodium* FusM gene. It was found that the FusM protein is essential for fusion of male and female gametes in *Plasmodium berghei* (FIG. 2). Thus, as predicted from the results in *Chlamydomonas*, interference with the *Plasmodium* FusM gene blocks the sexual life cycle of this deadly protozoan parasite.

Generation of a *Plasmodium* mutant clone containing a disrupted FusM gene. Using an established method for generation of gene targeting constructs in *Plasmodium berghei* (Menard and Janse, 1997), a strain was produced in which the FusM gene (PbFusM) was disrupted. Subcloning using standard methods followed by PCR analysis confirmed the absence of the wild-type gene.

The FusM mutant *Plasmodium* strain exhibited no detectable phenotype in the asexual phases of its life cycle, but the mutant gametes failed to fuse and failed to produce ookinetes. Blood from mice infected with the FusM mutant strain was incubated in vitro under conditions that stimulated release of microgametes and macrogametocytes from red blood cells (Billker et al., 1998). Examination of the samples by light microscopy revealed that macrogametocytes underwent exflagellation and produced flagellated microgametes whose morphology and motile properties were indistinguishable from wild-type cells.

In addition, the mutant macrogametes exhibited wild-type morphology. Analysis by light microscopy, however, indicated that the male gametes exhibited a non-wild-type interaction with the female gametes. Whereas wild-type gametes approached the female, briefly interacted, and then merged with the female, no merging of the cells could be detected in the mutant cultures. Furthermore, analysis of the cultures 24 hours after beginning of the incubation utilizing an immunofluorescence assay (Winger et al., 1988) demonstrated that no ookinetes had formed. And, finally, examination of the midguts of female *Anopheles* mosquitoes that had fed on mice containing wild-type and FusM mutant forms of *Plasmodium*, revealed that only mosquitoes that had fed on wild-type mice contained *Plasmodium* oocysts. Mosquitoes that had fed on the mice containing *Plasmodium* whose FusM gene was disrupted did not contain any oocysts. Thus, based on multiple, well-accepted scientific criteria, FusM was found to be essential for zygote formation in *Plasmodium*. Therefore, FusM is a critical target for vaccination.

FusM is essential only in male gametes. Since both the male and female gametes produced by the mutant strain possessed the disrupted FusM gene, additional studies were carried out to determine whether FusM was required in the male or female gamete or both. Blood containing the FusM mutant strain was mixed with blood from a mutant strain incapable of producing male gametes (Billker et al., 2004) or with blood from a mutant strain incapable of producing female gametes (Reininger et al., 2005). Analysis of the samples showed that when FusM mutant samples were mixed with blood from a mutant that produced only female gametes, no ookinetes were formed. On the other hand, when FusM mutant samples were mixed with blood from a mutant that produced only male gametes, ookinetes were formed. These results indicated that FusM mutant female gametes were capable of fusion, whereas FusM mutant male gametes were incapable of fusion. Thus, FusM is essential only in the male gamete.

Example 2

Unlike FUS1, which is species-specific (13, 16), FusM is widely conserved and contains no previously described domains. Mori et al. had reported that in addition to its presence in higher plants (including rice), database searches showed homologs in *Chlamydomonas* and red algae, a slime mold, and *Plasmodium* and *Leishmania*. Using PSI-BLAST the family was expanded, finding members in many other non-pathogenic and pathogenic protists, and importantly in multicellular animals including *hydra* and sea anemone (7). The presence of FusM in protists, higher plants, and some metazoans is in marked contrast with the rapid evolution of other genes involved in gamete interactions (16, 17). It was then determined whether the function of FusM in fertilization was conserved between *Chlamydomonas* and malaria parasites (genus *Plasmodium*), whose transmission to the mosquito relies on sexual reproduction. Sexual precursor stages, the gametocytes, form in the vertebrate host inside infected erythrocytes but remain quiescent until ingested by a susceptible *Anopheles* mosquito. In the bloodmeal, gametocytes emerge from their host cells and within minutes differentiate into gametes. Each female (macro) gametocyte gives rise to a single immotile macrogamete, while microgametocytes generate up to eight flagellated microgametes in a process termed exflagellation; within minutes after release, the gametes meet, adhere tightly for a few seconds, and then fuse to form a zygote (18). Microgamete adhesion to macrogametes requires the surface protein and transmission-blocking vaccine candidate P48/45 (19). Its role in microgamete adhesion may be direct or indirect, since P48/45 is known to interact physically with at least one other microgametocyte protein, P230 (20) and in *P. falciparum* is required to retain the complex on the surface of the microgamete (21). Within 15-20 h the zygote transforms into a motile ookinete, which penetrates the midgut epithelium and establishes the infection in the mosquito by forming an oocyst between the midgut epithelial cells and their underlying basal lamina. Thus, gamete adhesion and fusion are obligate steps in transmission and attractive targets for transmission-blocking vaccines. In the rodent malaria parasite *P. berghei*, gametocytes respond efficiently to well-characterized developmental triggers (22) in vitro, and gametogenesis, fertilization and ookinete formation are accessible to analysis in culture.

Targeted deletion of *P. berghei* FusM (GenBank accession number XM_671808) resulted in two knock-out clones (FIG. 2, A-C). RT-PCR detected FusM transcripts in wt gametocytes, but not in fusm gametocytes or in wt asexual erythrocytic stages of a gametocyte-deficient parasite strain (FIG. 2D). Consistent with this sexual stage-specific transcription, fusm clones showed normal asexual intraerythrocytic parasite development in mice. Neither the rate of gametocyte formation nor the sex ratio were affected (data not shown), but mosquitoes that had fed on mice infected with fusm parasites failed to develop oocysts on their midguts (FIG. 2E). The complete block in malaria transmission in vivo correlates with the absence of formation of ookinetes (FIG. 2F) in vitro, a process that occurs efficiently in wt parasites. Genetic complementation of the *P. berghei* fusm mutant restored ookinete formation. Thus, results in both *Chlamydomonas* and *Plasmodium* pointed to a role for FusM in fertilization.

Figure 3A:
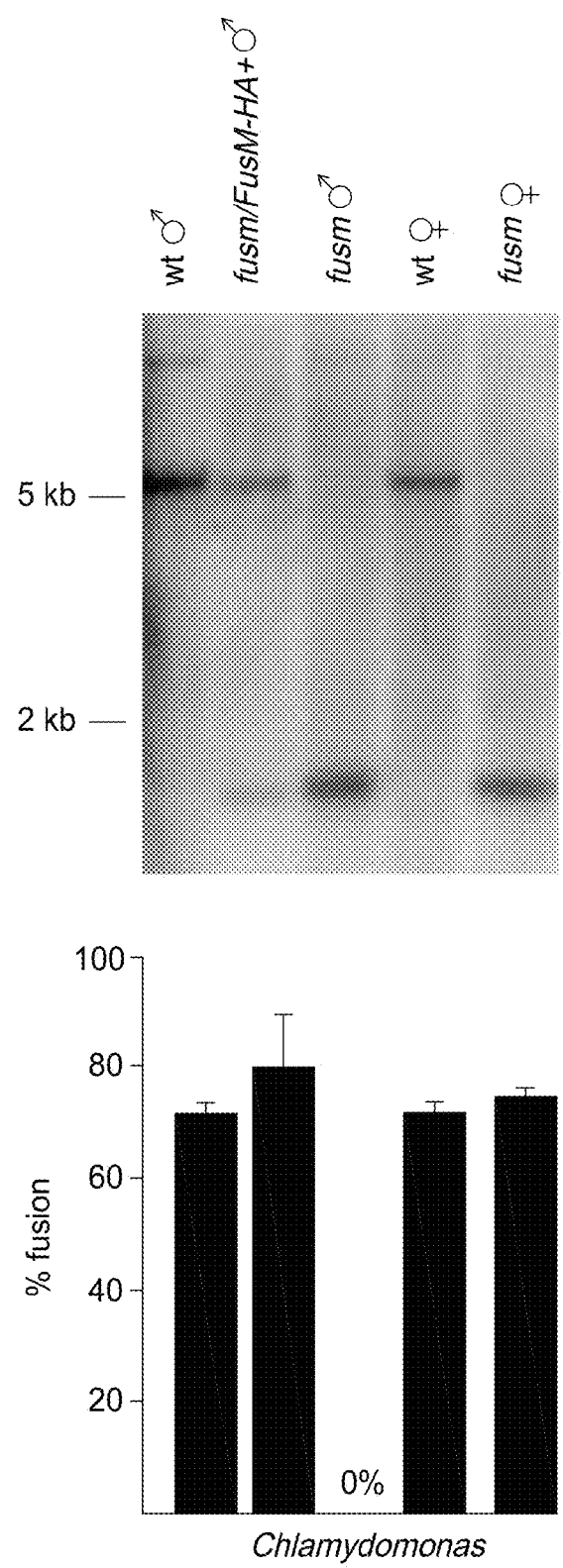
Figure 3B:
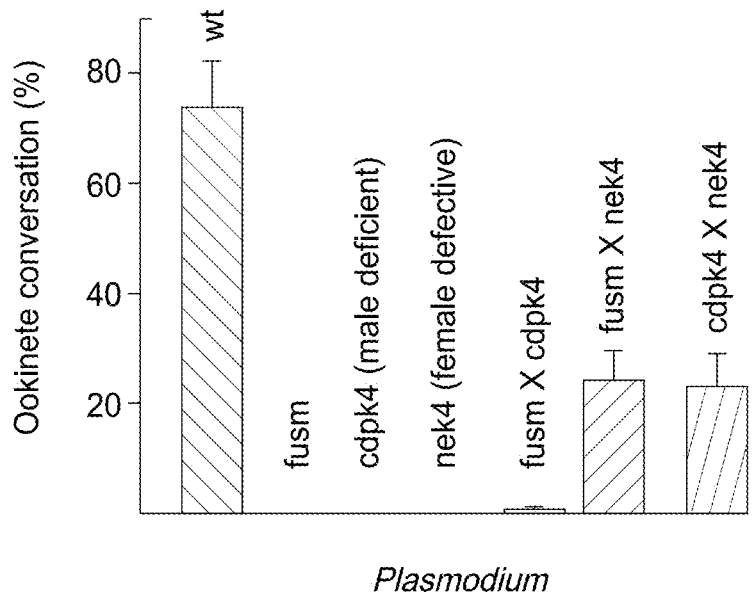

To dissect the function of FusM in *Chlamydomonas* fertilization, it was next determined whether FusM is required in male or female gametes or both. Briefly, wt females were crossed with 63B10 males that had been rendered fusion-competent by transformation with the wild type FusM gene, and selected female progeny that contained only the disrupted FusM gene (Southern blot, FIG. 3A, upper panel). Female gametes that lacked a functional FusM gene exhibited no detectable mutant phenotype as vegetative cells or gametes and underwent gamete fusion similarly to wt (FIG. 3A, lower panel). Consistent with results of Mori et al. (7) a strong RT-PCR signal for FusM in male gametes of *Chlamydomonas* and low amounts in female gametes was detected, although it was also detected in low amounts in male vegetative cells (data not shown). Thus, in spite of the detection of FusM transcripts in females, FusM is essential in fusion of *Chlamydomonas* male gametes only. In malaria parasites, gender-specific sterility phenotypes are revealed in cross-fertilization experiments with known sexual development mutants, such as the male-deficient cdpk4 or the female-defective nek4 mutant (23, 24). Neither cdpk4 nor nek4 strains produced ookinetes when cultured on their own, but when gametocytes of both mutants were mixed, nek4 microgametes productively fertilized cdpk4 macrogametes, restoring the capacity to form ookinetes (FIG. 3B). The fusm mutant was successfully cross-fertilized by nek4 male gametes, showing that fusm macrogametes were fusion competent. Taken together these results demonstrate that during fertilization in both *Chlamydomonas* and *Plasmodium* FusM is essential in male gametes only.

Figure 3C:
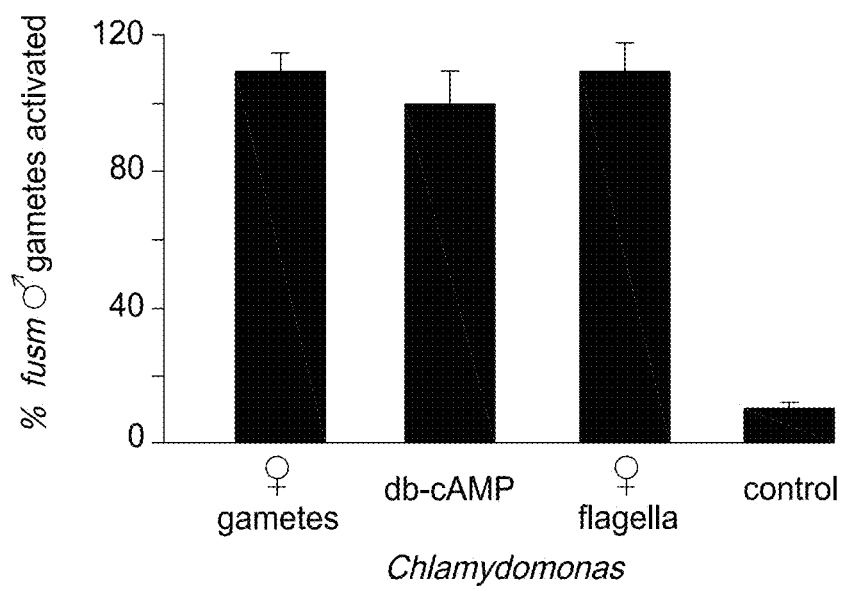

Unlike many organisms whose gametes possess an extracellular matrix that must be removed before fusion, *Plasmodium*'s gametes are "naked" (18). Therefore, it was determined whether FusM would also function at a step in *Chlamydomonas* fertilization when the gametes are "naked," that is, after flagellar-adhesion-induced gamete activation and release of cell walls. Consistent with this prediction, in mixtures of wt females and 63B10 male gametes, flagellar adhesion led to activation of both gametes as assessed by wall loss (FIG. 3C) and activation of female mating structures (not shown). 63B10 gametes also responded to the activation-triggering agent, db-cAMP, by releasing their walls (FIG. 3C). Because our results pointed to a role for FusM late in gamete interactions, possibly at the site of membrane fusion, the properties of FusM in 63B10 gametes expressing an HA-tagged FusM were investigated. Immunoblotting (FIG. 3D) showed that FusM-HA was expressed only in gametes. The detection of two closely spaced isoforms of FusM-HA suggested that the protein undergoes posttranslational modification. The more slowly migrating form disappeared upon treatment of live cells with trypsin, indicating that one form of FusM is exposed on the external surface of gametes (FIG. 3E). Moreover, immunofluorescence imaging showed that FusM was present as a single spot near the bases of the two flagella, the location of the mating structure (FIG. 3F) (11). Thus, the topology and the location of FusM were consistent with a function in either adhesion or fusion at the fusogenic plasma membrane sites.

Figure 4A:
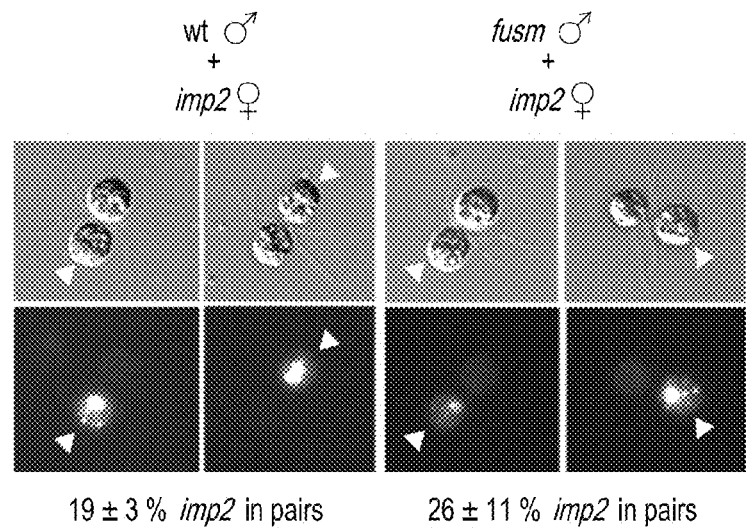
FIGS. 4A to 4C. FusM functions in the gamete fusion reaction downstream of gamete membrane adhesion.
Figure 4B:
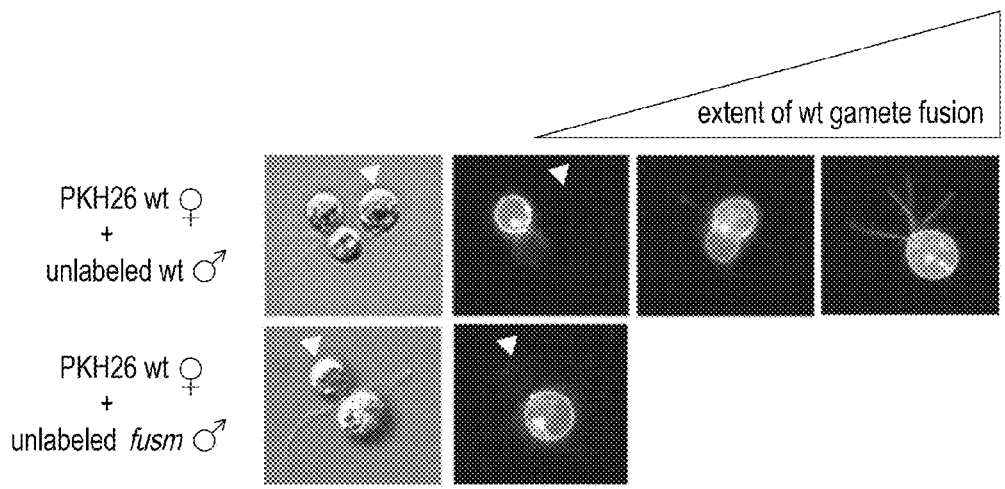

To examine the adhesion properties of the fusogenic membrane on 63B10 gametes without the interference of flagellar adhesion, 63B10 gametes were activated with db-cAMP and mixed them with similarly activated imp2 female gametes, which do not possess flagellar adhesion molecules. Surprisingly, the 63B10 males adhered tightly to the female gametes at the site where fusion normally occurs (FIG. 4A, right two panels), in a manner indistinguishable from adhesion of wild-type (wt) males and females at the site of fusion (13) (FIG. 4A, left two panels). Although the absence of zygote aggregates in 63B10/wt mixtures (FIG. 1D) demonstrated that cytoplasmic mixing of the two gametes and the consequent activation of the zygote developmental pathway (26) required FusM (26), it was possible that the 63B10 gametes underwent membrane fusion, and that FusM functioned after gamete membranes began to merge. Studies designed to assess membrane merger as detected by movement of a fluorescent lipid (PKH26) from the plasma membranes of labeled female gametes to wt and mutant males, however, ruled out this latter possibility. Whereas lipid mixing between wt females and wt males was evident soon after the mating structures interacted and complete mixing occurred immediately thereafter (FIG. 4B, upper panels), membrane merger was never detected in the hundreds of 63B10 male/wt female pairs examined in several independent experiments (FIG. 4B, lower panels). Taken together, these results demonstrated that male gametes employ a protein different from FusM to bind to the female-specific, mating structure adhesion protein FUS1, and that FusM is essential at a step in the gamete membrane fusion reaction immediately after species-specific adhesion of the fusogenic membranes.

Figure 4C:
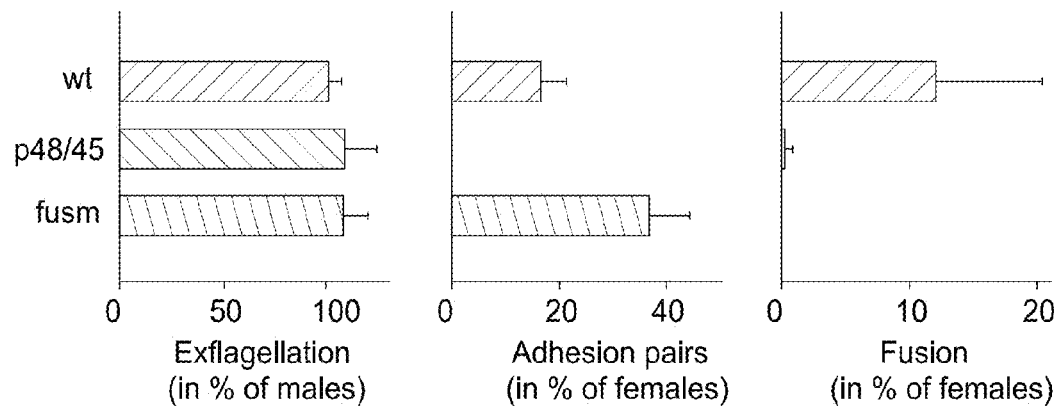

Similarly, FusM functions downstream of gamete adhesion in *Plasmodium*. Microscopic examination of fertilization in vitro showed that in the absence of FusM the incidence of male/female *Plasmodium* gamete pairs was approximately doubled compared to wild type (FIG. 4C); the failure to detect fertilization indicated that fusm pairs formed and persisted, but failed to progress from adhesion to membrane fusion. In marked contrast, in fertilization experiments with a p48/45 mutant, a complete lack of gamete binding explained fully the absence of fertilization (FIG. 4C), confirming the importance of the *Plasmodium*-specific P48/45 (19) complex in gamete adhesion.

The FusM mutants in *Chlamydomonas* and *Plasmodium* were used to genetically dissect the membrane fusion reaction in both species into molecularly distinct events of membrane adhesion and membrane fusion. Whether FusM functions directly as a fusogen, or has a more indirect role in the seconds between adhesion and fusion, may be determined. Membrane fusion reaction mechanisms are infrequent during evolution and the conserved function of FusM in gamete membrane fusion in two widely disparate organisms is consistent with a direct role for FusM in the final event of fertilization. Viruses use a single protein for both specific contact and for fusion itself, and the several classes of viral fusion proteins apparently evolved independently (4). Intracellular vesicle fusion employs distinct sets of conserved protein families for each step—rabs and their effectors for specific adhesion, and SNARES for membrane merger (1). These results show that the gamete membrane fusion reaction likewise depends on separate sets of proteins for specific adhesion and for fusion per se. In this manifestation of fusion, however, membrane adhesion depends on species-limited proteins, such as FUST, possibly reflecting their roles in speciation, whereas membrane merger depends on the broadly conserved FusM protein family. The obligate role of zygote formation in malaria transmission and the apparently strong selective pressure against mutations in FusM make it a potential target for transmission-blocking malaria interventions.

Example 3

Vaccination and production of antibodies against *Chlamydomonas* FusM protein. Expression and purification of recombinant FusM protein. Bacterial expression plasmid PYJ61 containing FusM cDNA (see below) was transformed into M15 bacteria strain for expression of His-tagged FusM recombinant protein. Protein production and purification were carried out as follows: 10 ml of overnight bacteria culture were inoculated into1 liter LB broth media with 100 ug/ml of Ampicillin. After shaking for 1 hr at 37° C., the culture was induced with 0.1 mM IPTG for 3 hrs at 37° C. (OD$_{600}$=0.6). Bacteria were harvested by centrifugation and suspended in 10 ml lysis buffer (20 mM Tris, 300 mM NaCl, 10 mM imidazole, protease inhibitor cocktail from Roach). Cell lysate were added with lysozyme to 1 mg/ml and incubated for 30 min on ice. 1.5% Sarkosyl (final concentration) was added to the lysate and the lysate was sonicated for 5 min. After sonication, the lysate was centrifuged at 12,000 g for 30 min. Triton-X-100 (final concentration 2%) was added to the supernatant, which was then passed through a 1 ml Ni-NTA affinity column (Qiagen). For maximum binding of protein, the lysate was incubated with Ni-NTA affinity beads for 1 hr. The column was washed with 50 ml wash buffer (20 mM imidazole, 20 mM Tris, 300 mM NaCl, 1% Triton, protease inhibitor cocktail). Bound recombinant protein was eluted with 10 ml elution buffer (20 mM Tris, 300 mM NaCl, 1% Triton, 250 mM imidazole, protease inhibitor cocktail). Eluted proteins were separated by SDS-PAGE. Recombinant FusM protein (75 Kd) was excised from the SDS-PAGE gel slice and electro-eluted for injection into animals.

CrFusM protein was affinity purified on an Ni-NTA column followed by SDS-PAGE. Coomassie stain shows the predominant band of CrFusM recombinant protein that runs as a 75 Kd protein (data not shown).

Vaccine production, immunization and antibody production and purification for immunoblotting and bioassays for gamete fusion. Rabbits were immunized with recombinant FusM protein using standard methods. Briefly, recombinant FusM protein purified as described and resuspended in phosphate buffered saline, was mixed with Freund's Complete adjuvant, final concentration of protein 1 mg/ml. After emulsification, the sample 0.5 ml was injected into a rabbit according to protocols approved Institutional Animal Care and Use Committee (IACCUC), subcutaneously in the flank. After 2-3 weeks the animals were boosted with 0.5 mg antigen in Freund's Incomplete Adjuvant subcutaneously. After 3 boosts over the course of 3 months, blood was collected from an ear vein by venous puncture using approved protocols. To prepare serum, the blood was allowed to clot, and the serum collected. Antibodies were affinity purified from the serum. Ten ml rabbit antiserum prepared against recombinant FusM protein was passed over a 2 ml protein A agarose antibody affinity column. The column was washed with 50 ml PBS, antibody was eluted with 10 ml 0.1M glycine (pH2.0) and antibody concentration was determined by absorbance at 280 nm. For gamete fusion bioassays, the purified antibody was dialyzed against 1 liter PBS or M-N media (nitrogen free media for *Chlamydomonas*). Antibody was stored at 2-8° C. with 0.2% sodium azide. For gamete fusion blocking experiments, no azide added.

Figure 5:
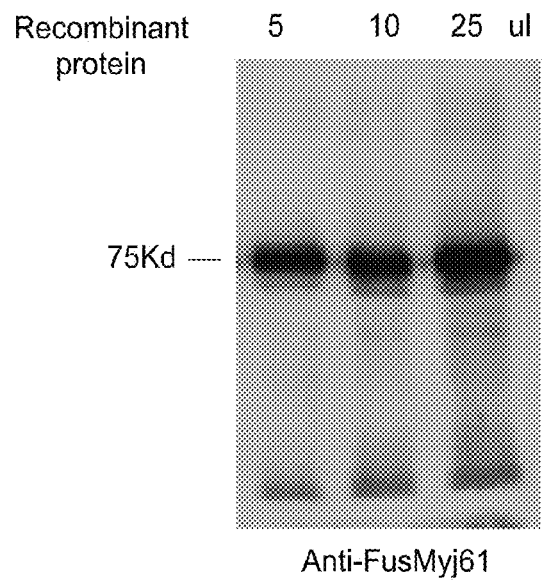
FIG. 5 shows the results of vaccination using the CrFusM antigen. Purified antibody against CrFusM stains recombinant FusM protein efficiently on immunoblots. Recombinant CrFusM protein was purified with Ni-NTA affinity column and loaded with increasing amounts on SDS-PAGE.

FIG. 5 shows that the vaccine was able to trigger a specific immune response. Purified antibody against CrFusM stains recombinant FusM protein efficiently on immunoblots. Recombinant CrFusM protein was purified with Ni-NTA affinity column and loaded with increasing amounts on SDS-PAGE.

Figure 6:
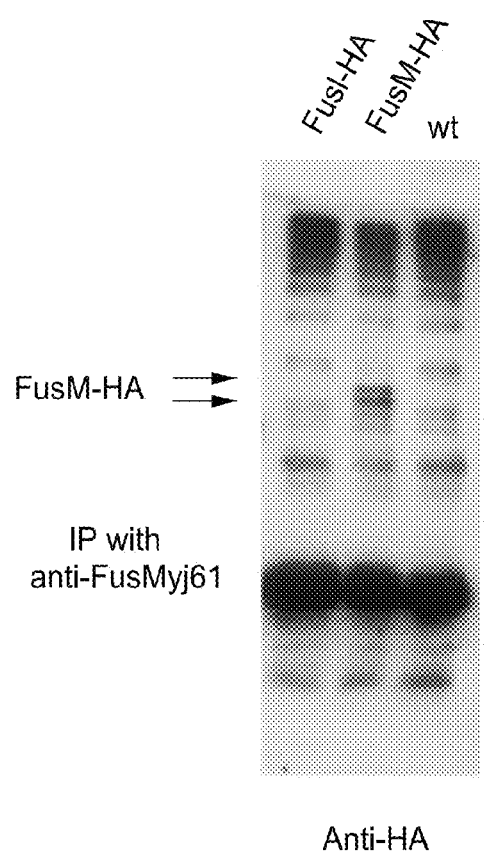
FIG. 6 the vaccine generated an immune response. Immunoblots show that purified anti-CrFusM antibodies immunoprecipitate endogenous FusM-HA protein. *Chlamydomonas* gametes of wild-type strain (wt) or strains expressing Fus1-HA (HA tagged Fus1 protein, a negative control) or FusM-HA were lysed and used for immunoprecipitation assay. Lysates were immunoprecipitated with purified anti-CrFusM antibodies and the immunoprecipitates were stained with anti-HA monoclonal antibody (Roach) on immunoblots. Only FusM-HA protein was immunoprecipitated by anti-CrFusM antibodies (two isoforms of FusM-HA shown with two arrows) and not Fus1-HA.

FIG. 6 demonstrates the specificity of the immune response by immunoblots show that purified anti-CrFusM antibodies immunoprecipitate endogenous FusM-HA protein. *Chlamydomonas* gametes of wild-type strain (wt) or strains expressing Fus1-HA (HA tagged Fus1 protein, a negative control) or FusM-HA were lysed and used for immunoprecipitation assay. Lysates were immunoprecipitated with purified anti-CrFusM antibodies and the immunoprecipitates were stained with anti-HA monoclonal antibody (Roach) on immunoblots. Only FusM-HA protein was immunoprecipitated by anti-CrFusM antibodies (two isoforms of FusM-HA shown with two arrows) and not Fus1-HA.

Anti-FusM antibodies for inhibition of gamete fusion. The vaccine was able to produce a FusM antigen-specific immune response that was able to block gamete formation. Briefly, Activated male ($5 \times 10^6$ cells/ml in M-N) were incubated with purified anti-recombinant FusM antibodies at 0.5, 1, 2.5 mg/ml final concentration for 1 hr, the treated gametes were mixed with an equal number of female gametes, and at 4 min after mixing the extent of gamete fusion was determined. As is indicated in the table below, antibody treatment in these initial experiments reduced fusion to 48% of the control cells (52% inhibition).

TABLE 2

Inhibition of gamete fusion by anti-FusM antibody

| Antibody concentration (mg/ml) | Gamete fusion (percent of control) |
| --- | --- |
| 0 (control) | 100% |
| 0.5 | 66% |
| 1 | 61%) |
| 2.5 | 48%) |

Figure 7:
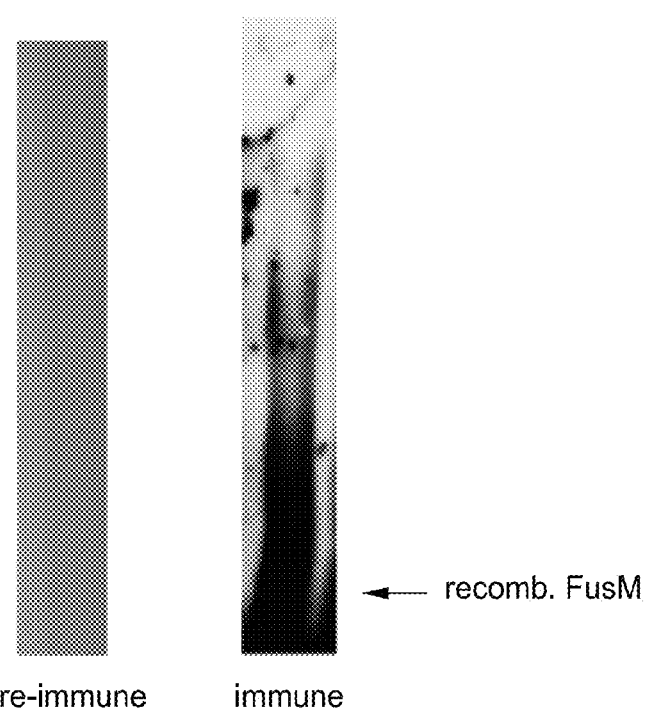
FIG. 7 shows the results of vaccinating a mouse. Immunoblots show that antiserum from mice injected with FusM protein for monoclonal antibody production recognizes recombinant CrFusM protein.
Figure 8:
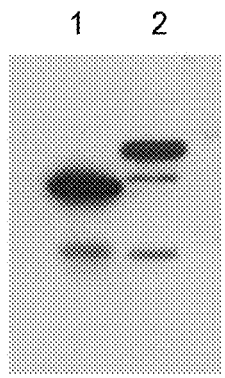
FIG. 8 is a Western blot of PbFusDomA and PbFusDomB expressed in pET46b and *E. coli* BL21 (DE3) pMico using anti-His$_6$ probe. 1; PbFusDomA expressed from total *E. coli* cell lysate, 2; PbFusDomB expressed from total cell lysate.
Figure 9:
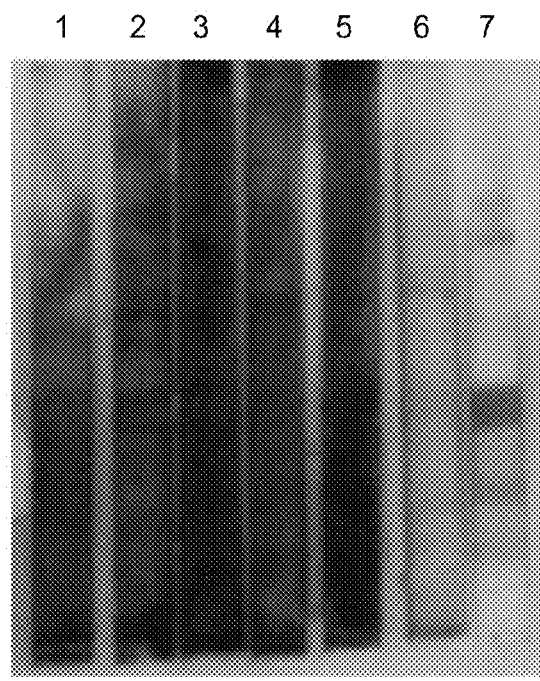
FIG. 9 shows the vaccination results as measured with a blot demonstrating serum response to recombinant PbFusDomA after first boost. 1; Sera from Mouse 1 (1 in 50) 2; Sera from Mouse 2 (1 in 50), 3; Sera from Mouse 3 (1 in 50), 4; Sera from Mouse 4 (1 in 50), 5; Sera from Mouse 5 (1 in 50), 6; negative control—pre-immune serum (1 in 50). 7; positive control—Anti His$_6$-probe (1 in 5000).

FIG. 7 shows the vaccination result from immunizing a different mammal. Immunoblots show that antiserum from mice injected with FusM protein for monoclonal antibody production recognizes recombinant CrFusM protein.

Example 4

Heterologous expression of *P. berghei* FusM in *E. coli* based expression systems. The FusM gene in *P. berghei* (locus PB-RP1579) consists of an open reading frame 2696 bp long, containing two exons, and an intron 209 bp long, located at position +228 within the gene. This gene encodes a protein 828 amino acids in length, with a single predicted transmembrane domain between residues 680 and 708, towards the C-terminus of the polypeptide. No other putative domains are identified via primary sequence homology, or bioinformatics-based secondary structure prediction algorithms. Initial attempts were made to clone and heterologously express regions of *P. berghei* FusM in appropriate *E. coli* (DE3) strains.

Initially, two sections of the gene were cloned into expression vectors. These sections corresponded to amino acids 82-371, and 255-660, and were named PbFusDomA and PbFusDomB respectively. PCR products were purified using a PCR purification kit (QIAGEN) and cloned into pET15b, pET46b and pET41b (Novagen). pET 15b and 46b produce N-terminal His$_6$ fusion proteins, whereas pET41b produces an N-terminal GST+His$_6$ fusion.

Each of these clones was confirmed initially by diagnostic PCR, followed by digestion, and finally, sequencing on both strands. Following sequencing, and the confirmation of the absence of any substitutions or frame shifts, the relevant constructs were cloned into *E. coli* BL21 (DE3) Star, *E. coli* BL21 (DE3) pLysS, *E. coli* Rosetta BL21 (DE3), *E. coli* Rosetta BL21 (DE3) pLysS and *E. coli* BL21 (DE3) pMico (Cinquin et al, *Mol. Biochem. Parasitol.* 117(2), pp 245-247 (2001)). The expression of each construct was then checked using standard *E. coli* T7 based expression methods. Expression was identified by SDS-PAGE and subsequent coomassie staining of *E. coli* lysates 5 hours post induction of expression, and western-blotting using an anti-His$_6$ antibody (His-probe from Pierce). Of all the constructs and cell lines used, only two gave demonstrated any detectable expression –PbFusDomA (31.2 kDa) and PbFusDomB (35.8 kDa) were only expressed in pET46b, using the *E. coli* BL21 (DE3) pMico cell line (FIG. 2). This expression resulted solely in polypeptide contained within inclusion bodies, and no soluble protein of interest was detected, even upon expression under a wide range of different temperatures. FIG. 3 shows the detection of PbFusDomA and PbFusDomB via western blot using an anti-$His_6$ antibody.

FIG. 8 is a Western blot of PbFusDomA and PbFusDomB expressed in pET46b and *E. coli* BL21 (DE3) pMico using anti-$His_6$ probe. Lane 1: PbFusDomA expressed from total *E. coli* cell lysate, Lane 2: PbFusDomB expressed from total cell lysate. For the production of antibodies, initially, SDS-PAGE gel slices containing approximately 250 μg PbFusMDomA and PbFusDomB were excised, ground to a fine powder, and resuspended in 1 ml MPL+TDM oil-in-water adjuvant (Sigma, M6536). For each of the two proteins to be investigated, a 200 μl dose was injected subcutaneously into five BalbC female mice, from which pre-immune sera had previously been collected. Each mouse was then boosted on day 21 (boost 1), and tail bled to a volume of 100 μl 4 days following this. Another two boosts followed this at 4 week intervals. Blood gleaned from tail bleeds was allowed to coagulate overnight at 4° C. overnight, and was then spun at 14,000 g for 20 mins. Separated sera was then removed from the resulting pellet, and stared at 4° C. until further use. To test for any immune response, sera were tested on a western blot against recombinant protein preparations of the appropriate *P. berghei* FusM domain. This sera was tested at the concentration of 1 in 50. The secondary antibody used was ECL Anti-mouse IgG, HRP linked whole antibody (from sheep; GE Healthcare NA931V). His-probe was used as a positive control, and pre-immune sera was used as a negative control. Immunisation using this method produced no obvious immune response to either of the FusM derived recombinant polypeptides, even after three boosts.

In order to investigate this further, for PbFusMDomA, a similar procedure was repeated, but this time, using a more powerful adjuvant (Freud's complete adjuvant for the initial immunization; Sigma, F5881, Freud's incomplete adjuvant for the boosts; Sigma, F5506). Also, protein preparations were not taken from SDS-PAGE gel slices, but from purified insoluble inclusion bodies following growth and induction of the appropriate *E. coli* expression strain. The immunization, boost and test-bleed protocols were as described previously. Following one boost, a potential immune response was seen at 35.8 kDa against recombinant PbFusMDomA in mouse 2A of 5 (FIG. 9).

FIG. 9 is a blot demonstrating serum response to recombinant PbFusDomA after first boost. 1; Sera from Mouse 1 (1 in 50) 2; Sera from Mouse 2 (1 in 50), 3; Sera from Mouse 3 (1 in 50), 4; Sera from Mouse 4 (1 in 50), 5; Sera from Mouse 5 (1 in 50), 6; negative control—pre-immune serum (1 in 50). 7; positive control—Anti $His_6$-probe (1 in 5000).

FIG. 10 is a Western blot demonstrating mouse 2A response to recombinant PbFusDomA. 1; Sera from Mouse 1 (1 in 200) 2; negative control—pre-immune serum (1 in 50).

Following this, mouse 2A was culled via cardiac puncture-resulting in 1.2 ml of blood. Sera was purified as described previously, and used on a western blot against recombinant PbFusMDomA. As can be clearly seen in FIG. 10, the serum from mouse 2 clearly recognizes recombinant FusM protein preparations (along with other *E. coli* proteins of varying sizes). A soluble version of *P. berghei* FusM (amino acids 355-660) coupled to an MBP molecule was produced. This polypeptide has been separated from *E. coli* Rosetta BL21 (DE3) pLysS cell lysates, and was used to immunize BalbC mice.

Nucleic acid sequences for use with the present invention may include at least portions of one or more of the following parasitic FusM genes:

*Plasmodium falciparum*

(SEQ ID NO.: 15)

```
ATGAACAAAAGGAAAAAGACAAAACACTTAAAAGTTAATTCTATATTGAGAATCTTTTTTTTTTTT

TTCCTTATTTCTTTTCTTTTTAGTAATTGTAAATTAAATGATTATATAAGAACAAAATACCCATTCA

TTCAATTTGTATATTCTTATTCCAAAAAAAAGGTATGTACATCTTCTACAGATGATTCCACATGTCG

TACTGTCGTTTATGGAGATTTAGATGTTTCTAATAATTCGGTGTTAAGGTTAAAGGTTTTAAGGTCT

GAGGGGAAAGGCTATTTTGTTACTATTCGAAGAGACTATGTAACAATATCTTACTATCTGAAATAT

ATGAAAGATATTCCTTTAAAGTATAGAGAAGTAGTTGATATATTTAATAATCATAAATATGAAAA

ATATACAGAGAAACAAATAAAGGATTTTACTTATAATTGTACTGCTATTAAAGTCGAAGATGCCA

ATAATACTGTAGGGGATTTTGCACCTCATTATCATGAATATACAAGAGGAGAATCTTGTATATGCC

CTTCATATCATCTTTTTAAAAATGACAATTCAATAAAAAGAGCAAAATTAAAATGCACTTATTTTA

ATATGTTATTTACAGATAGTGCTATAGTATATAGCCGTCATTGTGCTATAATGGATTTGTTTTATTT

TTCTGTTTATGAAATTGACTATCCTCCAATATTTAATACATATATAGATATAACAATACAAGAATA

TACATATGATGATGTATCAGGTATGTCACTGAATAAACATGATTTAGTTACAAAAGAAAAGAAAT

ATGAAATAAATGATTCGATGTCTGAAATAAGAGACGATTATTTTGATCTTTGGTTATTTTTAAGAG

GAGAAAGACATGGAAAAAGAACTTTAATTAATTTATCAAATGATTATGTTGTTATTCCATCTTCAC

CTTTAGATGATGCGGATGTAATAGAAACTGATGTTATGAGAAATTGTGGTTTGAAAGAAGATAAT

CCAGCTTTAAAAGGATGTGATTATAAACATGAATGTAACATTATACATCCATGTTTAGTAAAAGCA

ATGATGTTACCAAAATATCTTTTTGATTTAAGTGGTAAAACATGTAATAAATTAGGTGTATCGTTA
```

-continued

```
AATAAATGGAGAAATTCTGATGGGAATTTTTGTGGTTCTTCAGCTGGGTATTGTTTATCTGAGAAT
TTGTTTAAATATTATTACATACATAAAACATCTGTTGGGAATAGAAAACCTTCGAAATATAAAATT
AAAAATATATATGGGTCTGAACCACAGACAAAAGTCTATACATCTGCAAAATTACCTAATTATTTA
AAAGATAAGGTAGATAGTAATAATAATAAATCTTATGATATTAATGATATAGATAATAAAATATT
TTATAATGAAAACGCTGCTGCACATAGTCATTTTATTGATTACAAATATAATGGAAATCATACTGT
TGAAATTAAATTCGAAACTAATGCATTAGAAGTACATGAAATCAGACCTGTGTCATATGGAACTA
TTACACATATTACTATACCAAAAGATTGTTCATCAAATCAAACAAATTCTAAAGAATGTATTCTTG
TTGTACATACGTGGAATAATAATAAAACTATAGGAGCTAACTTCTCTTGTCATGTTTTATGTGTTG
ATAAAAGTACTCAACAAGTAGCAACACATATTAGTCCCATTAGTAAAATAAATGCACATATTGAT
GCAAATAAAAATTATGCCTTTTATTTCATTATTAAATTTTTAATAAATAAAAAATAACAAGTAAT
TGTACAGCAATACTAAAAGATGCTGATGGTAGGGAATGTTCAAAACTTTCATTTAATTTAACATCT
AAAGAAACAATAAATGTAGTAGAATCAGGAATAGTAGCACAACCTGTAGAAAGTGAAGCTCAAA
TAAATAAATATGATCCTGATGTATCAGGAGCATCTACGCCTACAGCTGATAAATGTGATTGTTATT
TTAATTTATTATGTTATATACTTAATTTGAATACATGTGTTTCATATTATACTAAATTAATTAAAGA
TTACCTTGGAAGATTTGTAACGATAGCTATATTAATTTTTCTTGCACCATCCTTAATACCCCTGTTA
CCATTTATCATTAAATTTTTTATATCATGTGCATCTCTCCCAATGAAATTATTTTCCAACTTTTCTTC
TTGGATGGAAAATAAAAAAAAAAGTAATAATAGTACAAAGCAAATAAAAATTATTTTCAAGG
AAATATGAAAATTTCAAAAAAAAGAGAACAAATATGAAGAAAAATAAATGTACATCATCTTCCGT
CTCTTCTTTAACAAATGTTTCAAGTATTTCTTCAAATAATACAATGAACAGTGATATAAAAAAGGA
CGTATCATTTAATAGGATTAAATCAAATAGGTACAATAAGGAGAATCATAAAAACAAAAAGAGG
AAAACAAAAGGTAACCATAGTAAATATAGTGGTACCTCGATGGAGAGTACACTAACAAATACAA
GTCCCTCAAGTACACCTGATAATTTAAGTGAATCTCATATAACATCTAATTCAAACAAAAATAATT
ATTCATCAAAAAAAAAAAACAAGTGTAATATGCTATATAAAAAAGAACATTCCAGGAAAAGTATA
AGAAAAAAATCTATGGGGATATCTGAATATTCTTCTTAA
```

Plasmodium berghei (SEQ ID NO.: 16)

```
ATGATTATTATTATTTTTTTTGTATTATTTTAAAGTATTATAAATGGTGTGACTTTAAAAATAAAG
TATTTTTCATTCAATTAGTGTATTCTTTTGCGAAAAAAAGTGTCTGTACTTCATCATTGGATGATTC
AACATGTCACACAGTAACTTTTGGTGAATTGGATGTTTCTAATAATTCGGTAGTGAGATTAAAGGT
GATGAGAAAAGGAGGAAAAGGGTATTTCCTGACAATTCGAAGAGATTACGTAACTGTCTCATATT
ATTTGAAGTATGTAAAGGACATTCCTTTAGAATTTAGGGAAATTATAGATATATTTAATAACCATA
AATTTGAGCAATACACACAAGAGCAAATAAATAAATATACATATACATGTAATGTACGTAAAATT
GAAGATATAGATAAATATGATGAAAAAAATCCAACTAAATTTCATGAATATACACGAGGAGAAGC
ATGCAGATGCCAAACATATAATTATTTTAAAGATGATGAATTTATAAAAAGAGCGAAATTAAAAT
GTATTTATTATAATATGCTATTTACTGAATCAGCGACAGTATATAGACATTGTCCTATTATAGATTT
AATGCATTTTGCAGTTTATGATATAGAATATCCACCAATATTTAATACAATTGTTAATATTACAAT
AGAAGAGTATTATTACAATGATGTATCATCTGTTTTGAACAATAAATCTGATTTAGTTACAAAAGA
AAAAAAATATCAATTAAATGATACTATAACAGAAATAAGAGATGATTATTTTGATTTATGGTTATT
TTTAAAAGGTGAAACACATGGAAAAAGAACCCTTGTTAATTTATCAAATGATTATATTGTTATTCC
ATCATCACCTATTAATAACAGAGATGTTATAGCTAGTGATATAACAAGAAATTGTGGACTATCACA
AAATTCACCATTATTAAAAGGTTGCAATTATTCAAGTATATGTAATATTATGCATCCATGCTTACG
```

-continued

```
AAAAGCTATGATGTTACCAAAATATATGTTTGATTTAAGTGGTAAAACATGTGGAAAGTTAGGTGT
ATCTTTAAATACTTGGAGGAAGTCAGAAGGTAATTTTTGTGGGTCAGAAGCTGGATATTGCATATC
AAATAATCTCAAAAAATATTATGATATTCATAATTCTGCATCTATAAAGATGGTATTTCTCTTTCA
AAGTATAAAATAAAAAATATATATAATTCAGAACCACAAACTAAAATATATGAATCCTATAAGTT
GCCTGATTATTTAAAAGATAAAATTAAGAATAATAATCATGCGGAAATGGATGAAAATGATTTAG
ATAATAAAATTTTTTATAAACCAAATGTAGCTGCACATAGCCAATTCATTGATTATAAATACAATG
GAAATCATAGTGTAGAAATAAAATTCGAAACAGATGCTATAGAAGTATATGAAATAAGACCCGTT
TCCATTGCAACAATTACTCATGTTACTATACCAAATGATTGTGCATCTAATAATTCTAATTCAAATG
AATGTGTCCTTATTATTCATGTATGGAATAATAGCAAATTTGTAGGTTCAAATTTCTCTTGCTCAAT
TGCATGCACAAATAAAGAAACTGACCAATTGGCTAGTCACATTAACCCTATCGCTCCTGTGCGTGC
ATTTATTGGACCAAATAAAAACTATGCTTTTTATTTTATAATAAAATTCTTAATAAATAAAGAAAT
TACAACATTGTGCAAAGCTATTGTAAAAGATTCTAATGGGAAAGAATGCTCTATAGAAGAATTCG
AATTACAATCAAAAGAAAGTGTACATATAGTTGAGTCAGAAGTAGATGAAACAACGGACCAAGT
AGTAGTAGAACATCATACACAATCACCTGATATTAAAAACCCTGATGAATATGTATGTAAATGTA
CTATTAATTTATTATGTTATGTAATTAATTTCAAAACATGCTCTAACTATTATATAAATACAGTTAA
AACGTTAATTGGGAAATTTGCTATTATAGCCATATTAATTATATTAGCACCTGCCTTAATACCTCTT
CTACCATTCTTTTTAAATTTCTTTTTCCTTTTTATATCTACTATACTTAAATTATATCAATCTATTAT
AAGCACAATAGGACAAATCAGAATACGAAATAATGATAAGCCTATTATTTATAAAAAAAAAATTC
ATGACATGAAAACCAACTACCTATCTGTTTCTTCATATTCGTCATTATCTGATTCAAGCAGTATATA
CTCCACTGATTCAGTATCTTCGATGAGAAAAAATAAAAAAAAATTCAATAAAAATAATATATCAA
GCAATATAAAACATAAAAAAGGGGGAAAAAGGTTAAACAAAAAGAGCCAAATAGAAATTCAAA
TCACACTTCCCATGAATATGCAGATACATCTCCGTCAGGTAAAAGTAAAATACCCCCATTGCGATA
A
```

Chlamydomonas reinhardtii
(SEQ ID NO.: 17)

```
ATGTGTCGTGCCATCGCGGTTGCGCTGATAGTTTACCTAGCCCAGCATTATATTCTTGCGCACGCT
GAGGTCATTGCAAGTGGGCGCTTGGAAAAATGCGTCGTCGATGGTGTTACCGAGGAGCTGGACTG
CCAGGAGAAGGTGGTGGTGACACTGACGGTCGGAAATGGGCAGAGCCTGCAGGCCGAGGCTCTG
GAATTCTCGCTCAGCTGCCTCAACAGCCCCGACGGACGCTGCCCCTGCAGCTGCAGCGCCGCCGA
CCCTACTTGCGCATGTCGTGACCTGGCGGCGCCGCTGCGCGTGTCGCTTACCAAGTCGCCGCTGTG
GGCCTCCTACCCGCTGCAGTACTTGTCGTCCTTTAACTGGAAACCCCTGGAAGTCATCCTGCGCCC
CAGCAACAAAGTTTGCAAGGACGGCGACTGGGAGGACTCGCCCACGTGTGGCTGGTTCAGCCAGG
GCGGTGTGCGGGTGGCGGACAGCCAGGGATTCTGCTGCGAGTGCAGCAGCAGCCAGGTGTGGGAC
GACACCTTCGGGTCCAGCAAGGAGCGCACTCGCGCCAACCTGGACTGTGACTTCTGGAGCGACCC
ACTGGACATACTGATTGGCCGCAAGCCGGTGTCCGCACACTGCCTCACATTCGACCCGCAGTGGT
ACAGCGGCTATGAGCTGGGCGCCGCCTCGCTGCAGTTCGAGATCGCCATCACCGTGGAGGTACCC
ACCGCCCCCTCCCCCACCACAGCCACCACCTCCGCCACTCCCCGCACCAACAACAGCAGTAGCGC
CAACAGCACCAACAGCACCAACAGCCCGGCGCCGCAGTTTCTGTCCCCGCCTGCGCCCAGCACGC
GGGAAGTGTTGCATCTGGGTCCCTCGGTGCCTCTGGCCAGCAGCGCGAGCCGCCTGCTGTCCGCCA
AGCTGCTGGGCGACCTGGCCATGTACACACAGCTGCCCGCAATCAGCAACCAGGTGCTGATGGTG
CCGCAGCCGCCAGCCGCCGCCGCCGCCACCGGCTCGCCCCTGGACGCCACCCTGGCGACCAACCG
CTCCGCCTGGATGCTGCTGGACAAGACCATGCTCAGCATGGACGGCCTGGCCTGCGACAAGGTGG
```

-continued

GGACCGGCTTCTCAGCCTTCCGCTACCAGCCCAGCGGCTGCGGCCGTGCCCCTCAGGCCTGTCTGT

CCGGCCAGCTCAAGGACCTGTGGGAGGCGGACCTGGCGCGTATCGCGGACGGCCGGGTGCCGCTG

TACATGATCACCAGGTTCACTGGCGGCAGCGACACCACGCTGCAGTCCTTCTCCGGGGGCCCGCT

GTCGTTCGCGCTGCCTGTCACCAGCCACAGCCAGAGCCTGGTGACGCTGAGTGTGGCGGCGGACG

GCGTGAGGCTGGTCACCAACCGCAGCCCGGGCAAGATTACAGGCGCGGCGGTGTGCCGTTTCGCC

GGCACTTCCTGTGGCGGCTTTGAGGCGGTGGCAGCTCGCGGCTACATCTACGTCAACATCACCAAC

ACCGGCCGCCTGGACAGTGACTACACACTCACAGTGTCCAACTGCTCGTCCAACGTGCGGCCCAT

CGAGGCGCGCACACTGGCCGTACGCGCGGGATCCGCCGCCAGCCTGGATCCGCCCATGGAGCTGT

ACGTGGAGGACCAGGCGGCAGCGGCGGCGCGCACGTGCACAGTCAGCCTGTACGACTCAGTCGG

CGCGGTGACGGACTCGCTCACGCTGTCCTTCTACACAAACGCCACCCAGCTGGTCGTCAAGCCCTC

CGGCGGGTACAACGGCACGGGGACGGCGCGGGCGTAAAGCGCAACGGCACCGATTGCAGCACG

GCCTGCACCAACCCGATTGACGTGCTGTGCTTCGTGACCAAGAAGTGCTGGTCCAAGTTCGGGCG

GCTTCTGGGCATCATCGGCGGCGCCCTGGTGGGGCTGGGCTGCTGGCAGTAGCACTCAAGTTCG

GGTGGCTGGCCTCCCTGGCGGCCTCGTGTTGTGGGGGAGGAGGAGGAGCAGCAGCAGGCGGGGCT

GGAGGCGGCATGGGGCTGGGGACCGGCGGCGGCGGAGGCTGTTTTGGAGGCGGGCAGCAGCAGC

AGCAGCAGCCGCCTGCTGCTAGCCATGCCATGTCGCCACCGCAGCAGCAGCAGCAGCGCTCGCAT

GCGGAGGTGGCAGCAGGGGCTGCAGTGGCAGGAGCAGGAGCCGCTGTTGCAGCAGCGGCGGTGC

TGGGAGCCAAACACGGCGGCGGCGGCGGCGCTCGTGGCAAGCAGCAGCATACCGACACCCGGCA

TTTGCAGGATCGCGACTCACGAGCCACCGCCGACGGAGCAAGCATTGACAGCAGCAGCGCCGGCG

GCAGTAGCAGTTTAAGCAGCTACACCCAGCCTCGTAAGGCCGGAGGCAGGCTGCTGCAGCCGCCG

GCAGCAGCAGTGTTTGTGCCTGAAGGCGGC

Trypanosome cruzi (SEQ ID NO.: 18)

ATGAGCCTGTCTTTGTCTCGTATGCTTTTTTCTTTATTGCTGTTTGCCCTGATGGTTGCAACAACTCC

TTTTGCCGCGGAGGGTTTACTGCTGGCGTCGTCTTCCATTGAACAGTGCGATCGTGTGGGAACCGA

CAACTCGCTGCCGTGTGAGAAAAAGTTGGTGGTGACGTTGTCGGTGGACAGTGATCAGGCGGAAG

ATGTGGAGGAGTTTGTGATTTTGCGCGATGCCGTGGACAAAACGAAAGGAACGGGGGAGGAGCA

CGTGGAATTTCAACCTATCCGTTTGACGACGAGCAAATCACGCGTGCAATACAGTTACCCTCTCTT

TTATGAAAGGAATTTCAATGCCAAGCCCTACGAGGAGGAAATTACAACGGAACTAGTTGGGTGCG

ATGATACATTTAGTCCGAAAGCAACATGCGGGCTGGCCATGGACACCGCGGGAAGGCCTATCCCG

TACAGTCAAGGTTTTTGTTGTCGATGTGGTCCCTGTCAGTTGTTGGGGTTATGTCCCGTGGGTAGCC

GCGGTCTTCAGGTATGCGACATATTCAGAGGGGCTGCATTAGCCTCATGTCTCCGTTTTGGAGAGC

TTTGGTACAGTGGGTACAGCATGGGTTCGGCTACTATCTGGTATCGCTTGTCGGTAAAACTGACGA

CTGACTCCCAAAATAACTCCAAGACAAAAGAAGCAGTTTTTGAGCTGGGACCGGATGTGCTTTCA

GGGTCTTCAGCGGAGTTTGGGGCTTGGGTCAGTCTAATTGGGGACTTTGTGCCGGCGGAATTACCA

TTGGTTCTAAGTAATAAAATGCTTTTTATTCCCTCTTCTCCAAGAATACACGAGCGTGTTTTGGCGG

GCCAAAAGGAGTGGTTAATTCTGGACAAGCACCATGTGAGCATGCAGGGTCGAGATTGTAACAAG

GTTGGGGTATCTTATGAAGCCTTTTCGGGTCAGGGGAGCAGGTGCCAATTAATTCGAGGGTCGTGT

CTGGCCGATCAGTTGGAGGACTACCGTTCGAGTGATTTGGCAGTTGAAGCCCGAGGGGGTAGAGG

CAAATACCTGGCTCGCTTTTTTGGAGACTTTGTTGTCAACAACGTCAACAACAGCAGAACAAGACT

CTCCTACTGGATGCGTGGGTCATTGGCGACGATGTTAACTGTTGTCATATCAGCGGACAGACTGCA

```
ATATCTGGTTTCTGTTTCCCCAGGTGAAATTGTCTCTGCGGTGATGTCGAAGTCGACAGTAGAGGA

AAGTTCGAGAGATGGATCCGTTTCTGTCATAGTGCGCAATATTGGCCACGTAACTGCGCAATACAC

GCTTGGTGTGGGGAACTGTTCGGGAAATGTTTTCCCCATTATGGCCCAGACCCTGAGTTTGAGACC

ACGAGGGACAGTGATACGCAGTTTTGATCTGAATATCCAAGATGTGGCGGAAGAGAGAATTGTGC

AATGCGACGTAACTTTACGAGACGCGAAAGGTGCTATCACGGACAAGAAGATTTTGAAGTTTCGA

GTAACAAGTAAAGTATTAACGAATGATACACAGGGCGGCAATGCACCAACTGGAGGTGGTGCCA

GCGTGGATGGTCAAGCCCCTCCAGCTTGCTCGCGTTGTGAGTGGTACAAGATTTCCTGTTTCCTGA

TTCATGGCTGTTGGTGGCAGCCACTGGTGTATGTTTTGATTGCCATTGCTATACTGCTGGGTATATA

TTATTTTTTCGGACTCTCTTCGCGCAGTAGTGAACCCAAATTACACGTGGTTCACTGA
```

Trypanosome brucei (SEQ ID NO.: 19)
```
ATGCCGACGGAGACGTTATCATCTGTTTTTGTGCTCGTCGTCCTTGTGACGACAAGCGGCCTTTTCC

CCTGCACTGAGGCGGCATTTGTGGCCTCGTCGTCCATCGAGTACTGCGAGCGCAGTAGTAATGGG

GAACCGTTTCCATGTGAAAAGAAGATGGTTGTGGGGCTCTCCGTGGGCAGCGAGCAAACAATTGA

GGCTGAAGAGGTTGTTCTTCTCCGCGAGGCAGTTGACAAAACGGGTGACGAAAAGGGAAAGCGTG

TCGAGTTTGAACCAATCCGCCTAGTGACGACAAAATCACCGGTGCAGTACCGCTATCCTATTTATT

ACATAAGAAACTTCAATGCCAAACCATATGAGCAGCGTCTCAGAACAAGTGCAAGCAGTTGGTGC

GACGATTCTTCCAACCCTGGATCCGCGACATGCGGCGTGGCGCGTGATCGGAGAGGAGATGTGAT

TCCGTACAGTCAAGGTTTTTGCTGCTTATGTGGCGCTTGTGCATTGTCAGGAATTTGCAACCCAACT

AGCCGCAGCGTTGGAACTTGCAGCGTGACGGGGGATACTGGAATGGCATCATGCCTTCGTTTCAG

TGACCTCTGGTACGGTGGCTATACCATTGGTCGAGGTGTTGTATGGTATGAATTGCAGGTGAAATT

GTCAAGTGGGAACAACAGCACTGGGGGAGGCTCCACGGGCTCAAAGGAGTTCACGATGTCTTTGG

GGCCGGATAAGTTGACCGCCACGTCGACAGAGTTCGGCGCGTCTGCACGTCTTATAGGAGACTTC

GCACCCCCAGAAATGCCTCTTGACCTATCGGGAAAGATGTTGTTTATCCCCTCTGAACCGCGGGGT

CATGAGCGAGTGGGTGCTGGGTATAACGAATGGATTATTGTTGACACCCACCTTGTTTCTATTCGT

GGCACCGAATGTAATAAAGTGGGCGTGTCATATGAGGGTTTCGCCACTCAGGGGAGCCGGTGTGA

CGCGTATCCGGGCGCTTGCTTGGCGAATCAACTGGAGGATTATCGTGATCGGGACTTGGAAGCGG

AGACTAAGGGGCAACAAGGGAAATATATGGCTCGCTTTTTCGCTCCTTTTGGTTTTGACCCACTGG

CCAATGCCAGTGCCCCAGCTGTGGCTTACCAGGTGACAGGAACATTATCAACGATGGTGACGATA

ACAATATCCGCTGATAAGTTAAACTTTGTGTTGTCTGTGTCCTCGGGTGTGATTGTTGGTGCAACC

GTTTCAGGGAAGGTGGTGCATTCCTATTCGCGGGGAAGCACCATTACCGTGACGGTTCTTAACACT

GGGGACATCGAGGCACAGTACACGGTTGTTGTCGGCGAGTGTACGGTTAATGTTCAGCCGATGGT

TGCCCAAACTGTGTACATACCCCTACAAGGATCAGCGCAGCGACGTTTCACTCTGATCGTACAGG

ACAGTATTGAGGGAGAGGCCAAATGCAATGCAACGCTGAGAAACGCCAGGGGCGACGTTGTGGA

CACCCGCGCTATTTCGTTCGGTGTTAAAGCGCTCAAACCAAGCAATGGCTCTCAAGGTGGCAGCA

CCTTTGAAAATGGACGGTACAGTGAGGAGGCAAAGGGGGAGTCGCAGTGCCAACAGTGCAGTTG

GTTCAATCTTTTGTGTTTTCTGAGGCATCGATGCTGGTGGCAACCGCTGGTGTACGTCCTTCCTTCA

GTGACCCTGTTAATGCTGCTGCGCAGGTTCCTTGAGAGTCAGTCAAGGTCCCGCCCAAGACCCCAA

TTACACCCTGATGAGCATGAACTGAGAAATACCGGTGCCATCTCTTCGTGCCATCTTCCCCGCGCA

CCGTACGTTAACACAGTGCACTGA
```

-continued

Cryptosporidium hominis
(SEQ ID NO.: 20)
ATGTGGTGGAATGTTTACTTATCGAAGTCATGCCCAGTTTGGATACCACCATGGTGGACAGCTTTT

AGAATAGGTGGATGGAATTGGCAATACTCATTAGAGGTTGAATTATCTTGGTTTAGTCCAACAGA

ATCATCAATTAATAAGTTATCAAGTACAGAATTGGAAAATATGGAAAATGAATGTAAGAAAGAAA

ATAAAGATTCCACAATAGATTGTTCAAGAATAAGGCATAAAGAATCAGGAATTCAGACTTCTGTA

CATACATTAAATTCATCGTCTCCATCATTCTATGATCCAAATTTTGGAGCTTCAGTACAGGTAATA

AGTTCAGGACCGCCGTTTGGGAGTGCTAATGCAAAGGATTTGAATGGTTATTACATGTTACAACCA

ACATTTTCACCAAAAGGGATGCCTGCTAGTATTGCAATTCCTCCTTTAAGAAGTGGGTGTGGAAAA

GCTTCAAAAAACCAAACAGAAGAGGAAATGAATGATTGTTTAAAGCCAACATTAATTATTCCTCC

AGAAAATGCAGACTTTACAGGAGTTTCATGTGATAAGATAGGAACAAGTGTTCATACTTGGAGTT

CTGTGAATGGTAGATTTTGCTATCATCCACCTGGGACTTGTCAAAGAGCTCAGATAGCTCACTTTT

ATAAGAAAGTTATAGAAGATCATTCACTTGGAAAGATTTCACAATATTCAGTGAGAGCACAAAAT

TCTGGTTCTCCACAGTTGATTTTGGATTCATTGGGAGAAATTGGTCATGAAGAGGTGGATCAAAAT

GATATGGAAAATATAACTAATATACAATCACGTAGATTCTTTTTGGGATATAATTTTGATTCAATC

TTTGACACAGAAATAATGTTCTCAGTCGAAGCTTCTTCTGTGTCTTGGGTAGCAACATCTTCTCCTG

GAATTATTACATATATAGAACCACCACCTTTGGAGGCTTGCACAGCAATGAGTAGTTTTGGCTGTC

CTCTAAAGGTTTATATTAAGAATAGTGGTAAGTTTGAATATATATATACATTTCGAATTGAATTAA

AAATAACTTATCAAAAATATTCTATAGGGGATATTGATTCAGGTTTTGTAGTTCAAATACCTTATT

GTACAAAGTCAGGAGTACAAACAAGTGAGGTAGGTTTATATTTAACTCATTCAAATTTATATAATT

AA

Toxoplasma gondii
(SEQ ID NO.: 21)
ATGGATCCACCACTGCCGCGATGGAGAGCCGTGGCTGTGGCAGCTTTTCTCATCGCCACCATCTGT

CACAATGGCGTGGACGCCGACATTCCTCAGGCCGTGTCACGGCAACAGATCTGCACAGTCAATGG

CGCATATGGAAAGGATGATCCTAGACGAATGCAGTGCAAAGATACGATTCTAGGGACTCTGAGAA

TATCTAATAAAGAGAAATTTTCGTTTAATGTCATGCAAAACACCATCGATTCCCGGGACAAGACAT

ACGCTGACGTGGGAAATGTCGGATTCGTCGTGACCATTACGAAGACTCCCGTAACAATATCGCTG

CCTCTAGAGTACATCAAGGAGGTACCGTTCGATTATCGGGAAGAGATATACGAATATTCCCGGTG

GGAGGCTGGGCGACTGCCGGAGAAGTTTTGTTACGAAGACACGACAGACAAATGCTCTGAAGATG

GGAAGCTGGCGGTCCACCCTCACGGCAAGCCCTGTCATGGGCCCACGGCCGCTGCTGCTGGTGT

AGTGAAGTGCTGGCTTTCACGCATATCAACAACATGAAGAGGGGCAACTTCCGTTGCAATTGGTTT

GCCCCGCCCCGCGCCTTGGAACTGGTGACTGAAACCCTCTACGACCAGTGTGAAGCCGGGAAAAT

AGACGGCACCGTTCCATTGGACCGAGATTGCGAAAGAGAGAAGCACGAGCGCTTGGGCATCACC

GACAGAGTTTACACACTGAACTACACTACACCAGAAATCTTCGACCGTTCTGTCTATTGCAATACA

AAGTCTTGCTTGAAACACGCCATCATCTTGGACAAGGACTATGTTTCTGTCACGGGTTATGAATGC

GACAAAGTTGGCACCGGCCTCGATCGATGGGAGACATGAGAGGAGAGTTTTGCAATCTGTTACC

AGGGACTTGTATCACTGGCCAGCTTCGGAAATTCAAGGAAGTCGACAAGCTACGGATCGAACAAA

ATCTGGCACCATTATATGCACTGAAACGGGAGTTCGGGGGCTTCCCTCGATATGCGCCAAACCCG

ATGAATGGAACGGGTTTTTCAACAACAGGCACAAGACACTACCTCGGCTACGATTTTGGCGAGCA

GCACTACTCAGACATCCGTTTCGAGATGGATGCAACCGATGTCACATGGTTGAGGGCAACATCAC

CCGGTCACATAACCTTCATTGAGGTGCCTCAGCTAGACGCATGCTCGTCCAGTACCATTGGCGGGT

-continued

```
GTCCACTGAAAGCCTACGTCTGGAATTCAGGCAACGAAGATGCTGCATTTGCAGTAGAGGTACCC
TTTTGTATCGATTCGATTACAAAGGAGCGAACAATCGATGTAAATCCCATTACGCCAGTTCGGACG
ACAGTGCCTGCTGACAAAACGGTTGTTTTCACGTTAACCTTTAAAGCCATTTCTTCTAGTAGTCTTG
GCGTTACATGTTTCATGAAGCTGTACGATGCCCAGCATCTCATGCTCGACCAAAAGACATTCAATG
TGACGACGTCGGCTGCTCAGGCACACGACACACAGCACTCACACAAAATAACGAAGATGCCTCAG
AGAAAACTACTCGGGGGGGCTTTTACGAAAGCAGCCGTCGGTGCCACAGCAGCAATGGGTTTCTT
TGGTCGGAGAACGGGGAAGAAGAAGAAAGGAGACACAAATGTTGAGGCGCATTCTGTAACGCCA
CAATCGTTTGCCGAAGACGCAAGAGGTCCTGGGATCCAAGATAAACTTCAGGGAAAGGCTGACCC
GGCAGAAACGTCTCTGTTCGGGGAATCGGCCACGAGTCACGCAGCGAAGTTGAGCAAGAAGGAA
AAACGCAGTTTACGCAAACAAGCAAAGAAACAAAAAAGGCAAGAATATCAGCGGCAGGCAGCGG
CAGGGAACGCAGAAATTTGGGCAGGAGAAGGAGAAGCCACTGCGTCTAAAAAAGACATGGTTTC
CAAGAAGAATGGGGTCGAGGGGTCGCGGTCCTCGACTATGGGTATCGCCGACAACAACCAATCTG
CTTCAGCAGTCACGAAGTCAAAACCGCATATCATGAAGGAACAACGGGAGACAGGGGCCAAACG
AAGGCAAGGGGAGTGTGCAAGAACAAAGGAGGAAGATAAACGCGGGCACGTAGAAGGGAAACT
GAAGGAGAAACACTCTACCCAGAGCCAACCGGATCATCCTCTCTCTGCAGGAAACAAGGGCACGA
GCACAACTCAACAGATCAGGAGTCAGATTGAACATAAATCCTCCATTTTCATGGGAAACGACAAT
CAGACACCTCTCGAAGTAGAGCTAGAAGGACAACTGCGGAAACATCTAGGTCAAGATGACTCTGA
TTCGCACCCGTCAAAGGCCGGAAAAGACAAGGTGCTTGAGCACGGGCAAACACCCGTCGAGAGG
GAAAAAGAAGGCAACGAAGAGGATAGCGCAGATAGGGGAAAGAACGATCAAACGTTGGGATC
ACTGGTGCAGCAGGGAAGATGAGGAAGTTCCTGCACAGAAAAAGGGATGAAATCGAATACCAAG
AAGGCCGTGAAGAGGCGGGATTAGACGCAGTGTCCATCAGTAGAGGAAGTACACAATGCACCCG
TGCACGGAAGGCGAAGAGAAAGAAGCAGCATTTGAAGGAACCGCGAACACCGCAAGAAGAAAA
CCCAGAAGATGACATCGAAGAACAGGACAGAGATGAAGAAGGCGAATCCGATACACTAAGGGAT
ACGACTGACCAAGGAGGCGCATCACCGCAGACAGCACGACCAGAGCTCACCACAGTAGTGGCAC
ATGAACCCGAAACACGGGGGGAAAAATACATTGAAGGGAGTTTCTCGACTCTACCCTCTGTGGAA
ATCGAGGAACACAAAGAGATTCAGATGGTCGAAACAAATCCTAGTTACTGTGTTTCAATGAGGTA
G
```

*Theileria parva*

(SEQ ID NO.: 22)
```
ATGAGCTCTTTAGGCCCTTTTAGAAGTGTGTTCACTTCCCTTATATACTTCTCAATCCTACACATTC
TCGGCTTTACATCACTATTCAATTTTTACACCACTGATAGCACTGGTTTCTTCTTTGTTGACTCAGC
AGTGACCGGAAACATAACCCAATGTGTTAGAAATAGCGATAAACTCTTCGATGATCAAACTTGTG
TACAAAGATTGCACACCAACGTCGATGTCTCACATGGACTCAGGGAGTACCATTACATATATAGA
AGAAAAGATGATTTATCTAAGGGATTATACTTGGTGTTAAAGACCTCAAACACTTCTCTACTCTAC
ACTCTCAATTATCAAACTATGGTCCCGTTGTATTATACGGATCATACGGAGAGGTGGACGTATAGT
GAGATTTCAGGTGAGTTGAAGACCTCGTGTAAGAGTGTGCAAAATTCTAAATGCACTAAAAAAAC
TCAAGTTCCACCAGGTATTGATTTCTTACCCAGAGTCTGCTGTATCTGCGGACTGAACGTACATAA
ACCAACGCCAAGAGCTGATTTTAAATGCGGAGGATTTCTGGCTATGGGAGGTAGGACAGCGTTGA
GTATGAGTTGTTTGGAGATAAGTGAGCCCTGGTATAAGCTTTACAAGACCAGTTACCCACCAGCCA
TAAGCAGAAGTGTTACTGTTAACATTTACAAATTCGATTCATCCACTGGAATTATCCCAGACGTGA
CATTGGAGGATGAGGATAAATTTGATAATTATGACTTTAAGAAGCGGGAGAAGAAGGACCCGGTG
ATCAAGTCACCGGAGATCAAATCACGCTCCACTAAAGAAATAACGGGAAAAAAGATGAATTAC
```

-continued

```
ACCCCAATTTCAGACGCATCATCATCGATGATACCGTCAAAGAAGAACATATCAATGATTTGGAT
GTGAAGATAACGCTGTTGTCGAGTAATACGAAGGATGGCTCTGCGCCCCCGTTATTTGATAAATAC
GTAGCCATACCATCATTCCCAAGAACCAATGAAACCGTCAAAGGCTCATCACTCATGGACAAATG
TCAAGACAGCACCTGGAAAACCAAACCCGAATGTCCCAAATATATGAATCCATCGTTGTGTGATA
TATGGCGTTGTACGTTGAATATGAGGACTGTGAAGATGAGTGCGGTGGATACGGATGGGTTGATG
TGTGATAAAATCGGCTTATCAATGAAGAGGTGGGCAAACCAAGAGGAAATTTGTAACTCAAGCCC
CGGCTCATGCCTCAAAAATCAGCTGAAACACTACTTCGATCAGGAAAAAGATGAGGCCAAATTAC
CAAAATTGTACGGAGTAGAGCCAACGTTTACAGCGGTTAAAAAAGATCTGTCATTACCAGCAGTA
AAGGAAGCAAATAAAACAACTCTGGATGATCCAAACAGAATTCACACTCTCACTTATATCCACTC
TAAGGACGATGTTACCAGACTTAAAATCGATACCTTCGACGCCACAGTCACCGAAATCATCTCCG
ATTTCCCCGGGTTCATCGTCTCCGCAAAGATGGACGGAGAGTGTGAGGTATCTTCGGAGAAAGGC
TGTAACATGGAATTGGACGTTAAAAACATGGGTAAATTTACACACAAAAATAGTATTTTAGGGGT
TAAGAAGTCGGAATTTACCGTTAGAGCGAATTGTTATGATGATCCTGACCTTAAAAATGAAGTTGC
TCAGATTTCTGAAACTACACTCAGTATCGACGGGAATAAAAATAAAACCGTCTCTATACCAATCA
AACTCACAGGATCACTCGCTAGTGAAAAAGGATACTGCAACATCATTCTCCTTTCCGGAAAGAAG
GAGATGTTGGATGGTATGAAGATGGAGATAAAGGTGAAGGTGAAGAAGGAGACGTTTGGTAAGG
ATCCGGTTAAGGTCCAGGATATAGTGGCTGCTCCTAGTCCTAAGGATAAATTAACCACTCCTCAAG
TGATTAACCCGATTGTCATTAACCAACCCGGGTCTAAAAATGACACTAAAAAAGAGGAAGAGTCA
CAATGCAAATGCGCGTCCTGGAATATCTTCTGCATGCTCATCAACTTTAAGATATGTGTTTCGTCTT
ATGTGAGTAAGGTATTATTTTACGTGTTGATTGCACTTGGAATTTTATTGCTTTTGATTTTGTTGCC
GGTGTTGATTCCGTTAATTGTTAGTCTCTTTAAGGCTCTCGCTGGACTCATCAAAACACCACTCGA
AGCCCTCGAACAAAGAAGATTAAAGAAAAAAAACAATACACAACTTGAAGTTTAA
```

Eimeria tenella (SEQ ID NO.: 23)

```
GCAGCTGCTGCTGCTGCGGCTGCAGCCTCCCGCAGTGTCTCGACACATCAGTAGCAACGTGCTGCC
GCAAATGAATTTTTATTTGTGGCTTCTAGGGGTAGGCTTGTATACCCCTTCACTGCAGCAGCAGAT
GATGATACCGTCTCGGAACAGGGTTTTCATTTTGACGCTACATGGTTTGCGCGGTCTCGAGCAAAG
AATGTCAATTCCGATTGTGGCACTTCAAGCTACGGTAATGCTTTACGTGACGAAGTGCTTTTCCAG
TTCTTTCTCCCGATGAGCTTTTTAATTTCAGGCTCACCATTTTGTAACCCTAAGAGCTGTCTGAGGC
ATATGATCGTCCTAGACGAACAACACGTCACAGTGGATGGCAGCACGTGTGATCTCCCGGGAGTT
TCACTGCAGCAATGGGAAGAGACGGCTTTTGTGATTACGCACAAGGAACGTGCTTTGCGAAAAA
CTTGAAGTGGTTTCATGAATACAACGAACAGGCCGCA
```

Leishmania major (SEQ ID NO.: 24)

```
ATGGGGGGCACCGCCACGGCAACGGCCTACGTGCGGTCCTGCGACGGAGCCTCGCCACCCACGCC
GCCTGGGTGCGGGCTCAAGCTGGTGGTGGACCTCACCCTCGACGACAGCATTCTCACCGGCTCCGT
CTTGGAGACAGAGGTGATGGTGACGCACGCGTTGCATGAGTCACTCTTTCCCCGTGACGCGGCGTC
CGATGCCGCTGGCACAGCTGCCACCTCTCTGCAGGTGTCTCTGCCTCCCATCACGGTGGCAATGCG
GCGTGGCGCTGTGCAGATGCGCTACGGGCTCACCTACCTACGCACGTTCCCGGCGGCATTGCGAG
ACTCTGTGCGGGTACTGAAGACGGCCATGTCGTGCGACGACGGCGTCACGCGCTGTCCTTCCTACA
TGAGCATGACAGGGACGCTTGTGTCGGCGCCGCTCGGATTGTGCTGCCTCTGCACCAGCGTGGAGT
GCGCCCTCACAAGCGACCTGTGCAACGCTTCGATGCGCGCGCACTTTTGCTTCCGCACCGGTGCAG
```

-continued

```
CCGGAATCACGTGCGTACAGAGCGAGGGCATCACCTACCACGGATGGGCCGTGGGATCGTCGTCG

CCCTACTACATGATGCACCTATCCGCGAGCGGGCGAGGGATCGCACCGACGACACTGCAGCTCAC

GACGGACGCCCCTGAGGTGCAGAAGGGTGCGTCTGCTCTGCAGATTCTTCGGGCCTCTGGTGTTTT

GCCCGGAGAGTCAAACCCCACGGTTGATATTTCCGGGCGCGTTCTCTTTGTCCCCTCTGCAGAACA

CAGCAGTGCCAGCCGCAGCATCAGCACCGGGCCTGTGCGCGACGACGACCCGGCAGAGTGGCTGT

TGCTCCCGGCGCCGCTTGTCAGCGTCTCCGGCAATGATTGCGACAAGGTCGGCATCTCACCAGACT

ATTTCTACTCGCTCTCCAGCACTAAGCAGTGCAACGCGCAGAAGGGGACGTGCGTGCGACACCAG

CTAGCAGACTACCGTGCGGCGGACCTGGAACAGATCGCCCAGGGCGTCGGCGGACGCTATATCGC

CGCCTCTCTGGGCACCTTCACGCGGCAGGCGATGAGGGAACAGGAGTTCCTGCTCGATGCGGTGG

AGCGCACGGGTGGGGCGATGCTGCGGTGGACGGTGAATGCGACGGCCTCGTGTTCCAGCCGCTT

CCGGTACACGGTGTACTGGATGCTATCAAGTTTGACAGCAGCACAGGCATCCTCTACGTCACGGTT

CGCAACAACAACACATATGGTGGCCTCTACTACGTTGCCGTTGGTCAGTGTCGGGGAGCACGCGC

ATCGAACTGCGATAGCGACGGCGTGACACACGAGTGTGGTCGCACGGCTTTGGTGGCCGGGGCTA

ACACCTCCTCGCTGTTGCAGTTCAGCATGGTGAGCGACCTGCCCGAGGAGGTGGGGAGCACCGCC

TCATGCACCGTCGTCTTTCGCGACGCGGCCGCAGCGCTGCTGGCCTCTGCAAACATTTCCTGGACG

GTCGAGCACACGACCACTACGCCGGCGCCGAATGCCCCCAAAGCGGAGCAGTGCAGACGCTGCG

CCTTTCGCGACCTGCGGTGTCTTTTCAGCACCGTCTGCGAGTGGCAGATGCTCCTGTGGACAGCGG

TGGCGGTGGCGGTGACGTGGACGCCGTATGCCATCTTGGCCTACTGGCGTATGGCGTGGCACGTTG

GCGCCAAGCTCTTGGCGTGTCTGAACTGA
```

CrFusM recombinant protein sequence (confirmed by mass spectrometry).
                                                              (SEQ ID NO.: 25)

```
MRGSHHHHHHGSACELHAEVIASGRLEKCVVDGVTEELDCQEKVVVTLTVGNGQSLQTEALEFSLSC

LNSPDGRCPCSCSAADPTCACRDLAAPLRVSLTKSPLWASYPLQYLSSFNWKPLEVILRPSNKVCKDG

DWEDSPTCGWFSQGGVRVADSQGFCCECSSSQVWDDTFGSSKERTRANLCDCFWSDPLDILIGRKPVS

AHCLTFDPQWYSGYELGAASLQFEIAITVEVPTAPSPTTATTSATPRTNNSSSANSTNSTNSPAPQFLSPP

APSTREVLHLGPSVPLASSASRLLSAKLLGDLAMYTQLPAISNQVLMVPQPPAAAAATGSPLDATLAT

NRSAWMLLDKTMLSMDGLACDKVGTGFSAFRYQPSGCGRAPQACLSGQLKDLWEADLARIADGRVP

LYMITRFTGGSDTTLQSFSGGPLSFALPVTSHSQSLVTLSVAADGVRLVTNRSPGKITGAAVCRFAGTS

CGGFEAVAARGYIYVNITNTGRLDSDYTLTVSNCSSNVRPIEARTLAVRAGSAASLDPPMELYVEDQA

AAAARTCTVSLYDSVGAVTDSLTLSFYTNATQLVVKPSGGYNGTGDGAGVKRNGTDCSTACTNPIDV

LCFVTKKCWSKFGRLLGIIGGALVGLGLLAVALKFGWLASLAASCCGGGGGAAAGGAGGGMGLGTG

GGGGCFGGGQQQQQ
```

DNA constructs sequence for expressing recombinant protein. FusM cDNA of Chlamydomonas was cloned into pQE30 vector (Qiagen) to generate pYJ61. PYJ61 DNA construct sequence.
                                                              (SEQ ID NO.: 26)

```
CTCGAGAAATCATAAAAAATTTATTTGCTTTGTGAGCGGATAACAATTATAATAGATTCAATTGTG

AGCGGATAACAATTTCACACAGAATTCATTAAAGAGGAGAAATTAACTATGAGAGGATCGCATCA

CCATCACCATCACGGATCCGCATGCGAGCTCCACGCTGAGGTCATTGCAAGTGGGCGCTTGGAAA

AATGCGTCGTCGATGGTGTTACCGAGGAGCTGGACTGCCAGGAGAAGGTGGTGGTGACACTGACG

GTCGGAAATGGGCAGAGCCTGCAGaCCGAGGCTCTGGAATTCTCGCTCAGCTGCCTCAACAGCCCC

GACGGACGCTGCCCCTGCAGCTGCAGCGCCGCCGACCCTACTTGCGCATGTCGTGACCTGGCGGC

GCCGCTGCGCGTGTCGCTTACCAAGTCGCCGCTGTGGGCCTCCTACCCGCTGCAGTACTTGTCGTC

CTTTAACTGGAAACCCCTGGAAGTCATCCTGCGCCCCAGCAACAAAGTTTGCAAGGACGGCGACT
```

-continued

```
GGGAGGACTCGCCCACGTGTGGCTGGTTCAGCCAGGGCGGTGTGCGGGTGGCGGACAGCCAGGG
ATTCTGCTGCGAGTGCAGCAGCAGCCAGGTGTGGGACGACACCTTCGGGTCCAGCAAGGAGCGCA
CTCGCGCCAACCTGGACTGTGACTTCTGGAGCGACCCACTGGACATACTGATTGGCCGCAAGCCG
GTGTCCGCACACTGCCTCACATTCGACCCGCAGTGGTACAGCGGCTATGAGCTGGGCGCCGCCTC
GCTGCAGTTCGAGATCGCCATCACCGTGGAGGTACCCACCGCCCCCTCCCCCACCACAGCCACCA
CCTCCGCCACTCCCCGCACCAACAACAGCAGTAGCGCCAACAGCACCAACAGCACCAACAGCCCG
GCGCCGCAGTTTCTGTCCCCGCCTGCGCCCAGCACGCGGGAAGTGTTGCATCTGGGTCCCTCGGTG
CCTCTGGCCAGCAGCGCGAGCCGCCTGCTGTCCGCCAAGCTGCTGGGCGACCTGGCCATGTACAC
ACAGCTGCCCGCaATCAGCAACCAGGTGCTGATGGTGCCGCAGCcGCCAGCCGCCGCCGCCGCCAC
CGGCTCGCCCCTGGACGCCACCCTGGCGACCAACCGCTCCGCCTGGATGCTGCTGGACAAGACCA
TGCTCAGCATGGACGGCCTGGCCTGCGACAAGGTGGGGACCGGCTTCTCAGCCTTCCGCTACCAG
CCCAGCGGCTGCGGCCGTGCCCCTCAGGCCTGTCTGTCCGGCCAGCTCAAGGACCTGTGGGAGGC
GGACCTGGCGCGTATCGCGGACGGCCGGGTGCCGCTGTACATGATCACCAGGTTCACTGGCGGCA
GCGACACCACGCTGCAGTCCTTCTCCGGGGGCCCGCTGTCGTTCGCGCTGCCTGTCACCAGCCACA
GCCAGAGCCTGGTGACGCTGAGTGTGGCGGCGGACGGCGTGAGGCTGGTCACCAACCGCAGCCCG
GGCAAGATTACAGGCGCGGCGGTGTGCCGTTTCGCCGGCACTTCCTGTGGCGGCTTTGAGGCGGT
GGCAGCTCGCGGCTACATCTACGTCAACATCACCAACACCGGCCGCCTGGACAGTGACTACACAC
TCACAGTGTCCAACTGCTCGTCCAACGTGCGGCCCATCGAGGCGCGCACACTGGCCGTACGCGCG
GGATCCGCCGCCAGCCTGGATCCGCCCATGGAGCTGTACGTGGAGGACCAGGCGGCAGCGGCGGC
GCGCACGTGCACAGTCAGCCTGTACGACTCAGTCGGCGCGGTGACGGACTCGCTCACGCTGTCCTT
CTACACAAACGCCACCCAGCTGGTCGTCAAGCCCTCCGGCGGGTACAACGGCACGGGGGACGGCG
CGGGCGTAAAGCGCAACGGCACCGATTGCAGCACGGCCTGCACCAACCCGATTGACGTGCTGTGC
TTCGTGACCAAGAAGTGCTGGTCCAAGTTCGGGCGGCTTCTGGGCATCATCGGCGGCGCCCTGGTG
GGGCTGGGGCTGCTGGCAGTAGCACTCAAGTTCGGGTGGCTGGCCTCCCTGGCGGCCTCGTGTTGT
GGGGGAGGAGGAGGAGCAGCAGCAGGCGGGGCTGGAGGCGGCATGGGGCTGGGGACCGGCGGC
GGCGGAGGCTGTTTTGGAGGCGGGCAGCAGCAGCAGCAGCCTGCTGCTAGCCATGCCATGTCGCC
ACCGCAGCAGCAGCAGCGCTCGCATGCGGAGGTGGCAGCAGGGGCTGCAGTGGCAGGAGCA
GGAGCCGCTGTTGCAGCAGCGGCGGTGCTGGGAGCCAAACACGGCGGCGGCGGCGGCGCTCGTG
GCAAGCAGCAGCATACCGACACCCGGCATTTGCAGGATCGCGACTCACGAGCCACCGCCGACGGA
GCAAGCATTGACAGCAGCAGCGCCGGCGGCAGTAGCAGTTTAAGCAGCTACACCCAGCCTCGTAA
GGCCGGAGGCAGGCTGCTGCAGCCGCCGGCAGCAGCAGTGTTTGTGCCTGAAGGCGGCATCACTA
GTGAATTCGCGGCCGCCTGCAGGTCGAAGCTTAATTAGCTGAGCTTGGACTCCTGTTGATAGATCC
AGTAATGACCTCAGAACTCCATCTGGATTTGTTCAGAACGCTCGGTTGCCGCCGGGCGTTTTTTAT
TGGTGAGAATCCAAGCTAGCTTGGCGAGATTTTCAGGAGCTAAGGAAGCTAAAATGGAGAAAAA
AATCACTGGATATACCACCGTTGATATATCCCAATGGCATCGTAAAGAACATTTTGAGGCATTTCA
GTCAGTTGCTCAATGTACCTATAACCAGACCGTTCAGCTGGATATTACGGCCTTTTTAAAGACCGT
AAAGAAAAATAAGCACAAGTTTTATCCGGCCTTTATTCACATTCTTGCCCGCCTGATGAATGCTCA
TCCGGAATTTCGTATGGCAATGAAAGACGGTGAGCTGGTGATATGGGATAGTGTTCACCCTTGTTA
CACCGTTTTCCATGAGCAAACTGAAACGTTTTCATCGCTCTGGAGTGAATACCACGACGATTTCCG
GCAGTTTCTACACATATATTCGCAAGATGTGGCGTGTTACGGTGAAAACCTGGCCTATTTCCCTAA
```

-continued

```
AGGGTTTATTGAGAATATGTTTTTCGTCTCAGCCAATCCCTGGGTGAGTTTCACCAGTTTTGATTTA

AACGTGGCCAATATGGACAACTTCTTCGCCCCCGTTTTCACCATGGGCAAATATTATACGCAAGGC

GACAAGGTGCTGATGCCGCTGGCGATTCAGGTTCATCATGCCGTCTGTGATGGCTTCCATGTCGGC

AGAATGCTTAATGAATTACAACAGTACTGCGATGAGTGGCAGGGCGGGGCGTAATTTTTTTAAGG

CAGTTATTGGTGCCCTTAAACGCCTGGGGTAATGACTCTCTAGCTTGAGGCATCAAATAAAACGAA

AGGCTCAGTCGAAAGACTGGGCCTTTCGTTTTATCTGTTGTTTGTCGGTGAACGCTCTCCTGAGTA

GGACAAATCCGCCGCTCTAGAGCTGCCTCGCGCGTTTCGGTGATGACGGTGAAAACCTCTGACAC

ATGCAGCTCCCGGAGACGGTCACAGCTTGTCTGTAAGCGGATGCCGGGAGCAGACAAGCCCGTCA

GGGCGCGTCAGCGGGTGTTGGCGGGTGTCGGGGCGCAGCCATGACCCAGTCACGTAGCGATAGCG

GAGTGTATACTGGCTTAACTATGCGGCATCAGAGCAGATTGTACTGAGAGTGCACCATATGCGGT

GTGAAATACCGCACAGATGCGTAAGGAGAAAATACCGCATCAGGCGCTCTTCCGCTTCCTCGCTC

ACTGACTCGCTGCGCTCGGTCTGTCGGCTGCGGCGAGCGGTATCAGCTCACTCAAAGGCGGTAAT

ACGGTTATCCACAGAATCAGGGGATAACGCAGGAAAGAACATGTGAGCAAAAGGCCAGCAAAAG

GCCAGGAACCGTAAAAAGGCCGCGTTGCTGGCGTTTTTCCATAGGCTCCGCCCCCCTGACGAGCA

TCACAAAAATCGACGCTCAAGTCAGAGGTGGCGAAACCCGACAGGACTATAAAGATACCAGGCG

TTTCCCCCTGGAAGCTCCCTCGTGCGCTCTCCTGTTCCGACCCTGCCGCTTACCGGATACCTGTCCG

CCTTTCTCCCTTCGGGAAGCGTGGCGCTTTCTCAATGCTCACGCTGTAGGTATCTCAGTTCGGTGTA

GGTCGTTCGCTCCAAGCTGGGCTGTGTGCACGAACCCCCCGTTCAGCCCGACCGCTGCGCCTTATC

CGGTAACTATCGTCTTGAGTCCAACCCGGTAAGACACGACTTATCGCCACTGGCAGCAGCCACTG

GTAACAGGATTAGCAGAGCGAGGTATGTAGGCGGTGCTACAGAGTTCTTGAAGTGGTGGCCTAAC

TACGGCTACACTAGAAGGACAGTATTTGGTATCTGCGCTCTGCTGAAGCCAGTTACCTTCGGAAAA

AGAGTTGGTAGCTCTTGATCCGGCAAACAAACCACCGCTGGTAGCGGTGGTTTTTTTGTTTGCAAG

CAGCAGATTACGCGCAGAAAAAAAGGATCTCAAGAAGATCCTTTGATCTTTTCTACGGGGTCTGA

CGCTCAGTGGAACGAAAACTCACGTTAAGGGATTTTGGTCATGAGATTATCAAAAAGGATCTTCA

CCTAGATCCTTTTAAATTAAAAATGAAGTTTTAAATCAATCTAAAGTATATATGAGTAAACTTGGT

CTGACAGTTACCAATGCTTAATCAGTGAGGCACCTATCTCAGCGATCTGTCTATTTCGTTCATCCAT

AGCTGCCTGACTCCCCGTCGTGTAGATAACTACGATACGGGAGGGCTTACCATCTGGCCCCAGTGC

TGCAATGATACCGCGAGACCCACGCTCACCGGCTCCAGATTTATCAGCAATAAACCAGCCAGCCG

GAAGGGCCGAGCGCAGAAGTGGTCCTGCAACTTTATCCGCCTCCATCCAGTCTATTAATTGTTGCC

GGGAAGCTAGAGTAAGTAGTTCGCCAGTTAATAGTTTGCGCAACGTTGTTGCCATTGCTACAGGCA

TCGTGGTGTCACGCTCGTCGTTTGGTATGGCTTCATTCAGCTCCGGTTCCCAACGATCAAGGCGAG

TTACATGATCCCCCATGTTGTGCAAAAAAGCGGTTAGCTCCTTCGGTCCTCCGATCGTTGTCAGAA

GTAAGTTGGCCGCAGTGTTATCACTCATGGTTATGGCAGCACTGCATAATTCTCTTACTGTCATGC

CATCCGTAAGATGCTTTTCTGTGACTGGTGAGTACTCAACCAAGTCATTCTGAGAATAGTGTATGC

GGCGACCGAGTTGCTCTTGCCCGGCGTCAATACGGGATAATACCGCGCCACATAGCAGAACTTTA

AAAGTGCTCATCATTGGAAAACGTTCTTCGGGGCGAAAACTCTCAAGGATCTTACCGCTGTTGAGA

TCCAGTTCGATGTAACCCACTCGTGCACCCAACTGATCTTCAGCATCTTTTACTTTCACCAGCGTTT

CTGGGTGAGCAAAAACAGGAAGGCAAAATGCCGCAAAAAAGGGAATAAGGGCGACACGGAAAT
```

-continued

```
GTTGAATACTCATACTCTTCCTTTTTCAATATTATTGAAGCATTTATCAGGGTTATTGTCTCATGAG

CGGATACATATTTGAATGTATTTAGAAAAATAAACAAATAGGGGTTCCGCGCACATTTCCCCGAA

AAGTGCCACCTGACGTCTAAGAAACCATTATTATCATGACATTAACCTATAAAAATAGGCGTATCA

CGAGGCCCTTTCGTCTTCAC
```

General Methods. *Plasmodium*: Deletion of the FusM gene: To replace all protein-coding sequence of the FusM gene (GenBank accession number XM_671808) with a *T. gondii* dhfr/ts expression cassette conveying resistance to pyrimethamine, a targeting vector was constructed in plasmid pBS-DHFR[1]. A 736 bp fragment comprising 5' flanking sequence immediately upstream of the start codon was amplified from *P. berghei* genomic DNA using primers ol527 (5'-CCCCGGGCCCGCGCGTTATTATTATTCGGGC (SEQ ID NO.: 27), restriction site underlined) and ol528 (5'-GGGG AAGCTTTTTTTCTAAATGAAATATTAAAGAATGGC) (SEQ ID NO.: 28) and inserted into ApaI and HindIII restriction sites upstream of the dhfr/ts cassette of pBS-DHFR. A 967 bp fragment of 3' flanking sequence was then generated using primers ol529 (5'-CCCC GAATTCATTACATGGAATAGTATTTGCAAATTTG) (SEQ ID NO.: 29) and ol530 (5'-GGGG TCTAGACAATATACATGCTGATAACCTCC) (SEQ ID NO.: 30) and inserted downstream of the dhfr/ts cassette using EcoRI and XbaI restriction sites. The replacement construct was excised as a ApaI/XbaI fragment and used for the electroporation of cultured *P. berghei* schizonts as described[2]. Following dilution cloning of drug resistant parasites, genotyping of two fusm clones was done by Southern blot hybridization on EcoRI digested genomic DNA using the ApaI/HindIII fragment of 5' targeting sequence as a probe. Diagnostic PCR analysis used primers ol525 (5'-CTC-GAATATGTAGATATATCCAGATG) (SEQ ID NO.: 31) and ol526 (5'-CAGAGATGTTATAGCTAGTGATATAAC) (SEQ ID NO.: 32) specific for FusM, and primers ol524 (5'-CTAAGTAGCAACTATTTTGTAAAATTATATC) (SEQ ID NO.: 33) and ol70[3] to span the predicted 5' integration site.

RT-PCR analysis of FusM expression: *P. berghei* RNA was isolated from equivalent numbers of purified wild type and fusm gametocytes and strain 233 asexual parasites using TRIzol reagent (Invitrogen) according to the manufacturer's protocol. Any residual gDNA was removed by treatment with RQ1 RNase-free DNase (Promega) and the resulting RNA was extracted with phenol/chloroform, precipitated with ethanol, resuspended in DEPC-treated water, and quantified by 0.8% agarose gel electrophoresis. First-strand cDNA synthesis from one µg of total RNA was done with M-MLV Reverse Transcriptase (Invitrogen) at 37° C. for 50 min. Following heat inactivation for 15 min at 70° C., 2 µl of cDNAs were used per PCR reaction. Primers selected to amplify sections of the FusM ORF (spanning the 209 bp intron) were: Forward: 5'-GCA TAA GAT TCA CAA ATA CAA AAA GG (SEQ ID NO.: 34) and Reverse: 5'-GGT CTT CCT CTA AGT ATT-3' (SEQ ID NO.: 35). The expected RT amplicon was 1203 bp, whereas the gDNA amplicon was 1412 bp. The ubiquitously expressed alpha tubulin gene PB300720.00.0 was amplified for each sample to ensure amplifiability of cDNA from respective RNA samples (Forward: 5'-CCA GAT GGT CAA ATG CCC-3' (SEQ ID NO.: 36) Reverse 5'-CTG TGG TGA TGG CCA TGA AC-3') (SEQ ID NO.: 37). The expected products were 432 bp (cDNA) and 592 bp (gDNA). Thirty RT-PCR cycles were carried out with denaturation at 94° C. for 1 min, annealing at 50° C. for 45 s, and extension at 68° C. for 1.5 min and products visualised on a 0.8% agarose gel.

*Chlamydomonas*: Insertional mutagenesis and TAIL-PCR: Insertional mutants were generated using the plasmid pSI103 linearized with PvuII and transformed into B215 cells using the glass bead method with selection on agar plates containing 10 µg/ml paromomycin (Sigma, St. Louis, Mo., United States) in M medium[4,5]. Approximately 2500 transformed colonies were induced to undergo gametogenesis by transferring them into 96 well plates containing M-N medium. After agitation on a reciprocal shaker for 2 h, 5 µl from each well was transferred into a duplicate 96 well plate containing M media to maintain a stock of the cells in vegetative growth. After continued agitation overnight, samples from each well of the plate with M-N were mixed with wild-type mt+ gametes. Each well was scored on an inverted microscope for flagellar agglutination at 10 min, 4 h, and 12-18 h. Zygote formation, as determined by the presence of large aggregates of zygotes visible in the inverted microscope, was assessed at 4 h and 12-18 h. The absence of zygotes in mixtures with 63B10 was confirmed by phase contrast microscopy.

PCR and TAIL-PCR (Thermal Asymmetric Interlaced PCR): TAIL-PCR was used to identify genomic sequence in the 5'-flanking region of the inserted aphVIII plasmid in clone 63B10 cells. The specific, nested primers were the following: primary: Aph.p22 (5'-GCGCCCTCATAGCCCGC-CAAATC) (SEQ ID NO.: 38); secondary: Aph.p21 (5'-CCGCCAAATCAGTCCTGTAGCTTC) (SEQ ID NO.: 39); and tertiary: Aph.p20 (5'-TGCGCGCTTGGCGTAAT-CATGGTC) (SEQ ID NO.: 40). The arbitrary degenerate primer was Ad.p24 [(G/C)TAGA(G/C)T(G/C)A(G/C)C(A/T)CA(G/C)] (SEQ ID NO.: 41) (personal communication, Carolyn Silflow, University of Minnesota, St. Paul, Minn.). For the tertiary reaction, primers aph.p20 and aph.p21 were used. The PCR product from the tertiary reaction, which was cloned and sequenced, is the following (single underlined sequence is C_530033; dashed underlined sequence is an *E. coli* cytosine methylase presumably from the plasmid host bacterium; and the non-underlined sequence is from the aphVIII plasmid): (5'-CCGCCAAATCAGTCCTGTAGCTTC-CATATCTGATTCGCAATCTTGCCTTGCACCTGCCTG-CCACGCTCATACCATGTCGCCGTGACCCCAAAACA-GGCCTGTCTGTCCGGCCAGCTCAAGGACCTGTGG-GAGGCGGACCTGGCGCGTACCGCGGACGGCCGG-GTGCCGCTGTACATGATCACCAGGTTCACTGGCG-GCAGCGAGGGCTAATCGCGCCG GAAAATATATCAG-TAACCGATTCATACAGCACCGGGAATGCCGCAC-AGGCAATG CTGGAGAAACTGCTGCAAATTTATGAT-GTTAAAACGTTGGTGGCGCAGCTTAATG GTGTAG-GTGAGAATCACTGGAGCGCGGCAATTTTAAAACG-TGCGCTGGCGAATG ACTCGGCATGGCACCGTTTAA-GTGAGAAAGAGTTCGCCCATCTGCAAACGTTATT ACCCAAACCACCGGCACATCATCCGCATTATGCG-TTTCGCTTTATCGATCTATTC GCCGGAATTGGCGGC-ATCCGTCGCGGTTTTGAATCGATTGGCGGACAG-TGCGTGT TTTCCAGCGAATGGAACAAACATGCGG-TACGCACTTATAAAGCCAACCATTATT GCGATCCG- GCGACGCATCATTTTAATGAAGATATCCGCGACATCACCCTCAGCC ATAAAGAAGGCGTGAGTGATGAGGCGGCGGCGGCGGAACATATTCGTCAACAATTC ACACAGGAAACAGCTATGACCATGATTACGCCAAGCGCGCA) (SEQ ID NO.: 42). Other primers used for PCR were the following: FusM.p1 (5'-ATGTCGCCGTGACCCCAAAACAG) (SEQ ID NO.: 43); FusM.p2 (5'-CTGGCTGGTGACAGGCAGCGCGAA) (SEQ ID NO.: 44); and Aph.p17: (5'-TTGGCTGCGCTCCTTCTGGCGC) (SEQ ID NO.: 45).

Figure 10:
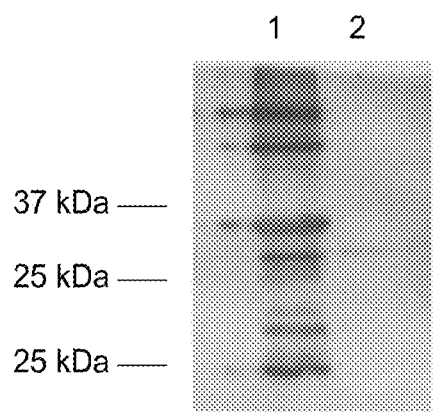
FIG. 10 is a Western blot using sera from mice vaccinated with the PbFusDomA antigen. The Western blot demonstrating mouse 2A response to recombinant PbFusDomA. 1; Sera from Mouse 1 (1 in 200) 2; negative control—pre-immune serum (1 in 50).

Transformation of *Chlamydomonas* with FusM constructs: FusM-HA: The 8.3 kb SstI fragment from DNA BAC clone 20L3 obtained from the Clemson University Genomics Institute, Clemson University containing gene model C_530033 was inserted into the SstI site of pUC119 to generate pYJ36. Standard methods were used to insert a PCR product encoding three copies of the 9-amino acid hemagglutinin (HA) epitope[7] into the NheI site of pYJ36 to generate pYJ58. To obtain 63B10 cells containing the FusM-HA construct, we carried out co-transformation with the glass bead method using pYJ58 and plasmid pmn56 encoding the nitrate reductase gene[8]. For the experiment shown in FIG. 1b, 63B10 cells were co-transformed with the gel-purified 8.3 kb Sst1 fragment of BAC clone 20L3 and pmn56. Transformants were selected for their ability to undergo fusion with wt mt+ gametes.

Generation of an mt+ strain containing only disrupted FusM: 63B10 gametes rescued for fusion by transgenic HA-tagged FusM protein were crossed with 21gr gametes and the progeny were grown using procedures described previously[9]. Colonies formed by germinated zygotes on 2% agar plates were pooled and inoculated into a growth flask containing M Media. Progeny cells were sub-cloned on agar selection plates containing 10 µg/ml paromomycin and screened for mt+ progeny that contained the disrupted fusm allele from the 63B10 cells and lacked both the wt allele and the FusM-HA insert. To confirm the genotype of the transformant, Southern blotting was carried out with genomic DNA digested with NotI. The probe was a cloned PCR product generated using p21 and aph.p20 primers with 63B10 genomic DNA as template and labeled using a Random Primed DNA labeling kit (Roche Applied Science).

Indirect immunofluorescence: Gametes were washed with MT buffer (30 mM Tris-acetate, pH 7.3, 5 mM MgSO4, 5 mM EDTA, 25 mM KCl, 1 mM dithiothreitol) and loaded onto 8-well slides coated with 0.1% polyethylenimine for 10 min[10]. Cells were fixed in 100% ice-cold methanol at −20° C. for 20 min, washed 3 times for 5 min in PBS, and blocked for 30 min with blocking serum (1% cold water fish gelatin, 0.1% bovine serum albumin, 5% goat serum in PBS). The slides with fixed cells were incubated with rat monoclonal anti-HA antibody (Roche Applied Science, diluted 100-fold) for 2 h, rinsed three times in PBS and then incubated for 1 h with fluorescein-conjugated goat anti-rat IgG (ICN/CAPPEL, 1:400 dilution) in blocking serum. The slides were rinsed in PBS and mounted in Fluoromount-G (Southern Biotech, Birmingham, Ala.). Fluorescence microscopy was performed using an Ultraview ERS spinning disk confocal microscope (Perkin Elmer). Final composite images were constructed using Image J (NIH, USA) and Adobe Photoshop (Adobe Systems, San Jose, Calif.).

Assessing gamete activation: To test whether 63B10 gametes were capable of gamete activation, 250 µl of 63B10 gametes at $1.6 \times 10^7$ cell/ml were mixed for 30 min with an equal number of 21gr (mt+) gametes, with dibutyryl cAMP, or with flagella isolated from 21gr gametes. For the experiment with isolated flagella, 10 cell equivalents of flagella were added at 5 min intervals[11]. Cell wall loss was determined as previously described[11]. The data shown are averages from three independent experiments, each done in duplicate, and the error bars are s.e.m.

Assessing membrane fusion: The plasma membranes of activated female gametes ($2 \times 10^7$ cells/ml in M-N medium) were labeled by mixing the cells with an equal volume of Staining Solution containing PKH26 red fluorescent dye (Sigma; final concentration $2 \times 10^{-3}$ mM) for 10 min at 23 C. The reaction was stopped by addition of BSA to a final concentration of 1% for 1 minute, and cells were washed three times with M-N medium by centrifugation. The labeled gametes were mixed with unlabeled wt or 63B10 male gametes and examined by epifluorescence and differential interference contrast microscopy.

Sequence analysis: PSI-BLAST[12] was used to search the nr database (March 15th; 4,655,816 sequences; 1,607,282,285 total letters) for FusM homologs. The query sequence was FusM protein from *Chlamydomonas reinhardtii* (accession number: ABO29824) and the inclusion e-value cutoff was 0.001. NCBI Accession numbers for representative sequences found with significant e-values (<0.001) during PSI-BLAST searches are: AAY51998 (*Arabidopsis thaliana*), AB029824 (*Chlamydomonas reinhardtii*), XP_667362 (*Cryptosporidium hominis*), XP_643321 (*Dictyostelium discoideum* A), XP_645269 (*Dictyostelium discoideum* B), ABN45755 (*Hydra magnipapillata*), XP_843157 (*Leishmania major* A), AAY42350 (*Leishmania major* B), BAE71142 (*Lilium longiflorum*), NP_001055054 (*Oryza sativa*), BAE71144 (*Physarum polycephalum*), XP_676900 (*Plasmodium berghei*), NP_700613 (*Plasmodium falciparum*), XP_725086 (*Plasmodium yoelii*), XP_001030543 (*Tetrahymena thermophile*), $XP_{13}$ 764209 (*Theileria parva*), XP_973371 (*Tribolium castaneum*), XP_823296 (*Trypanosoma brucei*), and XP_814894 (*Trypanosoma cruzi*). FusM proteins were also retrieved from publicly available genome databases for the following species: *Cyanidioschyzon merolae* (CMK076C)[13], *Monosiga brevicollis* (8819: http://genome.jgi-psf.org/Monbr1/Monbr1.info.html), *Naegleria gruberi* (http://genome.jgi-psf.org/Naegr1/Naegr1.home.html), *Nematostella vectensis* (http://genome.jgi-psf.org/Nemve1/Nemve1.home.html), *Paramecium tetraurelia*, *Toxoplasma gondii* (9840; Preliminary sequence data was obtained from The Institute for Genomic Research website at http://www.tigr.org.), and *Volvox carteri*, the relevant sequences for which are incorporated herein by reference. Each of these FusM proteins shows significant sequence similarities to FusM proteins available in NCBI databases (PSI-BLAST e-value<0.001). The *V. carteri* genome sequencing work was performed by the Joint Genome Institute (http://www.jgi.doe.gov/) under the auspices of the US Department of Energy's Office of Science, Biological and Environmental Research Program and the University of California, Lawrence Livermore National Laboratory under Contract No. W-7405-ENG-48, Lawrence Berkeley National Laboratory under contract No. DE-AC03-765F00098 and Los Alamos National Laboratory under contract No. W-7405-ENG-36 and was provided for use in this publication only. The *Apis mellifera* FusM was assembled by searching the *Apis mellifera* genome sequences using TBLASTN and based on comparison with the *Tribolium* FusM. A TBLASTN search starting from *Arabidopsis thaliana* FusM (accession number: AAY51998) against the est_others database in NCBI found several *Zea mays* est sequences (gi|76914610, gi|26457309, gi|78074749, and gi|76936583) with significant e-values (<0.001), that are likely to be FusM homologs. The maize protein was not included in the alignment or the phylogenetic analysis due to the partial sequence.

Multiple sequence alignment of FusM protein homologs was generated by PROMALS (available at pro-data.swmed.edu/promals)[14] (Figure S1), which uses information from database homologs and predicted secondary structures to improve alignment quality. For phylogenetic analysis, we removed from the alignment the N-terminal divergent segments including the signal peptide, and C-terminal divergent segments including the transmembrane segments. Highly gapped positions (gap fraction larger than 0.5) were also removed from the alignment. A maximum-likelihood tree (Figure S2 b) was built using the MOLPHY package (version 2.3). The local estimates of bootstrap percentages were obtained by the RELL method[15], as implemented in the program ProtML of MOLPHY[16]. A quartet puzzling tree was obtained by the TREE-PUZZLE program[17]. Both MOLPHY and TREE-PUZZLE trees were reconstructed with a JTT amino acid substitution model[18]. For the TREE-PUZZLE tree, substitution rate heterogeneity was modeled by discrete gamma distribution with eight rate categories.

METHOD REFERENCES

1. Dessens, J. T. et al. CTRP is essential for mosquito infection by malaria ookinetes. *EMBO J.* 18, 6221-7 (1999).
2. Janse, C. J. et al. High efficiency transfection of *Plasmodium berghei* facilitates novel selection procedures. *Mol Biochem Parasitol* 145, 60-70 (2006).
3. Billker, O. et al. Calcium and a calcium-dependent protein kinase regulate gamete formation and mosquito transmission in a malaria parasite. *Cell* 117, 503-514 (2004).
4. Kindle, K. L., Schnell, R. A., Fernandez, E. & Lefebvre, P. A. Stable nuclear transformation of *Chlamydomonas* using the *Chlamydomonas* gene for nitrate reductase. *J Cell Biol* 109, 2589-601 (1989).
5. Fang, S. C., de los Reyes, C. & Umen, J. G. Cell size checkpoint control by the retinoblastoma tumor suppressor pathway. *PLoS Genetics* 2, e167 (2006).
6. Liu, Y. G., Chen, Y. & Zhang, Q. Amplification of genomic sequences flanking T-DNA insertions by thermal asymmetric interlaced polymerase chain reaction. *Methods Mol Biol* 286, 341-8 (2005).
7. Silflow, C. D. et al. The VFL1 Protein in *Chlamydomonas* localizes in a rotationally asymmetric pattern at the distal ends of the basal bodies. *J Cell Biol* 153, 63-74 (2001).
8. Nelson, J. A., Savereide, P. B. & Lefebvre, P. A. The CRY1 gene in *Chlamydomonas reinhardtii*: structure and use as a dominant selectable marker for nuclear transformation. *Mol Cell Biol* 14, 4011-9 (1994).
9. Goodenough, U. W., Hwang, C. & Martin, H. Isolation and genetic analysis of mutant strains of *Chlamydomonas reinhardi* defective in gametic differentiation. *Genetics* 82, 169-86 (1976).
10. Mahjoub, M. R., Qasim Rasi, M. & Quarmby, L. M. A NIMA-related kinase, Fa2p, localizes to a novel site in the proximal cilia of *Chlamydomonas* and mouse kidney cells. *Mol Biol Cell* 15, 5172-86 (2004).
11. Snell, W. J. Study of the release of cell wall degrading enzymes during adhesion of *Chlamydomonas* gametes. *Exp Cell Res* 138, 109-19 (1982).
12. Altschul, S. F. et al. Gapped BLAST and PSI-BLAST: a new generation of protein database search programs. *Nuc Acids Res* 25, 3389-402 (1997).
13. Matsuzaki, M. et al. Genome sequence of the ultrasmall unicellular red alga *Cyanidioschyzon merolae* 10D. *Nature* 428, 653-7 (2004).
14. Pei, J. & Grishin, N. V. PROMALS: towards accurate multiple sequence alignments of distantly related sequences. *Bioinformatics* In Press (2007).
15. Kishino, H., Miyata, T. & Hasegawa, M. Maximum likelihood inference of protein phylogeny and the origin of chloroplasts. *J Mol Evol* 31, 151-160 (1990).
16. Adachi, J. & Hasegawa, M. MOLPHY: version 2.3: Programs for molecular phylogenetics based on maximum likelihood. *Mol Phylogen and Evol* Inst. Stat. Math. Tokyo., 72-6 (1996).
17. Schmidt, H. A., Strimmer, K., Vingron, M. & von Haeseler, A. TREE-PUZZLE: maximum likelihood phylogenetic analysis using quartets and parallel computing. *Bioinformatics* 18, 502-4 (2002).
18. Jones, D. T., Taylor, W. R. & Thornton, J. M. The rapid generation of mutation data matrices from protein sequences. *Comput Appl Biosci* 8, 275-82 (1992).
19. Pei, J. & Grishin, N. V. AL2CO: calculation of positional conservation in a protein sequence alignment. *Bioinformatics* 17, 700-12 (2001).

Attached Table 1. Multiple sequence alignment of FusM proteins generated by PROMALS. Secondary structure predictions are colored (red: alpha-helix; blue: beta-strand) for representative sequences (with cyan sequence names) and consensus secondary structure predictions are shown below the sequences ('h': alpha-helix; 'e': beta-strand). A conservation index number is shown for highly conserved positions (conservation index>=6) above the sequences. Sequence conservation was calculated using the program AL2CO[19]. *Dictyostelium discoideum*, *Leishmania major*, and *Paramecium tetraurelia* have two copies of FusMs labeled as 'A' and 'B'. *Dictyostelium discoideum* B sequence is not complete. We also identified distant homologs of FusM in *Plasmodium* species (not shown in the alignment).

Attached Table 2. a, Phylogenetic tree of FusM proteins generated by MOLPHY. b, Phylogenetic tree of FusM proteins generated by TREE-PUZZLE. Both trees are rooted artificially in the middle of the branch that separates the Apicomplexa species (*Plasmodium*, *Toxoplasma*, *Cryptosporidium*, and *Theileria*) from the rest of the species. Supporting values are shown above or below any internal branch.

It is contemplated that any embodiment discussed in this specification can be implemented with respect to any method, kit, reagent, or composition of the invention, and vice versa. Furthermore, compositions of the invention can be used to achieve methods of the invention. It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

GENERAL REFERENCES

Billker, O., Dechamps, S., Tewari, R., Wenig, G., Franke-Fayard, B., and Brinkmann, V. (2004). Calcium and a calcium-dependent protein kinase regulate gamete formation and mosquito transmission in a malaria parasite. Cell 117, 503-514.

Billker, O., Lindo, V., Panico, M., Etienne, A. E., Paxton, T., Dell, A., Rogers, M., Sinden, R. E., and Morris, H. R. (1998). Identification of xanthurenic acid as the putative inducer of malaria development in the mosquito. Nature 392, 289-292.

Breman, J. G., Alilio, M. S., and Mills, A. (2004). Conquering the intolerable burden of malaria: what's new, what's needed: a summary. Am J Trop Med Hyg 71, 1-15.

Dessens, J. T., Siden-Kiamos, I., Mendoza, J., Mahairaki, V., Khater, E., Vlachou, D., Xu, X. J., Kafatos, F. C., Louis, C., Dimopoulos, G., and Sinden, R. E. (2003). SOAP, a novel malaria ookinete protein involved in mosquito midgut invasion and oocyst development. Mol Microbiol 49, 319-329.

Ferris, P. J., Woessner, J. P., and Goodenough, U. W. (1996). A sex recognition glycoprotein is encoded by the plus mating-type gene fus1 of Chlamydomonas reinhardtii. Mol Biol Cell 7, 1235-1248.

Goodenough, U. W. (1991). Chlamydomonas mating reactions., In Microbial Cell-Cell Interactions, M. Dworkin, ed. (New York: American Society for Microbiology), pp. 71-112.

Inoue, N., Ikawa, M., Isotani, A., and Okabe, M. (2005). The immunoglobulin superfamily protein Izumo is required for sperm to fuse with eggs. Nature 434, 234-238.

Johnson, M. A., von Besser, K., Zhou, Q., Smith, E., Aux, G., Patton, D., Levin, J. Z., and Preuss, D. (2004). Arabidopsis hapless mutations define essential gametophytic functions. Genetics 168, 971-982.

Reininger, L., Billker, O., Tewari, R., Mukhopadhyay, A., Fennell, C., Dorin-Semblat, D., Doerig, C., Goldring, D., Harmse, L., Ranford-Cartwright, L., and Packer, J. (2005). A nima-related protein kinase is essential for completion of the sexual cycle of malaria parasites. J Biol Chem 280, 31957-31964.

Kindle, K. L., Schnell, R. A., Fernandez, E., and Lefebvre, P. A. (1989). Stable nuclear transformation of Chlamydomonas using the Chlamydomonas gene for nitrate reductase. J Cell Biol 109, 2589-2601.

Liu, Y. G., Chen, Y., and Zhang, Q. (2005). Amplification of genomic sequences flanking T-DNA insertions by thermal asymmetric interlaced polymerase chain reaction. Methods Mol Biol 286, 341-348.

Milek, R. L., Roeffen, W. F., Kocken, C. H., Jansen, J., Kaan, A. M., Eling, W. M., Sauerwein, R. W., Konings, R. N. (1998). Immunological properties of recombinant proteins of the transmission blocking vaccine candidate, Pfs48/45, of the human malaria parasite Plasmodium falciparum produced in Escherichia coli. Parasite Immunol 8:377-85.

Misamore, M. J., Gupta, S., and Snell, W. J. (2003). The Chlamydomonas Fus1 protein is present on the mating type plus fusion organelle and required for a critical membrane adhesion event during fusion with minus gametes. Mol Biol Cell 6:2530-2542

Mori, T., Kuroiwa, H., Higashiyama, T., and Kuroiwa, T. (2006). Generative Cell Specific 1 is essential for angiosperm fertilization. Nat Cell Biol 8, 64-71.

Pan, J., and Snell, W. J. (2000). Signal transduction during fertilization in the unicellular green alga, Chlamydomonas. Curr Opin Microbiol 3, 596-602.

Pollock, S. V., Colombo, S. L., Prout, D. L., Jr., Godfrey, A. C., and Moroney, J. V. (2003). Rubisco activase is required for optimal photosynthesis in the green alga Chlamydomonas reinhardtii in a low-CO(2) atmosphere. Plant Physiol 133, 1854-1861.

Quakyi, I. A., Carter, R., Rener, J., Kumar, N., Good, M. F., and Miller, L. H. (1987). The 230-kDa gamete surface protein of Plasmodium falciparum is also a target for transmission-blocking antibodies. J Immunol 139:4213-7.

Roberts, L. S., and Janovy, J. (2005). Gerald D. Schmidt and Larry S. Robert's Foundations of Parasitology, 7 edn (New York: McGraw-Hill).

Sinden, R. E. (1983). Sexual development of malarial parasites. Adv Parasitol 22, 153-216.

Winger L. A, Tirawanchai, N., Nicholas, J., Carter, H. E., Smith, J. E., and Sinden, R. E. (1988). Ookinete antigens of Plasmodium berghei. Appearance on the zygote surface of an Mr 21 kD determinant identified by transmission-blocking monoclonal antibodies. Parasite Immunol. 10:193-207.

What is claimed is:

1. A composition comprising:
   an isolated recombinant immunogenic portion of a protozoan Fusion protein Male (FusM) mating protein fusion protein, wherein the protozoan FusM mating protein sequence is at least 90% homologous to SEQ ID NO: 70; and
   an effective amount of an adjuvant, and at least one of an absorption enhancer, a release-rate controlling polymer, or a stability enhancer, wherein the adjuvant is selected from Complete Freund's Adjuvant, Incomplete Freund's Adjuvant, alum, a carrier virus, high molecular weight polysaccharides, glycoproteins, microparticles, liposomes or combinations thereof.

2. The composition of claim 1, further comprising a pharmaceutically acceptable salt, an excipient, a preservative, a binder or a pharmaceutically acceptable liquid.

3. The composition of claim 1, wherein the FusM protein is from a protozoan that is heat-killed, attenuated, chemically-inactivated, mechanically inactivated, lyophilized, vacuum-dried, vacuum heat-dried, freeze-sprayed.

4. The composition of claim 1, wherein the FusM protein is recombinant and the portion selected triggers a cytotoxic T-cell immune response, a humoral immune response, a mucosal immune response or a combination thereof.

5. The composition of claim 1, wherein the isolated immunogenic portion of the FusM protein is inserted for expression in an attenuated bacterium.

6. The composition of claim 1, wherein the protozoan is selected from the group consisting of Phylum Apicomplexa or the Class Kinetoplastida.

7. The composition of claim 1, wherein the protozoan is *Plasmodium falciparum*.

8. The composition of claim 1, formulated for oral, subcutaneous, intramuscular, nasal, intradermal, pulmonary, intraalveolar, intravaginal, intrarectal, intraperitoneal or intravenous administration.

9. The composition of claim 1, wherein the protozoan FusM mating protein is SEQ ID NO: 70.

10. The composition of claim 1, wherein the isolated recombinant immunogenic portion of a protozoan Fusion protein Male (FusM) mating protein fusion protein is an inclusion body.

11. The composition of claim 1, wherein the fusion protein is a short peptide or a full length protein.

* * * * *

SEQUENCE LISTING

<160> NUMBER OF SEQ ID NOS: 73

<210> SEQ ID NO 1
<211> LENGTH: 69
<212> TYPE: PRT
<213> ORGANISM: Chlamydomonas reinhardtii

<400> SEQUENCE: 1

Lys Ser Pro Leu Trp Ala Ser Tyr Pro Leu Gln Tyr Leu Ser Ser Phe
1               5                   10                  15

Asn Trp Lys Pro Leu Glu Val Ile Leu Arg Pro Ser Asn Lys Val Cys
            20                  25                  30

Lys Asp Gly Asp Trp Glu Asp Ser Pro Thr Cys Gly Trp Phe Ser Gln
        35                  40                  45

Gly Gly Val Arg Val Ala Asp Ser Gln Gly Phe Cys Cys Glu Cys Ser
    50                  55                  60

Ser Ser Gln Val Trp
65

<210> SEQ ID NO 2
<211> LENGTH: 69
<212> TYPE: PRT
<213> ORGANISM: Arabidopsis thaliana

<400> SEQUENCE: 2

Lys Ser Ala Ala Tyr Ala Leu Tyr Asp Leu Tyr Thr Ile Arg Asp Val
1               5                   10                  15

Pro Tyr Lys Pro Gln Glu Tyr His Val Thr Thr Arg Lys Cys Glu Pro
            20                  25                  30

Asp Ala Gly Pro Asp Ile Val Gln Ile Cys Glu Arg Leu Arg Asp Glu
        35                  40                  45

Lys Gly Asn Val Leu Glu Gln Thr Gln Pro Ile Cys Cys Pro Cys Gly
    50                  55                  60

Pro Gln Arg Arg Met
65

<210> SEQ ID NO 3
<211> LENGTH: 70
<212> TYPE: PRT
<213> ORGANISM: Lilium longiflorum

<400> SEQUENCE: 3

Lys Ser Ala Ala Tyr Ala Leu Tyr Lys Leu Ile Tyr Leu Arg Asp Val
1               5                   10                  15

Ala Tyr Lys Pro Glu Glu Phe His His Val Glu Thr Arg Cys Glu
            20                  25                  30

Pro Asp Ala Pro Tyr Glu Ile Leu Gly Glu Cys Gln Gly Leu Arg Asp
        35                  40                  45

Gln Asn Gly Asn Ile Ile Glu Asn Thr Gln Pro Val Cys Cys Pro Cys
    50                  55                  60

Gly Pro Glu Gly Arg Tyr
65                  70

<210> SEQ ID NO 4
<211> LENGTH: 64
<212> TYPE: PRT
<213> ORGANISM: Hydra sp.

<400> SEQUENCE: 4

```
Lys Ser Pro Val Tyr Leu Asn Phe Pro Phe Phe Asn Gly Ile Thr
 1               5                  10                  15

Val Asn Asn Gln Pro Tyr Glu Glu Ile Ile Leu Ser Lys Asn Arg Arg
             20                  25                  30

Gln Cys Leu Asp Asp Glu His Pro Thr Gly Tyr Gln Tyr Thr Arg Ile
         35                  40                  45

Trp Asp Ser Gln Gly Phe Cys Cys Tyr Cys Thr Gln Asp Leu Lys Asn
 50                  55                  60
```

<210> SEQ ID NO 5
<211> LENGTH: 69
<212> TYPE: PRT
<213> ORGANISM: Trypanosoma brucei

<400> SEQUENCE: 5

```
Lys Ser Pro Val Gln Tyr Arg Tyr Pro Ile Tyr Tyr Ile Arg Asn Phe
 1               5                  10                  15

Asn Ala Lys Pro Tyr Glu Gln Arg Leu Arg Thr Ser Ala Ser Ser Trp
             20                  25                  30

Cys Asp Asp Ser Ser Asn Pro Gly Ser Ala Thr Val Ala Arg Asp Arg
         35                  40                  45

Arg Gly Asp Val Ile Pro Tyr Ser Gln Gly Phe Cys Cys Leu Cys Gly
 50                  55                  60

Ala Cys Ala Leu Ser
 65
```

<210> SEQ ID NO 6
<211> LENGTH: 72
<212> TYPE: PRT
<213> ORGANISM: Toxoplasma gondii

<400> SEQUENCE: 6

```
Lys Thr Pro Val Thr Ile Ser Leu Pro Leu Glu Tyr Ile Lys Glu Val
 1               5                  10                  15

Pro Phe Asp Tyr Arg Glu Glu Ile Tyr Glu Tyr Ser Arg Trp Lys Phe
             20                  25                  30

Cys Tyr Glu Asp Thr Thr Asp Lys Cys Ser Glu Asp Gly Lys Leu Ala
         35                  40                  45

Val His Pro His Gly Lys Pro Leu Ser Trp Ala His Gly Arg Cys Cys
 50                  55                  60

Trp Cys Ser Glu Val Leu Ala Phe
 65                  70
```

<210> SEQ ID NO 7
<211> LENGTH: 67
<212> TYPE: PRT
<213> ORGANISM: Plasmodium berghei

<400> SEQUENCE: 7

```
Arg Asp Tyr Val Thr Val Ser Tyr Leu Lys Tyr Val Lys Asp Ile
 1               5                  10                  15

Pro Leu Glu Phe Arg Glu Ile Ile Asp Ile Phe Asn Asn His Gln Tyr
             20                  25                  30

Thr Gln Glu Gln Ile Asn Lys Tyr Thr Tyr Thr Cys Asn Val Arg Lys
         35                  40                  45

Ile Phe His Glu Tyr Thr Arg Gly Glu Ala Cys Arg Cys Gln Thr Tyr
 50                  55                  60

Asn Tyr Phe
```

<210> SEQ ID NO 8
<211> LENGTH: 75
<212> TYPE: PRT
<213> ORGANISM: Chlamydomonas reinhardtii

<400> SEQUENCE: 8

Ser Ala Trp Met Leu Leu Asp Lys Thr Met Leu Ser Met Asp Gly Leu
1               5                   10                  15

Ala Cys Asp Lys Val Gly Thr Gly Phe Ser Ala Phe Arg Tyr Gln Pro
            20                  25                  30

Ser Gly Cys Gly Arg Ala Pro Gln Ala Cys Leu Ser Gly Gln Leu Lys
        35                  40                  45

Asp Leu Trp Glu Ala Asp Leu Ala Arg Ile Ala Asp Gly Arg Val Pro
    50                  55                  60

Leu Tyr Met Ile Thr Arg Phe Thr Gly Gly Ser
65                  70                  75

<210> SEQ ID NO 9
<211> LENGTH: 75
<212> TYPE: PRT
<213> ORGANISM: Arabidopsis thaliana

<400> SEQUENCE: 9

Ser Met Trp Met Leu Leu Glu Arg Val Arg Phe Thr Leu Asp Gly Leu
1               5                   10                  15

Glu Cys Asn Lys Ile Gly Val Gly Tyr Glu Ala Phe Asn Thr Gln Pro
            20                  25                  30

Asn Phe Cys Ser Ser Pro Tyr Trp Ser Cys Leu His Asn Gln Leu Trp
        35                  40                  45

Asn Phe Arg Glu Ser Asp Ile Asn Arg Ile Asp Arg His Gln Leu Pro
    50                  55                  60

Leu Tyr Gly Leu Glu Gly Arg Phe Glu Arg Ile
65                  70                  75

<210> SEQ ID NO 10
<211> LENGTH: 75
<212> TYPE: PRT
<213> ORGANISM: Lilium longiflorum

<400> SEQUENCE: 10

Ser Lys Trp Met Leu Leu Glu Arg Glu Arg Phe Thr Leu Asp Gly Leu
1               5                   10                  15

Glu Cys Asn Lys Ile Gly Val Ser Tyr Asp Ala Tyr Arg Ser Gln Pro
            20                  25                  30

Asn Phe Cys Ser Ser Pro Leu Trp Ser Cys Leu His Asn Gln Leu Trp
        35                  40                  45

His Phe Trp Glu Ala Asp Gln Asn Gln Ile Arg Arg Asn Gln Pro Pro
    50                  55                  60

Glu Tyr Val Val Glu Gly Arg Phe Lys Arg Ile
65                  70                  75

<210> SEQ ID NO 11
<211> LENGTH: 73
<212> TYPE: PRT
<213> ORGANISM: Hydra sp.

<400> SEQUENCE: 11

```
Ser Lys Trp Met Ile Ile Pro Arg Asp Leu Val Ser Thr Asp Ala Lys
1               5                   10                  15

Gln Cys Asp Met Ile Gly Val Gly Tyr Ser Ala Phe Arg Gly Tyr Gly
            20                  25                  30

Cys Arg Ala Lys Lys Gly Ser Cys Leu Ala Asn Gln Pro Tyr Asn Lys
            35                  40                  45

Phe Met Asp Asp Glu Asp Arg Leu Glu Lys Gly Lys Met Pro Trp Tyr
        50                  55                  60

Phe Pro Ala Arg Tyr Gly Lys Leu Ala
65                  70

<210> SEQ ID NO 12
<211> LENGTH: 75
<212> TYPE: PRT
<213> ORGANISM: Trypanosoma brucei

<400> SEQUENCE: 12

Asn Glu Trp Ile Ile Val Asp Thr His Leu Val Ser Ile Arg Gly Thr
1               5                   10                  15

Glu Cys Asn Lys Val Gly Val Ser Tyr Glu Gly Phe Ala Thr Gln Gly
            20                  25                  30

Ser Arg Cys Asp Ala Tyr Pro Gly Ala Cys Leu Ala Asn Gln Leu Glu
            35                  40                  45

Asp Tyr Arg Asp Arg Asp Leu Glu Ala Glu Thr Lys Gly Gln Gln Gly
        50                  55                  60

Lys Tyr Met Ala Arg Phe Phe Ala Pro Phe Gly
65                  70                  75

<210> SEQ ID NO 13
<211> LENGTH: 76
<212> TYPE: PRT
<213> ORGANISM: Toxoplasma gondii

<400> SEQUENCE: 13

Lys His Ala Ile Ile Leu Asp Lys Asp Tyr Val Ser Val Thr Gly Tyr
1               5                   10                  15

Glu Cys Asp Lys Val Gly Thr Gly Leu Asp Arg Trp Gly Asp Met Arg
            20                  25                  30

Gly Glu Phe Cys Asn Leu Leu Pro Gly Thr Cys Ile Thr Gly Gln Leu
            35                  40                  45

Arg Lys Phe Lys Glu Val Asp Lys Leu Arg Ile Glu Gln Asn Leu Ala
        50                  55                  60

Pro Leu Tyr Ala Leu Lys Arg Glu Phe Gly Gly Phe
65                  70                  75

<210> SEQ ID NO 14
<211> LENGTH: 73
<212> TYPE: PRT
<213> ORGANISM: Plasmodium berghei

<400> SEQUENCE: 14

Arg Lys Ala Met Met Leu Pro Lys Tyr Met Phe Asp Leu Ser Gly Lys
1               5                   10                  15

Thr Cys Gly Lys Leu Gly Val Ser Leu Asn Thr Trp Arg Lys Ser Glu
            20                  25                  30

Gly Asn Phe Cys Gly Ser Glu Ala Gly Tyr Cys Ile Ser Asn Asn Leu
            35                  40                  45

Lys Lys Tyr Tyr Asp Ile His Asn Ser Ala Ser Ile Lys Ser Lys Tyr
```

Lys Ile Lys Asn Ile Tyr Asn Ser Glu
65                  70

<210> SEQ ID NO 15
<211> LENGTH: 2670
<212> TYPE: DNA
<213> ORGANISM: Plasmodium falciparum

<400> SEQUENCE: 15

| | | | | | |
|---|---|---|---|---|---|
| atgaacaaaa | ggaaaaagac | aaaacactta | aaagttaatt | ctatattgag | aatcttttt | 60 |
| tttttttcc | ttatttcttt | tcttttagt | aattgtaaat | taaatgatta | tataagaaca | 120 |
| aaatacccat | tcattcaatt | tgtatattct | tattccaaaa | aaaaggtatg | tacatcttct | 180 |
| acagatgatt | ccacatgtcg | tactgtcgtt | tatggagatt | tagatgtttc | taataattcg | 240 |
| gtgttaaggt | taaaggtttt | aaggtctgag | gggaaaggct | atttttgttac | tattcgaaga | 300 |
| gactatgtaa | caatatctta | ctatctgaaa | tatatgaaag | atattccttt | aaagtataga | 360 |
| gaagtagttg | atatatttaa | taatcataaa | tatgaaaaat | atacagagaa | acaaataaag | 420 |
| gattttactt | taattgtac | tgctattaaa | gtcgaagatg | ccaataatac | tgtaggggat | 480 |
| tttgcacctc | attatcatga | atatacaaga | ggagaatctt | gtatatgccc | ttcatatcat | 540 |
| ctttttaaaa | atgacaattc | aataaaaaga | gcaaaattaa | aatgcactta | ttttaatatg | 600 |
| ttatttacag | atagtgctat | agtatatagc | cgtcattgtg | ctataatgga | tttgttttat | 660 |
| ttttctgttt | atgaaattga | ctatcctcca | atatttaata | catatataga | tataacaata | 720 |
| caagaatata | catatgatga | tgtatcaggt | atgtcactga | taaacatga | tttagttaca | 780 |
| aaagaaaaga | aatatgaaat | aaatgattcg | atgtctgaaa | taagagacga | ttattttgat | 840 |
| ctttggttat | tttaagagg | agaaagacat | ggaaaaagaa | ctttaattaa | tttatcaaat | 900 |
| gattatgttg | ttattccatc | ttcaccttta | gatgatgcgg | atgtaataga | aactgatgtt | 960 |
| atgagaaatt | gtggttttgaa | agaagataat | ccagctttaa | aaggatgtga | ttataaacat | 1020 |
| gaatgtaaca | ttatacatcc | atgtttagta | aaagcaatga | tgttaccaaa | atatcttttt | 1080 |
| gatttaagtg | gtaaaacatg | taataaaatta | ggtgtatcgt | taaataaatg | gagaaaattct | 1140 |
| gatgggaatt | tttgtggttc | ttcagctggg | tattgtttat | ctgagaattt | gtttaaatat | 1200 |
| tattacatac | ataaaacatc | tgttgggaat | agaaaacctt | cgaaatataa | aattaaaaat | 1260 |
| atatatgggt | ctgaaccaca | gacaaaagtc | tatacatctg | caaaattacc | taattattta | 1320 |
| aaagataagg | tagatagtaa | taataataaa | tcttatgata | ttaatgatat | agataataaa | 1380 |
| atattttata | atgaaaacgc | tgctgcacat | agtcatttta | ttgattacaa | atataatgga | 1440 |
| aatcatactg | ttgaaattaa | attcgaaact | aatgcattag | aagtacatga | aatcagacct | 1500 |
| gtgtcatatg | gaactattac | acatattact | ataccaaaag | attgttcatc | aaatcaaaca | 1560 |
| aattctaaag | aatgtattct | tgttgtacat | acgtggaata | taataaaaac | tataggagct | 1620 |
| aacttctctt | gtcatgtttt | atgtgttgat | aaaagtactc | aacaagtagc | aacacatatt | 1680 |
| agtcccatta | gtaaaataaa | tgcacatatt | gatgcaaata | aaaattatgc | cttttatttc | 1740 |
| attattaaat | tttaataaa | taaaaaaata | acaagtaatt | gtacagcaat | actaaaagat | 1800 |
| gctgatggta | gggaatgttc | aaaactttca | tttaatttaa | catctaaaga | aacaataaat | 1860 |
| gtagtagaat | caggaatagt | agcacaacct | gtagaaagtg | aagctcaaat | aaataaatat | 1920 |
| gatcctgatg | tatcaggagc | atctacgcct | acagctgata | aatgtgattg | ttatttttaat | 1980 |

```
ttattatgtt atatacttaa tttgaataca tgtgtttcat attatactaa attaattaaa      2040
gattaccttg gaagatttgt aacgatagct atattaattt ttcttgcacc atccttaata      2100
cccctgttac catttatcat taaattttt atatcatgtg catctctccc aatgaaatta       2160
ttttccaact tttcttcttg gatggaaaat aaaaaaaaaa gtaataatag tacaaagcaa      2220
aataaaaatt attttcaaag gaaatatgaa aatttcaaaa aaagagaac aaatatgaag       2280 aaaaataaat gtacatcatc ttccgtctct tctttaacaa atgtttcaag tatttcttca     2340
aataatacaa tgaacagtga tataaaaaag gacgtatcat ttaataggat taaatcaaat     2400
aggtacaata aggagaatca taaaaacaaa aagaggaaaa caaaaggtaa ccatagtaaa     2460
tatagtggta cctcgatgga gagtacacta acaaatacaa gtccctcaag tacacctgat    2520
aatttaagtg aatctcatat aacatctaat tcaaacaaaa ataattattc atcaaaaaaa    2580
aaaaacaagt gtaatatgct atataaaaaa gaacattcca ggaaaagtat aagaaaaaaa    2640
tctatgggga tatctgaata ttcttcttaa                                     2670

<210> SEQ ID NO 16
<211> LENGTH: 2439
<212> TYPE: DNA
<213> ORGANISM: Plasmodium berghei

<400> SEQUENCE: 16
atgattatta ttatttttt ttgtattatt ttaaagtatt ataaatggtg tgactttaaa      60
aataaagtat ttttcattca attagtgtat tcttttgcga aaaaagtgt ctgtacttca      120 tcattggatg attcaacatg tcacacagta acttttggtg aattggatgt ttctaataat    180
tcggtagtga gattaaaggt gatgagaaaa ggaggaaaag ggtatttcct gacaattcga    240
agagattacg taactgtctc atattatttg aagtatgtaa aggacattcc tttagaattt     300
agggaaatta tagatatatt taataaccat aaatttgagc aatacacaca agagcaaata    360
aataaatata catatacatg taatgtacgt aaaattgaag atatagataa atatgatgaa    420
aaaaatccaa ctaaatttca tgaatataca cgaggagaag catgcagatg ccaaacatat    480
aattatttta agatgatga atttataaaa agagcgaaat taaaatgtat ttattataat     540 atgctatttta ctgaatcagc gacagtatat agacattgtc ctattataga tttaatgcat  600
tttgcagttt atgatataga atatccacca atatttaata caattgttaa tattacaata    660
gaagagtatt attacaatga tgtatcatct gttttgaaca ataaatctga tttagttaca    720
aaagaaaaaa aatatcaatt aaatgatact ataacagaaa taagagatga ttattttgat    780
ttatggttat ttttaaaagg tgaaacacat ggaaaaagaa cccttgttaa ttatcaaat    840 gattatattg ttattccatc atcacctatt aataacagag atgttatagc tagtgatata   900
acaagaaatt gtggactatc acaaaattca ccattattaa aaggttgcaa ttattcaagt   960
atatgtaata ttatgcatcc atgcttacga aaagctatga tgttaccaaa atatatgttt   1020
gatttaagtg gtaaaacatg tggaaagtta ggtgtatctt taaatacttg gaggaagtca   1080
gaaggtaatt tttgtgggtc agaagctgga tattgcatat caaataatct caaaaaatat   1140
tatgatattc ataattctgc atctataaaa gatggtattt ctctttcaaa gtataaaata   1200
aaaaatatat ataattcaga accacaaact aaaatatatg aatcctataa gttgcctgat   1260
tatttaaaag ataaaattaa gaataataat catgcggaaa tggatgaaaa tgatttagat   1320
aataaaattt tttataaacc aaatgtagct gcacatagcc aattcattga ttataaatac   1380 aatggaaaatc atagtgtaga aataaaattc gaaacagatg ctatagaagt atatgaaata   1440
```

```
agacccgttt ccattgcaac aattactcat gttactatac caaatgattg tgcatctaat    1500
aattctaatt caaatgaatg tgtccttatt attcatgtat ggaataatag caaatttgta    1560
ggttcaaatt tctcttgctc aattgcatgc acaaataaag aaactgacca attggctagt    1620
cacattaacc ctatcgctcc tgtgcgtgca tttattggac caaataaaaa ctatgctttt    1680
tattttataa taaaattctt aataaataaa gaaattacaa cattgtgcaa agctattgta    1740
aaagattcta atgggaaaga atgctctata gaagaattcg aattacaatc aaagaaagt     1800 gtacatatag ttgagtcaga agtagatgaa acaacggacc aagtagtagt agaacatcat    1860
acacaatcac ctgatattaa aaaccctgat gaatatgtat gtaaatgtac tattaattta    1920
ttatgttatg taattaattt caaaacatgc tctaactatt atataaatac agttaaaacg    1980
ttaattggga aatttgctat tatagccata ttaattatat tagcacctgc cttaatacct    2040
cttctaccat tctttttaaa tttcttttc cttttatat ctactatact taaattatat      2100
caatctatta taagcacaat aggacaaatc agaatacgaa ataatgataa gcctattatt    2160
tataaaaaaa aaattcatga catgaaaacc aactacctat ctgtttcttc atattcgtca    2220
ttatctgatt caagcagtat atactccact gattcagtat cttcgatgag aaaaaataaa    2280
aaaaaattca ataaaaataa tatatcaagc aatataaaac ataaaaaagg ggggaaaaag    2340
gttaaacaaa aagagccaaa tagaaattca aatcacactt cccatgaata tgcagataca    2400
tctccgtcag gtaaaagtaa aataccccca ttgcgataa                          2439

<210> SEQ ID NO 17
<211> LENGTH: 2436
<212> TYPE: DNA
<213> ORGANISM: Chlamydomonas reinhardtii

<400> SEQUENCE: 17
atgtgtcgtg ccatcgcggt tgcgctgata gtttacctag cccagcatta tattcttgcg      60
cacgctgagg tcattgcaag tgggcgcttg gaaaaatgcg tcgtcgatgg tgttaccgag     120
gagctggact gccaggagaa ggtggtggtg acactgacgg tcggaaatgg gcagagcctg     180
caggccgagc tctggaattc tcgctcagc tgcctcaaca gccccgacgg acgctgcccc      240
tgcagctgca cgccgccga ccctacttgc gcatgtcgtg acctggcggc gccgctgcgc      300
gtgtcgctta ccaagtcgcc gctgtggggcc tcctacccgc tgcagtactt gtcgtccttt    360
aactggaaac cctggaagt catcctgcgc cccagcaaca agtttgcaa ggacggcgac       420 tgggaggact cgcccacgtg tggctggttc agccagggcg gtgtgcgggt ggcggacagc     480
cagggattct gctgcgagtg cagcagcagc caggtgtggg acgacacctt cgggtccagc     540
aaggagcgca ctcgcgccaa cctggactgt gacttctgga cgacccact ggacatactg      600 attggccgca agccggtgtc cgcacactgc ctcacattcg acccgcagtg gtacagcggc     660
tatgagctgg gcgccgcctc gctgcagttc gagatcgcca tcaccgtgga ggtacccacc    720 gcccctcc ccaccacagc caccacctcc gccactcccc gcaccaacaa cagcagtagc      780
gccaacagca ccaacagcac caacagccc gcgccgcagt ttctgtcccc gcctgcgccc     840
agcacgcggg aagtgttgca tctgggtccc tcggtgcctc tggccagcag cgcgagccgc     900
ctgctgtccg ccaagctgct gggcgacctg gccatgtaca cacagctgcc cgcaatcagc     960
aaccaggtgc tgatggtgcc gcagccgcca gcgccgccg ccgccaccgg ctcgcccctg     1020
gacgccaccc tggcgaccaa ccgctccgcc tggatgctgc tggacaagac catgctcagc    1080
```

```
atggacggcc tggcctgcga caaggtgggg accggcttct cagccttccg ctaccagccc    1140
agcggctgcg gccgtgcccc tcaggcctgt ctgtccggcc agctcaagga cctgtgggag    1200
gcggacctgg cgcgtatcgc ggacggccgg gtgccgctgt acatgatcac caggttcact    1260
ggcggcagcg acaccacgct gcagtccttc tccgggggcc cgctgtcgtt cgcgctgcct    1320
gtcaccagcc acagccagag cctggtgacg ctgagtgtgg cggcggacgg cgtgaggctg    1380
gtcaccaacc gcagcccggg caagattaca ggcgcggcgg tgtgccgttt cgccggcact    1440
tcctgtggcg gctttgaggc ggtggcagct cgcggctaca tctacgtcaa catcaccaac    1500
accggccgcc tggacagtga ctacacactc acagtgtcca actgctcgtc caacgtgcgg    1560
cccatcgagg cgcgcacact ggccgtacgc gcgggatccg ccgccagcct ggatccgccc    1620
atggagctgt acgtggagga ccaggcggca gcggcggcgc gcacgtgcac agtcagcctg    1680
tacgactcag tcggcgcggt gacggactcg ctcacgctgt ccttctacac aaacgccacc    1740
cagctggtcg tcaagccctc cggcgggtac aacggcacgg gggacggcgc gggcgtaaag    1800
cgcaacggca ccgattgcag cacggcctgc accaacccga ttgacgtgct gtgcttcgtg    1860
accaagaagt gctggtccaa gttcgggcgg cttctgggca tcatcggcgg cgccctggtg    1920
gggctggggc tgctggcagt agcactcaag ttcgggtggc tggcctccct ggcggcctcg    1980
tgttgtgggg aggaggagg agcagcagca ggcggggctg gaggcggcat ggggctgggg    2040
accggcggcg gcggaggctg ttttggaggc gggcagcagc agcagcagca gccgcctgct    2100
gctagccatg ccatgtcgcc accgcagcag cagcagcagc gctcgcatgc ggaggtggca    2160
gcaggggctg cagtggcagg agcaggagcc gctgttgcag cagcggcggt gctgggagcc    2220
aaacacggcg gcggcggcgg cgctcgtggc aagcagcagc ataccgacac ccggcatttg    2280
caggatcgcg actcacgagc caccgccgac ggagcaagca ttgacagcag cagcgccggc    2340
ggcagtagca gtttaagcag ctacacccag cctcgtaagg ccggaggcag gctgctgcag    2400
ccgccggcag cagcagtgtt tgtgcctgaa ggcggc                              2436
```

<210> SEQ ID NO 18
<211> LENGTH: 1767
<212> TYPE: DNA
<213> ORGANISM: Trypanosoma cruzi

<400> SEQUENCE: 18

```
atgagcctgt ctttgtctcg tatgcttttt tctttattgc tgtttgccct gatggttgca      60
acaactcctt tgccgcgga gggtttactg ctggcgtcgt cttccattga acagtgcgat     120
cgtgtgggaa ccgacaactc gctgccgtgt gagaaaaagt tggtggtgac gttgtcggtg     180
gacagtgatc aggcggaaga gtggaggag tttgtgattt gcgcgatgc cgtggacaaa      240 acgaaaggaa cggggagga gcacgtggaa tttcaaccta tccgtttgac gacgagcaaa     300
tcacgcgtgc aatacagtta ccctctcttt tatgaaagga atttcaatgc caagccctac     360
gaggaggaaa ttacaacgga actagttggg tgcgatgata catttagtcc gaaagcaaca     420
tgcgggctgg ccatggacac cgcgggaagg cctatcccgt acagtcaagg ttttttgttgt    480 cgatgtggtc cctgtcagtt gttggggtta tgtcccgtgg gtagccgcgg tcttcaggta     540
tgcgacatat tcagagggc tgcattagcc tcatgtctcc gttttggaga gctttggtac      600
agtgggtaca gcatgggttc ggctactatc tggtatcgct tgtcggtaaa actgacgact     660
gactcccaaa ataactccaa gacaaaagaa gcagttttg agctgggacc ggatgtgctt     720
tcagggtctt cagcggagtt tggggcttgg gtcagtctaa ttgggggactt tgtgccggcg    780
```

```
gaattaccat tggttctaag taataaaatg cttttattc cctcttctcc aagaatacac      840
gagcgtgttt tggcgggcca aaaggagtgg ttaattctgg acaagcacca tgtgagcatg      900
cagggtcgag attgtaacaa ggtggggta tcttatgaag ccttttcggg tcaggggagc      960
aggtgccaat taattcgagg gtcgtgtctg gccgatcagt tggaggacta ccgttcgagt     1020
gatttggcag ttgaagcccg aggggtaga ggcaaatacc tggctcgctt ttttggagac     1080
tttgttgtca acaacgtcaa caacagcaga acaagactct cctactggat gcgtgggtca     1140
ttggcgacga tgttaactgt tgtcatatca gcggacagac tgcaatatct ggtttctgtt     1200
tccccaggtg aaattgtctc tgcggtgatg tcgaagtcga cagtagagga aagttcgaga     1260
gatggatccg tttctgtcat agtgcgcaat attggccacg taactgcgca atacacgctt     1320
ggtgtgggga actgttcggg aaatgttttc cccattatgg cccagaccct gagtttgaga     1380
ccacgaggga cagtgatacg cagttttgat ctgaatatcc aagatgtggc ggaagagaga     1440
attgtgcaat gcgacgtaac tttacgagac gcgaaaggtg ctatcacgga caagaagatt     1500
ttgaagtttc gagtaacaag taaagtatta cgaatgata cacagggcgg caatgcacca     1560
actggaggtg gtgccagcgt ggatggtcaa gcccctccag cttgctcgcg ttgtgagtgg     1620
tacaagattt cctgtttcct gattcatggc tgttggtggc agccactggt gtatgttttg     1680
attgccattg ctatactgct gggtatatat tattttttcg gactctcttc gcgcagtagt     1740
gaacccaaat tacacgtggt tcactga                                         1767
```

<210> SEQ ID NO 19
<211> LENGTH: 1857
<212> TYPE: DNA
<213> ORGANISM: Trypanosoma brucei

<400> SEQUENCE: 19

```
atgccgacgg agacgttatc atctgttttt gtgctcgtcg tccttgtgac gacaagcggc       60
cttttcccct gcactgaggc ggcatttgtg gcctcgtcgt ccatcgagta ctgcgagcgc      120
agtagtaatg gggaaccgtt tccatgtgaa aagaagatgg ttgtggggct ctccgtgggc      180
agcgagcaaa caattgaggc tgaagaggtt gttcttctcc gcgaggcagt tgacaaaacg      240
ggtgacgaaa agggaaagcg tgtcgagttt gaaccaatcc gcctagtgac gacaaaatca      300
ccggtgcagt accgctatcc tatttattac ataagaaact tcaatgccaa accatatgag      360
cagcgtctca gaacaagtgc aagcagttgg tgcgacgatt cttccaaccc tggatccgcg      420
acatgcggct ggcgcgtga tcggagagga gatgtgattc cgtacagtca aggttttgc       480 tgcttatgtg gcgcttgtgc attgtcagga atttgcaacc caactagccg cagcgttgga      540
acttgcagcg tgacggggga tactggaatg gcatcatgcc ttcgtttcag tgacctctgg      600
tacggtggct ataccattgg tcgaggtgtt gtatggtatg aattgcaggt gaaattgtca      660
agtgggaaca cagcactgg gggaggctcc acgggctcaa aggagttcac gatgtctttg      720
gggccggata agttgaccgc cacgtcgaca gagttcggcg cgtctgcacg tcttatagga      780
gacttcgcac ccccagaaat gcctcttgac ctatcgggaa agatgttgtt tatcccctct      840
gaaccgcggg gtcatgagcg agtgggtgct gggtataacg aatggattat tgttgacacc      900
caccttgttt ctattcgtgg caccgaatgt aataaagtgg gcgtgtcata tgagggtttc      960
gccactcagg ggagccggtg tgacgcgtat ccgggcgctt gcttggcgaa tcaactggag     1020
gattatcgtg atcgggactt ggaagcggag actaagggga acaagggaa atatatggct     1080
```

```
cgcttttcg ctcctttgg ttttgaccca ctggccaatg ccagtgcccc agctgtggct    1140
taccaggtga caggaacatt atcaacgatg gtgacgataa caatatccgc tgataagtta    1200
aactttgtgt tgtctgtgtc ctcgggtgtg attgttggtg caaccgtttc agggaaggtg    1260
gtgcattcct attcgcgggg aagcaccatt accgtgacgg ttcttaacac tgggacatc    1320 gaggcacagt acacggttgt tgtcggcgag tgtacggtta atgttcagcc gatggttgcc    1380
caaactgtgt acatacccct acaaggatca gcgcagcgac gtttcactct gatcgtacag    1440
gacagtattg agggagaggc caaatgcaat gcaacgctga gaaacgccag ggcgacgtt    1500 gtggacaccc cgcgctattc gttcggtgtt aaagcgctca aaccaagcaa tggctctcaa    1560
ggtggcagca ccttttgaaaa tggacggtac agtgaggagg caaggggga gtcgcagtgc    1620 caacagtgca gttggttcaa tcttttgtgt tttctgaggc atcgatgctg gtggcaaccg    1680
ctggtgtacg tccttccttc agtgaccctg ttaatgctgc tgcgcaggtt ccttgagagt    1740
cagtcaaggt cccgcccaag accccaatta caccctgatg agcatgaact gagaaatacc    1800
ggtgccatct cttcgtgcca tcttccccgc gcaccgtacg ttaacacagt gcactga    1857

<210> SEQ ID NO 20
<211> LENGTH: 1185
<212> TYPE: DNA
<213> ORGANISM: Cryptosporidium hominis

<400> SEQUENCE: 20
atgtggtgga atgtttactt atcgaagtca tgcccagttt ggataccacc atggtggaca     60
gcttttagaa taggtggatg gaattggcaa tactcattag aggttgaatt atcttggttt    120
agtccaacag aatcatcaat taataagtta tcaagtacag aattggaaaa tatggaaaat    180
gaatgtaaga agaaaataa agattccaca atagattgtt caagaataag gcataaagaa    240
tcaggaattc agacttctgt acatacatta aattcatcgt ctccatcatt ctatgatcca    300
aattttggag cttcagtaca ggtaataagt tcaggaccgc cgtttgggag tgctaatgca    360
aaggatttga atggttatta catgttacaa ccaacatttt caccaaaagg gatgcctgct    420
agtattgcaa ttcctccttt aagaagtggg tgtggaaaag cttcaaaaaa ccaaacagaa    480
gaggaaatga atgattgttt aaagccaaca ttaattattc ctccagaaaa tgcagacttt    540
acaggagttt catgtgataa gataggaaca agtgttcata cttggagttc tgtgaatggt    600
agattttgct atcatccacc tgggacttgt caaagagctc agatagctca cttttataag    660
aaagttatag aagatcattc acttggaaag atttcacaat attcagtgag agcacaaaat    720
tctggttctc cacagttgat tttggattca ttgggagaaa ttggtcatga gaggtggat    780 caaaatgata tggaaatat aactaatata caatcacgta gattcttttt gggatataat    840
tttgattcaa tctttgacac agaaataatg ttctcagtcg aagcttcttc tgtgtcttgg    900
gtagcaacat cttctcctgg aattattaca tatatagaac caccacctt ggaggcttgc    960 acagcaatga gtagttttgg ctgtcctcta aggtttata ttaagaatag tggtaagttt   1020
gaatatatat atacatttcg aattgaatta aaaataactt atcaaaaata ttctataggg   1080
gatattgatt caggttttgt agttcaaata ccttattgta caagtcagg agtacaaaca   1140 agtgaggtag gtttatattt aactcattca aatttatata attaa               1185

<210> SEQ ID NO 21
<211> LENGTH: 2919
<212> TYPE: DNA
<213> ORGANISM: Toxoplasma gondii
```

<400> SEQUENCE: 21

```
atggatccac cactgccgcg atggagagcc gtggctgtgg cagcttttct catcgccacc      60
atctgtcaca atggcgtgga cgccgacatt cctcaggccg tgtcacggca acagatctgc     120
acagtcaatg gcgcatatgg aaaggatgat cctagacgaa tgcagtgcaa agatacgatt     180
ctagggactc tgagaatatc taataaagag aaattttcgt ttaatgtcat gcaaaacacc     240
atcgattccc gggacaagac atacgctgac gtgggaaatg tcggattcgt cgtgaccatt     300
acgaagactc ccgtaacaat atcgctgcct ctagagtaca tcaaggaggt accgttcgat     360
tatcgggaag agatatacga atattcccgg tgggaggctg gcgactgcc ggagaagttt      420
tgttacgaag acacgacaga caaatgctct gaagatggga agctggcggt ccaccctcac     480
ggcaagcccc tgtcatgggc ccacggccgc tgctgctggt gtagtgaagt gctggctttc     540
acgcatatca acaacatgaa gagggcaac ttccgttgca attggtttgc cccgccccgc      600
gccttggaac tggtgactga aaccctctac gaccagtgtg aagccgggaa aatagacggc     660
accgttccat tggaccgaga ttgcgaaaga gagaagcacg agcgcttggg catcaccgac     720
agagtttaca cactgaacta cactacacca gaaatcttcg accgttctgt ctattgcaat     780
acaaagtctt gcttgaaaca cgccatcatc ttggacaagg actatgtttc tgtcacgggt     840
tatgaatgcg acaaagttgg caccggcctc gatcgatggg gagacatgag aggagagttt     900
tgcaatctgt taccagggac ttgtatcact ggccagcttc ggaaattcaa ggaagtcgac     960
aagctacgga tcgaacaaaa tctggcacca ttatatgcac tgaaacggga gttcggggc     1020
ttccctcgat atgcgccaaa cccgatgaat ggaacgggtt tttcaacaac aggcacaaga     1080
cactacctcg gctacgattt tggcgagcag cactactcag acatccgttt cgagatggat     1140
gcaaccgatg tcacatggtt gagggcaaca tcacccggtc acataacctt cattgaggtg     1200
cctcagctag acgcatgctc gtccagtacc attggcgggt gtccactgaa agcctacgtc     1260
tggaattcag gcaacgaaga tgctgcattt gcagtagagg taccctttg tatcgattcg      1320
attacaaagg agcgaacaat cgatgtaaat cccattacgc cagttcggac gacagtgcct     1380
gctgacaaaa cggttgtttt cacgttaacc tttaaagcca tttcttctag tagtcttggc     1440
gttacatgtt tcatgaagct gtacgatgcc cagcatctca tgctcgacca aaagacattc     1500
aatgtgacga cgtcggctgc tcaggcacac gacacacagc actcacacaa aataacgaag     1560
atgcctcaga gaaaactact cggggggct tttacgaaag cagccgtcgg tgccacagca     1620
gcaatgggtt tctttggtcg gagaacgggg aagaagaaga aggagacac aaatgttgag     1680
gcgcattctg taacgccaca atcgtttgcc gaagacgcaa gaggtcctgg gatccaagat     1740
aaacttcagg gaaaggctga cccggcagaa acgtctctgt cgggggaatc ggccacgagt     1800
cacgcagcga agttgagcaa gaaggaaaaa cgcagtttac gcaaacaagc aaagaaacaa     1860
aaaaggcaag aatatcagcg gcaggcagcg gcagggaacg cagaaatttg gcaggagaa     1920
ggagaagcca ctgcgtctaa aaaagacatg gtttccaaga gaatgggggt cgagggggtcg    1980
cggtcctcga ctatgggtat cgccgacaac aaccaatctg cttcagcagt cacgaagtca     2040
aaaccgcata tcatgaagga caacgggag acaggggcca aacgaaggca aggggagtgt     2100
gcaagaacaa aggaggaaga taacgcggg cacgtagaag ggaaactgaa ggagaaacac      2160
tctacccaga gccaaccgga tcatcctctc tctgcaggaa acaagggcac gagcacaact     2220
caacagatca ggagtcagat tgaacataaa tcctccattt tcatgggaaa cgacaatcag     2280
```

| | |
|---|---|
| acacctctcg aagtagagct agaaggacaa ctgcggaaac atctaggtca agatgactct | 2340 |
| gattcgcacc cgtcaaaggc cggaaaagac aaggtgcttg agcacgggca acacccgtc | 2400 |
| gagagggaaa aagaaggcaa cgaagaggat agcgcagata gagggaaaga acgatcaaac | 2460 |
| gttgggatca ctggtgcagc agggaagatg aggaagttcc tgcacagaaa aagggatgaa | 2520 |
| atcgaatacc aagaaggccg tgaagaggcg ggattagacg cagtgtccat cagtagagga | 2580 |
| agtacacaat gcacccgtgc acggaaggcg aagagaaaga agcagcattt gaaggaaccg | 2640 |
| cgaacaccgc aagaagaaaa cccagaagat gacatcgaag aacaggacag agatgaagaa | 2700 |
| ggcgaatccg atacactaag ggatacgact gaccaaggag gcgcatcacc gcagacagca | 2760 |
| cgaccagagc tcaccacagt agtggcacat gaacccgaaa cacgggggga aaaatacatt | 2820 |
| gaagggagtt tctcgactct accctctgtg gaaatcgagg aacacaaaga gattcagatg | 2880 |
| gtcgaaacaa atcctagtta ctgtgtttca atgaggtag | 2919 |

<210> SEQ ID NO 22
<211> LENGTH: 2280
<212> TYPE: DNA
<213> ORGANISM: Theileria parva

<400> SEQUENCE: 22

| | |
|---|---|
| atgagctctt taggccctttt tagaagtgtg ttcacttccc ttatatactt ctcaatccta | 60 |
| cacattctcg gctttacatc actattcaat ttttacacca ctgatagcac tggtttcttc | 120 |
| tttgttgact cagcagtgac cggaaacata acccaatgtg ttagaaatag cgataaactc | 180 |
| ttcgatgatc aaacttgtgt acaaagattg cacaccaacg tcgatgtctc acatggactc | 240 |
| agggagtacc attacatata tagaagaaaa gatgatttat ctaagggatt atacttggtg | 300 |
| ttaaagacct caaacacttc tctactctac actctcaatt atcaaactat ggtcccgttg | 360 |
| tattatacgg atcatacgga gaggtggacg tatagtgaga tttcaggtga gttgaagacc | 420 |
| tcgtgtaaga gtgtgcaaaa ttctaaatgc actaaaaaaa ctcaagttcc accaggtatt | 480 |
| gatttcttac ccagagtctg ctgtatctgc ggactgaacg tacataaacc aacgccaaga | 540 |
| gctgatttta aatgcggagg atttctggct atgggaggta ggacagcgtt gagtatgagt | 600 |
| tgtttggaga taagtgagcc ctggtataag ctttacaaga ccagttaccc accagccata | 660 |
| agcagaagtg ttactgttaa catttacaaa ttcgattcat ccactggaat tatcccagac | 720 |
| gtgacattgg aggatgagga taaatttgat aattatgact ttaagaagcg ggagaagaag | 780 |
| gacccggtga tcaagtcacc ggagatcaaa tcacgctcca ctaaagaaat aacgggaaaa | 840 |
| aaagatgaat tacaccccaa tttcagacgc atcatcatcg atgataccgt caaagaagaa | 900 |
| catatcaatg atttggatgt gaagataacg ctgttgtcga gtaatacgaa ggatggctct | 960 |
| gcgcccccgt tatttgataa atacgtagcc ataccatcat tcccaagaac caatgaaacc | 1020 |
| gtcaaaggct catcactcat ggacaaatgt caagacagca cctggaaaac caaacccgaa | 1080 |
| tgtcccaaat atatgaatcc atcgttgtgt gatatatggc gttgtacgtt gaatatgagg | 1140 |
| actgtgaaga tgagtgcggt ggatacggat gggttgatgt gtgataaaat cggcttatca | 1200 |
| atgaagaggt gggcaaacca agaggaaatt tgtaactcaa gccccggctc atgcctcaaa | 1260 |
| aatcagctga acactactt cgatcaggaa aaagatgagg ccaaattacc aaaattgtac | 1320 |
| ggagtagagc caacgtttac agcggttaaa aagatctgt cattaccagc agtaaaggaa | 1380 |
| gcaaataaaa caactctgga tgatccaaac agaattcaca ctctcactta tatccactct | 1440 |
| aaggacgatg ttaccagact taaaatcgat accttcgacg ccacagtcac cgaaatcatc | 1500 |

-continued

```
tccgatttcc ccgggttcat cgtctccgca aagatggacg gagagtgtga ggtatcttcg   1560
gagaaaggct gtaacatgga attggacgtt aaaaacatgg gtaaatttac acacaaaaat   1620
agtattttag gggttaagaa gtcggaattt accgttagag cgaattgtta tgatgatcct   1680
gaccttaaaa atgaagttgc tcagatttct gaaactacac tcagtatcga cgggaataaa   1740
aataaaaccg tctctatacc aatcaaactc acaggatcac tcgctagtga aaaaggatac   1800
tgcaacatca ttctcctttc cggaaagaag gagatgttgg atggtatgaa gatggagata   1860
aaggtgaagg tgaagaagga gacgtttggt aaggatccgg ttaaggtcca ggatatagtg   1920
gctgctccta gtcctaagga taaattaacc actcctcaag tgattaaccc gattgtcatt   1980
aaccaacccg ggtctaaaaa tgacactaaa aaagaggaag agtcacaatg caaatgcgcg   2040
tcctggaata tcttctgcat gctcatcaac tttaagatat gtgtttcgtc ttatgtgagt   2100
aaggtattat tttacgtgtt gattgcactt ggaattttat tgcttttgat tttgttgccg   2160
gtgttgattc cgttaattgt tagtctcttt aaggctctcg ctggactcat caaaacacca   2220
ctcgaagccc tcgaacaaag aagattaaag aaaaaaaaca atacacaact tgaagtttaa   2280
```

```
<210> SEQ ID NO 23
<211> LENGTH: 498
<212> TYPE: DNA
<213> ORGANISM: Eimeria tenella

<400> SEQUENCE: 23
gcagctgctg ctgctgcggc tgcagcctcc cgcagtgtct cgacacatca gtagcaacgt     60
gctgccgcaa atgaattttt atttgtggct tctaggggta ggcttgtata ccccttcact    120
gcagcagcag atgatgatac cgtctcggaa cagggttttc attttgacgc tacatggttt    180
gcgcggtctc gagcaaagaa tgtcaattcc gattgtggca cttcaagcta cggtaatgct    240
ttacgtgacg aagtgctttt ccagttcttt ctcccgatga gctttttaat ttcaggctca    300
ccattttgta accctaagag ctgtctgagg catatgatcg tcctagacga acaacacgtc    360
acagtggatg gcagcacgtg tgatctcccg ggagtttcac tgcagcaatg ggaagagac     420 ggcttttgtg attacgcaca aggaacgtgc tttgcgaaaa acttgaagtg gtttcatgaa    480
tacaacgaac aggccgca                                                  498
```

```
<210> SEQ ID NO 24
<211> LENGTH: 1731
<212> TYPE: DNA
<213> ORGANISM: Leishmania major

<400> SEQUENCE: 24
atggggggca ccgccacggc aacggcctac gtgcggtcct gcgacggagc ctcgccaccc     60
acgccgcctg ggtgcgggct caagctggtg gtggacctca ccctcgacga cagcattctc    120
accggctccg tcttggagac agaggtgatg gtgacgcacg cgttgcatga gtcactcttt    180
ccccgtgacg cggcgtccga tgccgctggc acagctgcca cctctctgca ggtgtctctg    240
cctcccatca cggtggcaat gcggcgtggc gctgtgcaga tgcgctacgg gctcacctac    300
ctacgcacgt tcccggcggc attgcgagac tctgtgcggg tactgaagac ggccatgtcg    360
tgcgacgacg gcgtcacgcg ctgtccttcc tacatgagca tgacagggac gcttgtgtcg    420
gcgccgctcg gattgtgctg cctctgcacc agcgtggagt gcgccctcac aagcgacctg    480
tgcaacgctt cgatgcgcgc gcacttttgc ttccgcaccg gtgcagccgg aatcacgtgc    540
```

-continued

```
gtacagagcg agggcatcac ctaccacgga tgggccgtgg gatcgtcgtc gccctactac    600
atgatgcacc tatccgcgag cgggcgaggg atcgcaccga cgacactgca gctcacgacg    660
gacgccctg aggtgcagaa gggtgcgtct gctctgcaga ttcttcgggc ctctggtgtt     720
ttgcccggag agtcaaaccc cacgttgat atttccgggc gcgttctctt tgtcccctct     780
gcagaacaca gcagtgccag ccgcagcatc agcaccgggc ctgtgcgcga cgacccg       840
gcagagtggc tgttgctccc ggcgccgctt gtcagcgtct ccggcaatga ttgcgacaag    900
gtcggcatct caccagacta tttctactcg ctctccagca ctaagcagtg caacgcgcag    960
aaggggacgt gcgtgcgaca ccagctagca gactaccgtg cggcggacct ggaacagatc   1020
gcccagggcg tcggcggacg ctatatcgcc gcctctctgg gcaccttcac gcggcaggcg   1080
atgagggaac aggagttcct gctcgatgcg gtggagcgca cgggtggggc gatgctgcgg   1140
tggacggtga atgcggacgg cctcgtgttc cagccgcttc cggtacacgg tgtactggat   1200
gctatcaagt ttgacagcag cacaggcatc ctctacgtca cggttcgcaa caacaacaca   1260
tatggtggcc tctactacgt tgccgttggt cagtgtcggg gagcacgcgc atcgaactgc   1320
gatagcgacg gcgtgacaca cgagtgtggt cgcacggctt tggtggccgg ggctaacacc   1380
tcctcgctgt tgcagttcag catggtgagc gacctgcccg aggaggtggg gagcaccgcc   1440
tcatgcaccg tcgtctttcg cgacgcggcc gcagcgctgc tggcctctgc aaacatttcc   1500
tggacggtcg agcacacgac cactacgccg gcgccgaatg cccccaaagc ggagcagtgc   1560
agacgctgcg cctttcgcga cctgcggtgt cttttcagca ccgtctgcga gtggcagatg   1620
ctcctgtgga cagcggtggc ggtggcggtg acgtggacgc cgtatgccat cttggcctac   1680
tggcgtatgg cgtggcacgt tggcgccaag ctcttggcgt gtctgaactg a            1731
```

<210> SEQ ID NO 25
<211> LENGTH: 692
<212> TYPE: PRT
<213> ORGANISM: Artificial sequence
<220> FEATURE:
<223> OTHER INFORMATION: Syntehtic peptide.

<400> SEQUENCE: 25

```
Met Arg Gly Ser His His His His His Gly Ser Ala Cys Glu Leu
1               5                   10                  15

His Ala Glu Val Ile Ala Ser Gly Arg Leu Glu Lys Cys Val Val Asp
            20                  25                  30

Gly Val Thr Glu Glu Leu Asp Cys Gln Glu Lys Val Val Thr Leu
            35                  40                  45

Thr Val Gly Asn Gly Gln Ser Leu Gln Thr Glu Ala Leu Glu Phe Ser
    50                  55                  60

Leu Ser Cys Leu Asn Ser Pro Asp Gly Arg Cys Pro Cys Ser Cys Ser
65                  70                  75                  80

Ala Ala Asp Pro Thr Cys Ala Cys Arg Asp Leu Ala Ala Pro Leu Arg
                85                  90                  95

Val Ser Leu Thr Lys Ser Pro Leu Trp Ala Ser Tyr Pro Leu Gln Tyr
            100                 105                 110

Leu Ser Ser Phe Asn Trp Lys Pro Leu Glu Val Ile Leu Arg Pro Ser
        115                 120                 125

Asn Lys Val Cys Lys Asp Gly Asp Trp Glu Asp Ser Pro Thr Cys Gly
    130                 135                 140

Trp Phe Ser Gln Gly Gly Val Arg Val Ala Asp Ser Gln Gly Phe Cys
145                 150                 155                 160
```

-continued

Cys Glu Cys Ser Ser Ser Gln Val Trp Asp Asp Thr Phe Gly Ser Ser
                165                 170                 175
Lys Glu Arg Thr Arg Ala Asn Leu Asp Cys Asp Phe Trp Ser Asp Pro
            180                 185                 190
Leu Asp Ile Leu Ile Gly Arg Lys Pro Val Ser Ala His Cys Leu Thr
        195                 200                 205
Phe Asp Pro Gln Trp Tyr Ser Gly Tyr Glu Leu Gly Ala Ala Ser Leu
    210                 215                 220
Gln Phe Glu Ile Ala Ile Thr Val Glu Val Pro Thr Ala Pro Ser Pro
225                 230                 235                 240
Thr Thr Ala Thr Thr Ser Ala Thr Pro Arg Thr Asn Asn Ser Ser Ser
                245                 250                 255
Ala Asn Ser Thr Asn Ser Thr Asn Ser Pro Ala Pro Gln Phe Leu Ser
            260                 265                 270
Pro Pro Ala Pro Ser Thr Arg Glu Val Leu His Leu Gly Pro Ser Val
        275                 280                 285
Pro Leu Ala Ser Ser Ala Ser Arg Leu Leu Ser Ala Lys Leu Leu Gly
    290                 295                 300
Asp Leu Ala Met Tyr Thr Gln Leu Pro Ala Ile Ser Asn Gln Val Leu
305                 310                 315                 320
Met Val Pro Gln Pro Pro Ala Ala Ala Ala Thr Gly Ser Pro Leu
                325                 330                 335
Asp Ala Thr Leu Ala Thr Asn Arg Ser Ala Trp Met Leu Leu Asp Lys
            340                 345                 350
Thr Met Leu Ser Met Asp Gly Leu Ala Cys Asp Lys Val Gly Thr Gly
        355                 360                 365
Phe Ser Ala Phe Arg Tyr Gln Pro Ser Gly Cys Gly Arg Ala Pro Gln
    370                 375                 380
Ala Cys Leu Ser Gly Gln Leu Lys Asp Leu Trp Glu Ala Asp Leu Ala
385                 390                 395                 400
Arg Ile Ala Asp Gly Arg Val Pro Leu Tyr Met Ile Thr Arg Phe Thr
                405                 410                 415
Gly Gly Ser Asp Thr Thr Leu Gln Ser Phe Ser Gly Pro Leu Ser
            420                 425                 430
Phe Ala Leu Pro Val Thr Ser His Ser Gln Ser Leu Val Thr Leu Ser
        435                 440                 445
Val Ala Ala Asp Gly Val Arg Leu Val Thr Asn Arg Ser Pro Gly Lys
    450                 455                 460
Ile Thr Gly Ala Ala Val Cys Arg Phe Ala Gly Thr Ser Cys Gly Gly
465                 470                 475                 480
Phe Glu Ala Val Ala Arg Gly Tyr Ile Tyr Val Asn Ile Thr Asn
                485                 490                 495
Thr Gly Arg Leu Asp Ser Asp Tyr Thr Leu Thr Val Ser Asn Cys Ser
            500                 505                 510
Ser Asn Val Arg Pro Ile Glu Ala Arg Thr Leu Ala Val Arg Ala Gly
        515                 520                 525
Ser Ala Ala Ser Leu Asp Pro Pro Met Glu Leu Tyr Val Glu Asp Gln
    530                 535                 540
Ala Ala Ala Ala Ala Arg Thr Cys Thr Val Ser Leu Tyr Asp Ser Val
545                 550                 555                 560
Gly Ala Val Thr Asp Ser Leu Thr Leu Ser Phe Tyr Thr Asn Ala Thr
                565                 570                 575

```
Gln Leu Val Val Lys Pro Ser Gly Gly Tyr Asn Gly Thr Gly Asp Gly
            580                 585                 590

Ala Gly Val Lys Arg Asn Gly Thr Asp Cys Ser Thr Ala Cys Thr Asn
        595                 600                 605

Pro Ile Asp Val Leu Cys Phe Val Thr Lys Lys Cys Trp Ser Lys Phe
    610                 615                 620

Gly Arg Leu Leu Gly Ile Ile Gly Gly Ala Leu Val Gly Leu Gly Leu
625                 630                 635                 640

Leu Ala Val Ala Leu Lys Phe Gly Trp Leu Ala Ser Leu Ala Ala Ser
            645                 650                 655

Cys Cys Gly Gly Gly Gly Ala Ala Ala Gly Gly Ala Gly Gly Gly
            660                 665                 670

Met Gly Leu Gly Thr Gly Gly Gly Gly Cys Phe Gly Gly Gly Gln
        675                 680                 685

Gln Gln Gln Gln
        690

<210> SEQ ID NO 26
<211> LENGTH: 5841
<212> TYPE: DNA
<213> ORGANISM: Artificial sequence
<220> FEATURE:
<223> OTHER INFORMATION: Synthetic oligonucleotide.

<400> SEQUENCE: 26
ctcgagaaat cataaaaaat ttatttgctt tgtgagcgga taacaattat aatagattca      60
attgtgagcg gataacaatt tcacacagaa ttcattaaag aggagaaatt aactatgaga     120
ggatcgcatc accatcacca tcacggatcc gcatgcgagc tccacgctga ggtcattgca     180
agtgggcgct tggaaaaatg cgtcgtcgat ggtgttaccg aggagctgga ctgccaggag     240
aaggtggtgg tgacactgac ggtcggaaat gggcagagcc tgcagaccga ggctctggaa     300
ttctcgctca gctgcctcaa cagccccgac ggacgctgcc cctgcagctg cagcgccgcc     360
gaccctactt gcgcatgtcg tgacctggcg cgccgctgc gcgtgtcgct taccaagtcg     420
ccgctgtggg cctcctaccc gctgcagtac ttgtcgtcct ttaactggaa ccccctggaa     480
gtcatcctgc gccccagcaa caaagttttgc aaggacggcg actgggagga ctcgcccacg     540
tgtggctggt cagccagggg cggtgtgcgg gtggcggaca ccagggatt ctgctgcgag     600 tgcagcagca gccaggtgtg ggacgacacc ttcgggtcca gcaaggagcg cactcgcgcc     660
aacctggact gtgacttctg gagcgaccca ctggacatac tgattggccg caagccggtg     720
tccgcacact gcctcacatt cgaccccgca gtggtacagcg gctatgagct gggcgccgcc     780
tcgctgcagt tcgagatcgc catcaccgtg gaggtaccca ccgccccctc cccaccaca     840 gccaccacct ccgccactcc ccgcaccaac aacagcagta gcgccaacag caccaacagc     900
accaacagcc cggcgccgca gtttctgtcc ccgcctgcgc ccagcacgcg ggaagtgttg     960
catctgggtc cctcggtgcc tctggccagc agcgcgagcc gcctgctgtc cgccaagctg    1020
ctgggcgacc tggccatgta cacacagctg cccgcaatca gcaaccaggt gctgatggtg    1080
ccgcagccgc cagccgccgc cgccgccacc ggctcgcccc tggacgccac cctggcgacc    1140
aaccgctccg cctggatgct gctggacaag accatgctca gcatggacgg cctggcctgc    1200
gacaaggtgg ggaccggctt ctcagccttc gctaccagc ccagcggctg cggccgtgcc    1260
cctcaggcct gtctgtccgg ccagctcaag gacctgtggg aggcggacct ggcgcgtatc    1320
gcggacggcc gggtgccgct gtacatgatc accaggttca ctggcggcag cgacaccacg    1380
```

```
ctgcagtcct tctccggggg cccgctgtcg ttcgcgctgc ctgtcaccag ccacagccag   1440
agcctggtga cgctgagtgt ggcggcggac ggcgtgaggc tggtcaccaa ccgcagcccg   1500
ggcaagatta caggcgcggc ggtgtgccgt ttcgccggca cttcctgtgg cggctttgag   1560
gcggtggcag ctcgcggcta catctacgtc aacatcacca acaccggccg cctggacagt   1620
gactacacac tcacagtgtc caactgctcg tccaacgtgc ggcccatcga ggcgcgcaca   1680
ctggccgtac gcgcgggatc cgccgccagc ctggatccgc ccatggagct gtacgtggag   1740
gaccaggcgg cagcggcggc gcgcacgtgc acagtcagcc tgtacgactc agtcggcgcg   1800
gtgacggact cgctcacgct gtccttctac acaaacgcca cccagctggt cgtcaagccc   1860
tccggcgggt acaacggcac gggggacggc gcgggcgtaa agcgcaacgg caccgattgc   1920
agcacggcct gcaccaaccc gattgacgtg ctgtgcttcg tgaccaagaa gtgctggtcc   1980
aagttcgggc ggcttctggg catcatcggc ggcgccctgg tggggctggg gctgctggca   2040
gtagcactca agttcgggtg gctggcctcc ctggcggcct cgtgttgtgg gggaggagga   2100
ggagcagcag caggcggggc tggaggcggc atggggctgg ggaccggcgg cggcggaggc   2160
tgttttggag gcgggcagca gcagcagcag cctgctgcta gccatgccat gtcgccaccg   2220
cagcagcagc agcagcgctc gcatgcggag gtggcagcag gggctgcagt ggcaggagca   2280
ggagccgctg ttgcagcagc ggcggtgctg ggagccaaac acggcggcgg cggcggcgct   2340
cgtggcaagc agcagcatac cgacacccgg catttgcagg atcgcgactc acgagccacc   2400
gccgacggag caagcattga cagcagcagc gccggcggca gtagcagttt aagcagctac   2460
acccagcctc gtaaggccgg aggcaggctg ctgcagccgc cggcagcagc agtgtttgtg   2520
cctgaaggcg gcatcactag tgaattcgcg gccgcctgca ggtcgaagct taattagctg   2580
agcttggact cctgttgata gatccagtaa tgacctcaga actccatctg gatttgttca   2640
gaacgctcgg ttgccgccgg gcgtttttta ttggtgagaa tccaagctag cttggcgaga   2700
ttttcaggag ctaaggaagc taaaatggag aaaaaaatca ctggatatac caccgttgat   2760
atatcccaat ggcatcgtaa agaacatttt gaggcatttc agtcagttgc tcaatgtacc   2820
tataaccaga ccgttcagct ggatattacg gcctttttaa agaccgtaaa gaaaaataag   2880
cacaagtttt atccggcctt tattcacatt cttgcccgcc tgatgaatgc tcatccggaa   2940
tttcgtatgg caatgaaaga cggtgagctg gtgatatggg atagtgttca cccttgttac   3000
accgttttcc atgagcaaac tgaaacgttt tcatcgctct ggagtgaata ccacgacgat   3060
ttccggcagt ttctacacat atattcgcaa gatgtggcgt gttacggtga aaacctggcc   3120
tatttcccta aagggtttat tgagaatatg ttttcgtct cagccaatcc ctgggtgagt   3180
ttcaccagtt tgatttaaa cgtggccaat atggacaact tcttcgcccc cgttttcacc   3240
atgggcaaat attatacgca aggcgacaag gtgctgatgc cgctggcgat tcaggttcat   3300
catgccgtct gtgatggctt ccatgtcggc agaatgctta atgaattaca acagtactgc   3360
gatgagtggc agggcggggc gtaatttttt taaggcagtt attggtgccc ttaaacgcct   3420
ggggtaatga ctctctagct tgaggcatca aataaaacga aaggctcagt cgaaagactg   3480
ggcctttcgt tttatctgtt gtttgtcggt gaacgctctc ctgagtagga caaatccgcc   3540
gctctagagc tgcctcgcgc gtttcggtga tgacggtgaa aacctctgac acatgcagct   3600
cccggagacg gtcacagctt gtctgtaagc ggatgccggg agcagacaag cccgtcaggg   3660
cgcgtcagcg ggtgttggcg ggtgtcgggg cgcagccatg acccagtcac gtagcgatag   3720
```

```
cggagtgtat actggcttaa ctatgcggca tcagagcaga ttgtactgag agtgcaccat    3780
atgcggtgtg aaataccgca cagatgcgta aggagaaaat accgcatcag gcgctcttcc    3840
gcttcctcgc tcactgactc gctgcgctcg tctgtcggc tgcggcgagc ggtatcagct    3900
cactcaaagg cggtaatacg gttatccaca gaatcagggg ataacgcagg aaagaacatg    3960
tgagcaaaag gccagcaaaa ggccaggaac cgtaaaaagg ccgcgttgct ggcgtttttc    4020
cataggctcc gcccccctga cgagcatcac aaaaatcgac gctcaagtca gaggtggcga    4080
aacccgacag gactataaag ataccaggcg tttccccctg gaagctccct cgtgcgctct    4140
cctgttccga ccctgccgct taccggatac ctgtccgcct ttctcccttc gggaagcgtg    4200
gcgctttctc aatgctcacg ctgtaggtat ctcagttcgg tgtaggtcgt tcgctccaag    4260
ctgggctgtg tgcacgaacc ccccgttcag cccgaccgct gcgccttatc cggtaactat    4320
cgtcttgagt ccaacccggt aagacacgac ttatcgccac tggcagcagc cactggtaac    4380
aggattagca gagcgaggta tgtaggcggt gctacagagt tcttgaagtg gtggcctaac    4440
tacggctaca ctagaaggac agtatttggt atctgcgctc tgctgaagcc agttaccttc    4500
ggaaaaagag ttggtagctc ttgatccggc aaacaaacca ccgctggtag cggtggtttt    4560
tttgtttgca agcagcagat tacgcgcaga aaaaaaggat ctcaagaaga tcctttgatc    4620
ttttctacgg ggtctgacgc tcagtggaac gaaaactcac gttaagggat tttggtcatg    4680
agattatcaa aaaggatctt cacctagatc cttttaaatt aaaaatgaag ttttaaatca    4740
atctaaagta tatatgagta aacttggtct gacagttacc aatgcttaat cagtgaggca    4800
cctatctcag cgatctgtct atttcgttca tccatagctg cctgactccc cgtcgtgtag    4860
ataactacga tacgggaggg cttaccatct ggccccagtg ctgcaatgat accgcgagac    4920
ccacgctcac cggctccaga tttatcagca ataaaccagc cagccggaag ggccgagcgc    4980
agaagtggtc ctgcaacttt atccgcctcc atccagtcta ttaattgttg ccgggaagct    5040
agagtaagta gttcgccagt taatagtttg cgcaacgttg ttgccattgc tacaggcatc    5100
gtggtgtcac gctcgtcgtt tggtatggct tcattcagct ccggttccca acgatcaagg    5160
cgagttacat gatcccccat gttgtgcaaa aaagcggtta gctccttcgg tcctccgatc    5220
gttgtcagaa gtaagttggc cgcagtgtta tcactcatgg ttatggcagc actgcataat    5280
tctcttactg tcatgccatc cgtaagatgc ttttctgtga ctggtgagta ctcaaccaag    5340
tcattctgag aatagtgtat gcggcgaccg agttgctctt gcccggcgtc aatacgggat    5400
aataccgcgc cacatagcag aactttaaaa gtgctcatca ttggaaaacg ttcttcgggg    5460
cgaaaactct caaggatctt accgctgttg agatccagtt cgatgtaacc cactcgtgca    5520
cccaactgat cttcagcatc ttttactttc accagcgttt ctgggtgagc aaaaacagga    5580
aggcaaaatg ccgcaaaaaa gggaataagg gcgacacgga aatgttgaat actcatactc    5640
ttcctttttc aatattattg aagcatttat cagggttatt gtctcatgag cggatacata    5700
tttgaatgta tttagaaaaa taaacaaata ggggttccgc gcacatttcc ccgaaaagtg    5760
ccacctgacg tctaagaaac cattattatc atgacattaa cctataaaaa taggcgtatc    5820
acgaggccct ttcgtcttca c                                              5841
```

<210> SEQ ID NO 27
<211> LENGTH: 31
<212> TYPE: DNA
<213> ORGANISM: Artificial sequence
<220> FEATURE:
<223> OTHER INFORMATION: Synthetic oligonucleotide.

```
<400> SEQUENCE: 27
ccccgggccc gcgcgttatt attattcggg c                              31

<210> SEQ ID NO 28
<211> LENGTH: 39
<212> TYPE: DNA
<213> ORGANISM: Artificial sequence
<220> FEATURE:
<223> OTHER INFORMATION: Synthetic oligonucleotide.

<400> SEQUENCE: 28
ggggaagctt tttttctaaa tgaaatatta aagaatggc                      39

<210> SEQ ID NO 29
<211> LENGTH: 38
<212> TYPE: DNA
<213> ORGANISM: Artificial sequence
<220> FEATURE:
<223> OTHER INFORMATION: Synthetic oligonucleotide.

<400> SEQUENCE: 29
ccccgaattc attacatgga atagtatttg caaatttg                       38

<210> SEQ ID NO 30
<211> LENGTH: 33
<212> TYPE: DNA
<213> ORGANISM: Artificial sequence
<220> FEATURE:
<223> OTHER INFORMATION: Synthetic oligonucleotide.

<400> SEQUENCE: 30
ggggtctaga caatatacat gctgataacc tcc                            33

<210> SEQ ID NO 31
<211> LENGTH: 26
<212> TYPE: DNA
<213> ORGANISM: Artificial sequence
<220> FEATURE:
<223> OTHER INFORMATION: Synthetic oligonucleotide.

<400> SEQUENCE: 31
ctcgaatatg tagatatatc cagatg                                    26

<210> SEQ ID NO 32
<211> LENGTH: 27
<212> TYPE: DNA
<213> ORGANISM: Artificial sequence
<220> FEATURE:
<223> OTHER INFORMATION: Synthetic oligonucleotide.

<400> SEQUENCE: 32
cagagatgtt atagctagtg atataac                                   27

<210> SEQ ID NO 33
<211> LENGTH: 31
<212> TYPE: DNA
<213> ORGANISM: Artificial sequence
<220> FEATURE:
<223> OTHER INFORMATION: Synthetic oligonucleotide.

<400> SEQUENCE: 33
ctaagtagca actattttgt aaaattatat c                              31

<210> SEQ ID NO 34
```

```
<211> LENGTH: 26
<212> TYPE: DNA
<213> ORGANISM: Artificial sequence
<220> FEATURE:
<223> OTHER INFORMATION: Synthetic oligonucleotide.

<400> SEQUENCE: 34
gcataagatt cacaaataca aaaagg                                          26

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide.

<400> SEQUENCE: 35
ggtcttcctc taagtatt                                                   18

<210> SEQ ID NO 36
<211> LENGTH: 18
<212> TYPE: DNA
<213> ORGANISM: Artificial sequence
<220> FEATURE:
<223> OTHER INFORMATION: Synthetic oligonucleotide.

<400> SEQUENCE: 36
ccagatggtc aaatgccc                                                   18

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide.

<400> SEQUENCE: 37
ctgtggtgat ggccatgaac                                                 20

<210> SEQ ID NO 38
<211> LENGTH: 23
<212> TYPE: DNA
<213> ORGANISM: Artificial sequence
<220> FEATURE:
<223> OTHER INFORMATION: Synthetic oligonucleotide.

<400> SEQUENCE: 38
gcgccctcat agcccgccaa atc                                             23

<210> SEQ ID NO 39
<211> LENGTH: 24
<212> TYPE: DNA
<213> ORGANISM: Artificial sequence
<220> FEATURE:
<223> OTHER INFORMATION: Synthetic oligonucleotide.

<400> SEQUENCE: 39
ccgccaaatc agtcctgtag cttc                                            24

<210> SEQ ID NO 40
<211> LENGTH: 24
<212> TYPE: DNA
<213> ORGANISM: Artificial sequence
<220> FEATURE:
<223> OTHER INFORMATION: Synthetic oligonucleotide.

<400> SEQUENCE: 40
```
tgcgcgcttg gcgtaatcat ggtc                                          24

<210> SEQ ID NO 41
<211> LENGTH: 21
<212> TYPE: DNA
<213> ORGANISM: Artificial sequence
<220> FEATURE:
<223> OTHER INFORMATION: Synthetic oligonucleotides

<400> SEQUENCE: 41
gctagagctg cagccatcag c                                             21

<210> SEQ ID NO 42
<211> LENGTH: 749
<212> TYPE: DNA
<213> ORGANISM: Artificial sequence
<220> FEATURE:
<223> OTHER INFORMATION: Synthetic oligonucleotide.

<400> SEQUENCE: 42
ccgccaaatc agtcctgtag cttccatatc tgattcgcaa tcttgccttg cacctgcctg     60
ccacgctcat accatgtcgc cgtgacccca aaacaggcct gtctgtccgg ccagctcaag    120
gacctgtggg aggcggacct ggcgcgtacc gcggacggcc gggtgccgct gtacatgatc    180
accaggttca ctggcggcag cgagggctaa tcgcgccgga aaatatatca gtaaccgatt    240
catacagcac cgggaatgcc gcacaggcaa tgctggagaa actgctgcaa atttatgatg    300
ttaaaacgtt ggtggcgcag cttaatggtg taggtgagaa tcactggagc gcggcaattt    360
taaaacgtgc gctggcgaat gactcggcat ggcaccgttt aagtgagaaa gagttcgccc    420
atctgcaaac gttattaccc aaaccaccgg cacatcatcc gcattatgcg tttcgcttta    480
tcgatctatt cgccggaatt ggcggcatcc gtcgcggttt tgaatcgatt ggcggacagt    540
gcgtgttttc cagcgaatgg aacaaacatg cggtacgcac ttataaagcc aaccattatt    600
gcgatccggc gacgcatcat tttaatgaag atatccgcga catcaccctc agccataaag    660
aaggcgtgag tgatgaggcg gcggcggaac atattcgtca caatttcac acaggaaaca     720 gctatgacca tgattacgcc aagcgcgca                                     749

<210> SEQ ID NO 43
<211> LENGTH: 23
<212> TYPE: DNA
<213> ORGANISM: Artificial sequence
<220> FEATURE:
<223> OTHER INFORMATION: Synthetic oligonucleotide.

<400> SEQUENCE: 43
atgtcgccgt gaccccaaaa cag                                           23

<210> SEQ ID NO 44
<211> LENGTH: 24
<212> TYPE: DNA
<213> ORGANISM: Artificial sequence
<220> FEATURE:
<223> OTHER INFORMATION: Synthetic oligonucleotide.

<400> SEQUENCE: 44
ctggctggtg acaggcagcg cgaa                                          24

<210> SEQ ID NO 45
<211> LENGTH: 22
<212> TYPE: DNA

<213> ORGANISM: Artificial sequence
<220> FEATURE:
<223> OTHER INFORMATION: Synthetic oligonucleotide.

<400> SEQUENCE: 45
ttggctgcgc tccttctggc gc                                                22

<210> SEQ ID NO 46
<211> LENGTH: 572
<212> TYPE: PRT
<213> ORGANISM: Dictyostelium discoideum A

<400> SEQUENCE: 46

Met Ile Lys Lys Leu Ile Phe Phe Ser Ile Phe Ile Phe Phe Ile Lys
1               5                   10                  15

Ile Asn Leu Ile Trp Cys Gly Ile Ile Ser Ser Ser Ile Glu Ser
            20                  25                  30

Cys Thr Leu Asp Gly Thr Glu Leu Ala Asp Gln Asp Lys Thr Asn Leu
            35                  40                  45

Lys Cys Asp Lys Lys Leu Val Val Ser Leu Tyr Ile Asp Ser Gln Lys
    50                  55                  60

Glu Asn Ser Glu Thr Phe Asn Phe Gln Val Ser Glu Ile Lys Asp Glu
65              70                  75                  80

Asn Gly Lys Leu Lys Thr Leu Val Ile Pro Ile Ser Val Lys Phe Lys
                85                  90                  95

Lys Ser Glu Thr Phe Ile Asn Tyr Pro Leu Val Tyr Val Gln Asn Val
            100                 105                 110

Ala Tyr Gln Pro Lys Glu Thr Val Ile Tyr Lys Thr Asp Tyr Val Leu
        115                 120                 125

Thr Ser Gly Cys Lys Asp Lys Pro Thr Asp His Thr Cys Pro Gly Ala
130                 135                 140

Ile Asp Ala Asn Gly Lys Leu Ile Arg Asp Ser Gln Gly Phe Cys Cys
145                 150                 155                 160

Ser Cys Ser Phe Ser Asp Tyr Val Gly Ala Asp Gln Asn Ser Arg Ala
                165                 170                 175

Asn Leu Gly Cys Ser Leu Leu Gly Ser Lys Ser Ser Ala His Cys
            180                 185                 190

Leu Ser Phe Ser Ser Val Lys Tyr Asp Val Tyr Asn Val Ala Lys Thr
        195                 200                 205

Gln Val Glu Tyr Thr Ile Thr Ala Thr Leu Tyr Ser Tyr Asn Gln
    210                 215                 220

Asn Pro Ile Thr Gln Asp Ile Ile Leu Ser Asn Ser Ala Pro Met Gly
225                 230                 235                 240

Met Asp Thr Phe Ser Gln Ala Ile Val Arg Ile Ile Gly Asp Phe Gln
                245                 250                 255

Ser Ser Thr Gln Ile Asn Gln Phe Thr Asp Lys Lys Val Phe Pro
            260                 265                 270

Tyr Asn Gln Pro Asn Ser Ile Asn Thr Cys Met Val Leu Asp Gln Asn
        275                 280                 285

Phe Phe Asp Leu Ser Gly Leu Thr Cys Asn Lys Ile Gly Val Ser Tyr
    290                 295                 300

Ser Ala Phe Gln Asn Gln Pro Asn Ser Cys Ala Ala Leu Phe Gly Ser
305                 310                 315                 320

Cys Leu Gln Asn Gln Ile Ala Asp Tyr Tyr Asn Ala Asp Val Ala Leu
                325                 330                 335

Ile Ser Ser Gly Lys Lys Gly Asn Tyr Ile Ala Ser Gln Leu Gly Thr
            340                 345                 350

Lys Val Gln Ile Ala Gly Asn Gln Asp Ser Arg Ser Leu Lys Ile Arg
        355                 360                 365

Phe Asp Glu Ser His Arg Thr Met Leu Thr Ile Thr Leu Lys Ala Asp
    370                 375                 380

Ser Leu Gln Tyr Ile Val Asn Ile Ser Pro Gly Lys Ile Ile Asn Tyr
385                 390                 395                 400

Gln Ile Asp Arg Phe Glu Ser Met Ser Lys Asn Gly Val Leu Arg Val
                405                 410                 415

Asn Val Gln Asn Thr Gly Thr Ile Asn Ala Asp Tyr Thr Met Thr Ile
            420                 425                 430

Ile Asn Cys Thr Gly Asp Ile Asn Pro Ile Asn Asn Gln Gln Val Thr
        435                 440                 445

Ile Lys Ser Lys Glu Ile Tyr Ser Phe Val Phe Gln Val Tyr Thr Thr
    450                 455                 460

Ser Lys Leu Asp Ser Ser Tyr His Cys Phe Gly Asp Leu Tyr Asn Glu
465                 470                 475                 480

Val Ala Gln Val Ile Asp Ser Ile Arg Ile Asn Phe Asn Thr Ser Asp
                485                 490                 495

Thr Glu Ile Asp Asn Gly Ala Gln Ser Gly Asp Asn Ser Leu Asp Gly
            500                 505                 510

Asp Ser Leu Asn Ile Gly Ser Glu Phe Thr Cys Asp Asp Val Cys Pro
        515                 520                 525

Asn Leu Tyr Val Ile Lys Asn Asn Asn Asn Asn Asn Asn Asn Asn Asn
    530                 535                 540

Asn Asn Asn Asn Asn Asn Asn Asn Asn Asn Asn Asn Asn Asn Asn Asn
545                 550                 555                 560

Asn Asn Asn Asn Asn Asn Asn Asn Lys Lys Asn
                565                 570

<210> SEQ ID NO 47
<211> LENGTH: 327
<212> TYPE: PRT
<213> ORGANISM: Dictyostelium discoideum B

<400> SEQUENCE: 47

Met Ser Asp Tyr Ile Asp Ala Asp Gln Asn Ser Arg Ala Asn Leu Gly
1               5                   10                  15

Cys Ser Leu Leu Gly Ser Gln Ser Ser Ser Ala His Cys Leu Ser Phe
            20                  25                  30

Ser Pro Met Lys Tyr Asp Val Tyr Asn Ile Ala Lys Thr Gln Val Glu
        35                  40                  45

Tyr Lys Ile Thr Ala Thr Leu Thr Tyr Ser Tyr Asn Gln Asn Pro Ile
    50                  55                  60

Thr Gln Asp Ile Ile Leu Ser Asn Ser Asn Pro Met Gly Met Asp Ser
65                  70                  75                  80

Phe Ser Gln Ala Met Ile Arg Ile Val Gly Asp Phe Gln Ser Ser Thr
                85                  90                  95

Gln Ile Asn Gln Phe Thr Asp Lys Lys Val Val Phe Pro Tyr Asn Gln
            100                 105                 110

Pro Asn Ser Ile Asn Thr Ala Met Leu Leu Asp Gln Asn Phe Phe Asp
        115                 120                 125

Leu Ser Gly Leu Thr Cys Asn Lys Ile Gly Val Ser Tyr Ser Ala Phe
    130                 135                 140

Gln Asn Gln Pro Asn Lys Cys Ala Ala Leu Phe Gly Ser Cys Leu Gln
145                 150                 155                 160

Asn Gln Ile Ala Asp Tyr Tyr Asn Ala Asp Val Thr Leu Ile Ser Asn
            165                 170                 175

Gly Lys Lys Gly Asn Tyr Ile Ala Ser Gln Phe Gly Thr Lys Val Ala
            180                 185                 190

Gly Asp Gln Asn Ser Arg Ser Leu Lys Ile Arg Phe Asp Glu Ser His
            195                 200                 205

Arg Thr Met Leu Thr Ile Thr Leu Lys Ala Asp Ser Leu Gln Tyr Arg
210                 215                 220

Val Asp Ile Ser Pro Gly Lys Ile Ile Ser Tyr Gln Ile Asp Arg Phe
225                 230                 235                 240

Glu Ser Met Ser Lys Asn Gly Ile Leu Arg Val Lys Val Gln Asn Ile
            245                 250                 255

Gly Thr Ile Asn Ser Asp Tyr Thr Leu Ala Ile Val Asn Cys Ser Gly
            260                 265                 270

Asp Ile Asn Pro Ile Asp Ser Lys Asp Val Thr Ile Lys Ser Lys Glu
            275                 280                 285

Ile Tyr Ser Phe Glu Phe Gln Ile Phe Thr Thr Ser Lys Leu Asp Ser
290                 295                 300

Ser Tyr Gln Cys Phe Gly Asp Leu Tyr Asn Glu Val Ala Gln Val Ile
305                 310                 315                 320

His Ser Cys Pro Cys Gln Asn
            325

<210> SEQ ID NO 48
<211> LENGTH: 672
<212> TYPE: PRT
<213> ORGANISM: Hydra magnipapillata

<400> SEQUENCE: 48

Met Lys Met Ile Phe Lys Met Lys Lys Gln Leu Leu Ser Ser Phe Phe
1               5                   10                  15

Asn Ile Thr Val Asn Ile Ile Phe Val Gly Gly Leu Ile Leu Ser Lys
            20                  25                  30

Ser Ser Ile Glu Phe Cys Glu Asn Thr Gly Ser Ser Asn Asp Leu Lys
        35                  40                  45

Asp Pro Thr Asn Val Val Thr Gln Ser Ala Cys Glu Lys Lys Met Val
    50                  55                  60

Val Leu Leu Ser Val Gly Asn Lys Gln Gly Glu Thr Glu Lys Leu Gln
65                  70                  75                  80

Ala Val Val Ser Val Val Gln Asn Ser Ala Thr Asn Glu Phe Ala Arg
                85                  90                  95

Leu Tyr Asn Pro Phe Met Ile Thr Val Ser Lys Ser Pro Val Tyr Leu
            100                 105                 110

Asn Phe Pro Phe Phe Phe Asn Gly Ile Thr Val Asn Asn Gln Pro Tyr
        115                 120                 125

Glu Glu Ile Ile Leu Ser Lys Asn Arg Trp Tyr Val Ser Asp Ser Ser
    130                 135                 140

Arg Gln Cys Leu Asp Gln Trp Gln Val Glu Glu Asp Asp Glu His
145                 150                 155                 160

Pro Thr Cys Gly Tyr Gln Tyr Thr Asn Ser Thr Gln Lys Gln Thr Asp
            165                 170                 175

Gly Thr Trp Lys Thr Val Lys Thr Arg Ile Trp Asp Ser Gln Gly Phe

-continued

```
              180                 185                 190
Cys Cys Tyr Cys Thr Gln Asp Leu Lys Asn Tyr Tyr Ile Lys Lys Asp
            195                 200                 205
Ile Gln Asp Ala Asn Arg Ala Gly Ile Ile Cys Lys Pro Leu Thr Asn
210                 215                 220
Ser Pro Gln Ala Ser Ala His Cys Met Arg Met Ser Asn Leu Trp Tyr
225                 230                 235                 240
Thr Leu Asn Glu Phe Thr Glu Ser Tyr Arg Asp Phe Ser Ile Tyr Val
                245                 250                 255
Lys Ala Phe Asp Gln Ile Thr Lys Val Val Gln Asn Lys Ser Tyr Ile
                260                 265                 270
Asp Tyr Val Asn Gly Gly Glu Ile Leu Leu Ser Pro Ser Gln Lys Ser
            275                 280                 285
Ala Thr Gly Ser Tyr Asn Arg Ile Thr Gly Asn Tyr Val Gly Asp Leu
            290                 295                 300
Gln Pro Ile Lys Ser Tyr Pro Val Leu Thr Asn Asn Tyr Phe Leu Ile
305                 310                 315                 320
Pro Phe Ser Ser Thr Asn Val Asp Pro Lys Lys Glu Pro Gln Leu Lys
                325                 330                 335
Ser Gly Ile Ser Lys Trp Met Ile Ile Pro Arg Asp Leu Val Ser Thr
                340                 345                 350
Asp Ala Lys Gln Cys Asp Met Ile Gly Val Gly Tyr Ser Ala Phe Arg
            355                 360                 365
Asn Gln Ala Ala Tyr Gly Thr Gly Tyr Gly Cys Arg Ala Lys Lys Gly
            370                 375                 380
Ser Cys Leu Ala Asn Gln Pro Tyr Asn Lys Phe Met Asp Asp Glu Asp
385                 390                 395                 400
Arg Leu Glu Lys Gly Lys Met Pro Trp Tyr Phe Pro Ala Arg Tyr Gly
                405                 410                 415
Lys Leu Ala Gly Val Lys Gln Asn Ile Gly Asp Asn Lys Tyr Leu
                420                 425                 430
Leu Thr Tyr Glu Leu Asp Asp Glu Gln Ile Ser Leu Val Thr Leu Gln
                435                 440                 445
Ile Ser Ala Asp Asp Val Val Leu Val Tyr Asn Arg Ala Thr Gly Ile
450                 455                 460
Ile Thr Arg Thr Ala Ile Gln Asp Phe Glu Ala Leu Ser Leu Glu Gly
465                 470                 475                 480
Gln Leu Ser Val Asp Val Leu Asn Thr Gly Tyr Val Ser Ser Asp Phe
                485                 490                 495
Arg Ile Ser Ile Pro Ser Cys Thr Ser Gly Val Gln Pro Ile Glu Glu
                500                 505                 510
Lys Arg Ile Thr Ile Asp Pro Gln Met Thr Glu Thr Ile Thr Phe Lys
                515                 520                 525
Met Met Thr Ser Thr Asp Lys Lys Ser Ala His Asp Cys Thr Ile Asn
            530                 535                 540
Leu Tyr Asp Ser Lys Asn Ile Leu Leu Gln Ser Arg Asn Phe Thr Phe
545                 550                 555                 560
Ser Thr Lys Ala Pro Cys Val Cys Glu Val Gln Ser Cys Lys Cys Asp
                565                 570                 575
Cys Ser Glu Gly Gly Val Lys Cys Val Gln Ala Glu Gly Lys Phe
            580                 585                 590
Ile Asp Asn Pro Asn Leu Phe Val Pro Gln Ser Thr Gly Phe Leu Asp
            595                 600                 605
```

Lys Leu Trp Ser Ser Ile Lys Ser Phe Pro Ser Ile Ile Gly Asn Phe
610                 615                 620

Phe Ser Gly Ile Phe Gly Ser Leu Phe Gly Asp Leu Val Gln Tyr Ala
625                 630                 635                 640

Ile Phe Ala Ala Ile Ala Leu Val Val Ile Cys Leu Cys Cys Asn Cys
            645                 650                 655

Gly Gly Phe Arg Leu Leu Lys Arg Phe Ile Pro Lys Phe Asn Lys Lys
            660                 665                 670

<210> SEQ ID NO 49
<211> LENGTH: 853
<212> TYPE: PRT
<213> ORGANISM: Nematostella vectensis

<400> SEQUENCE: 49

Met Gly Arg Gly Gln Ile Ile Met Ile Leu Val Gly Leu Leu Cys Leu
1               5                   10                  15

Ala Asn Glu Ser Tyr Ser Asp Val Ile Ala Lys Ser Ser Leu Gln Met
            20                  25                  30

Cys Glu Asn Thr Gly Asn Ser Asp Asp Pro Tyr Asn Val Val Asp Gln
        35                  40                  45

Lys Ala Cys Glu Lys Lys Leu Ile Val Thr Leu Ser Val Arg Ser Gly
50                  55                  60

Gln Asn Gly Thr Glu Phe Leu Lys Ala Val Thr Asn Val Ser Lys Val
65                  70                  75                  80

Tyr Asp Gln Thr Glu Lys Glu Met Ala Arg Leu Tyr Asn Pro Phe Ile
            85                  90                  95

Ile Thr Leu Ala Lys Thr Pro Val Lys Leu Thr Tyr Pro Tyr Tyr Tyr
            100                 105                 110

Leu Ala Met Val Asn Asn Lys Pro Thr Glu Arg Val Val Ile Ser Asp
            115                 120                 125

Ser Lys Trp His Ala Ser Gly Ser Tyr His Ala Cys Ser Asp Ala Trp
130                 135                 140

Asp Asp Glu Asp Ala Leu Cys Gly Phe Tyr Thr Asp Ala Glu Gly Lys
145                 150                 155                 160

Pro Ile Trp Asp Ser Gln Gly Phe Cys Cys Arg Cys Thr Glu Gln Glu
            165                 170                 175

Lys Trp Arg Gly Ser Phe Asn Asp Lys Asn Pro Tyr Ser Arg Ala Gly
            180                 185                 190

Ile Asn Cys Lys Leu Phe Gly Thr Gln Ala Ala His Cys Met Thr
            195                 200                 205

Phe Asp Asp Leu Trp Tyr Thr Val Asn Glu Val Gly Leu Trp Gln Met
210                 215                 220

Asp Phe Ser Ile His Val Lys Ala Tyr Asp Leu Val Val Glu Lys Val
225                 230                 235                 240

Gly Asn Lys Thr Gln Ser Lys Trp Val Asp Gly Glu Ile Val Ile
            245                 250                 255

Gly Pro Thr Ile Arg Ser Gly Val Gly Val His Gly Arg Leu His Ala
            260                 265                 270

Thr Phe Ile Gly Glu Phe Gln Ser His Lys Gln Phe Pro Val Leu Thr
            275                 280                 285

Thr Lys Tyr Leu Leu Ile Pro Tyr Val Ser Glu Lys Val Asp Pro Lys
290                 295                 300

Thr His Pro Gln Phe Arg Asn Gly Pro His Asp Tyr Met Leu Ile Asp

```
            305                 310                 315                 320
Lys His Glu Val Asn Tyr Lys Ser Ser Gly Pro His Glu Cys Asp Lys
                    325                 330                 335

Ile Gly Val Ser Phe Ser Ala Phe Arg Ala Gln Ala Pro Met Gly Cys
                    340                 345                 350

Ser Gln Lys Gln Gly Asp Cys Leu His Asn Gln Pro Lys Asp Tyr Phe
                    355                 360                 365

Glu Glu Asp Thr Lys Arg Arg Ala Ser Gly Lys Thr Pro Tyr Tyr Phe
            370                 375                 380

Pro Gln Lys Phe Gly Lys Leu Leu Gly Val Asn Gln Arg Lys Asp Asn
385                 390                 395                 400

Asn His Phe Val Leu Thr Tyr Glu Val Asp Glu Val Met Thr Ser Met
                    405                 410                 415

Val Thr Leu Gln Ile Ser Ala Asp Asp Val Ile Leu Ile Tyr Asn Arg
                    420                 425                 430

Ala Glu Gly Lys Ile Leu Arg Ala Tyr Ala Gln Asp Phe Glu Ala Leu
                    435                 440                 445

Ser Arg Asp Gly Asn Leu Tyr Val Ile Val Gln Asn Ile Gly Leu Val
            450                 455                 460

Thr Ala Asp Phe Tyr Val Val Ile Lys Glu Cys Ser Val Gly Ile Gly
465                 470                 475                 480

Lys Leu Leu Glu Lys Ala Ala Ser Ile Asn Pro Gln Gln Thr His Ser
                    485                 490                 495

Phe Thr Phe Ser Val Lys Ala Gln Gln Trp Lys Gly Gly Asp Asn Phe
                    500                 505                 510

Cys Ile Val Gln Leu Tyr Asp Ala Arg Arg Lys Met Val Asp Ser Ser
                    515                 520                 525

Asn Val Thr Phe Arg Thr Thr Glu Pro Cys Val Cys Ala Ser Ser Cys
            530                 535                 540

Gly Cys Ser Cys Phe Lys Asn Gly Phe Lys Cys Thr Lys Arg Glu Asp
545                 550                 555                 560

Arg Asp Phe Thr Lys Thr Lys Pro Lys Asp Ser Gly Leu Asp Leu Gly
                    565                 570                 575

Phe Phe Pro Lys Leu Trp Asn Lys Ile Lys Asn Val Trp Asp Thr Val
                    580                 585                 590

Thr Ser Val Phe Asn Phe Met Glu Ser Gly Trp Ala Leu Leu Gly Thr
            595                 600                 605

Ala Leu Gly Leu Leu Ser Leu Gly Gly Leu Lys Ala Phe Leu Gly Phe
610                 615                 620

Arg Lys Thr Gly Ser Arg Ile Ala Arg Phe Gly Phe Gly Gly Ala Asn
625                 630                 635                 640

Lys Gly Arg Val Arg Arg Asp Gly Ser Gly Arg Met Val Thr Met
                    645                 650                 655

Glu Phe Asn Glu Thr Gly Asp Arg Ile Asp Pro Glu Thr Lys Glu Val
            660                 665                 670

Ile Glu Pro Arg Asn Lys Lys Glu Leu Leu Asn Leu Phe Phe
                    675                 680                 685

Phe Phe Ile Leu Pro Phe Leu Leu Ile Tyr His Leu Val Gly Trp Ile
                    690                 695                 700

Arg Trp Arg Met Arg Lys Pro Gly Ser Glu Asp Glu Gln Ala Gly
705                 710                 715                 720

Thr Gly Asp Glu Gln Gly Gly Ala Ser Pro Leu His Asn Ile Glu Ala
                    725                 730                 735
```

-continued

```
Arg Ala Ala Val Asp Gln Phe Leu Gln Pro Asp Thr Ile Val Tyr His
            740                 745                 750

Ser Tyr Ser Gln Asp Asp Tyr Val Ala Gln Phe Leu Ile Asn Pro Gly
            755                 760                 765

Lys Arg Phe Cys Met Ala Gly Arg Met Thr Ser Leu Ser Gly Pro Ser
            770                 775                 780

Ala Asp Gln Phe Arg Phe Asp Leu Leu Gln Ala Ile Gln Ile Tyr Glu
785                 790                 795                 800

Val Ile Asp Asn Lys Arg Arg Leu Glu Ser Val Asn Ser Leu Asn
            805                 810                 815

Ala His Tyr Phe Ser Arg Leu Leu Asn Ala Glu Ala Met Ile Asp Cys
            820                 825                 830

Leu Ser Leu Lys Pro Ala Phe Pro Cys Leu Asn Val Asn Arg Lys Arg
            835                 840                 845

Lys Pro Lys Gln Lys
            850

<210> SEQ ID NO 50
<211> LENGTH: 588
<212> TYPE: PRT
<213> ORGANISM: Trypanosoma cruzi

<400> SEQUENCE: 50

Met Ser Leu Ser Leu Ser Arg Met Leu Phe Ser Leu Leu Leu Phe Ala
1               5                   10                  15

Leu Met Val Ala Thr Thr Pro Phe Ala Ala Glu Gly Leu Leu Leu Ala
            20                  25                  30

Ser Ser Ser Ile Glu Gln Cys Asp Arg Val Gly Thr Asp Asn Ser Leu
            35                  40                  45

Pro Cys Glu Lys Lys Leu Val Val Thr Leu Ser Val Asp Ser Asp Gln
        50                  55                  60

Ala Glu Asp Val Glu Glu Phe Val Ile Leu Arg Asp Ala Val Asp Lys
65                  70                  75                  80

Thr Lys Gly Thr Gly Glu Glu His Val Glu Phe Gln Pro Ile Arg Leu
            85                  90                  95

Thr Thr Ser Lys Ser Arg Val Gln Tyr Ser Tyr Pro Leu Phe Tyr Glu
            100                 105                 110

Arg Asn Phe Asn Ala Lys Pro Tyr Glu Glu Ile Thr Thr Glu Leu
            115                 120                 125

Val Gly Cys Asp Asp Thr Phe Ser Pro Lys Ala Thr Cys Gly Leu Ala
            130                 135                 140

Met Asp Thr Ala Gly Arg Pro Ile Pro Tyr Ser Gln Gly Phe Cys Cys
145                 150                 155                 160

Arg Cys Gly Pro Cys Gln Leu Leu Gly Leu Cys Pro Val Gly Ser Arg
            165                 170                 175

Gly Leu Gln Val Cys Asp Ile Phe Arg Gly Ala Ala Leu Ala Ser Cys
            180                 185                 190

Leu Arg Phe Gly Glu Leu Trp Tyr Ser Gly Tyr Ser Met Gly Ser Ala
            195                 200                 205

Thr Ile Trp Tyr Arg Leu Ser Val Lys Leu Thr Thr Asp Ser Gln Asn
            210                 215                 220

Asn Ser Lys Thr Lys Glu Ala Val Phe Glu Leu Gly Pro Asp Val Leu
225                 230                 235                 240

Ser Gly Ser Ser Ala Glu Phe Gly Ala Trp Val Ser Leu Ile Gly Asp
```

```
                    245                 250                 255
Phe Val Pro Ala Glu Leu Pro Leu Val Leu Ser Asn Lys Met Leu Phe
            260                 265                 270

Ile Pro Ser Ser Pro Arg Ile His Glu Arg Val Leu Ala Gly Gln Lys
            275                 280                 285

Glu Trp Leu Ile Leu Asp Lys His His Val Ser Met Gln Gly Arg Asp
            290                 295                 300

Cys Asn Lys Val Gly Val Ser Tyr Glu Ala Phe Ser Gly Gln Gly Ser
305                 310                 315                 320

Arg Cys Gln Leu Ile Arg Gly Ser Cys Leu Ala Asp Gln Leu Glu Asp
                325                 330                 335

Tyr Arg Ser Ser Asp Leu Ala Val Glu Ala Arg Gly Gly Arg Gly Lys
            340                 345                 350

Tyr Leu Ala Arg Phe Phe Gly Asp Phe Val Val Asn Asn Val Asn Asn
            355                 360                 365

Ser Arg Thr Arg Leu Ser Tyr Trp Met Arg Gly Ser Leu Ala Thr Met
        370                 375                 380

Leu Thr Val Val Ile Ser Ala Asp Arg Leu Gln Tyr Leu Val Ser Val
385                 390                 395                 400

Ser Pro Gly Glu Ile Val Ser Ala Val Met Ser Lys Ser Thr Val Glu
                405                 410                 415

Glu Ser Ser Arg Asp Gly Ser Val Ser Val Ile Val Arg Asn Ile Gly
            420                 425                 430

His Val Thr Ala Gln Tyr Thr Leu Gly Val Gly Asn Cys Ser Gly Asn
            435                 440                 445

Val Phe Pro Ile Met Ala Gln Thr Leu Ser Leu Arg Pro Arg Gly Thr
    450                 455                 460

Val Ile Arg Ser Phe Asp Leu Asn Ile Gln Asp Val Ala Glu Glu Arg
465                 470                 475                 480

Ile Val Gln Cys Asp Val Thr Leu Arg Asp Ala Lys Gly Ala Ile Thr
                485                 490                 495

Asp Lys Lys Ile Leu Lys Phe Arg Val Thr Ser Lys Val Leu Thr Asn
            500                 505                 510

Asp Thr Gln Gly Gly Asn Ala Pro Thr Gly Gly Gly Ala Ser Val Asp
        515                 520                 525

Gly Gln Ala Pro Pro Ala Cys Ser Arg Cys Glu Trp Tyr Lys Ile Ser
    530                 535                 540

Cys Phe Leu Ile His Gly Cys Trp Trp Gln Pro Leu Val Tyr Val Leu
545                 550                 555                 560

Ile Ala Ile Ala Ile Leu Leu Gly Ile Tyr Tyr Phe Phe Gly Leu Ser
                565                 570                 575

Ser Arg Ser Ser Glu Pro Lys Leu His Val Val His
            580                 585

<210> SEQ ID NO 51
<211> LENGTH: 618
<212> TYPE: PRT
<213> ORGANISM: Trypanosoma brucei

<400> SEQUENCE: 51

Met Pro Thr Glu Thr Leu Ser Ser Val Phe Val Leu Val Leu Val
1               5                   10                  15

Thr Thr Ser Gly Leu Phe Pro Cys Thr Glu Ala Ala Phe Val Ala Ser
            20                  25                  30
```

```
Ser Ser Ile Glu Tyr Cys Glu Arg Ser Ser Asn Gly Glu Pro Phe Pro
         35                  40                  45

Cys Glu Lys Lys Met Val Val Gly Leu Ser Val Gly Ser Glu Gln Thr
 50                  55                  60

Ile Glu Ala Glu Glu Val Val Leu Leu Arg Glu Ala Val Asp Lys Thr
 65                  70                  75                  80

Gly Asp Glu Lys Gly Lys Arg Val Glu Phe Glu Pro Ile Arg Leu Val
                 85                  90                  95

Thr Thr Lys Ser Pro Val Gln Tyr Arg Tyr Pro Ile Tyr Tyr Ile Arg
            100                 105                 110

Asn Phe Asn Ala Lys Pro Tyr Glu Gln Arg Leu Arg Thr Ser Ala Ser
            115                 120                 125

Ser Trp Cys Asp Asp Ser Ser Asn Pro Gly Ser Ala Thr Cys Gly Val
        130                 135                 140

Ala Arg Asp Arg Arg Gly Asp Val Ile Pro Tyr Ser Gln Gly Phe Cys
145                 150                 155                 160

Cys Leu Cys Gly Ala Cys Ala Leu Ser Gly Ile Cys Asn Pro Thr Ser
                165                 170                 175

Arg Ser Val Gly Thr Cys Ser Val Thr Gly Asp Thr Gly Met Ala Ser
            180                 185                 190

Cys Leu Arg Phe Ser Asp Leu Trp Tyr Gly Gly Tyr Thr Ile Gly Arg
        195                 200                 205

Gly Val Val Trp Tyr Glu Leu Gln Val Lys Leu Ser Ser Gly Asn Asn
        210                 215                 220

Ser Thr Gly Gly Ser Thr Gly Ser Lys Glu Phe Thr Met Ser Leu
225                 230                 235                 240

Gly Pro Asp Lys Leu Thr Ala Thr Ser Thr Glu Phe Gly Ala Ser Ala
                245                 250                 255

Arg Leu Ile Gly Asp Phe Ala Pro Pro Glu Met Pro Leu Asp Leu Ser
            260                 265                 270

Gly Lys Met Leu Phe Ile Pro Ser Glu Pro Arg Gly His Glu Arg Val
        275                 280                 285

Gly Ala Gly Tyr Asn Glu Trp Ile Ile Val Asp Thr His Leu Val Ser
290                 295                 300

Ile Arg Gly Thr Glu Cys Asn Lys Val Gly Val Ser Tyr Glu Gly Phe
305                 310                 315                 320

Ala Thr Gln Gly Ser Arg Cys Asp Ala Tyr Pro Gly Ala Cys Leu Ala
                325                 330                 335

Asn Gln Leu Glu Asp Tyr Arg Arg Asp Leu Glu Ala Glu Thr Lys
            340                 345                 350

Gly Gln Gln Gly Lys Tyr Met Ala Arg Phe Phe Ala Pro Phe Gly Phe
            355                 360                 365

Asp Pro Leu Ala Asn Ala Ser Ala Pro Ala Val Ala Tyr Gln Val Thr
        370                 375                 380

Gly Thr Leu Ser Thr Met Val Thr Ile Thr Ile Ser Ala Asp Lys Leu
385                 390                 395                 400

Asn Phe Val Leu Ser Val Ser Ser Gly Val Ile Val Gly Ala Thr Val
                405                 410                 415

Ser Gly Lys Val Val His Ser Tyr Ser Arg Gly Ser Thr Ile Thr Val
            420                 425                 430

Thr Val Leu Asn Thr Gly Asp Ile Glu Ala Gln Tyr Thr Val Val Val
        435                 440                 445

Gly Glu Cys Thr Val Asn Val Gln Pro Met Val Ala Gln Thr Val Tyr
```

```
                450                 455                 460
Ile Pro Leu Gln Gly Ser Ala Gln Arg Arg Phe Thr Leu Ile Val Gln
465                 470                 475                 480

Asp Ser Ile Glu Gly Glu Ala Lys Cys Asn Ala Thr Leu Arg Asn Ala
                485                 490                 495

Arg Gly Asp Val Val Asp Thr Arg Ala Ile Ser Phe Gly Val Lys Ala
                500                 505                 510

Leu Lys Pro Ser Asn Gly Ser Gln Gly Gly Ser Thr Phe Glu Asn Gly
                515                 520                 525

Arg Tyr Ser Glu Glu Ala Lys Gly Glu Ser Gln Cys Gln Gln Cys Ser
                530                 535                 540

Trp Phe Asn Leu Leu Cys Phe Leu Arg His Arg Cys Trp Trp Gln Pro
545                 550                 555                 560

Leu Val Tyr Val Leu Pro Ser Val Thr Leu Met Leu Leu Arg Arg
                565                 570                 575

Phe Leu Glu Ser Gln Ser Arg Ser Arg Pro Arg Pro Gln Leu His Pro
                580                 585                 590

Asp Glu His Glu Leu Arg Asn Thr Gly Ala Ile Ser Ser Cys His Leu
                595                 600                 605

Pro Arg Ala Pro Tyr Val Asn Thr Val His
                610                 615

<210> SEQ ID NO 52
<211> LENGTH: 917
<212> TYPE: PRT
<213> ORGANISM: Leishmania major A

<400> SEQUENCE: 52

Met Pro Gly Ala Asp Ala Val Thr Arg His Pro Ala Ala Thr Glu Asn
1               5                   10                  15

Ala Met Leu His His Arg Leu His Ser Ser Glu Gly Val Lys Ser Gly
                20                  25                  30

Val Leu Pro Ser Ser Arg Val Ser Leu Leu Ala Thr Leu Cys Gly Cys
                35                  40                  45

Leu Thr Leu Thr Val Ala Leu Val Ala Ser Ala Pro Thr Gln Lys Gly
            50                  55                  60

Gly Leu Val Val Leu Leu Val Trp Ala Tyr Arg Met Val Arg Glu Thr
65              70                  75                  80

Met Arg Val Tyr Leu Ala Pro Gln Ser Arg Cys Ser Leu Tyr Arg Ser
                85                  90                  95

Pro Lys Pro His Arg His Ala Leu Ala Gln Gly Ala Val Cys Ile Ala
                100                 105                 110

Val Leu Tyr Val Ser Leu Leu Val Trp Leu Ala Arg Pro Ala Arg Ala
                115                 120                 125

Ala Phe Val Ser Ser Ser Leu Ile Ser Tyr Cys Ser Asp Ser Gly Asp
                130                 135                 140

Glu Asn Ile Ser Cys Thr Lys Lys Met Val Val Thr Val Thr Val Glu
145                 150                 155                 160

Gly Glu Gln Leu Pro Gly Glu Glu Ser Leu Leu Phe Leu Asn Ser Ala
                165                 170                 175

Thr Asp Met Thr Val Asn Asn Gly Thr Ser Val Gln Phe Ser Pro Leu
                180                 185                 190

Arg Ile Thr Thr Ser Arg Ser Ala Val Arg Tyr Arg Tyr Pro Leu Phe
                195                 200                 205
```

-continued

Tyr Val Gln Asn Tyr Asn Ala Lys Pro Tyr Glu Ala Thr Val Lys Gly
    210                 215                 220

Ser Leu Leu Asn Gln Cys Asn Ala Asp Phe Asn Ala Asp Thr Ala Thr
225                 230                 235                 240

Cys Gly Leu Ala Tyr Asp Ala Ala Gly Lys Ala Ile Pro Tyr Ser Gln
                245                 250                 255

Gly Phe Cys Cys Asp Cys Ser Met Cys Gln Thr Leu Gly Leu Cys Gln
                260                 265                 270

Pro Asp Ala Arg Ala Asn Ala Ala Cys Asn Val Phe Gly Lys Tyr Thr
                275                 280                 285

Thr Ala Ser Cys Leu Arg Phe Ala Gln Arg Trp Tyr Ser Gly Tyr Thr
    290                 295                 300

Ile Gly Gly Tyr Met Thr Trp Tyr Thr Val Asn Leu Thr Leu Ser Arg
305                 310                 315                 320

Asn Val Ser Asp Ser Gly Ala Gly Ala Ala Glu Lys Val Val Met
                325                 330                 335

Arg Leu Ser Pro Ser Asn Gly Glu Val Ala Gly Glu Gly Trp Asp
                340                 345                 350

Val Met Ala Arg Ile Val Gly Thr Tyr Ala Pro Val Asp Gln Pro Leu
                355                 360                 365

Asp Leu Thr Ser Arg Met Leu Phe Ala Pro Ala Ile Pro Pro Asn Asp
    370                 375                 380

Ala Arg Val Gln Ala Gly Ala Ala Glu Trp Leu Leu Pro Thr Asn
385                 390                 395                 400

Leu Val Thr Leu Asp Gly Arg Glu Cys Asp Lys Val Gly Val Ser Tyr
                405                 410                 415

Glu Ala Phe Ala Ser Gln Gly Asn Lys Cys Asn Leu Arg Pro Gly Ser
                420                 425                 430

Cys Leu Ser Ser Gln Leu Glu Asp Tyr Arg Thr Ala Asp Leu Gln Arg
    435                 440                 445

Ile Ala Ala Gly Asn Lys Gly Gln Tyr Met Ala Thr Ser Phe Gly Asp
    450                 455                 460

Phe Asn Leu Glu Asn Asp Ala Ala Thr Ser Pro Tyr Ile Ser Tyr Leu
465                 470                 475                 480

Ala Ala Ser Pro Ala Ala Thr Met Ile Ser Ile Thr Val Ser Ala Asp
                485                 490                 495

Asp Leu Glu Tyr Thr Val Gly Leu Ala Ser Gly Lys Ile Ile Ser Thr
                500                 505                 510

Asp Met Asn Lys Pro Thr Leu Gln Ala Gly Thr Ala Asp Gly Val Met
    515                 520                 525

Thr Val Met Val Arg Asn Thr Ala Ala Val Thr Gly Arg Leu Val Val
530                 535                 540

Gly Thr Leu Asn Cys Ser Asp Gly Val Phe Pro Met Thr Ala Gln Lys
545                 550                 555                 560

Leu Ser Leu Ala Ala Gln Gln Gln Ser Ala Val Thr Phe Lys Val Tyr
                565                 570                 575

Val Gln Ser Ser His Ala Ser Gly Asn Ala Ser Cys Thr Val Val Val
                580                 585                 590

Arg Asn Ala His Glu Val Ile Thr Asp Leu Arg Val Ser Trp Lys
                595                 600                 605

Val Ser Ser Thr Asn Phe His Asn Gly Thr Gln Gly Gly Ser Ala Ala
    610                 615                 620

Asp Gly Ser Gly Gly Gly Ser Thr Glu Glu Ser Ser Ala Ala Ser Cys

```
            625                 630                 635                 640
Leu Asn Cys Arg Thr Leu Asp Ile Ala Cys Ala Val Arg Arg Arg Cys
                645                 650                 655

Trp Gln Leu Ile Leu Leu Asp Leu Phe Val Tyr Leu Ile Ile Ala
                660                 665                 670

Val Ile Leu Cys Val Ile Phe Phe Trp Arg Val Phe Cys Cys Leu
                675                 680                 685

Tyr Leu Leu Gly Arg Gln His Arg Arg Gly Ser Ala Gly Glu Ala Glu
                690                 695                 700

Pro Lys Asn Glu Ala Ser Arg Trp Gly Ala Tyr Trp Lys Arg Gly
705                 710                 715                 720

Glu Ser Asp Ala Thr Ser Ser Arg Gln Thr Asp His Lys Asn Ser
                725                 730                 735

Gly Ser Ser Asp Val Leu Leu Gln Ala Ala Pro Val Ser Pro Ala
                740                 745                 750

Pro Pro Pro Ala Pro Ala Met Met Tyr Val Pro Ile Pro Val Ser Tyr
                755                 760                 765

Glu Pro Ala Pro Phe Ala Thr Arg Ser Gly Gly Glu Ala Ala Ser
770                 775                 780

Pro Ala Ala Ser Phe Thr Pro Phe Leu Gln Ala Leu Pro Pro Pro
785                 790                 795                 800

Ala Ala Ala His Pro Leu Ala Leu Met Pro Pro Arg Trp Cys Pro
                805                 810                 815

Tyr Gly Asn Glu Glu Ala Ile Asp Pro Gly Glu Gly Pro Cys Ala Thr
                820                 825                 830

His Ala Phe Pro Pro His Ser Pro Ile Gly Ser Phe Ala Phe Ala Ala
                835                 840                 845

Pro Pro Ala Cys Pro Ala Pro Arg Tyr Gly Glu Glu Trp Ser Gly Cys
                850                 855                 860

Gly Ser Val Thr Ser Thr Ser Pro Leu Thr Pro Ser Arg Ser Thr Gln
865                 870                 875                 880

Glu Gly Ser Pro Tyr Asn Lys Glu Ala Arg Cys Thr Pro Arg Ala Phe
                885                 890                 895

Gln Arg Ser Trp Ala Ser Thr Pro Arg Arg Pro Pro Ser Pro Gly Ala
                900                 905                 910

His Ala Pro Tyr Leu
                915

<210> SEQ ID NO 53
<211> LENGTH: 1058
<212> TYPE: PRT
<213> ORGANISM: Monosiga brevicollis

<400> SEQUENCE: 53

Met Leu Trp Phe Thr Ala Leu Leu Ala Cys Phe Thr Ile Met Gly Leu
1               5                   10                  15

Ser Pro Ala Val Gln Ala Gln Ile Lys Ala Ala Gly Gln Ile Glu Arg
                20                  25                  30

Cys Leu Arg Asp Gly Ser Leu Glu Pro Asn Cys Glu Arg Lys Met Val
            35                  40                  45

Leu Asn Leu Gly Val Leu Gly Ser Thr Gly Gly Glu Tyr Tyr His
        50                  55                  60

Leu Thr Gln Ser Arg Thr Glu Asp Gly Ala Ile Ser Asp Ser Glu Asn
65                  70                  75                  80
```

-continued

```
Glu Phe Ile Ile Val Val Gln Lys Thr Ser Val Ser Ile Glu Tyr Pro
                 85                  90                  95

Leu Arg Tyr Arg Gly Val Val Asn Asn Lys Pro Tyr Glu Ile Ala Gln
            100                 105                 110

Pro Val Gln Thr Leu Leu Gly Gly Leu Phe Gly Ser Gly Asp Lys Thr
        115                 120                 125

Gly Cys Lys Asp Ser Pro Tyr His Ser Ser Pro Ser Cys Gly Trp Leu
    130                 135                 140

Ile Asp Gly Gly Lys Lys Val Glu Gly Ser Gln Gly Phe Cys Cys
145                 150                 155                 160

Arg Cys Ser Thr Ala Asp Gln Leu Gly Ile Gly Met Pro Thr Asp Ser
                165                 170                 175

Tyr Arg Ala Asn Leu Asp Cys Gly Leu Phe Gly Lys Gly Gln Gln Ser
            180                 185                 190

Ala His Cys Phe Arg Tyr Ser Asp Glu Leu Trp Tyr Gly Val Tyr Asp
        195                 200                 205

Phe Asp Pro Gly His Ile Arg Phe Lys Val Tyr Val Ser Ile Tyr Arg
    210                 215                 220

Lys Tyr Ala Val Gly Pro Gly Tyr Ser His Ala Thr Gln Asp Asp Val
225                 230                 235                 240

Pro Ala Ala Ser Pro Asp Cys Thr Val Glu Leu Pro Asp Glu Tyr Ala
                245                 250                 255

Asp Phe Arg Cys Gln Gly Val Leu Glu Val Gly Pro His Leu Arg Gly
            260                 265                 270

Gly Leu Thr Ser Asp Gly Ala Val Ser Val Phe Gly Gly Asp Phe
        275                 280                 285

Ala Thr Pro Val Gln Leu Arg Asp Met Ser Ser Lys Thr Leu Leu Ala
    290                 295                 300

Pro Ile Leu Glu Thr Val Asp Asn Trp His Thr His Glu Gln Thr Lys
305                 310                 315                 320

Asp Gly Met Asp Thr Tyr Leu Val Val Asp Lys Ser Asp Ile Asp Met
                325                 330                 335

Thr Gly Ser Thr Cys Asp Lys Ile Gly Val Glu Pro Leu Ala Phe Tyr
            340                 345                 350

Leu His Gly Lys Gly Gly Cys Gly Val Ser Glu Gly Thr Cys Leu
        355                 360                 365

Asn Asn Gln Pro Arg Asp Phe Phe Leu Ala Asp Gln Ala Leu Val Asn
    370                 375                 380

Ala Gly Lys Arg Pro Phe Asn Leu Leu Ser Ala Tyr Asn Pro Tyr Gly
385                 390                 395                 400

Phe Ala Gln Val Glu Asp Asp Glu Ser Arg Tyr Gly Ile Arg Phe
                405                 410                 415

Pro Val Glu Gln His Ile Ser Ser Ile Thr Ile Ser Val Asn Ala Asp
            420                 425                 430

Asp Leu Thr Val Tyr Thr Ala Val Cys Arg Asp Met Thr Leu Ala Leu
        435                 440                 445

Gly Ser Pro Asn Phe Glu Ala Leu Ser Gly Asn Gly Phe Ile Leu Ala
    450                 455                 460

Asn Ile Tyr Ser Asn Cys Pro Asn Met Thr Ala Leu Val Ser Val Ser
465                 470                 475                 480

Val Ile Cys His Gly Asn Ala Arg Gly Ser Ala Ser Tyr Glu Arg Glu
                485                 490                 495

Ile Thr Ser Phe Ile Gln Leu Gln Leu Pro Ile Tyr Val Val Ser Glu
```

```
                500             505             510
    Glu Ala Gly Asp His Phe Cys Asp Val Leu Val Phe Asp Ala Val Gly
                515             520             525
    Tyr Leu Val Val Asn Lys Ser Val Thr Phe Ser Thr Ser Ala Val Cys
                530             535             540
    Tyr Cys Leu Gly Gly Cys Asp Cys Asp Cys Asn Asn Thr Val Val Glu
    545             550             555             560
    Asp Cys Val Glu Asp Phe Asn Pro Glu Ile Asp Asp Glu Val Thr Ser
                    565             570             575
    Gly Gly Gly Phe Gly Leu Gly Asp Leu Phe Asp Ala Leu His Leu Ser
                580             585             590
    Trp Ala Thr Gly Leu Ala Leu Phe Ser Ser Leu Ile Ser Leu Ile Leu
                595             600             605
    Leu Cys Ala Val Val Tyr Leu Met Arg Met Cys Cys Pro Glu Arg Met
                610             615             620
    Cys Ser His Arg His Ala Trp Thr Glu Pro Ala Val Ala Thr Gly Glu
    625             630             635             640
    Pro Ala Thr Gly Tyr Val Gly Pro Val Lys Gly Thr Ser Ser Pro Ala
                    645             650             655
    Leu Tyr Ala Ser Pro Pro His Pro Arg Pro Ala Pro Asp Gly Ala Glu
                    660             665             670
    Asp Ala Ala Thr His Asn Ala Arg Ala Ser Arg Val Arg Gln Gly Gly
                675             680             685
    Arg Ala Leu Arg Gln Ala Ala Leu Ala Ala Gly Thr Ala Val Gly Ala
                690             695             700
    Ala Cys Gly His Leu Tyr Arg Trp Ser Ala Ala Arg Trp Ala Ala Arg
    705             710             715             720
    His Arg Ala Ala Ala Arg Ala Ser Leu Gly Ala Glu Pro Glu His Arg
                    725             730             735
    Arg Thr His Gly Pro Thr Val Ser Trp Thr Arg Pro Glu Ala Ala Pro
                    740             745             750
    Gly Asn Glu Leu Ala Leu Met Ser Pro Arg Leu Ala Met Ser Met Pro
                755             760             765
    Ala Gln Leu Glu Ser Val Pro Pro Trp Thr Pro Asp Leu Ser Pro
    770             775             780
    Ser Leu Leu Pro Pro Ser Pro Val Met His Asp Ala Pro Ala Leu Pro
    785             790             795             800
    Leu Pro Pro Val Pro Pro Pro Ser Arg Pro Leu Leu Pro Ser
                    805             810             815
    Gln Ser Pro Ile Pro Lys Ser Met Ser Gln Met Ser Gln Ala Ser Leu
                    820             825             830
    Ser Val Gly Thr Ser Gly Glu Gly Arg Arg Ser Ser Phe Pro Asp
                835             840             845
    Leu Arg Glu Pro Ser Val Leu Gly Arg Phe Val Asp Arg Trp Arg Pro
                850             855             860
    Ser Pro Ala Ala Thr Ala Gly Ser Thr Asn Pro Gly Ala Val Ser Val
    865             870             875             880
    Ser Val Ser Gln Ser Ser Phe Trp Gln Glu Asp Leu Ala Cys Arg
                    885             890             895
    Ser Ser Thr Arg Ala Asn Ala Thr Gln Pro Leu Pro Ala Phe Thr Arg
                    900             905             910
    Gln Gln Tyr Pro Tyr Ser Arg Gln Arg Thr Gln Arg Gln Thr Gln
                915             920             925
```

```
Val Leu Ala Arg Leu Leu Gln Ala Asp Gln Thr Arg Leu Met Val Asp
    930                 935                 940

Gly Gly Asp Asp Gly Thr Phe Val Leu His Gly Leu Leu Glu Pro Ala
945                 950                 955                 960

Thr Pro Gly Ser Gly Leu Tyr Glu Phe His Pro Ala Asn Thr Ala Ser
            965                 970                 975

Ile Glu Gln Ser Thr Val Arg Asn Leu Leu Ser Leu Thr His Ser Leu
        980                 985                 990

Ala Asp Gly Ile Met Leu His Gly Thr Trp Ser His Cys Cys Ala Gln
    995                 1000                1005

Leu Pro Ala Thr Cys Val Gly Asp Asp Ala Arg Arg Ser His Ser
    1010                1015                1020

Ser Thr Gly Arg Asn Ala Ala Arg Gln Gln Pro Gln Ala Ala Thr
    1025                1030                1035

Asn Gln Leu Ala Tyr His Asp Pro Pro His Ser Arg Arg Ser Arg
    1040                1045                1050

Arg Leu Cys Leu Val
    1055

<210> SEQ ID NO 54
<211> LENGTH: 748
<212> TYPE: PRT
<213> ORGANISM: Chlamydomonas reinhardtii

<400> SEQUENCE: 54

Met Cys Arg Ala Ile Ala Val Ala Leu Ile Val Tyr Leu Ala Gln His
1               5                   10                  15

Tyr Ile Leu Ala His Ala Glu Val Ile Ala Ser Gly Arg Leu Glu Lys
            20                  25                  30

Cys Val Val Asp Gly Val Thr Glu Glu Leu Asp Cys Gln Glu Lys Val
        35                  40                  45

Val Val Thr Leu Thr Val Gly Asn Gly Gln Ser Leu Gln Thr Glu Ala
    50                  55                  60

Leu Glu Phe Ser Leu Ser Cys Leu Asn Ser Pro Asp Gly Arg Cys Pro
65                  70                  75                  80

Cys Ser Cys Ser Ala Ala Asp Pro Thr Cys Ala Cys Arg Asp Leu Ala
                85                  90                  95

Ala Pro Leu Arg Val Ser Leu Thr Lys Ser Pro Leu Trp Ala Ser Tyr
            100                 105                 110

Pro Leu Gln Tyr Leu Ser Ser Phe Asn Trp Lys Pro Leu Glu Val Ile
        115                 120                 125

Leu Arg Pro Ser Asn Lys Val Cys Lys Asp Gly Asp Trp Glu Asp Ser
    130                 135                 140

Pro Thr Cys Gly Trp Phe Ser Gln Gly Gly Val Arg Val Ala Asp Ser
145                 150                 155                 160

Gln Gly Phe Cys Cys Glu Cys Ser Ser Ser Gln Val Trp Asp Asp Thr
                165                 170                 175

Phe Gly Ser Ser Lys Glu Arg Thr Arg Ala Asn Leu Asp Cys Asp Phe
            180                 185                 190

Trp Ser Asp Pro Leu Asp Ile Leu Ile Gly Arg Lys Pro Val Ser Ala
        195                 200                 205

His Cys Leu Thr Phe Asp Pro Gln Trp Tyr Ser Gly Tyr Glu Leu Gly
    210                 215                 220

Ala Ala Ser Leu Gln Phe Glu Ile Ala Ile Thr Val Glu Val Pro Thr
```

```
            225                 230                 235                 240
Ala Pro Ser Pro Thr Thr Ala Thr Thr Ser Ala Thr Pro Arg Thr Asn
                245                 250                 255

Asn Ser Ser Ser Ala Asn Ser Thr Asn Ser Thr Asn Ser Pro Ala Pro
                260                 265                 270

Gln Phe Leu Ser Pro Pro Ala Pro Ser Thr Arg Glu Val Leu His Leu
                275                 280                 285

Gly Pro Ser Val Pro Leu Ala Ser Ser Ala Ser Arg Leu Leu Ser Ala
                290                 295                 300

Lys Leu Leu Gly Asp Leu Ala Met Tyr Thr Gln Leu Pro Ala Ile Ser
305                 310                 315                 320

Asn Gln Val Leu Met Val Pro Gln Gln Pro Ala Ala Ala Ala Ala Thr
                325                 330                 335

Gly Ser Pro Leu Asp Ala Thr Leu Ala Thr Asn Arg Ser Ala Trp Met
                340                 345                 350

Leu Leu Asp Lys Thr Met Leu Ser Met Asp Gly Leu Ala Cys Asp Lys
                355                 360                 365

Val Gly Thr Gly Phe Ser Ala Phe Arg Tyr Gln Pro Ser Gly Cys Gly
                370                 375                 380

Arg Ala Pro Gln Ala Cys Leu Ser Gly Gln Leu Lys Asp Leu Trp Glu
385                 390                 395                 400

Ala Asp Leu Ala Arg Ile Ala Asp Gly Arg Val Pro Leu Tyr Met Ile
                405                 410                 415

Thr Arg Phe Thr Gly Ser Asp Thr Thr Leu Gln Ser Phe Ser Gly
                420                 425                 430

Gly Pro Leu Ser Phe Ala Leu Pro Val Thr Ser His Ser Gln Ser Leu
                435                 440                 445

Val Thr Leu Ser Val Ala Ala Asp Gly Val Arg Leu Val Thr Asn Arg
                450                 455                 460

Ser Pro Gly Lys Ile Thr Gly Ala Ala Val Cys Arg Phe Ala Gly Thr
465                 470                 475                 480

Ser Cys Gly Gly Phe Glu Ala Val Ala Ala Arg Gly Tyr Ile Tyr Val
                485                 490                 495

Asn Ile Thr Asn Thr Gly Arg Leu Asp Ser Asp Tyr Thr Leu Thr Val
                500                 505                 510

Ser Asn Cys Ser Ser Asn Val Arg Pro Ile Glu Ala Arg Thr Leu Ala
                515                 520                 525

Val Arg Ala Gly Ser Ala Ala Ser Leu Asp Pro Pro Met Glu Leu Tyr
                530                 535                 540

Val Glu Asp Gln Ala Ala Ala Ala Arg Thr Cys Thr Val Ser Leu
545                 550                 555                 560

Tyr Asp Ser Val Gly Ala Val Thr Asp Ser Leu Thr Leu Ser Phe Tyr
                565                 570                 575

Thr Asn Ala Thr Gln Leu Val Val Lys Pro Ser Gly Tyr Asn Gly
                580                 585                 590

Thr Gly Asp Gly Ala Gly Val Lys Arg Asn Gly Thr Asp Cys Ser Thr
                595                 600                 605

Ala Cys Thr Asn Pro Ile Asp Val Leu Cys Phe Val Thr Lys Lys Cys
                610                 615                 620

Trp Ser Lys Phe Gly Arg Leu Leu Gly Ile Ile Gly Gly Ala Leu Val
625                 630                 635                 640

Gly Leu Gly Leu Leu Ala Val Ala Leu Lys Phe Gly Trp Leu Ala Ser
                645                 650                 655
```

```
Leu Ala Ala Ser Cys Cys Gly Gly Gly Ala Ala Gly Gly
            660             665             670

Ala Gly Gly Gly Met Gly Leu Gly Thr Gly Gly Gly Cys Phe
        675             680             685

Gly Gly Gly Gln Gln Gln Gln Gln Pro Pro Ala Ala Ser His Ala
        690             695             700

Met Ser Pro Pro Gln Gln Gln Gln Arg Ser His Ala Glu Val Ala
705             710             715                     720

Ala Gly Ala Ala Val Ala Gly Ala Gly Ala Ala Val Ala Ala Ala
            725             730             735

Val Leu Gly Ala Lys His Gly Gly Gly Gly Ala
            740             745

<210> SEQ ID NO 55
<211> LENGTH: 611
<212> TYPE: PRT
<213> ORGANISM: Leishmania major B

<400> SEQUENCE: 55

Met Pro Pro Pro Thr Arg Val Ala Phe Ile Ala Leu Leu Ala Leu
1               5                   10                  15

Val Tyr Ala Ser Gln Gly Leu Cys Ala Gly Pro Thr Val Gly Gly Leu
            20                  25                  30

Ala Asp Gly Met Gly Gly Thr Ala Thr Ala Thr Ala Tyr Val Arg Ser
        35                  40                  45

Cys Asp Gly Ala Ser Pro Pro Thr Pro Pro Gly Cys Gly Leu Lys Leu
50                  55                  60

Val Val Asp Leu Thr Leu Asp Asp Ser Ile Leu Thr Gly Ser Val Leu
65                  70                  75                  80

Glu Thr Glu Val Met Val Thr His Ala Leu His Glu Ser Leu Phe Pro
                85                  90                  95

Arg Asp Ala Ala Ser Asp Ala Ala Gly Thr Ala Ala Thr Ser Leu Gln
            100                 105                 110

Val Ser Leu Pro Pro Ile Thr Val Ala Met Arg Arg Gly Ala Val Gln
        115                 120                 125

Met Arg Tyr Gly Leu Thr Tyr Leu Arg Thr Phe Pro Ala Ala Leu Arg
130                 135                 140

Asp Ser Val Arg Val Leu Lys Thr Ala Met Ser Cys Asp Asp Gly Val
145                 150                 155                 160

Thr Arg Cys Pro Ser Tyr Met Ser Met Thr Gly Thr Leu Val Ser Ala
                165                 170                 175

Pro Leu Gly Leu Cys Cys Leu Cys Thr Ser Val Glu Cys Ala Leu Thr
            180                 185                 190

Ser Asp Leu Cys Asn Ala Ser Met Arg Ala His Phe Cys Phe Arg Thr
        195                 200                 205

Gly Ala Ala Gly Ile Thr Cys Val Gln Ser Glu Gly Ile Thr Tyr His
    210                 215                 220

Gly Trp Ala Val Gly Ser Ser Pro Tyr Tyr Met Met His Leu Ser
225                 230                 235                 240

Ala Ser Gly Arg Gly Ile Ala Pro Thr Thr Leu Gln Leu Thr Thr Asp
                245                 250                 255

Ala Pro Glu Val Gln Lys Gly Ala Ser Ala Leu Gln Ile Leu Arg Ala
            260                 265                 270

Ser Gly Val Leu Pro Gly Glu Ser Asn Pro Thr Val Asp Ile Ser Gly
```

```
            275                 280                 285
Arg Val Leu Phe Val Pro Ser Ala Glu His Ser Ser Ala Arg Ser
    290                 295                 300

Ile Ser Thr Gly Pro Val Arg Asp Asp Pro Ala Glu Trp Leu Leu
305                 310                 315                 320

Leu Pro Ala Pro Leu Val Ser Val Ser Gly Asn Asp Cys Asp Lys Val
                325                 330                 335

Gly Ile Ser Pro Asp Tyr Phe Tyr Ser Leu Ser Ser Thr Lys Gln Cys
                340                 345                 350

Asn Ala Gln Lys Gly Thr Cys Val Arg His Gln Leu Ala Asp Tyr Arg
                355                 360                 365

Ala Ala Asp Leu Glu Gln Ile Ala Gln Gly Val Gly Gly Arg Tyr Ile
370                 375                 380

Ala Ala Ser Leu Gly Thr Phe Thr Arg Gln Ala Met Arg Glu Gln
385                 390                 395                 400

Phe Leu Leu Asp Ala Val Glu Arg Thr Gly Gly Ala Met Leu Arg Trp
                405                 410                 415

Thr Val Asn Ala Asp Gly Leu Val Phe Gln Pro Leu Pro Val His Gly
                420                 425                 430

Val Leu Asp Ala Ile Lys Phe Asp Ser Ser Thr Gly Ile Leu Tyr Val
                435                 440                 445

Thr Val Arg Asn Asn Thr Tyr Gly Gly Leu Tyr Tyr Val Ala Val
                450                 455                 460

Gly Gln Cys Arg Gly Ala Arg Ala Ser Asn Cys Asp Ser Asp Gly Val
465                 470                 475                 480

Thr His Glu Cys Gly Arg Thr Ala Leu Val Ala Gly Ala Asn Thr Ser
                485                 490                 495

Ser Leu Leu Gln Phe Ser Met Val Ser Asp Leu Pro Glu Glu Val Gly
                500                 505                 510

Ser Thr Ala Ser Cys Thr Val Val Phe Arg Asp Ala Ala Ala Ala Leu
                515                 520                 525

Leu Ala Ser Ala Asn Ile Ser Trp Thr Val Glu His Thr Thr Thr Thr
                530                 535                 540

Pro Ala Pro Asn Ala Pro Lys Ala Glu Gln Cys Arg Arg Cys Ala Phe
545                 550                 555                 560

Arg Asp Leu Arg Cys Leu Phe Ser Thr Val Cys Glu Trp Gln Met Leu
                565                 570                 575

Leu Trp Thr Ala Val Ala Val Ala Val Thr Trp Thr Pro Tyr Ala Ile
                580                 585                 590

Leu Ala Tyr Trp Arg Met Ala Trp His Val Gly Ala Lys Leu Leu Ala
                595                 600                 605

Cys Leu Asn
    610

<210> SEQ ID NO 56
<211> LENGTH: 708
<212> TYPE: PRT
<213> ORGANISM: Cyanidioschyzon merolae

<400> SEQUENCE: 56

Met Lys Val Ile Phe Arg Arg Ser Leu Phe Val Leu Leu Phe Phe Gln
1               5                   10                  15

Val Pro Leu Trp Leu Val Ala Pro Phe Phe Ser Ala Ser Val Gly Gly
                20                  25                  30
```

-continued

```
Ser Leu Thr Gly Val Gly Ser Ile Val Thr Cys Leu Asp Ser Gly Arg
         35                  40                  45

Pro Gly Ser Ile Pro Cys Ser Lys Lys Trp Val Leu Thr Leu Ala Val
 50                  55                  60

Glu Asn Gly Ala Thr Ala Ala Ser Ser Val Ser Ala Thr Gln Ala
 65                  70                  75                  80

Val Tyr Gly Ser Ser Ser Ala Asn Ala Thr Val Arg Ser Ala Asp Asn
                     85                  90                  95

Pro Asn Thr Val Tyr Ala Phe Lys Tyr Gln Val His Ile Thr Leu Thr
                100                 105                 110

Lys Ser Arg Ile Arg Leu Asp Tyr Pro Leu Tyr Tyr Gln Ser Asp Phe
                115                 120                 125

Asn Asn Lys Pro Tyr Glu Ile Val Tyr Lys Tyr Asn Gln Lys Gly Pro
        130                 135                 140

Leu Asn Trp Leu Asp Asn Gln Cys Val Ala Thr Trp Gly Ser Ser Asp
145                 150                 155                 160

Pro Thr Cys Gly Tyr Ala Tyr Asn Pro Ser Trp Ser Thr Lys Pro Ala
                165                 170                 175

Asp Arg Ile Leu Tyr Ser Gln Gly Phe Cys Asp Cys Asn Ala Gly
                180                 185                 190

Asp Leu Leu Gly Leu Ser Pro Asn Arg Ile Arg Gly Gly Leu Asp Cys
                195                 200                 205

Ser Leu Leu Asn Phe Asp Asn Pro Thr Glu Ser Ala His Cys Leu Arg
        210                 215                 220

Phe Asp Ser Leu Trp Tyr Ser Ala Phe Gln Ile Gly Glu Pro Asp Val
225                 230                 235                 240

Asn Phe Val Ile Leu Val Asn Val Thr Lys Cys Pro Leu Ala Asn Ser
                245                 250                 255

Thr Ile Lys Ser Ile Ser Gly Leu Val Gly Asn Gln Asp Gln Ala Ile
                260                 265                 270

Gln Asn Cys Ser Thr Glu Ile Ile Ser Leu Ser Pro Ser Ser Pro Ile
                275                 280                 285

Gly Tyr Ala Ser Asn Gly Lys Ile Ser Ala Gln Ala Ile Gly Asp Phe
        290                 295                 300

Ala Pro Trp Glu Gly Thr Pro Ser Tyr Ser Glu Lys Leu Phe Phe Val
305                 310                 315                 320

Pro Ser Val Cys Thr Asp Thr Ser Glu Ala Trp Cys Val Asp Arg Ile
                325                 330                 335

Ser Tyr Ile Pro Thr Glu Ile Asn Arg Trp Met Leu Ile Asp Asn Asp
                340                 345                 350

Leu Val Thr Ile Thr Gly Asp Thr Cys Asp Lys Ile Gly Val Ser Tyr
                355                 360                 365

Ser Ala Phe Thr Asn Glu Gly Gln Arg Cys Glu Arg Pro Thr Gln Ser
        370                 375                 380

Cys Leu His Asp Gln Leu Gln Asp Tyr Tyr Asp Ser Asp Leu Ala Leu
385                 390                 395                 400

Glu Gln Thr Gly Lys Val Gly Ser Tyr Phe Val Gln Phe Phe Gly Asp
                405                 410                 415

Phe Asp Val Ser Gly Leu Thr Pro Arg Asn Pro Leu Leu Arg Phe Phe
                420                 425                 430

Thr Asn Arg Thr Gln Ala Thr Glu Val Val Leu Gln Phe Ala Ala Glu
        435                 440                 445

Glu Leu Phe Tyr Thr Ile Tyr Leu Ala Pro Ala Arg Phe Leu Arg His
```

```
                450                 455                 460
Leu Ser Lys Ile Asn Pro Phe Thr Ser Gln Ser Lys Gly Gly Leu Ile
465                 470                 475                 480

Asp Leu Trp Ile Val Ser Glu Gly Thr Gly Gln Asn Ala Ala Gln Phe
                485                 490                 495

Thr Val Ser Ala Ser Cys Glu Pro Asn Val Glu Pro Ile Gln Ala Gln
                500                 505                 510

Ile Val Thr Leu Ala Pro Gly Gln Leu Val Ser Ile Ser Leu Pro Ile
                515                 520                 525

Ile Glu Thr Lys Ala Thr Gly Gly Ala Gly Val Cys Asn Cys Thr Leu
530                 535                 540

Arg Asn Ala Leu Gly Gln Val Leu Asp Val Leu Val Leu Glu Phe Asn
545                 550                 555                 560

Ala Ser Ser Val Arg Thr Thr Asp Gly Ala Gln Gly Gly Ser Ala Ser
                565                 570                 575

Thr Thr Ser Gly Asn Leu Thr His Thr Gly Ser Ser Pro Tyr Pro Ser
                580                 585                 590

Gly Gly Cys Gly Ser Cys Gly Gly Leu Leu Asp Ile Gly Cys Ile Phe
                595                 600                 605

Ala Asn Val Cys Ile Leu Asn Ile Leu Phe Phe Ile Gly Leu Leu Phe
                610                 615                 620

Leu Ile Leu Leu Leu Cys Cys Cys Arg Thr Cys Ile Trp Arg Cys
625                 630                 635                 640

Cys Cys Gly Cys Cys Gly Leu Leu Gly Lys Gly Phe Ser Leu Pro Pro
                645                 650                 655

Gly Leu Arg Ala Arg Thr Gln Arg Arg Gly Tyr Phe Thr Ser Val Thr
                660                 665                 670

Ala Leu Pro Gly Gln Thr Leu Pro Ala Leu Pro Lys Ala Ala Leu Val
                675                 680                 685

Arg Ser Val Ser Leu Glu Gly Pro Ser Met Leu Gln Thr Val Ala Cys
                690                 695                 700

Ser Lys Ala Arg
705

<210> SEQ ID NO 57
<211> LENGTH: 808
<212> TYPE: PRT
<213> ORGANISM: Physarum polycephalum

<400> SEQUENCE: 57

Met Gly Gly Val Phe Leu Cys Ile Leu Phe Leu Phe Tyr Leu Phe Ser
1               5                   10                  15

Thr Leu His Ala Asp Leu Ile Ala Ser Ser Gln Ile Thr Asn Cys Val
                20                  25                  30

Leu Asp Gly Ser Ser Glu Asp Thr Ile Leu Asn Cys Gln Lys Lys Phe
            35                  40                  45

Val Val Ser Leu Ser Val Asp Asn Gly Gln Asn Lys Thr Glu Ala Val
        50                  55                  60

Gln Phe Thr Ile Ser Ser Ala Thr Asp Gly Asn Thr Thr Leu Gln Phe
65                  70                  75                  80

Val Asn Pro Trp Thr Ile Thr Leu Ser Lys Ser Pro Val Ala Ile Tyr
                85                  90                  95

Tyr Pro Ile Ser Tyr Leu Gln Thr Val Asn Ala Asp Pro Ser Glu Ala
            100                 105                 110
```

```
Val Ile Tyr Thr Arg Asp Trp Ile Val Val Ser Ser Cys Gln Ser Gly
        115                 120                 125
Ala Tyr Ser Asp Asn Pro Thr Cys Gly Trp Tyr Lys Asp Ser Asn Gly
    130                 135                 140
Asn Asn Ile Pro Asp Ser Gln Gly Phe Cys Cys Ser Cys Asn Leu Ala
145                 150                 155                 160
Glu Tyr Leu Gly Ile Ser Asp Asp Gln Thr Arg Ala Gly Leu Thr Cys
                165                 170                 175
Ser Phe Phe Ser Gly Ser Ser Ser Ala His Cys Leu Arg Phe Asp
                180                 185                 190
Asp Asn Gly Trp Tyr Asp Ile Phe Gln Ile Ala Asn Ala Gln Asp Met
            195                 200                 205
Tyr Thr Ile Asp Ile Asp Ile Ser Gln Gly Gly Thr Asn Thr Thr
    210                 215                 220
Val Thr Leu Ser Pro Ser Thr Thr Ile Ser Ser Ser Ser Val Ile
225                 230                 235                 240
Ala Arg Leu Leu Gly Asp Phe Ser Pro Phe Gln Gln Leu Pro Val Tyr
                245                 250                 255
Ser Thr Lys Tyr Leu Ala Val Pro Ser Ser Gly Asn Pro Arg Glu Thr
        260                 265                 270
Asp Gly Met Asp Thr Trp Met Met Ile Asp Thr Asp Leu Phe Asp Leu
    275                 280                 285
Ser Gly Thr Val Cys Asn Lys Ile Gly Val Ser Phe Ala Gly Phe Asn
        290                 295                 300
Ser Glu Ala Ser His Cys Lys Leu Leu Val Asn Ser Cys Leu Gly Tyr
305                 310                 315                 320
Gln Ile Glu Asp Tyr Tyr Gln Ser Asp Leu Gln Leu Gln Lys Ala Asn
                325                 330                 335
Arg Ile Gly Asn Tyr Phe Leu Ser Phe Phe Gly Gly Leu Tyr Tyr Ala
                340                 345                 350
Glu Thr Tyr Thr Ser Ser Leu Thr Asn Arg Phe Leu Ala Phe Asp Leu
        355                 360                 365
Thr Gly Leu Gln Ser Ser Val Ile Thr Leu Thr Phe Ser Ala Asp Asp
    370                 375                 380
Ile Arg Phe Val Thr Asn Glu Ser Pro Gly Gln Ile Val Ser Ala Tyr
385                 390                 395                 400
Val Glu Glu Phe Glu Ala Leu Ser Lys Asp Gly Arg Met His Val Val
                405                 410                 415
Val Val Asn Asn Gly Thr Ile Asn Ala Gln Tyr Glu Ile Thr Val Thr
        420                 425                 430
Gln Cys Ser Thr Gly Ile Ala Thr Ile Gln Ala Gln Glu Pro Thr Leu
    435                 440                 445
Val Pro Arg Lys Gln Thr Glu Phe Ile Phe Asn Ile Gln Ser Glu Asn
450                 455                 460
Ala Leu Gln Lys Ser Tyr Gln Cys Lys Val Ser Leu Leu Asp Ser Gln
                470                 475                 480
Ala Val Leu Leu Asp Tyr Arg Ile Val Tyr Phe Asn Thr Ser Ala Thr
                485                 490                 495
Asn Phe Gln Thr Thr Ala Gln Gly Gly Asp Thr Ser Gly Asp Ser Gly
        500                 505                 510
Asp Asp Leu Lys Ser Asp Lys His Ser Ser Cys Ser Gln Ala Cys Ser
        515                 520                 525
Ala Phe Tyr Asp Ile Ile Cys Phe Leu Ser His Lys Cys Trp Lys Asn
```

-continued

```
            530                 535                 540
Val Phe Ser Phe Leu Gly Thr Ile Ile Gly Ile Ala Ala Gly Leu Phe
545                 550                 555                 560

Ile Leu Tyr Lys Leu Lys Gln His Phe Gly Met Cys Gly Leu Cys Ser
                565                 570                 575

Lys Ile Cys Cys Gly Cys Cys Gly Ser Ser Asn Asp Lys Lys
                580                 585                 590

Lys Lys Lys Lys Lys Ala Lys Lys Glu Lys Leu Lys Arg Glu Lys Ser
                595                 600                 605

Val Lys Met Lys Lys Met Lys Lys Glu Lys Ser Thr Lys His Arg Glu
                610                 615                 620

Glu Thr Arg Gly Lys Pro Ser Asp Tyr Glu Lys Thr Arg Gly Asn Ser
625                 630                 635                 640

Ser Asp Tyr Ser Ser Asp Ser Ser Tyr Thr Tyr Ser Ser Gly Ser Glu
                645                 650                 655

Gly Ser Tyr Ser Ser Tyr Thr Ser Gly Ser Asp Tyr Asp Ser Ser Ser
                660                 665                 670

Ser Glu Tyr Glu Leu Glu Glu Gly Arg Arg Arg Gly Ala Met Gly
                675                 680                 685

Leu Ser Ser Ser Glu Met Ser Leu Ser Ala Gln Arg His Thr Pro Val
                690                 695                 700

Tyr Leu Cys Phe Ser Gly Ala Lys Asn Thr Pro Leu Tyr Lys Pro Gly
705                 710                 715                 720

Ala Gln Phe Cys Leu Ile Gly Glu Ile Glu Lys Thr Lys Asn Asn Phe
                725                 730                 735

Glu Phe Asn Leu Glu Ala Tyr Pro Ser Gln Thr Lys Tyr Leu Gln Val
                740                 745                 750

Ser Thr Gln Arg Tyr Ala Arg Leu Gln Thr Pro Arg Pro Ile Asp Val
                755                 760                 765

Glu Leu Phe Arg Met Pro Leu Asn Asp Gly Gln Val Arg Lys Ser Leu
                770                 775                 780

Thr Thr Asn Pro Pro Ala Met Tyr Thr Cys Ile Asn Lys Pro Tyr Ala
785                 790                 795                 800

Thr Lys Lys Ala Lys Asn Lys Lys
                805
```

<210> SEQ ID NO 58
<211> LENGTH: 1087
<212> TYPE: PRT
<213> ORGANISM: Apis mellifera

<400> SEQUENCE: 58

```
Met Ser Ala Thr Arg Thr Pro Tyr Val Ser Glu Phe Glu Tyr Val Pro
1               5                   10                  15

Gln Leu His Pro Ser Arg Asn Pro Asp Cys Pro Ser Arg Phe Ile Ser
                20                  25                  30

Asp Arg Gln Val Arg Lys Asp Ser Asp Glu Trp Asp Arg Pro Leu Ile
                35                  40                  45

Glu Ile Arg Ala Val Leu Ser His Cys Pro Leu Leu Gly Asn Glu Lys
                50                  55                  60

Thr Arg Gln Gly Val His Val Arg Arg Lys Arg Arg His Asp Glu Glu
65                  70                  75                  80

Gln Asn Pro Asp Thr Met Arg Asn Cys Thr Arg Lys Ile Ile Ile Ser
                85                  90                  95
```

```
Met Arg Phe Asn Asn Ile Gly Lys Thr Glu Ile Glu Asp Lys Phe Val
                100                 105                 110
Val Ile Asp His Val Leu Asp Pro Phe Thr Met Glu Lys Ile Pro Leu
            115                 120                 125
Gln Asn Pro Tyr Val Ile Lys Val Arg Gln Asp Thr Ile Leu Gln Phe
        130                 135                 140
Tyr Gly Leu Lys Phe Gln Ser Val Val Asn Ala Glu Ala Arg Glu Glu
145                 150                 155                 160
Val Ile Asn Asn Arg Ser Pro Asn Phe Thr Gly Cys Ser Val Thr Glu
                165                 170                 175
His Pro Thr Cys Gly Arg Ser Phe Ile His Gly Lys Pro Val Pro Tyr
            180                 185                 190
Ser Glu Gly Phe Cys Cys Ser Cys Asn Ser Thr Phe Glu Arg His Asp
        195                 200                 205
Leu Pro Asp Ser Ser Glu Pro Thr Arg Ser Cys Asn Asp Lys Ala Lys
    210                 215                 220
Ser Asn Tyr Glu Ala Ala Ala Asn Lys Ser Cys Asn Arg Phe Gln Ser
225                 230                 235                 240
Glu Ser Gly Trp Met Asp Arg Glu Asp Asn Ser Val Ala Arg Gly Gln
                245                 250                 255
Pro Ala Arg Gly Glu Ala Pro Phe Arg Gln Lys Pro Asn Val Ser Arg
            260                 265                 270
Ile Pro Gly Asn Glu Thr Ile Glu Phe Gly Thr Leu Tyr Asn Thr Arg
        275                 280                 285
Asn Gly Ile Gln Ile Ile Leu Ser Lys Lys Gln Pro Leu Val Asn Lys
    290                 295                 300
Glu Thr Val Ser Asn Ala Ser Arg Lys Ser Glu Gly Ser Glu Phe Pro
305                 310                 315                 320
Ala Thr Ile Trp Thr Lys Glu Asp Arg Trp Tyr Gly Lys Gly Phe
                325                 330                 335
Glu Thr Ser Thr Gly Val Ser Ser Tyr Leu Glu Val Ile Val Gly Glu
            340                 345                 350
Leu Leu Asp Val Thr Thr Thr Gly Gly Asp Arg Ala Leu Thr Arg Glu
        355                 360                 365
Gly Ile Ala Ser Ala Lys Gly Gly Asn Gly Lys Pro Ile Gly Lys Glu
    370                 375                 380
Gly Ser Ser Lys Gln Arg Gln Ser Thr Val Pro Val Lys Asn Ser Gly
385                 390                 395                 400
Leu Ala Arg Glu Asp Gly Gly Lys Arg His Glu Lys Gln Glu Glu Glu
                405                 410                 415
Glu Glu Gln Ile Gln Pro Ser Asn Leu Asp Tyr Gly Val Lys Trp Arg
            420                 425                 430
Asp Arg Asp Lys Phe Ser Ser Arg Glu Gln Arg Gly Arg Asn Met Arg
        435                 440                 445
Ser Thr Gly Lys Gly Thr Ala Asn Glu Ser Arg Ala Lys Glu Gln Arg
    450                 455                 460
Gln Ile Arg Gly Gly Gln Asp Cys Ser Asp Pro Arg His Pro Pro Asn
465                 470                 475                 480
Val Asp Ala Leu Lys Tyr Leu Glu Ser Ala His Cys Leu Arg Phe Ser
                485                 490                 495
Asp Leu Trp Tyr Ser Val Tyr Gln Leu Glu Glu Pro Ile Val Val His
            500                 505                 510
Lys Val Asp Leu Arg Leu Tyr Val Lys His Thr Leu Pro Asp Gly Ser
```

```
                515                 520                 525
Ile Leu Trp Lys Asp Leu Ser Asn Gly Ser Ile Ile Arg Leu Gly Thr
    530                 535                 540

Phe Asp Lys Tyr Tyr Arg Asn Lys Gly Asn Thr Val Ala Leu Lys Tyr
545                 550                 555                 560

Asn Glu Met Arg Ser Pro Ser Gly Ile Glu Tyr Asn Leu Asp Pro Thr
                565                 570                 575

Lys Asp Arg Leu Leu Val Pro Ser Arg Leu Ser Glu Glu Arg Ala Lys
            580                 585                 590

Tyr Ser Glu Ala Lys Gly Trp Ser Ser Glu Tyr Leu Val Val Glu Ala
        595                 600                 605

Asn Lys Ile Ser Gly Asp Val Asp Glu Cys Asp Lys Ala Gly Val Gly
    610                 615                 620

Phe Thr Ala Phe Ala Gly Gln Pro Asp Arg Cys Glu His Val Ser Gly
625                 630                 635                 640

Thr Cys Leu Lys Asn Gln Pro Leu Asp Tyr Trp Arg His Asp Ile Val
                645                 650                 655

Arg Met Thr Ser Ala Ile Asn Glu Ala Ile Glu Ala Arg Lys Ser Gly
            660                 665                 670

Arg Ala Gly Cys Tyr Phe Leu Ser Asn Phe Ala Arg Val Pro Ser Glu
        675                 680                 685

Ala Ile Lys Tyr Asn Val Asn Gly Thr Gly Ser His Glu Phe Leu Ala
    690                 695                 700

Leu Glu Tyr His Ser Met His Val Ser Val Ile Asp Val Glu Leu Arg
705                 710                 715                 720

Glu Asp Tyr Asn Ser Leu Leu Lys Pro Gly Ser Ile Gly Gln Ile Asp
                725                 730                 735

Glu Ile His Ile Asp Asn Thr Glu Ile Asp Asn Thr Val Ile Thr Val
            740                 745                 750

Leu Ile Thr Asn Lys Gly Pro Ser Pro Ser Ser Tyr Arg Leu Arg Ile
        755                 760                 765

Thr Asp Cys Pro Lys Gly Leu Pro Pro Ser Trp Phe Asn Val Glu Lys
    770                 775                 780

Glu Thr Lys Thr Ile Pro Pro His His Asp His Glu Ile Thr Leu Asn
785                 790                 795                 800

Leu Tyr Gly Lys Leu Pro Leu Glu Glu Phe Ser Cys Ser Ala Ile Leu
                805                 810                 815

Met Asn Arg Tyr Asp Gln Leu Val Ala Arg Arg Ile Asn Val Lys
            820                 825                 830

Lys Gly Asn Arg Cys Ser Cys Val Lys Ser Ser Glu Cys Thr Cys Ile
        835                 840                 845

Asn Lys Asn Asp Glu Thr Asn Thr Arg Tyr Lys His Val Lys Met Lys
    850                 855                 860

Asp Tyr His Val Ala His Leu Glu Glu Lys Lys Leu Ser Pro Lys Val
865                 870                 875                 880

Pro Glu Glu Pro Lys Val Ser Pro Thr Ile Trp Pro Gly Val Met Thr
                885                 890                 895

Ile Ser Trp Pro Asn Val Met Thr Ile Val Cys Ser Val Ser Thr Ile
            900                 905                 910

Leu Leu Leu Phe Leu Leu Leu Gly Phe Phe Lys Trp Met Phe Gly
        915                 920                 925

Leu Cys Val Pro Thr Val Ser Arg Trp Gly Leu Asp Thr Leu Ile Asp
    930                 935                 940
```

Thr Glu Lys Met Glu Arg Tyr Phe Glu Lys Asp Leu Arg Ser Arg Ser
945                 950                 955                 960

Val Ile Phe Asn Glu Leu Gly Gln Pro Val His Pro Asp Thr Tyr Gln
                965                 970                 975

Lys Ser Val Arg Val Cys Asn Arg Ile Ser Glu Phe Ile Leu Asn Leu
            980                 985                 990

Ser Phe Phe Phe Val Tyr Pro Phe Met Ala Leu Phe Gln Asn Pro Arg
        995                 1000                1005

Ala Lys Pro Gln Pro Pro Ser His Gln Ile Ser Thr Thr Ser Thr
    1010                1015                1020

Thr Asn Thr Thr Thr Ser Thr Lys Glu Ser Lys Ala Ser Leu Leu
    1025                1030                1035

Ser Glu Lys Asp Glu Ser Ser Thr Met Ile Arg Val Ile Thr Tyr
    1040                1045                1050

Gly Asp Thr Ile Asn Ser Lys Met Glu Glu Asp Thr Lys Tyr
    1055                1060                1065

Val Ile Asp Glu Leu Lys Lys Ser Gln Glu Ser Leu Gln Lys Asn
    1070                1075                1080

Arg Tyr Lys Cys
    1085

<210> SEQ ID NO 59
<211> LENGTH: 501
<212> TYPE: PRT
<213> ORGANISM: Volvox carteri

<400> SEQUENCE: 59

Ser Ala Ala Arg Ser Pro Ser Gly Ile Cys Pro Cys Pro Cys Asn Ala
1               5                   10                  15

Ala Val Asp Glu Gly Cys Ser Cys Arg Asp Leu Ala Glu Pro Leu Val
            20                  25                  30

Val Glu Tyr Asn Lys Glu Ala Leu Tyr Val Ser His Met Leu Asn Tyr
        35                  40                  45

Thr Gly Thr Tyr Asn Tyr Lys Pro Tyr Glu Val Leu Asp Ile Asn Pro
    50                  55                  60

Leu Lys Leu Cys Glu Gln Asp Ala Pro Thr Asp Asp Trp Pro Gln Cys
65                  70                  75                  80

Gly Trp Gln Lys Val Asp Gly Lys Arg Val Pro Asp Ser Gln Gly Phe
                85                  90                  95

Cys Cys Trp Cys Asp Arg Lys Val Ile Trp Asp Gln Thr Gly Arg Asn
            100                 105                 110

Pro Ala Leu Arg Arg Ala Asn Lys Ala Cys Asp Glu Asn Met Phe Pro
        115                 120                 125

Glu Leu Glu Arg Glu Pro Val Ser Ala His Cys Leu Arg Leu Asp Asp
    130                 135                 140

Gln Trp Tyr Arg Val Ser Thr Thr Thr Gly Val Gln Leu Gly Met
145                 150                 155                 160

Phe Val Thr Gln Tyr Arg Leu Gly Tyr Asn Leu Arg Pro Gly Gly Thr
                165                 170                 175

Leu Gln Phe Gly Val Arg Leu Glu Val His Ile Pro Thr Ala Gly Lys
            180                 185                 190

Pro Ala Ser Met Ala Tyr Val Asn Gly Thr Leu Arg Ile Ser Lys Ser
        195                 200                 205

Thr Val Ile Thr Arg Ser Glu Ser Leu Asp Leu Thr Leu Ala Gly Pro

```
            210                 215                 220
Leu Val Thr Thr Ser Asn Lys Met Thr Ser Ala Arg Leu Leu Gly Asp
225                 230                 235                 240

Leu Ser Ser Tyr Ala Gln Val Pro Gly Leu Ser Cys Asp Lys Ile Gly
                245                 250                 255

Thr Ser Tyr Thr Ala Phe Arg Asn Gln Gln Asn Ala Cys Gln Thr Cys
            260                 265                 270

Leu Arg Asn Gln Leu Lys Asp Leu Phe Glu Gly Asp Gln Lys Arg Ile
        275                 280                 285

Gly Ser Gly Met Thr Pro Leu Tyr Leu Leu Ser Gln Phe Asn Gly Val
    290                 295                 300

Asn Gly Met Ala Val Arg Cys Leu Asn Pro Arg Met Arg Asn Pro His
305                 310                 315                 320

Asn Trp Gln Ala Pro Val Ala Thr Tyr Thr Gln Leu Ser Asn Leu Arg
                325                 330                 335

Met Cys Glu Phe Gly Ser Thr Thr Ser Cys Gly Ser Leu Gly Phe Ile
            340                 345                 350

Thr Arg Gly His Ile Phe Leu Ser Val Ala Asn Met Gly Leu Leu Pro
        355                 360                 365

Ala Asp Tyr Ile Ile Val Val Ser Asp Cys Ser Leu Asn Asn Val Trp
    370                 375                 380

Pro Ile Glu Ala Arg Met Ile Thr Val Asn Ala Gly Gln Thr Val Asn
385                 390                 395                 400

Leu Ser Pro Pro Ile Pro Ile Tyr Met Asn Asp Thr Thr Lys Glu
                405                 410                 415

Arg Ser Cys Ala Val Gln Leu Tyr Asp Ala Cys Ala Asn Pro Ala Gly
            420                 425                 430

Val Ser Cys Phe Ile Glu Asn Asp Cys Pro Ala Lys Met Gly Arg Phe
        435                 440                 445

Leu Gly Ile Leu Ala Ala Ile Leu Ala Gly Ile Thr Leu Met Val Leu
    450                 455                 460

Ala Cys Lys Tyr Ser Trp Phe Ser Lys Leu Tyr Gly Cys Cys Cys Asn
465                 470                 475                 480

Asp Ala Gly Cys Met Leu Gly Gly Gly Ser Arg Arg Gly Gly Leu
                485                 490                 495

Asp Leu Gly Tyr Gly
            500

<210> SEQ ID NO 60
<211> LENGTH: 685
<212> TYPE: PRT
<213> ORGANISM: Paramecium tetraurelia A

<400> SEQUENCE: 60

Met Ser Val Phe Leu Leu Thr Leu Leu Arg Leu Thr Ser Gln Glu Pro
1               5                   10                  15

Leu Thr Thr Ser Gln Ile Lys Val Cys Asp Ser Asn Lys Asn Ala Asp
                20                  25                  30

Cys Ser Glu Asn Met Leu Ile Ser Leu Thr Ile Glu Asn Ser Phe Ser
            35                  40                  45

Thr Ser Thr Glu Gln Ile Gln Ile Asn Ser Thr Ile Leu Asn Asn Gln
        50                  55                  60

Thr Val Gln Leu Ser Thr Pro Phe Thr Leu Thr Ile Thr Lys Thr Pro
65                  70                  75                  80
```

-continued

```
Val Tyr Ala Tyr Tyr Pro Leu Lys Tyr Phe Gln Asn Tyr Asn Ser Gln
                 85                  90                  95

Pro Tyr Glu Leu Gln Ile Pro Ser Ala Val Asn Pro Cys Asp Asp Asn
            100                 105                 110

Trp Thr Ser Asn Ser Pro Thr Cys Gly Phe Gln Tyr Ser Ser Thr Asn
            115                 120                 125

Lys Val Gln Asp Ser Gln Gly Phe Cys Cys Ser Cys Gly Ser Ser Glu
            130                 135                 140

Tyr Ser Gly Gln Asn Asp Gln Ser Val Arg Ile Asn Ile Cys Lys Asn
145                 150                 155                 160

Ala Ser Val Ala Thr Met Ala Phe Cys Leu Arg Tyr Ser Pro Leu Trp
                165                 170                 175

Tyr Ser Ser Tyr Asn Ile Ser Lys Phe Val Ile His Tyr Asn Ile Thr
            180                 185                 190

Ile Ser Ile Lys Tyr Ser Asn Asp Glu Val Glu Gln Tyr Thr Leu Gly
            195                 200                 205

Ser Glu Val Lys Glu Val Lys Gly Glu Ser Ser Ile Ala Lys Ile Ile
    210                 215                 220

Ser Asp Tyr Ile Pro Ser Asn Gln Pro Pro Ser Leu Glu Ser Phe Met
225                 230                 235                 240

Leu Met Lys Pro Ser Ser Pro Thr Ser His Asn Arg Val Gln Ala Gly
                245                 250                 255

Ser Ala Ala Tyr Met Phe Val Pro Lys Glu Phe Leu Gly Gln Gly Glu
            260                 265                 270

Cys Asn Lys Ile Gly Val Ser Tyr Thr Ser Phe Lys Asn Glu Arg Asn
            275                 280                 285

Ser Cys Lys Lys Leu Ile Arg Ser Cys Leu Gln Asn Gln Leu Glu Asp
    290                 295                 300

Leu Tyr Gln Asn Asp Ile Ala Gln Leu Asn Asn Ser Gln Pro Thr
305                 310                 315                 320

Tyr Leu Ile Gln Lys Tyr Gly Glu Phe Lys Gln Ile Asn Ile Asn Asn
                325                 330                 335

Asp Gln Tyr Leu Gln Phe Ser Ile Asp Gln Gln Met Phe Thr Thr Ile
            340                 345                 350

Thr Leu Glu Ile Asn Thr Thr Gly Arg Ile Ser Tyr Ile Gly Asn Lys
            355                 360                 365

Gln Glu Ser Val Lys Gly Gln Ile Asp Leu Val Glu Ile His Asn Phe
    370                 375                 380

Ser Ile Ala Ser Gly Ser Gly Leu Leu Tyr Ala Gln Ile Thr Asn Thr
385                 390                 395                 400

Gly Gly Ser Leu Ser Glu Phe Lys Ser Phe Asn Cys Ser Thr Asn
                405                 410                 415

Thr Ile Thr Ile Asn Ser Thr Glu Leu Glu Pro Leu Gln Ser Ile Ile
            420                 425                 430

Ile Gln Gln Asp Ile Asn Val Ser Ile Asp Ile Lys Lys Ser Thr Ser
            435                 440                 445

Cys Asn Phe Ser Leu Leu Ser Asn Glu Gly Ala Leu Leu Asp Trp Lys
    450                 455                 460

Ile Val Tyr Leu Asn Gln Phe Asp Asn Asn Thr Asn Gln Ser Asn Asn
465                 470                 475                 480

Tyr Asn Gln Thr Ile Thr Ser Glu Gly Lys Val Cys Glu Ile Lys Cys
                485                 490                 495

Ser Gln Phe Ile Asp Ile Ser Cys Tyr Leu Gln Asn Asn Cys Glu Lys
```

```
            500                 505                 510
Asp Ala Ile Thr Phe Phe Thr Val Leu Gly Gly Ile Leu Leu Thr Phe
            515                 520                 525

Ser Phe Cys Cys Leu Tyr Val Gly Gln Lys Arg Asn Ser Cys Cys Phe
            530                 535                 540

Trp Ser Lys Asn Lys Arg Met Ser Ile Ile Pro Leu Glu Ser Val
545                 550                 555                 560

Leu Tyr Gln Gln Asn Ser Gln Met Lys Arg Arg Ile Gly Gly Ser Glu
                565                 570                 575

Ser Ser Tyr Glu Gln Ile Ser Gln Leu Gln Ile Ser Ile Leu Ser Ala
                580                 585                 590

Asn Leu Asn Lys Ile Met Tyr Leu Asn Leu Ala Leu Gly Thr Asp Pro
                595                 600                 605

Ile Ser Asn His Leu Gln Ser Asp Ala Ser Phe Glu Val Leu Ala Thr
                610                 615                 620

Tyr Gln Asn Lys Asp Leu Val Glu Leu Ser Ile Lys Arg Arg Ser Pro
625                 630                 635                 640

Phe Val Arg Ile Phe Lys Glu Ile Tyr Gly Leu Gln Asp Ala Asp Arg
                645                 650                 655

Asn Val Lys Lys Tyr Leu Glu Gly Lys Arg Glu Ser Ile Tyr Leu Phe
                660                 665                 670

Ser Asn Leu Leu Thr Glu Phe Pro Leu Phe Ser Ile Tyr
                675                 680                 685

<210> SEQ ID NO 61
<211> LENGTH: 698
<212> TYPE: PRT
<213> ORGANISM: Paramecium tetraurelia B

<400> SEQUENCE: 61

Met Ile Val Ile Ile Val Ser Ser Leu Ile Leu Lys Ser Met Ala Glu
1               5                   10                  15

Ile Ile Ser Gln Ser Gln Ile Asn Lys Cys Tyr Ser Asn Ser Thr Asn
                20                  25                  30

Asn Thr Glu Cys Ser Glu Lys Met Leu Ile Ser Leu Thr Val Glu Asn
            35                  40                  45

Ala Gln Asn Thr Val Thr Glu Tyr Ile Lys Ile Ser Glu Thr Thr Ile
        50                  55                  60

Asp Asn Gln Thr Ser Gln Leu Lys Thr Pro Ile Ile Ser Ile Thr
65                  70                  75                  80

Lys Thr Pro Val Tyr Ala Phe Tyr Pro Leu Lys Tyr Thr Glu Asp Tyr
                85                  90                  95

Asn Ser Gln Pro Tyr Glu Val Lys Ile Ala Gly Ala Ile Leu Ser Cys
            100                 105                 110

Asp Asp Ser Trp Tyr Ser Asn Ser Pro Thr Cys Gly Phe Gln Tyr Glu
        115                 120                 125

Lys Lys Glu Lys Ile Phe Asp Ser Gln Gly Phe Cys Cys Ser Cys Gly
    130                 135                 140

Ile Leu Asp Leu Ile Gly Leu Ser Asp Glu Phe Ala Arg Gly Asn Ile
145                 150                 155                 160

Cys His Lys Ala Gly Leu Thr Thr Ala Thr Met Ala Phe Cys Leu Arg
                165                 170                 175

Tyr Ser Thr Leu Trp Tyr Ser Ala Tyr Glu Ile Ser Thr Tyr Ser Ile
            180                 185                 190
```

```
Tyr Tyr Asn Ile Thr Ile Ser Ile Thr Tyr Ser Asn Gln Glu Glu
            195                 200                 205

Glu Leu Gln Leu Gly Ser Glu Val Lys Val Val Gln Gly Lys Thr Leu
210                 215                 220

Ile Gly Arg Ile Ile Gly Asp Phe Thr Pro Leu Asn Pro Pro Pro Ser
225                 230                 235                 240

Leu Glu Ser Phe Tyr Phe Met Arg Pro Ser Ser Pro Asn Ser His Ala
                245                 250                 255

Arg Val Gln Ala Gly Ser Ala Ala Phe Met Ile Val Ser Lys Asp Gln
            260                 265                 270

Val Gly Arg Gly Glu Cys Asn Lys Ile Gly Val Ser Tyr Ser Ala Phe
            275                 280                 285

Arg Thr Glu Ala Glu Arg Cys Lys Lys Gln Val Lys Ser Cys Leu Lys
290                 295                 300

Asn Gln Leu Glu Asp Phe Tyr Ile Glu Asp Gln Ala Leu Ile Ala Asn
305                 310                 315                 320

Asn Ser Gln Pro Lys Tyr Leu Leu Ser Arg Tyr Gly Lys Phe Lys Ser
                325                 330                 335

Ile Tyr Leu Asn Asn Glu Thr Tyr Leu Gln Tyr Ser Val Glu Gly Ser
            340                 345                 350

Met Gln Thr Met Ile Thr Leu Glu Ile Thr Thr Gly Leu Ile Ser
            355                 360                 365

Tyr Val Val Asn Leu Gly Lys Gly Lys Ile Asp Leu Ala Glu Ile Gln
            370                 375                 380

Asp Phe Glu Ala Lys Ser Gly Asn Gly Leu Leu Tyr Ala Gln Ile Thr
385                 390                 395                 400

Asn Val Gly Asp Ile Glu Ser Glu Phe Asn Thr Tyr Leu Asn Cys Ser
                405                 410                 415

Ile Asn Val Ile Pro Ile Asn Ser Ala Ala Leu Tyr Leu Lys Pro Leu
            420                 425                 430

Glu Ser Tyr Ile Val Lys Lys Asp Val Asn Val Leu Ser Asp Met Asn
            435                 440                 445

Lys Ser Asn Ile Cys Thr Phe Ser Leu Leu Asn Asn Lys Gly Thr Leu
450                 455                 460

Leu Asp Gln Lys Gln Ile Glu Phe Asn Thr Thr Glu Ile Gln His Glu
465                 470                 475                 480

Ser Glu Gln Asn His Glu Glu Gln Asn Ile Lys Asp Asn Glu Val Leu
                485                 490                 495

Ala Ser Asp Glu Ser Gln Asp Asn Cys Tyr Ser Asp Cys Ser Val Phe
            500                 505                 510

Leu Asp Ile Thr Cys Tyr Ile Phe Asn Asp Cys Asn Ser Gln Ile Ile
            515                 520                 525

Thr Phe Phe Thr Val Leu Gly Ile Thr Phe Ile Phe Leu Ile Ile Cys
530                 535                 540

Leu Thr Cys Leu Ser Tyr Arg Lys Lys Leu Cys Cys Cys Lys Lys Ser
545                 550                 555                 560

His Lys Cys Lys Pro Ser Val Leu Glu Thr Ile Val Gln Lys Asp Tyr
                565                 570                 575

Lys Thr Asn Lys Lys Gln Gln Lys Arg Tyr Asp Asn Ser Ile Tyr Glu
            580                 585                 590

Asn Asn Ile Asp Leu Leu Glu Asn Ser Ser Leu Gln Leu Ile Glu Asn
            595                 600                 605

Arg Ile Met Tyr Leu Asn Leu Ala Ser Gly Ser Asp Pro Ile Ser Asn
```

```
                   610                 615                 620

Tyr Leu Gln Ser Asp Val Ser Phe Glu Val Leu Thr Ser Tyr Gln Arg
625                 630                 635                 640

Lys Gln Leu Ile Asn Met Lys Ile Lys Arg Asn Ser Asp Phe Leu Lys
                    645                 650                 655

Val Phe Gln Asn Val Tyr Gly Leu Glu Ser Leu Glu Arg Asn Val Lys
                660                 665                 670

Lys Tyr Phe Gln Lys Lys Cys Glu Ser Val Leu Leu Phe Asn Asn Leu
                675                 680                 685

Leu Thr Asp Leu Pro Leu Phe Ser Leu Leu
            690                 695

<210> SEQ ID NO 62
<211> LENGTH: 715
<212> TYPE: PRT
<213> ORGANISM: Tetrahymena thermophila

<400> SEQUENCE: 62

Met Lys Phe Leu Ala Phe Gly Leu Ile Tyr Phe His Phe Cys Ile Leu
1               5                   10                  15

Asn Arg Cys Glu Tyr Ile Thr Ser Ser Thr Ile Gln Lys Cys Tyr Asn
            20                  25                  30

Ser Ser Asn Glu Pro Asn Asn Cys Ser Gln Lys Ala Val Ile Val Leu
        35                  40                  45

Ser Leu Glu Asn Gly Gln Ile Ala Asn Thr Glu Gln Val Val Ala Thr
50                  55                  60

Leu Asn Gln Leu Ser Asp Ser Gly Val Asn Lys Gln Leu Gln Asn Ser
65                  70                  75                  80

Phe Ile Phe Glu Val Thr Lys Ser Pro Val Thr Ala Leu Phe Pro Leu
                85                  90                  95

Ile Tyr Leu Gln Asp Phe Asn Ser Gln Pro Leu Glu Gln Val Ile Ala
            100                 105                 110

Thr Thr Leu Phe Ser Cys Lys Asp Gly Phe Tyr Asp Ser Ser Pro Thr
        115                 120                 125

Cys Lys Phe Gln Tyr Asp Ser Lys Gly Gln Lys Ile Leu Asp Ser Gln
130                 135                 140

Gly Tyr Cys Cys Tyr Cys Ser Leu Ser Asp Ile Leu Gly Met Gly Asn
145                 150                 155                 160

Asp Leu Ser Arg Gly Lys Val Cys Tyr Ala Leu Asn Leu Gly Ala Gly
                165                 170                 175

Ser Ala Thr Ala His Cys Leu Lys Phe Ser Pro Leu Trp Tyr Ser Ala
            180                 185                 190

Phe Lys Ile Gln Gln Tyr Gln Leu Tyr Phe Glu Val Asn Ile Asn Ile
        195                 200                 205

Tyr Thr Val Asp Ser Gln Asn Gln Lys Asn Leu Lys Gln Thr Leu Lys
210                 215                 220

Leu Ser Thr Ser Asn Pro Thr Met Lys Ser Ser Asp Asn Ser Thr Ile
225                 230                 235                 240

Ser Lys Ile Ile Gly Thr Phe Thr Pro Thr Gln Pro Pro Ala Asp Leu
                245                 250                 255

Ser Ser Tyr Tyr Leu Val Lys Pro Ser Phe Pro Ala Thr Asp Pro Arg
            260                 265                 270

Val Leu Gln Gly Ile Ser Ser Trp Met Phe Val Asp Lys Thr Met Phe
        275                 280                 285
```

```
Thr Leu Asp Gly Thr Gln Cys Asn Lys Ile Gly Val Ser Tyr Ser Gly
    290                 295                 300
Phe Arg Gln Gln Ser Ser Ser Cys Ser Gln Pro Val Gly Ser Cys Leu
305                 310                 315                 320
Gln Asn Gln Leu Glu Asn Leu Tyr Gln Ser Asp Leu Ile Leu Leu Ser
                325                 330                 335
Gln Arg Leu Ser Gly Ser Ala Ser Thr Leu Ile Thr Ile Glu Ile Asp
            340                 345                 350
Ala Ala Gln Ile Lys Phe Val Thr Asn Leu Gly Ile Gly Cys Ile Ser
        355                 360                 365
Gln Cys Ser Ile Asn Asn Phe Glu Ser His Ser Gly Asn Gly Lys Leu
    370                 375                 380
Val Ala Leu Val Gln Asn Gln Gly Asn Tyr Ser Ala Glu Phe Val Leu
385                 390                 395                 400
Gly Phe Asn Cys Ser Ser Asn Val Gln Pro Ile Gln Gly Gln Lys Leu
                405                 410                 415
Phe Leu Thr Ala Asn Gln Leu Tyr Asn Phe Asn Cys Ser Val Ser Val
            420                 425                 430
Asn Ser Asp Ile Ser Ala Ile Asn Asn Cys Thr Ile Asn Leu Tyr
        435                 440                 445
Asp Ala Ile Gly Asn Gln Leu Asp Ser Lys Asn Ile Leu Phe Asn Thr
450                 455                 460
Thr Ser Thr Asn His Thr Ser Asn Gln Gly Asn Asn Thr Gly Gln Gln
465                 470                 475                 480
Gln Ser Ser Gln Glu Tyr Lys Ser Ser Gln Ser Cys Ser Asp Lys Cys
                485                 490                 495
Ser Ser Phe Trp Ser Phe Trp Cys Tyr Phe Ser Ala Gly Cys Ile Lys
            500                 505                 510
Glu Ala Phe Lys Ser Ile Ala Ser Ile Ala Gly Val Ala Ser Ala Leu
        515                 520                 525
Ala Leu Val Ile Phe Leu Ala Lys Asn Gly Tyr Leu Val Pro Ile Ile
    530                 535                 540
Arg Phe Leu Cys Cys Cys Cys Lys Ser Lys Lys Lys Glu Asn Glu
545                 550                 555                 560
Lys Asn Lys Asp Lys Thr Asp Lys Lys Ser Ile Gln Glu Ser Cys Ser
                565                 570                 575
Tyr Asp Arg Ser Cys Cys Ser His Ser Ile Ser Gln Ser Tyr Gln Val
            580                 585                 590
Glu Asn Lys Asn Lys Tyr Lys Arg Ser Lys Ile Gln Arg Ser Phe Ser
        595                 600                 605
Ser Glu Ser Cys Gln Asp Lys Ser Lys Lys Ile Asn Glu Leu Ser
    610                 615                 620
Asn Leu Glu Glu Thr Phe Glu Ala Asn Lys Leu Tyr Ala Asn Ile Asp
625                 630                 635                 640
Lys Asn Ser Ser Ile Phe Glu Tyr Phe Gly Phe Lys Lys Ser Phe Thr
                645                 650                 655
Phe Ile Leu Tyr Glu Arg Asn Asp Ile Leu Phe Leu Pro Gln Asn Ser
            660                 665                 670
Thr Ile Leu Asp Met Ile Gly Ala Leu Gln Pro Gln Lys Gly Ser Tyr
        675                 680                 685
Leu Ala Gln Lys Phe Leu Glu Ile Val Asn Lys Asn Ala Leu Lys Val
    690                 695                 700
Val Ser Thr Ser Pro Leu Tyr Leu Leu Ile Glu
```

<210> SEQ ID NO 63
<211> LENGTH: 394
<212> TYPE: PRT
<213> ORGANISM: Cryptosporidium hominis

<400> SEQUENCE: 63

Met Trp Trp Asn Val Tyr Leu Ser Lys Ser Cys Pro Val Trp Ile Pro
1 5 10 15

Pro Trp Trp Thr Ala Phe Arg Ile Gly Gly Trp Asn Trp Gln Tyr Ser
20 25 30

Leu Glu Val Glu Leu Ser Trp Phe Ser Pro Thr Glu Ser Ser Ile Asn
35 40 45

Lys Leu Ser Ser Thr Glu Leu Glu Asn Met Glu Asn Glu Cys Lys Lys
50 55 60

Glu Asn Lys Asp Ser Thr Ile Asp Cys Ser Arg Ile Arg His Lys Glu
65 70 75 80

Ser Gly Ile Gln Thr Ser Val His Thr Leu Asn Ser Ser Ser Pro Ser
85 90 95

Phe Tyr Asp Pro Asn Phe Gly Ala Ser Val Gln Val Ile Ser Ser Gly
100 105 110

Pro Pro Phe Gly Ser Ala Asn Ala Lys Asp Leu Asn Gly Tyr Tyr Met
115 120 125

Leu Gln Pro Thr Phe Ser Pro Lys Gly Met Pro Ala Ser Ile Ala Ile
130 135 140

Pro Pro Leu Arg Ser Gly Cys Gly Lys Ala Ser Lys Asn Gln Thr Glu
145 150 155 160

Glu Glu Met Asn Asp Cys Leu Lys Pro Thr Leu Ile Ile Pro Pro Glu
165 170 175

Asn Ala Asp Phe Thr Gly Val Ser Cys Asp Lys Ile Gly Thr Ser Val
180 185 190

His Thr Trp Ser Ser Val Asn Gly Arg Phe Cys Tyr His Pro Pro Gly
195 200 205

Thr Cys Gln Arg Ala Gln Ile Ala His Phe Tyr Lys Lys Val Ile Glu
210 215 220

Asp His Ser Leu Gly Lys Ile Ser Gln Tyr Ser Val Arg Ala Gln Asn
225 230 235 240

Ser Gly Ser Pro Gln Leu Ile Leu Asp Ser Leu Gly Glu Ile Gly His
245 250 255

Glu Glu Val Asp Gln Asn Asp Met Glu Asn Ile Thr Asn Ile Gln Ser
260 265 270

Arg Arg Phe Phe Leu Gly Tyr Asn Phe Asp Ser Ile Phe Asp Thr Glu
275 280 285

Ile Met Phe Ser Val Glu Ala Ser Ser Val Ser Trp Val Ala Thr Ser
290 295 300

Ser Pro Gly Ile Ile Thr Tyr Ile Glu Pro Pro Pro Leu Glu Ala Cys
305 310 315 320

Thr Ala Met Ser Ser Phe Gly Cys Pro Leu Lys Val Tyr Ile Lys Asn
325 330 335

Ser Gly Lys Phe Glu Tyr Ile Tyr Thr Phe Arg Ile Glu Leu Lys Ile
340 345 350

Thr Tyr Gln Lys Tyr Ser Ile Gly Asp Ile Asp Ser Gly Phe Val Val
355 360 365

```
Gln Ile Pro Tyr Cys Thr Lys Ser Gly Val Gln Thr Ser Glu Val Gly
        370                 375                 380

Leu Tyr Leu Thr His Ser Asn Leu Tyr Asn
385                 390
```

<210> SEQ ID NO 64
<211> LENGTH: 759
<212> TYPE: PRT
<213> ORGANISM: Theileria parva

<400> SEQUENCE: 64

```
Met Ser Ser Leu Gly Pro Phe Arg Ser Val Phe Thr Ser Leu Ile Tyr
1               5                   10                  15

Phe Ser Ile Leu His Ile Leu Gly Phe Thr Ser Leu Phe Asn Phe Tyr
            20                  25                  30

Thr Thr Asp Ser Thr Gly Phe Phe Val Asp Ser Ala Val Thr Gly
        35                  40                  45

Asn Ile Thr Gln Cys Val Arg Asn Ser Asp Lys Leu Phe Asp Asp Gln
    50                  55                  60

Thr Cys Val Gln Arg Leu His Thr Asn Val Asp Val Ser His Gly Leu
65                  70                  75                  80

Arg Glu Tyr His Tyr Ile Tyr Arg Arg Lys Asp Asp Leu Ser Lys Gly
                85                  90                  95

Leu Tyr Leu Val Leu Lys Thr Ser Asn Thr Ser Leu Leu Tyr Thr Leu
            100                 105                 110

Asn Tyr Gln Thr Met Val Pro Leu Tyr Tyr Thr Asp His Thr Glu Arg
        115                 120                 125

Trp Thr Tyr Ser Glu Ile Ser Gly Glu Leu Lys Thr Ser Cys Lys Ser
130                 135                 140

Val Gln Asn Ser Lys Cys Thr Lys Lys Thr Gln Val Pro Pro Gly Ile
145                 150                 155                 160

Asp Phe Leu Pro Arg Val Cys Cys Ile Cys Gly Leu Asn Val His Lys
                165                 170                 175

Pro Thr Pro Arg Ala Asp Phe Lys Cys Gly Gly Phe Leu Ala Met Gly
            180                 185                 190

Gly Arg Thr Ala Leu Ser Met Ser Cys Leu Glu Ile Ser Glu Pro Trp
        195                 200                 205

Tyr Lys Leu Tyr Lys Thr Ser Tyr Pro Pro Ala Ile Ser Arg Ser Val
210                 215                 220

Thr Val Asn Ile Tyr Lys Phe Asp Ser Ser Thr Gly Ile Ile Pro Asp
225                 230                 235                 240

Val Thr Leu Glu Asp Glu Asp Lys Phe Asp Asn Tyr Asp Phe Lys Lys
                245                 250                 255

Arg Glu Lys Lys Asp Pro Val Ile Lys Ser Pro Glu Ile Lys Ser Arg
            260                 265                 270

Ser Thr Lys Glu Ile Thr Gly Lys Lys Asp Glu Leu His Pro Asn Phe
        275                 280                 285

Arg Arg Ile Ile Ile Asp Asp Thr Val Lys Glu His Ile Asn Asp
290                 295                 300

Leu Asp Val Lys Ile Thr Leu Leu Ser Ser Asn Thr Lys Asp Gly Ser
305                 310                 315                 320

Ala Pro Pro Leu Phe Asp Lys Tyr Val Ala Ile Pro Ser Phe Pro Arg
                325                 330                 335

Thr Asn Glu Thr Val Lys Gly Ser Ser Leu Met Asp Lys Cys Gln Asp
            340                 345                 350
```

```
Ser Thr Trp Lys Thr Lys Pro Glu Cys Pro Lys Tyr Met Asn Pro Ser
        355                 360                 365

Leu Cys Asp Ile Trp Arg Cys Thr Leu Asn Met Arg Thr Val Lys Met
    370                 375                 380

Ser Ala Val Asp Thr Asp Gly Leu Met Cys Asp Lys Ile Gly Leu Ser
385                 390                 395                 400

Met Lys Arg Trp Ala Asn Gln Glu Glu Ile Cys Asn Ser Ser Pro Gly
                405                 410                 415

Ser Cys Leu Lys Asn Gln Leu Lys His Tyr Phe Asp Gln Glu Lys Asp
                420                 425                 430

Glu Ala Lys Leu Pro Lys Leu Tyr Gly Val Glu Pro Thr Phe Thr Ala
                435                 440                 445

Val Lys Lys Asp Leu Ser Leu Pro Ala Val Lys Glu Ala Asn Lys Thr
                450                 455                 460

Thr Leu Asp Asp Pro Asn Arg Ile His Thr Leu Thr Tyr Ile His Ser
465                 470                 475                 480

Lys Asp Asp Val Thr Arg Leu Lys Ile Asp Thr Phe Asp Ala Thr Val
                485                 490                 495

Thr Glu Ile Ile Ser Asp Phe Pro Gly Phe Ile Val Ser Ala Lys Met
                500                 505                 510

Asp Gly Glu Cys Glu Val Ser Ser Glu Lys Gly Cys Asn Met Glu Leu
                515                 520                 525

Asp Val Lys Asn Met Gly Lys Phe Thr His Lys Asn Ser Ile Leu Gly
                530                 535                 540

Val Lys Lys Ser Glu Phe Thr Val Arg Ala Asn Cys Tyr Asp Asp Pro
545                 550                 555                 560

Asp Leu Lys Asn Glu Val Ala Gln Ile Ser Glu Thr Thr Leu Ser Ile
                565                 570                 575

Asp Gly Asn Lys Asn Lys Thr Val Ser Ile Pro Ile Lys Leu Thr Gly
                580                 585                 590

Ser Leu Ala Ser Glu Lys Gly Tyr Cys Asn Ile Ile Leu Leu Ser Gly
                595                 600                 605

Lys Lys Glu Met Leu Asp Gly Met Lys Met Glu Ile Leu Val Lys Val
                610                 615                 620

Lys Lys Glu Thr Phe Gly Lys Asp Pro Val Lys Val Gln Asp Ile Val
625                 630                 635                 640

Ala Ala Pro Ser Pro Lys Asp Lys Leu Thr Thr Pro Gln Val Ile Asn
                645                 650                 655

Pro Ile Val Ile Asn Gln Pro Gly Ser Lys Asn Asp Thr Lys Lys Glu
                660                 665                 670

Glu Glu Ser Gln Cys Lys Cys Ala Ser Trp Asn Ile Phe Cys Met Leu
                675                 680                 685

Ile Asn Phe Lys Ile Cys Val Ser Ser Tyr Val Ser Lys Val Leu Phe
                690                 695                 700

Tyr Val Leu Ile Ala Leu Gly Ile Leu Leu Leu Ile Leu Leu Pro
705                 710                 715                 720

Val Leu Ile Pro Leu Ile Val Ser Leu Phe Lys Ala Leu Ala Gly Leu
                725                 730                 735

Ile Lys Thr Pro Leu Glu Ala Leu Glu Gln Arg Arg Leu Lys Lys Lys
                740                 745                 750

Asn Asn Thr Gln Leu Glu Val
                755
```

<210> SEQ ID NO 65
<211> LENGTH: 607
<212> TYPE: PRT
<213> ORGANISM: Toxoplasma gondii

<400> SEQUENCE: 65

Met Asp Pro Pro Leu Pro Arg Trp Arg Ala Val Ala Val Ala Ala Phe
1               5                   10                  15

Leu Ile Ala Thr Ile Cys His Asn Gly Val Asp Ala Asp Ile Pro Gln
            20                  25                  30

Ala Val Ser Arg Gln Gln Ile Cys Thr Val Asn Gly Ala Tyr Gly Lys
        35                  40                  45

Asp Asp Pro Arg Arg Met Gln Cys Lys Asp Thr Ile Leu Gly Thr Leu
    50                  55                  60

Arg Ile Ser Asn Lys Glu Lys Phe Ser Phe Asn Val Met Gln Asn Thr
65                  70                  75                  80

Ile Asp Ser Arg Asp Lys Thr Tyr Ala Asp Val Gly Asn Val Gly Phe
                85                  90                  95

Val Val Thr Ile Thr Lys Thr Pro Val Thr Ile Ser Leu Pro Leu Glu
            100                 105                 110

Tyr Ile Lys Glu Val Pro Phe Asp Tyr Arg Glu Ile Tyr Glu Tyr
        115                 120                 125

Ser Arg Trp Glu Ala Gly Arg Leu Pro Glu Lys Phe Cys Tyr Glu Asp
    130                 135                 140

Thr Thr Asp Lys Cys Ser Glu Asp Gly Lys Leu Ala Val His Pro His
145                 150                 155                 160

Gly Lys Pro Leu Ser Trp Ala His Gly Arg Cys Cys Trp Cys Ser Glu
                165                 170                 175

Val Leu Ala Phe Thr His Ile Asn Asn Met Lys Arg Gly Asn Phe Arg
            180                 185                 190

Cys Asn Trp Phe Ala Pro Pro Arg Ala Leu Glu Leu Val Thr Glu Thr
        195                 200                 205

Leu Tyr Asp Gln Cys Glu Ala Gly Lys Ile Asp Gly Thr Val Pro Leu
    210                 215                 220

Asp Arg Asp Cys Glu Arg Glu Lys His Glu Arg Leu Gly Ile Thr Asp
225                 230                 235                 240

Arg Val Tyr Thr Leu Asn Tyr Thr Thr Pro Glu Ile Phe Asp Arg Ser
                245                 250                 255

Val Tyr Cys Asn Thr Lys Ser Cys Leu Lys His Ala Ile Ile Leu Asp
            260                 265                 270

Lys Asp Tyr Val Ser Val Thr Gly Tyr Glu Cys Asp Lys Val Gly Thr
        275                 280                 285

Gly Leu Asp Arg Trp Gly Asp Met Arg Gly Glu Phe Cys Asn Leu Leu
    290                 295                 300

Pro Gly Thr Cys Ile Thr Gly Gln Leu Arg Lys Phe Lys Glu Val Asp
305                 310                 315                 320

Lys Leu Arg Ile Glu Gln Asn Leu Ala Pro Leu Tyr Ala Leu Lys Arg
                325                 330                 335

Glu Phe Gly Gly Phe Pro Arg Tyr Ala Pro Asn Pro Met Asn Gly Thr
            340                 345                 350

Gly Phe Ser Thr Thr Gly Thr Arg His Tyr Leu Gly Tyr Asp Phe Gly
        355                 360                 365

Glu Gln His Tyr Ser Asp Ile Arg Phe Glu Met Asp Ala Thr Asp Val
    370                 375                 380

```
Thr Trp Leu Arg Ala Thr Ser Pro Gly His Ile Thr Phe Ile Glu Val
385                 390                 395                 400

Pro Gln Leu Asp Ala Cys Ser Ser Thr Ile Gly Gly Cys Pro Leu
            405                 410                 415

Lys Ala Tyr Val Trp Asn Ser Gly Asn Glu Asp Ala Ala Phe Ala Val
            420                 425                 430

Glu Val Pro Phe Cys Ile Asp Ser Ile Thr Lys Glu Arg Thr Ile Asp
            435                 440                 445

Val Asn Pro Ile Thr Pro Val Arg Thr Thr Val Pro Ala Asp Lys Thr
450                 455                 460

Val Val Phe Thr Leu Thr Phe Lys Ala Ile Ser Ser Ser Leu Gly
465                 470                 475                 480

Val Thr Cys Phe Met Lys Leu Tyr Asp Ala Gln His Leu Met Leu Asp
                485                 490                 495

Gln Lys Thr Phe Asn Val Thr Thr Ser Ala Ala Gln Ala His Asp Thr
            500                 505                 510

Gln His Ser His Lys Ile Thr Lys Met Pro Gln Arg Lys Leu Leu Gly
            515                 520                 525

Gly Ala Phe Thr Lys Ala Ala Val Gly Ala Thr Ala Ala Met Gly Phe
530                 535                 540

Phe Gly Arg Arg Thr Gly Lys Lys Lys Gly Asp Thr Asn Val Glu
545                 550                 555                 560

Ala His Ser Val Thr Pro Gln Ser Phe Ala Glu Asp Ala Arg Gly Pro
                565                 570                 575

Gly Ile Gln Asp Lys Leu Gln Gly Lys Ala Asp Pro Ala Glu Thr Ser
            580                 585                 590

Leu Phe Gly Glu Ser Ala Thr Ser His Ala Ala Lys Leu Ser Lys
            595                 600                 605

<210> SEQ ID NO 66
<211> LENGTH: 665
<212> TYPE: PRT
<213> ORGANISM: Naegleria gruberi

<400> SEQUENCE: 66

Met Phe Arg Tyr Gly Ile Ala Phe Leu Leu Ile Leu Cys Cys Ser Ile
1               5                   10                  15

Asn Val Tyr Ser Leu Ser Ser Lys Val Val Ser Cys Thr Asp Ala Ser
                20                  25                  30

Cys Thr Thr Gln Leu Ala Val Gln Ile Ser Leu Ala Phe Gly Asn Gln
            35                  40                  45

Lys Ser Met Leu Val Glu Leu Ser Asp Thr Val Asn Glu Lys Gly Glu
50                  55                  60

Lys Val Asn Leu Arg Pro Ile Lys Ile Val Gln Lys Ser Ala Pro
65                  70                  75                  80

Lys Ala Val Tyr Pro Leu Leu Tyr Val Lys Thr Phe Asn Gly Lys Pro
                85                  90                  95

Thr Glu Ser Ile Ile Tyr Lys Asp Asp Ile Leu Val Pro Thr Cys Asp
            100                 105                 110

Asp Ser Ser Lys Ser Ala Ala Pro Thr Cys Gly Trp Val Lys Asp Ser
            115                 120                 125

Gln Gly Asn Lys Ile Pro Asp Ser Gln Gly Phe Cys Cys Ser Cys Ser
            130                 135                 140

Val Gly Gln Met Phe Gly Asp Ser Ser Ala Ser Asn Arg Gly Ala Leu
```

```
            145                 150                 155                 160
        Asn Cys Gly Phe Met Gln Met Lys Ser Ser Ala His Cys Leu Arg Leu
                            165                 170                 175

Gly Glu Val Tyr Trp Asp Ala Tyr Glu Ile Glu Gly Tyr Val Met Ser
                            180                 185                 190

Phe Glu Ile Ser Val Phe Ile Gly Glu Thr Gly Phe Asp Asp Ile Gly
                    195                 200                 205

Lys Val Thr Val Ser Pro Ser Ser Lys Leu Ala Gln Leu Pro Lys Gly
                    210                 215                 220

Gly Arg Val Glu Leu Glu Gly Asp Phe Ser Ala Tyr Lys Ser Val Pro
        225                 230                 235                 240

Leu Tyr Glu Ser Lys Tyr Leu Phe Ile Pro Ser Ser Pro Lys Thr Ser
                            245                 250                 255

Pro Ile Val Val Asn Gly Gln Ala Asn Trp Met Phe Ile Asp Lys Ser
                            260                 265                 270

Met Val Thr Leu Ser Gly Ser Glu Cys Asp Lys Ile Gly Val Ser Tyr
                    275                 280                 285

Ala Gln Phe Arg Asn Gln Pro Asn Ala Cys Ser Arg Pro Ala Leu Thr
                    290                 295                 300

Cys Leu Ala Asn Gln Ile Glu Asp Leu Arg Leu Ala Asp Val Glu Leu
        305                 310                 315                 320

Met Lys Ser Gly Leu Lys Ser Gly Lys Tyr Ile Val Ser Asn Phe Gly
                            325                 330                 335

Ser Phe Ala Val Asn Lys Thr Asn Thr Gly Asn Val Leu Glu Lys Tyr
                            340                 345                 350

Leu Asp Glu Asp Thr Asn Ser Gln Ile Asn Leu Tyr Ile Asn Gly Glu
                    355                 360                 365

Asn Val Lys Phe Leu Ile Thr Lys Ser Ala Ala Glu Ile Ser Glu Ala
                    370                 375                 380

Tyr Val Lys Thr Phe Thr Ser Leu Ser Lys Glu Gly Glu Met Leu Val
        385                 390                 395                 400

Ser Val Lys Asn Lys Gly Ala Asn Gly Cys Ser Tyr Val Val Thr Val
                            405                 410                 415

Thr Glu Cys Ser Asp Asn Ile Leu Thr Ile Val Gln Gln Thr Val Phe
                            420                 425                 430

Val Asp Ala Ser Asn Lys Lys Glu Leu Thr Phe Gln Val Arg Ser Glu
                    435                 440                 445

Gln Lys Leu Ala Thr Thr Asn Gln Cys Lys Val Thr Leu Leu Phe Ser
                    450                 455                 460

Asp Gly Glu Lys Ile Gln Asp Ile Thr Val Thr Phe Asp Ser Lys Asp
        465                 470                 475                 480

Tyr Ala Tyr Glu Asn Ala Met Glu Ser Ser Gly Glu Gln Thr Gly Lys
                            485                 490                 495

Val Glu Thr Glu Gly Asp His Ser Leu Gly Gln Cys Lys Cys Asn Ser
                            500                 505                 510

Pro Phe Asp Val Val Cys Ile Val Leu Asn Ser Ser Ser Cys Thr Ser
                    515                 520                 525

Tyr Ile Ile Gly Trp Val Ala Ser Ile Val Gly Ile Ile Ala Thr Pro
                    530                 535                 540

Val Ile Phe Val Phe Leu Trp Arg Cys Gly Leu Phe Gly Leu Met Phe
        545                 550                 555                 560

Lys Thr Cys Lys Cys Cys Ala Cys Cys Cys Ser Phe Leu Pro Thr Ser
                            565                 570                 575
```

```
Ile Met Asn Cys Leu Ile Gly Pro Tyr Lys Lys Ser Lys Ser
            580                 585                 590

Lys Lys Ser Lys Lys Lys Arg His His Ser Ser Asp Ser Glu
    595                 600                 605

Asp Glu Lys Lys Ser Lys Lys Lys Lys Ser Lys Lys Asn Lys
610                 615                 620

Lys Arg Arg Lys Arg Arg Gln Gln Arg Arg Asp Asp Phe Glu Met
625                 630                 635                 640

Asp Tyr Tyr Asn Asp Arg Tyr Ser Lys Arg Arg Ser His Lys Asp Ile
                645                 650                 655

Glu His Asp Pro Ile Ala Arg Tyr Lys
            660                 665

<210> SEQ ID NO 67
<211> LENGTH: 705
<212> TYPE: PRT
<213> ORGANISM: Arabidopsis thaliana

<400> SEQUENCE: 67

Met Val Asn Ala Ile Leu Met Ala Cys Ile Leu Ala Gly Ile Phe Val
1               5                   10                  15

Gly Met Phe Asn Glu Val Asp Gly Ile Gln Ile Leu Ser Lys Ser Lys
            20                  25                  30

Leu Glu Lys Cys Glu Lys Thr Ser Asp Ser Gly Asn Leu Asn Cys Ser
        35                  40                  45

Thr Lys Ile Val Leu Asn Leu Ala Val Pro Ser Gly Ser Ser Gly Gly
    50                  55                  60

Glu Ala Ser Ile Val Ala Glu Ile Val Glu Val Glu Asp Asn Ser Ser
65                  70                  75                  80

Ser Asn Met Gln Thr Val Arg Ile Pro Pro Val Ile Thr Val Asn Lys
                85                  90                  95

Ser Ala Ala Tyr Ala Leu Tyr Asp Leu Thr Tyr Ile Arg Asp Val Pro
            100                 105                 110

Tyr Lys Pro Gln Glu Tyr His Val Thr Thr Arg Lys Cys Glu Pro Asp
        115                 120                 125

Ala Gly Pro Asp Ile Val Gln Ile Cys Glu Arg Leu Arg Asp Glu Lys
    130                 135                 140

Gly Asn Val Leu Glu Gln Thr Gln Pro Ile Cys Cys Pro Cys Gly Pro
145                 150                 155                 160

Gln Arg Arg Met Pro Ser Ser Cys Gly Asp Ile Phe Asp Lys Met Ile
                165                 170                 175

Lys Gly Lys Ala Asn Thr Ala His Cys Leu Arg Phe Pro Gly Asp Trp
            180                 185                 190

Phe His Val Phe Gly Ile Gly Gln Arg Ser Leu Gly Phe Ser Val Arg
        195                 200                 205

Val Glu Leu Lys Thr Gly Thr Arg Val Ser Glu Val Ile Ile Gly Pro
    210                 215                 220

Glu Asn Arg Thr Ala Thr Ala Asn Asp Asn Phe Leu Lys Val Asn Leu
225                 230                 235                 240

Ile Gly Asp Phe Gly Gly Tyr Thr Ser Ile Pro Ser Phe Glu Asp Phe
                245                 250                 255

Tyr Leu Val Ile Pro Arg Glu Ala Ala Glu Ala Gly Gln Pro Gly Ser
            260                 265                 270

Leu Gly Ala Asn Tyr Ser Met Trp Met Leu Leu Glu Arg Val Arg Phe
```

-continued

```
              275                 280                 285
Thr Leu Asp Gly Leu Glu Cys Asn Lys Ile Gly Val Gly Tyr Glu Ala
    290                 295                 300
Phe Asn Thr Gln Pro Asn Phe Cys Ser Ser Pro Tyr Trp Ser Cys Leu
305                 310                 315                 320
His Asn Gln Leu Trp Asn Phe Arg Glu Ser Asp Ile Asn Arg Ile Asp
                325                 330                 335
Arg His Gln Leu Pro Leu Tyr Gly Leu Glu Gly Arg Phe Glu Arg Ile
            340                 345                 350
Asn Gln His Pro Asn Ala Gly Pro His Ser Phe Ser Ile Gly Val Thr
        355                 360                 365
Glu Thr Leu Asn Thr Asn Leu Met Ile Glu Leu Arg Ala Asp Asp Ile
    370                 375                 380
Glu Tyr Val Phe Gln Arg Ser Pro Gly Lys Ile Asn Ile Ala Ile
385                 390                 395                 400
Pro Thr Phe Glu Ala Leu Thr Gln Phe Gly Val Ala Ala Val Ile Ile
                405                 410                 415
Lys Asn Thr Gly Glu Val Glu Ala Ser Tyr Ser Leu Thr Phe Asp Cys
            420                 425                 430
Ser Lys Gly Val Ala Phe Val Glu Glu Gln Phe Phe Ile Ile Lys Pro
        435                 440                 445
Lys Ala Val Thr Thr Arg Ser Phe Lys Leu Tyr Pro Thr Lys Asp Gln
    450                 455                 460
Ala Ala Lys Tyr Ile Cys Thr Ala Ile Leu Lys Asp Ser Gln Phe Ser
465                 470                 475                 480
Glu Val Asp Arg Ala Glu Cys Gln Phe Ser Thr Thr Ala Thr Val Leu
                485                 490                 495
Asp Asn Gly Thr Gln Val Thr Asn Pro Phe Gln Ile Pro Glu Thr Gln
            500                 505                 510
Pro Lys Gly Phe Phe Asp Ser Ile Arg Ile Leu Trp Thr Lys Ile Ile
        515                 520                 525
Asn Gly Leu Val Asp Phe Ile Thr Gly Asp Thr Cys Arg Asn Lys Cys
    530                 535                 540
Ser Ser Phe Phe Asp Phe Ser Cys His Ile Gln Tyr Val Cys Leu Ser
545                 550                 555                 560
Trp Met Val Met Phe Gly Leu Leu Ala Leu Phe Pro Ile Thr Cys
                565                 570                 575
Leu Leu Leu Trp Leu Leu His Gln Lys Gly Leu Phe Asp Pro Cys Tyr
            580                 585                 590
Asp Trp Trp Glu Asp His Phe Asp Leu Asp His His Arg Arg Leu Leu
        595                 600                 605
Pro Ser Arg Ala Asp Val Val Asn Arg His His His His Lys His
    610                 615                 620
Arg His His His Asn His His Arg Arg Thr His Gln Arg His Lys His
625                 630                 635                 640
His His Gly Gln Asp Asp Val Leu Gln Lys Met Met Leu Glu Arg
                645                 650                 655
Asp His Ser Asp Ser His Tyr Tyr His Gln Leu His Arg Val His Lys
            660                 665                 670
Asp Ser Lys Gln Lys Gln Arg Arg Ala Lys His Gly Ile Val Leu
        675                 680                 685
Pro Arg Asp Val His Val Glu Arg Gln Arg Lys Gln Arg Leu Arg Glu
    690                 695                 700
```

Ser
705

<210> SEQ ID NO 68
<211> LENGTH: 698
<212> TYPE: PRT
<213> ORGANISM: Lilium longiflorum

<400> SEQUENCE: 68

```
Met Glu Thr Arg Ser Ser Pro Ala Ser Thr Phe Leu Leu Leu Leu
1               5                   10                  15

Leu Leu His Pro Leu Ser Thr Ala Val Glu Ile Leu Ser Lys Ser Arg
                20                  25                  30

Val Glu Arg Cys Thr Lys Thr Ser Asp Ser Asp Lys Leu Asp Cys Asn
            35                  40                  45

Asn Lys Ile Val Val Asp Leu Ala Val Pro Ser Gly Ser Ser Gly Gly
        50                  55                  60

Glu Ala Ser Ile Val Ala Gln Leu Val Glu Val Gln Arg Glu Asn
65                  70                  75                  80

Ala Thr Arg Lys Met His Thr Leu Arg Glu Pro Pro Val Ile Thr Ile
                85                  90                  95

Asn Lys Ser Ala Ala Tyr Ala Leu Tyr Lys Leu Ile Tyr Leu Arg Asp
                100                 105                 110

Val Ala Tyr Lys Pro Glu Glu Phe His Val Glu Thr Arg Arg Cys Glu
            115                 120                 125

Pro Asp Ala Pro Tyr Glu Ile Leu Gly Glu Cys Gln Gly Leu Arg Asp
130                 135                 140

Gln Asn Gly Asn Ile Ile Glu Asn Thr Gln Pro Val Cys Cys Pro Cys
145                 150                 155                 160

Gly Pro Glu Gly Arg Tyr Pro Thr Thr Cys Gly Ser Ile Phe Gln Val
                165                 170                 175

Phe Lys Gly Lys Thr Asn Thr Ala His Cys Leu Lys Phe Pro Gly Asp
            180                 185                 190

Trp Phe His Val Phe Ala Ile Gly Lys Arg Ser Leu Gly Phe Ser Val
        195                 200                 205

Arg Val Glu Val Arg Lys Gly Ser Gln Ser Glu Ala Ile Val Gly
210                 215                 220

Pro Asp Asn Arg Ala Val Leu Ser Glu Asp Asn Phe Leu Arg Val Asn
225                 230                 235                 240

Leu Ile Gly Asp Phe Val Gly Tyr Thr Ser Ile Pro Ser Phe Glu Asp
                245                 250                 255

Phe Tyr Leu Val Thr Pro Arg Leu Gly Ala Ala Gly Gln Pro Thr Asp
            260                 265                 270

Leu Gly Gly Asp Tyr Ser Lys Trp Met Leu Leu Glu Arg Glu Arg Phe
        275                 280                 285

Thr Leu Asp Gly Leu Glu Cys Asn Lys Ile Gly Val Ser Tyr Asp Ala
    290                 295                 300

Tyr Arg Ser Gln Pro Asn Phe Cys Ser Ser Pro Leu Trp Ser Cys Leu
305                 310                 315                 320

His Asn Gln Leu Trp His Phe Trp Glu Ala Asp Gln Asn Gln Ile Arg
                325                 330                 335

Arg Asn Gln Pro Pro Glu Tyr Val Val Glu Gly Arg Phe Lys Arg Ile
            340                 345                 350

Asn Gln His Pro Asn Ala Gly Thr His Ser Phe Ser Met Gly Ile Thr
```

```
                355                 360                 365
Glu Ala Leu Asn Thr Asn Leu Leu Ile Glu Leu Arg Ala Asp Asp Ile
370                 375                 380

Asp Tyr Val Tyr Gln Arg Ser Pro Gly Lys Val Leu Ala Ile Asn Ile
385                 390                 395                 400

Pro Thr Phe Glu Ala Leu Thr Gln Phe Gly Thr Ala Thr Val Thr Thr
                405                 410                 415

Lys Asn Thr Gly Lys Leu Glu Ala Ser Tyr Ser Leu Thr Phe Arg Cys
                420                 425                 430

Arg Ser Gly Val Ser Tyr Leu Glu Glu Gln Phe Tyr Ile Met Lys Pro
                435                 440                 445

Glu Glu Glu Val Ser Arg Ser Phe Arg Leu Tyr Leu Thr Ser Asp Leu
                450                 455                 460

Ala Ala Thr Tyr Glu Cys Ala Ala Ile Leu Lys Ala Ser Asp Phe Ser
465                 470                 475                 480

Glu Val Asp Arg Ala Asp Cys Gln Phe Thr Thr Thr Ala Thr Ile Leu
                485                 490                 495

Asp Asp Gly Ser Gln Ile Val Pro Ala Asn Glu Leu Lys Glu Lys Gly
                500                 505                 510

Ile Asn Gly Ile Phe Lys Ser Ile Lys Ser Ile Trp Gly Asn Ile Trp
                515                 520                 525

Glu Gly Leu Leu Glu Phe Phe Ser Gly Lys Thr Cys Arg Ser Lys Cys
530                 535                 540

Ser Ser Phe Phe Asn Phe Arg Cys His Met Gln Tyr Ile Cys Met Ser
545                 550                 555                 560

Trp Ile Leu Leu Leu Ser Leu Leu Ala Val Phe Pro Thr Gly Val
                565                 570                 575

Val Leu Leu Trp Leu Leu His Gln Gln Gly Leu Phe Asp Pro Ile Tyr
                580                 585                 590

Asp Trp Trp Tyr Asp Arg Tyr Gly Glu Gly Phe Gln Arg Ser Ser Ser
                595                 600                 605

Leu Phe Ser Leu Arg Asp Ser Arg Ser Ala Arg His Arg Gly Asp Asn
                610                 615                 620

Asn Ala Arg Leu Arg Asp Arg Lys His Ser Phe Tyr Glu Glu Lys Lys
625                 630                 635                 640

Arg Lys Arg Ser His Thr Ser Arg Met Leu His Glu Arg Ser His Ser
                645                 650                 655

Glu Ile Ala Ala Gly Asp His Tyr His His Arg His Glu Ser His Leu
                660                 665                 670

His Val His Lys Glu Arg His Lys Tyr Lys His Ser Lys Asp Leu Asp
                675                 680                 685

Glu His His Gly His Lys Ser Ser Lys Arg
                690                 695

<210> SEQ ID NO 69
<211> LENGTH: 722
<212> TYPE: PRT
<213> ORGANISM: Oryza sativa

<400> SEQUENCE: 69

Met Pro Arg Arg Gly Thr Pro Leu Pro Thr Ile Leu Leu Leu Leu
1               5                   10                  15

Ala Phe Val Gly Gly Ala Cys Gly Thr Glu Ile Leu Ser Lys Ser Arg
                20                  25                  30
```

-continued

```
Leu Glu Ser Cys Ser His Asp Ser Asp Ala Gly Gly Arg Leu Lys Cys
         35                  40                  45

Asp Arg Lys Leu Val Val Asp Leu Ala Val Pro Ser Gly Ala Ser Gly
 50                  55                  60

Gly Glu Ala Ser Leu Val Ala Arg Val Ala Gly Val Glu Glu Asn
 65                  70                  75                  80

Asp Thr Pro Ser Ala Thr Lys Ser Ile Arg Asp Pro Val Ile Thr
                     85                  90                  95

Val Ser Lys Ser Ala Thr Tyr Ala Leu Tyr Ala Leu Thr Tyr Leu Asp
                100                 105                 110

Arg Asp Val Ala Tyr Arg Pro Asp Glu Lys Tyr Val Lys Thr His Lys
                115                 120                 125

Cys Glu Pro Tyr Ala Gly Ala Lys Val Val Gly Glu Cys Glu Arg Leu
130                 135                 140

Trp Asp Glu Lys Gly Asn Val Ile Lys Gln Thr Glu Pro Ile Cys Cys
145                 150                 155                 160

Pro Cys Gly Pro His Arg Val Gln Ser Lys Cys Gly Asp Ile Trp Ser
                165                 170                 175

Lys Leu Thr Lys Gly Lys Ala Asn Thr Ala His Cys Val Arg Phe Pro
                180                 185                 190

Gly Asp Trp Phe His Val Phe Gly Ile Gly Ala Trp Ser Leu Arg Phe
                195                 200                 205

Ser Ile Arg Val Gln Val Lys Lys Gly Ser Ser Val Trp Asp Val Val
                210                 215                 220

Val Gly Pro Glu Asn Lys Thr Val Val Ser Gly Asp Asn Phe Leu Arg
225                 230                 235                 240

Val Lys Val Val Gly Asp Tyr Thr Gly Tyr Thr Ser Ile Pro Ser Phe
                245                 250                 255

Glu Asp Asn Tyr Leu Val Thr Pro Arg Lys Gly Thr Gly Ser Ser Gln
                260                 265                 270

Pro Gln Asp Leu Gly Asn Glu His Ser Lys Trp Met Ile Leu Asp Arg
                275                 280                 285

Val Arg Phe Thr Leu Asp Gly Leu Glu Cys Asp Lys Ile Gly Val Gly
                290                 295                 300

Tyr Glu Ala Tyr Arg Asn Gln Pro Asn Phe Cys Ser Ala Pro Tyr Gly
305                 310                 315                 320

Ser Cys Leu Gly Asn Gln Leu Trp Asn Phe Trp Glu Tyr Asp Lys Arg
                325                 330                 335

Arg Ile Asp Asn Ser Gln Leu Pro Leu Tyr Ile Val Glu Gly Arg Phe
                340                 345                 350

Gln Arg Ile Asn Gln His Pro Asn Ala Gly Ala His Thr Phe Ser Val
                355                 360                 365

Gly Val Thr Glu Asp Leu Asn Thr Asn Leu Leu Ile Glu Leu Met Ala
                370                 375                 380

Asp Asp Ile Glu Tyr Val Tyr Gln Arg Ser Pro Ala Lys Ile Ile Asp
385                 390                 395                 400

Ile Arg Val Pro Thr Phe Glu Ala Leu Ser Gln Val Gly Ile Ala Asn
                405                 410                 415

Val Thr Thr Lys Asn Ile Gly Lys Leu Glu Ser Ser Tyr Ser Leu Thr
                420                 425                 430

Phe Lys Cys Ser Ser Gly Ile Ser Pro Val Glu Glu Gln Leu Tyr Thr
                435                 440                 445

Met Lys Pro Asp Glu Val Ile Ala Arg Ser Phe Glu Leu Arg Ser Thr
```

```
            450                 455                 460
Thr Asp Gln Ala Ala Met His Gln Cys Glu Ala Ile Leu Lys Ala Ser
465                 470                 475                 480

Asp Phe Ser Glu Leu Asp Arg Glu Gly Tyr Arg Phe Ser Thr Ala Ala
                485                 490                 495

Thr Val Tyr Asn Asn Gly Ala Gln Ile Gly Pro Thr Asn Asp His Lys
            500                 505                 510

Lys Gly Gly Phe Trp Asp Ser Ile Lys Ala Leu Trp Arg Asn Leu Ile
        515                 520                 525

Asp Phe Leu Thr Gly Arg Leu Cys Trp Thr Lys Cys Pro Arg Leu Phe
    530                 535                 540

Asp Phe Gly Cys His Ile Gln Tyr Val Cys Ile Gly Trp Ile Leu Leu
545                 550                 555                 560

Leu Leu Leu Ile Pro Ala Ala Val Val Phe Leu Trp Leu Leu His Gln
                565                 570                 575

Glu Gly Leu Phe Asp Pro Leu Tyr Asp Trp Trp Gly Leu Glu Pro Asp
            580                 585                 590

Asp Asp Tyr Arg Ala Arg Arg Arg His Gln Lys Gly Arg His His Arg
        595                 600                 605

His His His Asp His Arg His Arg His Gly His Ser His Gly Asp His
    610                 615                 620

His His His Tyr His Gly Gly His His Gln Arg Arg Arg His His His
625                 630                 635                 640

Pro Pro Ala Trp Asp Val Glu Gly His His Asp Arg Gln Gln His
                645                 650                 655

Ser His Glu Ala Gly Arg Asn His His Arg Gly Tyr Gly Glu Val Val
            660                 665                 670

Ala Ala Gly Ala Ala Pro Leu Arg Leu Asp Arg Ala Ser Arg Pro Gly
        675                 680                 685

Gln Thr Glu Val Asp Ala Val Val Glu Tyr Arg Glu Arg Arg Ser Arg
    690                 695                 700

His Glu Arg His Gly Gly His Gly His Arg Asp Gly His Tyr Ser Pro
705                 710                 715                 720

Ser Val

<210> SEQ ID NO 70
<211> LENGTH: 889
<212> TYPE: PRT
<213> ORGANISM: Plasmodium falciparum

<400> SEQUENCE: 70

Met Asn Lys Arg Lys Thr Lys His Leu Lys Val Asn Ser Ile Leu
1               5                   10                  15

Arg Ile Phe Phe Phe Phe Phe Leu Ile Ser Phe Leu Phe Ser Asn Cys
                20                  25                  30

Lys Leu Asn Asp Tyr Ile Arg Thr Lys Tyr Pro Phe Ile Gln Phe Val
            35                  40                  45

Tyr Ser Tyr Ser Lys Lys Lys Val Cys Thr Ser Ser Thr Asp Asp Ser
        50                  55                  60

Thr Cys Arg Thr Val Val Tyr Gly Asp Leu Asp Val Ser Asn Asn Ser
65                  70                  75                  80

Val Leu Arg Leu Lys Val Leu Arg Ser Glu Gly Lys Gly Tyr Phe Val
                85                  90                  95

Thr Ile Arg Arg Asp Tyr Val Thr Ile Ser Tyr Tyr Leu Lys Tyr Met
```

-continued

```
            100                 105                 110
Lys Asp Ile Pro Leu Lys Tyr Arg Glu Val Asp Ile Phe Asn Asn
            115                 120                 125

His Lys Tyr Glu Lys Tyr Thr Glu Lys Gln Ile Lys Asp Phe Thr Tyr
        130                 135                 140

Asn Cys Thr Ala Ile Lys Val Glu Asp Ala Asn Asn Thr Val Gly Asp
145                 150                 155                 160

Phe Ala Pro His Tyr His Glu Tyr Thr Arg Gly Glu Ser Cys Ile Cys
                    165                 170                 175

Pro Ser Tyr His Leu Phe Lys Asn Asp Asn Ser Ile Lys Arg Ala Lys
                180                 185                 190

Leu Lys Cys Thr Tyr Phe Asn Met Leu Phe Thr Asp Ser Ala Ile Val
            195                 200                 205

Tyr Ser Arg His Cys Ala Ile Met Asp Leu Phe Tyr Phe Ser Val Tyr
        210                 215                 220

Glu Ile Asp Tyr Pro Pro Ile Phe Asn Thr Tyr Ile Asp Ile Thr Ile
225                 230                 235                 240

Gln Glu Tyr Thr Tyr Asp Asp Val Ser Gly Met Ser Leu Asn Lys His
                    245                 250                 255

Asp Leu Val Thr Lys Glu Lys Lys Tyr Glu Ile Asn Asp Ser Met Ser
                260                 265                 270

Glu Ile Arg Asp Asp Tyr Phe Asp Leu Trp Leu Phe Leu Arg Gly Glu
            275                 280                 285

Arg His Gly Lys Arg Thr Leu Ile Asn Leu Ser Asn Asp Tyr Val Val
        290                 295                 300

Ile Pro Ser Ser Pro Leu Asp Asp Ala Asp Val Ile Glu Thr Asp Val
305                 310                 315                 320

Met Arg Asn Cys Gly Leu Lys Glu Asp Asn Pro Ala Leu Lys Gly Cys
                    325                 330                 335

Asp Tyr Lys His Glu Cys Asn Ile Ile His Pro Cys Leu Val Lys Ala
                340                 345                 350

Met Met Leu Pro Lys Tyr Leu Phe Asp Leu Ser Gly Lys Thr Cys Asn
            355                 360                 365

Lys Leu Gly Val Ser Leu Asn Lys Trp Arg Asn Ser Asp Gly Asn Phe
        370                 375                 380

Cys Gly Ser Ser Ala Gly Tyr Cys Leu Ser Glu Asn Leu Phe Lys Tyr
385                 390                 395                 400

Tyr Tyr Ile His Lys Thr Ser Val Gly Asn Arg Lys Pro Ser Lys Tyr
                    405                 410                 415

Lys Ile Lys Asn Ile Tyr Gly Ser Glu Pro Gln Thr Lys Val Tyr Thr
                420                 425                 430

Ser Ala Lys Leu Pro Asn Tyr Leu Lys Asp Lys Val Asp Ser Asn Asn
            435                 440                 445

Asn Lys Ser Tyr Asp Ile Asn Asp Ile Asp Asn Lys Ile Phe Tyr Asn
        450                 455                 460

Glu Asn Ala Ala Ala His Ser His Phe Ile Asp Tyr Lys Tyr Asn Gly
465                 470                 475                 480

Asn His Thr Val Glu Ile Lys Phe Glu Thr Asn Ala Leu Glu Val His
                    485                 490                 495

Glu Ile Arg Pro Val Ser Tyr Gly Thr Ile Thr His Ile Thr Ile Pro
                500                 505                 510

Lys Asp Cys Ser Ser Asn Gln Thr Asn Ser Lys Glu Cys Ile Leu Val
            515                 520                 525
```

Val His Thr Trp Asn Asn Lys Thr Ile Gly Ala Asn Phe Ser Cys
    530                 535                 540

His Val Leu Cys Val Asp Lys Ser Thr Gln Gln Val Ala Thr His Ile
545                 550                 555                 560

Ser Pro Ile Ser Lys Ile Asn Ala His Ile Asp Ala Asn Lys Asn Tyr
                565                 570                 575

Ala Phe Tyr Phe Ile Ile Lys Phe Leu Ile Asn Lys Lys Ile Thr Ser
                580                 585                 590

Asn Cys Thr Ala Ile Leu Lys Asp Ala Asp Gly Arg Glu Cys Ser Lys
            595                 600                 605

Leu Ser Phe Asn Leu Thr Ser Lys Glu Thr Ile Asn Val Val Glu Ser
            610                 615                 620

Gly Ile Val Ala Gln Pro Val Glu Ser Glu Ala Gln Ile Asn Lys Tyr
625                 630                 635                 640

Asp Pro Asp Val Ser Gly Ala Ser Thr Pro Thr Ala Asp Lys Cys Asp
                645                 650                 655

Cys Tyr Phe Asn Leu Leu Cys Tyr Ile Leu Asn Leu Asn Thr Cys Val
                660                 665                 670

Ser Tyr Tyr Thr Lys Leu Ile Lys Asp Tyr Leu Gly Arg Phe Val Thr
                675                 680                 685

Ile Ala Ile Leu Ile Phe Leu Ala Pro Ser Leu Ile Pro Leu Leu Pro
690                 695                 700

Phe Ile Ile Lys Phe Phe Ile Ser Cys Ala Ser Leu Pro Met Lys Leu
705                 710                 715                 720

Phe Ser Asn Phe Ser Ser Trp Met Glu Asn Lys Lys Ser Asn Asn
                725                 730                 735

Ser Thr Lys Gln Asn Lys Asn Tyr Phe Gln Arg Lys Tyr Glu Asn Phe
                740                 745                 750

Lys Lys Lys Arg Thr Asn Met Lys Leu Asn Lys Cys Thr Ser Ser Ser
            755                 760                 765

Val Ser Ser Leu Thr Asn Val Ser Ser Ile Ser Ser Asn Asn Thr Met
770                 775                 780

Asn Ser Asp Ile Lys Lys Asp Val Ser Phe Asn Arg Ile Lys Ser Asn
785                 790                 795                 800

Arg Tyr Asn Lys Glu Asn His Lys Asn Lys Arg Lys Thr Lys Gly
                805                 810                 815

Asn His Ser Lys Tyr Ser Gly Thr Ser Met Glu Ser Thr Leu Thr Asn
                820                 825                 830

Thr Ser Pro Ser Ser Thr Pro Asp Asn Leu Ser Glu Ser His Ile Thr
            835                 840                 845

Ser Asn Ser Asn Lys Asn Asn Tyr Ser Ser Lys Lys Lys Asn Lys Cys
850                 855                 860

Asn Met Leu Tyr Lys Lys Glu His Ser Arg Lys Ser Ile Arg Lys Lys
865                 870                 875                 880

Ser Met Gly Ile Ser Glu Tyr Ser Ser
                885

<210> SEQ ID NO 71
<211> LENGTH: 828
<212> TYPE: PRT
<213> ORGANISM: Plasmodium yoelii

<400> SEQUENCE: 71

Met Lys Asn Lys Leu Ile Asn Leu Arg Ser Lys His Ile Tyr Lys Leu

-continued

```
1               5                   10                  15
Ile Ile Phe Phe Phe Phe Cys Ile Ile Leu Lys Tyr Tyr Lys Trp Cys
            20                  25                  30

Asp Ser Lys Asn Lys Val Phe Phe Ile Gln Leu Val Tyr Ser Phe Ala
            35                  40                  45

Lys Lys Ser Val Cys Thr Ser Ser Asp Asp Ser Thr Cys His Thr
            50                  55                  60

Val Thr Phe Gly Glu Leu Asp Val Ser Asn Asn Ser Val Val Arg Leu
65                      70                  75                  80

Lys Val Met Arg Lys Gly Gly Lys Gly Tyr Phe Leu Thr Ile Arg Arg
                85                  90                  95

Asp Tyr Val Thr Val Ser Tyr Tyr Leu Lys Tyr Val Lys Asp Ile Pro
                100                 105                 110

Leu Glu Phe Arg Glu Val Ile Asp Ile Phe Asn Asn His Lys Phe Glu
                115                 120                 125

Gln Tyr Thr Gln Glu Gln Ile Asn Lys Tyr Thr Tyr Thr Cys Asn Val
            130                 135                 140

Arg Lys Ile Glu Asp Ile Asp Lys Tyr Asp Glu Lys Asn Pro Thr Lys
145                 150                 155                 160

Phe His Glu Tyr Thr Arg Gly Glu Ala Cys Arg Cys Gln Ser Tyr Asn
                165                 170                 175

Tyr Phe Lys Asp Asp Glu Phe Ile Lys Arg Ala Lys Leu Lys Cys Ile
                180                 185                 190

Tyr Tyr Asn Met Leu Phe Thr Glu Ser Ala Thr Val Tyr Ser Arg His
                195                 200                 205

Cys Pro Phe Val Asp Leu Met His Phe Ala Val Tyr Asp Ile Glu Tyr
            210                 215                 220

Pro Pro Ile Phe Asn Thr Ile Val Asn Ile Thr Ile Glu Glu Tyr Tyr
225                 230                 235                 240

Tyr Asn Asp Val Ser Ser Val Leu Asn Asn Lys Ser Asp Leu Val Thr
                245                 250                 255

Lys Glu Lys Lys Tyr Gln Leu Asn Asp Thr Ile Thr Glu Ile Arg Asp
                260                 265                 270

Asp Tyr Phe Asp Leu Trp Leu Phe Leu Lys Gly Glu Thr His Gly Lys
                275                 280                 285

Arg Thr Leu Ile Asn Leu Ser Asn Asp Tyr Ile Val Ile Pro Ser Ser
            290                 295                 300

Pro Ile Asn Asn Lys Asp Val Ile Ala Ser Asp Ile Thr Arg Asn Cys
305                 310                 315                 320

Gly Leu Ser Gln Asn Ser Pro Leu Leu Lys Gly Cys Asn Tyr Ser Asn
                325                 330                 335

Val Cys Asn Thr Met His Pro Cys Leu Arg Lys Ala Met Met Leu Pro
                340                 345                 350

Lys Tyr Met Phe Asp Leu Ser Gly Lys Thr Cys Gly Lys Leu Gly Val
                355                 360                 365

Ser Leu Asn Thr Trp Arg Lys Ser Glu Gly Asn Phe Cys Gly Ser Glu
            370                 375                 380

Ala Gly Tyr Cys Ile Ser Asn Asn Leu Lys Lys Tyr Tyr Asp Ala His
385                 390                 395                 400

Asn Ser Ala Ser Thr Lys Asp Gly Val Ser Leu Ser Lys Tyr Lys Val
                405                 410                 415

Lys Asn Val Tyr Asn Ser Glu Pro Gln Thr Lys Ile Tyr Glu Ser Tyr
                420                 425                 430
```

```
Lys Val Pro Asp Tyr Leu Lys Asp Lys Ile Lys Ser Asn Asn His Ala
            435                 440                 445

Gln Ile Asp Glu Thr Asp Leu Asp Asn Lys Ile Phe Tyr Lys Pro Asn
    450                 455                 460

Val Ala Ala His Ser Gln Phe Ile Asp Tyr Lys Tyr Asn Gly Asn His
465                 470                 475                 480

Ser Val Glu Ile Lys Phe Glu Thr Asp Ala Leu Glu Val Tyr Glu Ile
                485                 490                 495

Arg Pro Ile Ser Asn Ala Thr Ile Thr His Val Thr Thr Pro Asn Asp
                500                 505                 510

Cys Ala Ser Thr Asn Ser Asn Ser Asn Glu Cys Val Leu Ile Ile His
            515                 520                 525

Val Trp Asn Asn Ser Lys Phe Val Gly Ser Asn Phe Ser Cys Ser Ile
            530                 535                 540

Thr Cys Thr Asn Lys Glu Thr Gly Gln Leu Ala Ser His Ile Asn Pro
545                 550                 555                 560

Ile Ala Pro Val Arg Ala Phe Ile Gly Pro Asn Lys Asn Tyr Ala Phe
                565                 570                 575

Tyr Phe Ile Ile Lys Phe Leu Ile Asn Lys Glu Ile Thr Thr Leu Cys
            580                 585                 590

Lys Ala Ile Val Lys Asp Ser Asn Gly Lys Glu Cys Ser Ile Glu Glu
            595                 600                 605

Phe Glu Leu Gln Ser Lys Glu Ser Val His Ile Val Glu Ser Glu Ile
    610                 615                 620

Asp Glu Gly Leu Pro Gln Val Val Val Glu His Pro Gln Ser Pro
625                 630                 635                 640

Asp Ile Lys Asn Pro Asp Glu Tyr Val Cys Lys Cys Thr Ile Asn Leu
                645                 650                 655

Leu Cys Tyr Val Ile Asn Phe Lys Thr Cys Ser Asn Tyr Tyr Ile Asn
                660                 665                 670

Ala Ala Lys Thr Leu Ile Gly Lys Phe Ala Ile Ile Ala Ile Leu Ile
            675                 680                 685

Ile Leu Ala Pro Ala Leu Ile Pro Leu Leu Pro Phe Phe Leu Asn Phe
            690                 695                 700

Phe Phe Ile Phe Ile Ser Thr Ile Leu Lys Leu Tyr Gln Ser Ile Ile
705                 710                 715                 720

Asn Thr Ile Gly Gln Ile Lys Ile Arg Asn Asn Asp Lys Pro Ile Ile
                725                 730                 735

Tyr Lys Lys Lys Ile Asn Asp Met Lys Thr Asn Tyr Leu Ser Ala Ser
                740                 745                 750

Ser Tyr Ser Ser Leu Ser Asp Ser Ser Ile Tyr Ser Thr Asp Ser
            755                 760                 765

Ile Ser Ser Met Arg Lys Asn Lys Lys Phe Asn Lys Gly Asn Met
770                 775                 780

Ser Ser Asn Ile Lys Gln Lys Lys Gly Glu Lys Val Lys Gln Lys
785                 790                 795                 800

Glu Pro Thr Arg Asn Ser Asn His Ile Ser His Glu Tyr Pro Asp Thr
                805                 810                 815

Ser Pro Ser Gly Lys Ser Lys Ile Tyr Pro Leu Arg
                820                 825
```

<210> SEQ ID NO 72
<211> LENGTH: 812

<212> TYPE: PRT
<213> ORGANISM: Plasmodium berghei

<400> SEQUENCE: 72

```
Met Ile Ile Ile Ile Phe Phe Cys Ile Ile Leu Lys Tyr Tyr Lys Trp
1               5                   10                  15

Cys Asp Phe Lys Asn Lys Val Phe Phe Ile Gln Leu Val Tyr Ser Phe
            20                  25                  30

Ala Lys Lys Ser Val Cys Thr Ser Ser Leu Asp Ser Thr Cys His
        35                  40                  45

Thr Val Thr Phe Gly Glu Leu Asp Val Ser Asn Asn Ser Val Val Arg
    50                  55                  60

Leu Lys Val Met Arg Lys Gly Gly Lys Gly Tyr Phe Leu Thr Ile Arg
65                  70                  75                  80

Arg Asp Tyr Val Thr Val Ser Tyr Tyr Leu Lys Tyr Val Lys Asp Ile
                85                  90                  95

Pro Leu Glu Phe Arg Glu Ile Ile Asp Ile Phe Asn Asn His Lys Phe
            100                 105                 110

Glu Gln Tyr Thr Gln Glu Gln Ile Asn Lys Tyr Thr Tyr Thr Cys Asn
        115                 120                 125

Val Arg Lys Ile Glu Asp Ile Asp Lys Tyr Asp Glu Lys Asn Pro Thr
130                 135                 140

Lys Phe His Glu Tyr Thr Arg Gly Glu Ala Cys Arg Cys Gln Thr Tyr
145                 150                 155                 160

Asn Tyr Phe Lys Asp Asp Glu Phe Ile Lys Arg Ala Lys Leu Lys Cys
                165                 170                 175

Ile Tyr Tyr Asn Met Leu Phe Thr Glu Ser Ala Thr Val Tyr Arg His
            180                 185                 190

Cys Pro Ile Ile Asp Leu Met His Phe Ala Val Tyr Asp Ile Glu Tyr
        195                 200                 205

Pro Pro Ile Phe Asn Thr Ile Val Asn Ile Thr Ile Glu Gly Tyr Tyr
    210                 215                 220

Tyr Asn Asp Val Ser Ser Val Leu Asn Asn Lys Ser Asp Leu Val Thr
225                 230                 235                 240

Lys Glu Lys Lys Tyr Gln Leu Asn Asp Thr Ile Thr Glu Ile Arg Asp
                245                 250                 255

Asp Tyr Phe Asp Leu Trp Leu Phe Leu Lys Gly Glu Thr His Gly Lys
            260                 265                 270

Arg Thr Leu Val Asn Leu Ser Asn Asp Tyr Ile Val Ile Pro Ser Ser
        275                 280                 285

Pro Ile Asn Asn Arg Asp Val Ile Ala Ser Ile Thr Arg Asn Cys
    290                 295                 300

Gly Leu Ser Gln Asn Ser Pro Leu Leu Lys Gly Cys Asn Tyr Ser Ser
305                 310                 315                 320

Ile Cys Asn Ile Met His Pro Cys Leu Arg Lys Ala Met Met Leu Pro
                325                 330                 335

Lys Tyr Met Phe Asp Leu Ser Gly Lys Thr Cys Gly Lys Leu Gly Val
            340                 345                 350

Ser Leu Asn Thr Trp Arg Lys Ser Glu Gly Asn Phe Cys Gly Ser Glu
        355                 360                 365

Ala Gly Tyr Cys Ile Ser Asn Asn Leu Lys Lys Tyr Tyr Asp Ile His
    370                 375                 380

Asn Ser Ala Ser Ile Lys Asp Gly Ile Ser Leu Ser Lys Tyr Lys Ile
385                 390                 395                 400
```

-continued

```
Lys Asn Ile Tyr Asn Ser Glu Pro Gln Thr Lys Ile Tyr Glu Ser Tyr
                405                 410                 415
Lys Leu Pro Asp Tyr Leu Lys Asp Lys Ile Lys Asn Asn His Ala
            420                 425                 430
Glu Met Asp Glu Asn Asp Leu Asp Asn Lys Ile Phe Tyr Lys Pro Asn
        435                 440                 445
Val Ala Ala His Ser Gln Phe Ile Asp Tyr Lys Tyr Asn Gly Asn His
    450                 455                 460
Ser Val Glu Ile Lys Phe Glu Thr Asp Ala Ile Glu Val Tyr Glu Ile
465                 470                 475                 480
Arg Pro Val Ser Ile Ala Thr Ile Thr His Val Thr Ile Pro Asn Asp
                485                 490                 495
Cys Ala Ser Asn Asn Ser Asn Ser Asn Glu Cys Val Leu Ile Ile His
            500                 505                 510
Val Trp Asn Asn Ser Lys Phe Val Gly Ser Asn Phe Ser Cys Ser Ile
        515                 520                 525
Ala Cys Thr Asn Lys Glu Thr Asp Gln Leu Ala Ser His Ile Asn Pro
    530                 535                 540
Ile Ala Pro Val Arg Ala Phe Ile Gly Pro Asn Lys Asn Tyr Ala Phe
545                 550                 555                 560
Tyr Phe Ile Ile Lys Phe Leu Ile Asn Lys Glu Ile Thr Thr Leu Cys
                565                 570                 575
Lys Ala Ile Val Lys Asp Ser Asn Gly Lys Glu Cys Ser Ile Glu Glu
            580                 585                 590
Phe Glu Leu Gln Ser Lys Glu Ser Val His Ile Val Glu Ser Glu Val
        595                 600                 605
Asp Glu Thr Thr Asp Gln Val Val Val Glu His His Thr Gln Ser Pro
    610                 615                 620
Asp Ile Lys Asn Pro Asp Glu Tyr Val Cys Lys Cys Thr Ile Asn Leu
625                 630                 635                 640
Leu Cys Tyr Val Ile Asn Phe Lys Thr Cys Ser Asn Tyr Tyr Ile Asn
                645                 650                 655
Thr Val Lys Thr Leu Ile Gly Lys Phe Ala Ile Ala Ile Leu Ile
            660                 665                 670
Ile Leu Ala Pro Ala Leu Ile Pro Leu Leu Pro Phe Phe Leu Asn Phe
        675                 680                 685
Phe Phe Leu Phe Ile Ser Thr Ile Leu Lys Leu Tyr Gln Ser Ile Ile
    690                 695                 700
Ser Thr Ile Gly Gln Ile Arg Ile Arg Asn Asn Asp Lys Pro Ile Ile
705                 710                 715                 720
Tyr Lys Lys Lys Ile His Asp Met Lys Thr Asn Tyr Leu Ser Val Ser
                725                 730                 735
Ser Tyr Ser Ser Leu Ser Asp Ser Ser Ile Tyr Ser Thr Asp Ser
            740                 745                 750
Val Ser Ser Met Arg Lys Asn Lys Lys Phe Asn Lys Asn Ile
        755                 760                 765
Ser Ser Asn Ile Lys His Lys Lys Gly Lys Lys Val Lys Gln Lys
    770                 775                 780
Glu Pro Asn Arg Asn Ser Asn His Thr Ser His Glu Tyr Ala Asp Thr
785                 790                 795                 800
Ser Pro Ser Gly Lys Ser Lys Ile Pro Pro Leu Arg
                805                 810
```

-continued

```
<210> SEQ ID NO 73
<211> LENGTH: 800
<212> TYPE: PRT
<213> ORGANISM: Tribolium castaneum

<400> SEQUENCE: 73
```

Met His Tyr Phe Ile Leu Ile Ile Ser Ile Leu His Gly Val Ser Ser
1               5                   10                  15

Leu Glu Arg Val Ser Thr Asn Leu Arg Lys Lys Leu Asp Ala Glu Glu
            20                  25                  30

Gln Asn Ala Ile Cys Cys Met His His Met Asp Cys Cys Arg Glu Ala
        35                  40                  45

Gln Lys Pro Thr Ser Phe Glu Val Lys Ser Met Met Thr Glu Cys Pro
    50                  55                  60

Asn Gln Asn Cys Leu Asn Trp Ser Asn Ala His Gln Val Ile Val Gln
65                  70                  75                  80

Arg Asn Lys Thr Thr Pro Glu Lys Leu Thr Asp Cys Lys Gln Lys Leu
                85                  90                  95

Leu Leu Thr Ile Lys Val Thr Asn Glu Gly Ile Pro Ser Asp Lys Ser
            100                 105                 110

Glu Tyr Val Ile Ile Asp His Ile Thr Asp Pro Thr Thr Leu Gln Lys
        115                 120                 125

Val Arg Ile Leu Asn Pro Tyr Ala Ile Arg Ile Arg Gln Gln Pro Met
    130                 135                 140

Leu Gln Ala Tyr Gln Leu Lys Phe Glu Arg Ala Val Asn Gly Glu Ala
145                 150                 155                 160

Lys Glu Gln Val Phe Asn Lys His Thr Arg Asn Tyr Arg Gly Cys Asp
                165                 170                 175

Thr Ser Tyr Glu Ser Pro Thr Cys Gly Leu Val Gln His Glu Gly Lys
            180                 185                 190

Met Val Pro Tyr Ser Thr Gly Phe Cys Cys Ser Cys Asp Ala Glu Lys
        195                 200                 205

Asn Arg Gln Leu Glu Glu His Gly Ser His Val Pro Leu Val Gln Trp
    210                 215                 220

Pro Leu Arg Asp Gly Val Pro Asp Tyr Arg Lys Asn Arg Pro Glu Glu
225                 230                 235                 240

Asn Asp Tyr Glu His Tyr Lys His Tyr Gly Phe Ile Arg Pro Asp Gly
                245                 250                 255

Lys Met Val Tyr Gly Arg Pro Gln Lys Arg Ala Asp Lys Ser Val Asn
            260                 265                 270

Tyr Gln Gln Phe Thr Glu Leu Lys Asp Gly Lys Ile Arg Gln Arg Arg
        275                 280                 285

Gly Gly Gln Thr Cys Asp Asp Ala Asp Leu Asn Ile Pro Glu Ser Phe
    290                 295                 300

Arg Glu Ser Thr His Cys Leu Thr Phe Ser Asn Met Trp Tyr Ser Val
305                 310                 315                 320

Tyr Gln Ile Ser Lys Pro Glu Ile Ile His Lys Leu Arg Ile Gln Ile
                325                 330                 335

Phe Gln Lys Tyr Glu Asp Cys His Gly Asn Thr His Trp Met Asp Ile
            340                 345                 350

Thr Gln Gly Lys Thr Ile Glu Leu Gly Thr Gln Thr Pro Leu Tyr Val
        355                 360                 365

Glu Lys Asp Ile Ile Ala Lys Tyr Cys Ser Glu Asp Ile Asp Phe Gln
    370                 375                 380

```
Asp Gln Ala Leu Asp Tyr Lys Asn Leu Lys Leu Leu Ile Pro Glu Arg
385                 390                 395                 400

Arg Val Val Asp Pro Glu Gln Phe Met Leu Leu Pro Lys Asn Ser Val
            405                 410                 415

Ser Asp Gly Arg Thr Cys Asp Thr Ala Gly Val Gly Tyr Glu Ala Phe
            420                 425                 430

Phe Lys Gln Arg Lys Arg Cys Ala Gln Pro Gln Gly Ser Cys Leu Gly
        435                 440                 445

Asn Gln Pro Asn Gln Leu His Glu Ser Asp Ala Glu Ala Val Lys Gln
        450                 455                 460

Gly Arg Val Gly Gln Tyr Phe Leu Lys Phe Tyr Gly Thr Leu Ala Glu
465                 470                 475                 480

Asp Pro Val Gly Tyr Asn Ser Ser Gly His Ile Gln Tyr Leu Lys Met
            485                 490                 495

Val Tyr Thr Lys Arg His Val Ser Thr Leu Ser Phe Glu Leu Asn Ala
            500                 505                 510

Asp Leu Val Thr Leu Leu Lys Pro Asn Ser Phe Ala Thr Ile Thr Glu
        515                 520                 525

Ala Tyr Thr Asp Ala Thr Asp Pro Ser Lys Ala Lys Ile Ile Val Lys
        530                 535                 540

Val Thr Asn Ser Gly Leu Leu Tyr Gly Val Phe Tyr Val Arg Met Ser
545                 550                 555                 560

Gly Cys Pro Leu Glu Val Ala Ala Thr Phe Asn Asn Ile Ala Ser Lys
            565                 570                 575

Ser Val Leu Ile Pro Pro Gln His Gln His Ile Phe Asn Leu Leu Val
            580                 585                 590

Glu Tyr Pro Leu Pro Met Lys Glu Phe Tyr Cys Ser Ile His Val His
        595                 600                 605

Asn Ile Asn Gln Glu Leu Ile Ala Val Arg Gln Val Arg Ile Met Thr
        610                 615                 620

Tyr Asp Arg Cys Ile Cys Ile Trp His Cys Glu Cys Ala Cys Tyr Val
625                 630                 635                 640

Ala Asp Lys Gly Leu Lys Cys Leu Pro Met Thr Leu Asp Asn Tyr His
            645                 650                 655

Ala Ala Gly Phe Gln Gly Gly Phe Pro Thr Glu Thr His Phe Val Glu
            660                 665                 670

Thr Ser Tyr Leu Asp Glu Met Leu Ala Met Met Phe Asn Met Phe Phe
        675                 680                 685

Phe Leu Val Leu Thr Leu Leu Ala Met Gly Leu Val Lys Ala Leu Leu
        690                 695                 700

Gly Leu Cys Ser Gln Glu Ile Ser Leu Trp Gly Leu Asp Thr Ile Leu
705                 710                 715                 720

Gly Thr Glu Ser Val Lys Lys Cys Gly Asp Lys Lys Cys Glu Tyr
            725                 730                 735

Lys Asn Asn Ser Gly Ile Ser Leu Ala Gly Gln Phe Cys Leu Asn Val
            740                 745                 750

Met Phe Phe Phe Leu Tyr Pro Leu Ala Leu Phe Asn Leu Cys Ile Arg
        755                 760                 765

His Tyr Cys Phe Ser Ala Tyr Thr Ile Glu Asp Asp Glu Cys Ser Cys
        770                 775                 780

Glu Glu Arg Trp Val Asn Tyr Glu Cys Asp Asp Glu Val Cys Arg Ala
785                 790                 795                 800
```